(12) United States Patent
Pramod et al.

(10) Patent No.: US 11,827,893 B2
(45) Date of Patent: Nov. 28, 2023

(54) PALE YELLOW LOCUS AND ITS APPLICATIONS IN TOBACCO

(71) Applicant: Altria Client Services LLC, Richmond, VA (US)

(72) Inventors: Sreepriya Pramod, Fredricksburg, VA (US); Andrew C. Adams, Midlothian, VA (US); Marcos Fernando de Godoy Lusso, Chesterfield, VA (US); Gregory A. Davis, Midlothian, VA (US); Jerry W. Morris, Jetersville, VA (US); Dongmei Xu, Glen Allen, VA (US); Jesse Frederick, Richmond, VA (US)

(73) Assignee: Altria Client Services LLC

( * ) Notice: Subject to any disclaimer, the term of this patent is extended or adjusted under 35 U.S.C. 154(b) by 117 days.

(21) Appl. No.: 17/067,289

(22) Filed: Oct. 9, 2020

(65) Prior Publication Data

US 2021/0108219 A1 Apr. 15, 2021

Related U.S. Application Data

(60) Provisional application No. 62/913,313, filed on Oct. 10, 2019, provisional application No. 62/913,414, filed on Oct. 10, 2019.

(51) Int. Cl.
*C12N 15/82* (2006.01)
*A01H 6/82* (2018.01)

(52) U.S. Cl.
CPC .............................. *C12N 15/8243* (2013.01)

(58) Field of Classification Search
None
See application file for complete search history.

(56) References Cited

U.S. PATENT DOCUMENTS

| | | |
|---|---|---|
| 4,516,590 A | 5/1985 | Teng |
| 4,528,993 A | 7/1985 | Sensabaugh, Jr. et al. |
| 4,660,577 A | 4/1987 | Sensabaugh, Jr. et al. |
| 4,848,373 A | 7/1989 | Lenkey |
| 4,897,355 A | 1/1990 | Eppstein et al. |
| 4,946,787 A | 8/1990 | Eppstein et al. |
| 4,987,907 A | 1/1991 | Townend |
| 5,049,386 A | 9/1991 | Eppstein et al. |
| 5,159,135 A | 10/1992 | Umbeck |
| 5,188,958 A | 2/1993 | Moloney et al. |
| 5,372,149 A | 12/1994 | Roth et al. |
| 5,463,174 A | 10/1995 | Moloney et al. |
| 5,538,880 A | 7/1996 | Lundquist et al. |
| 5,550,318 A | 8/1996 | Adams et al. |
| 5,591,616 A | 1/1997 | Hiei et al. |
| 5,750,871 A | 5/1998 | Moloney et al. |
| 5,824,877 A | 10/1998 | Hinchee et al. |
| 6,153,812 A | 11/2000 | Fry et al. |
| 6,160,208 A | 12/2000 | Lundquist et al. |
| 6,194,636 B1 | 2/2001 | McElroy et al. |
| 6,232,526 B1 | 5/2001 | McElroy et al. |
| 6,384,301 B1 | 5/2002 | Martinell et al. |
| 6,399,861 B1 | 6/2002 | Anderson et al. |
| 9,521,863 B2 * | 12/2016 | Lusso .................. A24B 15/245 |
| 2004/0216189 A1 | 10/2004 | Houmard et al. |
| 2005/0178398 A1 | 8/2005 | Breslin et al. |
| 2006/0191548 A1 | 8/2006 | Strickland et al. |
| 2006/0200878 A1 | 9/2006 | Lutfiyya et al. |
| 2014/0076339 A1 | 3/2014 | Lusso et al. |
| 2019/0216037 A1 | 7/2019 | Pramod et al. |
| 2019/0271000 A1 | 9/2019 | de Godoy Lusso et al. |

FOREIGN PATENT DOCUMENTS

| | | |
|---|---|---|
| CN | 108271341 A | 7/2018 |
| WO | WO 1991/16024 | 10/1991 |
| WO | WO 1991/17424 | 11/1991 |
| WO | WO 2004/041006 | 5/2004 |
| WO | WO 2011/027315 | 3/2011 |
| WO | WO 2016/210303 A1 | 12/2016 |
| WO | WO 2018/237107 | 12/2018 |
| WO | WO 2019/140297 | 7/2019 |

OTHER PUBLICATIONS 2019-2020 Burley and Dark Tobacco Production Guide, published by the University of Kentucky, The University of Tennessee, Virginia Tech, and North Carolina State University (2018).
Allen et al., "Evolution of microRNA genes by inverted duplication of target gene sequences in *Arabidopsis thaliana*," *Nature Genetics*, 36: 1282-1290 (2004).
Allen et al., "microRNA-Directed Phasing during Trans-Acting siRNA Biogenesis in Plants," *Cell*, 121(2): 207-221 (2005).
Altschul et al. "Basic local alignment search tool." Journal of Molecular Biology, 215(3): 403-410 (1990).
Altschul et al., "Gapped BLAST and PSI-BLAST: a new generation of protein database search programs," *Nucleic Acids Research*, 25(17): 3389-3402 (1997).
Bartel, "MicroRNAs: Genomics, Biogenesis, Mechanism, and Function," *Cell*, 116(2): 281-297 (2004).
Bindler et al., "A high density genetic map of tobacco (*Nicotiana tabacum* L.) obtained from large scale microsatellite marker development," *Theoretical and Applied Genetics*, 123: 219-230 (2011).
Bowman et al, "Revised North Carolina Grade Index for Flue-Cured Tobacco," *Tobacco Science*, 32: 39-40(1988).
Chaplin et al., "Association Between Percent Total Alkaloids and Other Traits in Flue-cured Tobacco," *Crop Science*, 16(3): 416-18 (1976).
Chaplin, "Inheritance and Possible Use of Pale Yellow Character in Tobacco," Crop Science, 9(2): 169-172 (1969).

(Continued)

*Primary Examiner* — Jason Deveau Rosen
(74) *Attorney, Agent, or Firm* — Arnold & Porter Kaye Scholer LLP

(57) ABSTRACT

The present disclosure relates to tobacco plants, tobacco seeds, compositions, and methods related to the identification and introgression of the Pale Yellow locus in tobacco. It also relates to generating novel mutations within the PY locus in tobacco.

20 Claims, 16 Drawing Sheets

Specification includes a Sequence Listing.

(56) References Cited

OTHER PUBLICATIONS

Chaplin, "Interrelationship Between the Pale-Yellow Character and Other Traits in Flue-Cured Tobacco," Crop Science, 17(1): 21-22 (1977).
Chapters 4B and 4C of *Tobacco, Production, Chemistry and Technology*, Davis & Nielsen Editions, Blackwell Publishing, Oxford, pp. 70-103. (1999).
Chenna et al., "Multiple sequence alignment with the Clustal series of programs," Nucleic Acids Research 31: 3497-3500 (2003).
Collins et al., "Determination of Nicotine Alkaloids in Tobacco Using the Autoanalyzer," *Tobacco Science*, 13: 79-81 (1969).
Dugas et al., "MicroRNA regulation of gene expression in plants," *Current Opinion in Plant Biology*, 7: 512-520 (2004).
Goldman et al., "Female sterile tobacco plants are produced by stigma-specific cell ablation," *EMBO Journal*, 13: 2976-2984 (1994).
Griffiths-Jones et al., "Rfam: an RNA family database," *Nucleic Acids Research*, 31: 439-441 (2003).
Hibi et al., "Putrescine N-Methyltransferase in Cultured Roots of *Hyoscyamus albus*," *Plant Physiology*, 100: 826-35 (1992).
Horsch et al., "A Simple and General Method for Transferring Genes into Plants," *Science*, 227(4691): 1229-1231 (1985).
International Search Report and Written Opinion dated Apr. 8, 2022—PCT/US2020/055055.
Jones-Rhoades et al., "Computational Identification of Plant MicroRNAs and Their Targets, Including a Stress-Induced miRNA," *Molecular Cell*, 14(6): 787-799 (2004).
Kajikawa et al., "Genomic Insights into the Evolution of the Nicotine Biosynthesis Pathway in Tobacco," *Plant Physiology*, 174: 999-1011 (2017).
Katoh et al., "Specific residues at every third position of siRNA shape its efficient RNAi activity," *Nucleic Acids Research*, 35(4): e27 (2007).
Khvorova et al., "Functional siRNAs and miRNAs Exhibit Strand Bias," *Cell*, 115(2): 209-216 (2003).
Kim, "MicroRNA biogenesis: coordinated cropping and dicing," *Nature Reviews Molecular Cell Biology*, 6: 376-385 (2005).
Larkin et al., "Clustal W and Clustal X version 2.0," *Bioinformatics*, 23(21): 2947-2948 (2007).
Legg et al., "Registration of La Burley 21 Tobacco Germplasm," *Crop Science*, 10: 212 (1970).
Mayo et al., "Genetic transformation of tobacco NT1 cells with Agrobacterium tumefaciens," *Nature Protocols*, 1: 1105-11 (2006).
Miller et al., "A Grade Index for Type 22 and 23 Fire-Cured Tobacco," *Tobacco Science*, 192: 55-57 (1990).
Murchison et al., "miRNAs on the move: miRNA biogenesis and the RNAi machinery," *Current Opinion in Cell Biology*, 16(3):223-229(2004).
Official Standard Grades for Burley Tobacco (U.S. Type 31 and Foreign Type 93), effective Nov. 5, 1990 (55 F.R. 40645).
Official Standard Grades for Flue-Cured Tobacco (U.S. Types 11, 12, 13, 14 and Foreign Type 92), effective Mar. 27, 1989 (54 F.R. 7925).
Official Standard Grades for Georgia and Florida Shade-Grown Cigar-Wrapper Tobacco (U.S. Type 62), Effective Apr. 1971.
Official Standard Grades for Ohio Cigar-Leaf Tobacco (U.S. Types 42, 43, and 44), effective Dec. 8, 1963 (28 F.R. 11719 and 28 F.R. 11926).
Official Standard Grades for Pennsylvania Seedleaf Tobacco (U.S. Type 41), effective Jan. 8, 1965 (29 F.R. 16854).
Official Standard Grades for Wisconsin Cigar-Binder Tobacco (U.S. Types 54 and 55), effective Nov. 20, 1969 (34 F.R. 17061).
Parizotto et al., "In vivo investigation of the transcription, processing, endonucleolytic activity, and functional relevance of the spatial distribution of a plant miRNA," *Genes & Development*, 18: 2237-2242 (2004).
Reynolds et al., "Rational siRNA design for RNA interference," *Nature Biotechnology*, 22: 326-330 (2004).
Rhoades et al., "Prediction of Plant MicroRNA Targets," *Cell*, 110(4): 513-520 (2002).
Shoji et al., "Clustered Transcription Factor Genes Regulate Nicotine Biosynthesis in Tobacco," *Plant Cell*, 22(10): 3390-3409 (2010).
Smith et al., "Comparison of Biosequences," *Advances in Applied Mathematics*, 2: 482-489 (1981).
Sunkar et al., "Novel and Stress-Regulated MicroRNAs and Other Small RNAs from *Arabidopsis*", *The Plant Cell*, 16(8): 2001-2019 (2004).
Thompson et al., "Clustal W: Improving the sensitivity of progressive multiple sequence alignment through sequence weighting, position-specific gap penalties and weight matrix choice," *Nucleic Acids Research*, 22: 4673-4680 (1994).
Tong et al., "Large-scale development of SSR markers in tobacco and construction of a linkage map in flue-cured tobacco," *Breeding Science*, 66(3): 381-390 (2016).
Tso "Chapter 1 in Tobacco, Production, Chemistry and Technology," Davis & Nielsen Editions, Blackwell Publishing, Oxford (1999).
Wang et al., "Post-translational coordination of chlorophyll biosynthesis and breakdown by BCMs maintains chlorophyll homeostasis during leaf development," *Nature Communications*, 11:1254 (2020).
Wernsman et al., "Chapter Seventeen. Tobacco. pp. 669-698 In: Cultivar Development. Crop Species." W. H. Fehr Edition, MacMillan Publishing Go., Inc., New York, N.Y. 761 pp. (1987).
Zeng et al., "Both Natural and Designed Micro RNAs Can Inhibit the Expression of Cognate mRNAs When Expressed in Human Cells," *Molecular Cell*, 9(6): 1327-1333 (2002).
Zhang et al., "PowerBLAST: a new network BLAST application for interactive or automated sequence analysis and annotation," *Genome Research*, 7(6): 649-656 (1997).
Agrawal et al., "RNA interference: biology, mechanism, and applications," *Microbiology and Molecular Biology Reviews* 67.4, pp. 657-685 (2003).
Biswas et al., "The Development of DNA based Methods for the Reliable and Efficient Identification of Nicotiana tabacum in Tobacco and Its Derived Products," *Int. J. Anal. Chem.*, Article ID 4352308 (Jul. 2016); available online: http://dx.doi.org/10.1155/2016/4352308.
Chinese Search Report issued in Chinese Patent Application No. 2020800839246, dated Mar. 18, 2023; with English translation.
Korchinski et al., "Detection of Nicotiana DNA in Tobacco Products Using a Novel Multiplex Real-Time PCR Assay," *Journal of AOAC International*, vol. 99, No. 4, pp. 1038-1042 (Nov. 2016); available online: DOI: 10.5740/jaoacint.16-0008.
Miller "Memorandum: Proposed Burley Tobacco Grade Index," Legacy Tobacco Document Library, The University of Tennessee Agricultural Experiment Station (Bates Document #523267826-523267833) (Jul. 1988) (Knoxville, USA).

* cited by examiner

G58899 RNAi T$_0$ plants g58917 Expression

Tobacco Variety

Figure 12

| | | |
|---|---|---|
| BCM2 | MGLPLLSCSSTRVTLSSSSSSSWCSSGSGGFRSSSKLFDSPACSRSDLKKRSGKRNSRLN | 60 |
| BCM1 | MELPLLSYASSASF----SRTGLCSSSSS---SSTSIYEFPERRRSLKLRFNGGE---- | 48 |
| g58899 | MEVPVLARCTNTPT----T------SFLG---CKVSLFDFPIRRKLNKRNYKAKF---- | 42 |

| | | |
|---|---|---|
| BCM2 | GLSLEKLRSIKASSSSAGQSSSEVIDDGDAAARGLAVTSGDVTSVGSFSSGEFVGAGSGG | 120 |
| BCM1 | -------RSRSVIA-------------SAERSSEGIEKTT-------DTVGGGGGGAGR | 81 |
| g58899 | -------SVLRVKA-------------MAERTST------------EASADARERESGG | 69 |

| | | |
|---|---|---|
| BCM2 | LAGPSGEVTSVG-EFVGGSGGDFKDWDKIGAIVRLSYGIGIYCGMAVAGRFICEVAGIDY | 179 |
| BCM1 | FAGTAMEVTTLDRGFANSTTVDFPIWDKIGAVVRLTYGIGIYGAMAVAGRFICSVTGIDS | 141 |
| g58899 | YTGTTMEVTTFHQSFSD---AQLPVWEKIGAVVRLSYGIGIYGAMALAGKFICSMTGIDC | 126 |

| | | |
|---|---|---|
| BCM2 | TGGFNASLDTIIAGLGYASPPIMALLFILDDEVVKLSPHARAIRDVEDDELRGFFQGMSA | 239 |
| BCM1 | SGGFDPSLDALLAGLGYATPPIMALLFILDDEVVKLSPHARAIRDVEDEELRSFFFGMSP | 201 |
| g58899 | TGGFSPSLDAIVEGLGYAAPPIMALLFILDDEVVKLSPHARAIRDVEDEELRNFFYGMSP | 186 |

| | | |
|---|---|---|
| BCM2 | WQFILVVTASSVGEELFYRAAFQGALADIFLRGTDLISDSRGMVALTGLLPPFVPFAQVF | 299 |
| BCM1 | WQFILIVAASSVGEELFYRVAVQGALADIFLKGTQLMTDSRGMASLTGVFPPFVPFAEVF | 261 |
| g58899 | WQFILIVAASSVGEELFYRAAVQGALADIFLRGSGFVTDARGMASLTGVLPPYVPFAQAF | 246 |

| | | |
|---|---|---|
| BCM2 | AATITAALTGSLYYIAASPKDFTYIMAPVLKTRSARDELKKLFAANYERRQMKKIYSPLL | 359 |
| BCM1 | AAVITATLTGSLYFLAASPKDFTYIVAPVLRS--RRDDFKKLLSANYEKRQMKKIYSPLL | 319 |
| g58899 | AAVITAALTGSLYYMAASPKDFTYVVAPVLKSHSGREDLKKLFAANYERRQMKKIYSPLL | 306 |

| | | |
|---|---|---|
| BCM2 | EGLLGLYLGFEWIQTNWKLAPIITHGIYSAVVLGNGLWKLHHRQQRLRLRVQKLETEGDW | 419 |
| BCM1 | EGLLALYLGIEWVQTDWILAPMMTHGIYSAVILGHGLWKIHDHRRRLRRRIEHIRSEATD | 379 |
| g58899 | EAMLALYLGFEWIQTNWIFAPIITHGIYSAVILGHGLWKIHDHRRRLHQRIQQLKQEGNW | 366 |

| | | |
|---|---|---|
| BCM2 | NSR*- | 422 |
| BCM1 | KLI*- | 382 |
| g58899 | SRWL* | 370 |

BCM2 = SEQ ID NO: 56
BCM1 = SEQ ID NO: 55
G58899 = SEQ ID NO: 30

SEQUENCE LISTING

<160> NUMBER OF SEQ ID NOS: 58

<210> SEQ ID NO 1
<211> LENGTH: 241
<212> TYPE: DNA
<213> ORGANISM: Nicotiana tabacum
<220> FEATURE:
<221> NAME/KEY: modified_base
<222> LOCATION: (121)..(121)
<223> OTHER INFORMATION: a, c, t, g, unknown or other

<400> SEQUENCE: 1
gtcaagcagt ttttgaacaa gttctaccca cccaataaga ttgccaagta agttgatcag     60
atattgagct tcagggagaa tccaactgaa cactacaag aaacgtaaga gaggttcaaa    120
nggatactgg ttaagtgtcc acatcatggt attccagatt agatgttggg gcaaatgttc    180
tacatgggat tgacagacag cttgaaggcc aatgttgatg cttcagcaag tggagcattt    240
t                                                                    241

<210> SEQ ID NO 2
<211> LENGTH: 241
<212> TYPE: DNA
<213> ORGANISM: Nicotiana tabacum
<220> FEATURE:
<221> NAME/KEY: modified_base
<222> LOCATION: (121)..(121)
<223> OTHER INFORMATION: a, c, t, g, unknown or other

<400> SEQUENCE: 2
cttcttctac gcgttcacaa ggtgctggtc acgttcgcga aggtatgagc tggtaaagct     60
ttgcattcgc gaagccgtgg tcgcatttgc gaagggtaag aattgtaaag tttcacgttc    120
ncgaaggatt aaattgtggg caatcgagtt gtgcttcgca aacgcaaggg acctgtcgtg    180
ttcgcgaaga agagaggtca ggacagaagg tttaagttca gaaatggga cttcgtccca    240 t                                                                    241

<210> SEQ ID NO 3
<211> LENGTH: 201
<212> TYPE: DNA
<213> ORGANISM: Nicotiana tabacum
<220> FEATURE:
<221> NAME/KEY: modified_base
<222> LOCATION: (101)..(101)
<223> OTHER INFORMATION: a, c, t, g, unknown or other

<400> SEQUENCE: 3
gagagcttcg tgctttaagt atggtatcgt ctttgttaga aagtgtttca cgttatatta     60
tggagttgtg caaatctgaa tttagtcggg gcccaatacg nagacaccag gtgggacact    120 aaaaagaaa agaaaaaaga ggagaaacaa agtccgaagt ctactagata caaatgcata    180
cgtctctatt aataaatttg t                                              201

<210> SEQ ID NO 4
<211> LENGTH: 241
<212> TYPE: DNA
<213> ORGANISM: Nicotiana tabacum
<220> FEATURE:
<221> NAME/KEY: modified_base
<222> LOCATION: (121)..(121)
<223> OTHER INFORMATION: a, c, t, g, unknown or other

<400> SEQUENCE: 4
aatagtacaa gatgagagca atttcatata gtcactctca actaattagg aaatatgagg     60

```
cgcttgactg attgaagttt gtatgttgaa tatactagaa cttctgatgt agacatgtag    120
nattctgtat attttagagc acatcactta taagcagccc aagaatatta ctgtatctaa    180
gacataattt agtaaataaa aagtatgttt tctttgaaag tttaagattt tttatgagat    240
g                                                                   241
```

<210> SEQ ID NO 5
<211> LENGTH: 241
<212> TYPE: DNA
<213> ORGANISM: Nicotiana tabacum
<220> FEATURE:
<221> NAME/KEY: modified_base
<222> LOCATION: (121)..(121)
<223> OTHER INFORMATION: a, c, t, g, unknown or other

<400> SEQUENCE: 5

```
tacctcggga gtgccgttgt tgatattttc ctattagtgt acttgtcttg attgttttat    60
ttttccttta atatgtaaat tcctgtttgt cttccgtgat gtattattcg cccttactct   120
nagcagttaa attctgacat actgcttact tgattcactc tcattgttat tattttatta   180
ttattattat tattattatt attattatta tattattata tattattatt attatatatt   240
a                                                                   241
```

<210> SEQ ID NO 6
<211> LENGTH: 241
<212> TYPE: DNA
<213> ORGANISM: Nicotiana tabacum

<400> SEQUENCE: 6

```
gtcaagcagt ttttgaacaa gttctaccca cccaataaga ttgccaagta agttgatcag    60
atattgagct tcagggagaa tccaactgaa acactacaag aaacgtaaga gaggttcaaa   120
aggatactgg ttaagtgtcc acatcatggt attccagatt agatgttggg gcaaatgttc   180
tacatgggat tgacagacag cttgaaggcc aatgttgatg cttcagcaag tggagcattt   240
t                                                                   241
```

<210> SEQ ID NO 7
<211> LENGTH: 241
<212> TYPE: DNA
<213> ORGANISM: Nicotiana tabacum

<400> SEQUENCE: 7

```
cttcttctac gcgttcacaa ggtgctggtc acgttcgcga aggtatgagc tggtaaagct    60
ttgcattcgc gaagccgtgg tcgcatttgc gaagggtaag aattgtaaag tttcacgttc   120
acgaaggatt aaattgtggg caatcgagtt gtgcttcgca aacgcaaggg acctgtcgtg   180
ttcgcgaaga agagaggtca ggacagaagg tttaagttca gaaaatggga cttcgtccca   240
t                                                                   241
```

<210> SEQ ID NO 8
<211> LENGTH: 201
<212> TYPE: DNA
<213> ORGANISM: Nicotiana tabacum

<400> SEQUENCE: 8

```
gagagcttcg tgctttaagt atggtatcgt ctttgttaga aagtgtttca cgttatatta    60
tggagttgtg caaatctgaa tttagtcggg gcccaatacg aagacaccag gtgggacact   120
```

```
aaaaaagaaa agaaaaaaga ggagaaacaa agtccgaagt ctactagata caaatgcata        180
cgtctctatt aataaatttg t                                                  201

<210> SEQ ID NO 9
<211> LENGTH: 241
<212> TYPE: DNA
<213> ORGANISM: Nicotiana tabacum

<400> SEQUENCE: 9
aatagtacaa gatgagagca atttcatata gtcactctca actaattagg aaatatgagg         60
cgcttgactg attgaagttt gtatgttgaa tatactagaa cttctgatgt agacatgtag        120
aattctgtat attttagagc acatcactta taagcagccc aagaatatta ctgtatctaa        180
gacataattt agtaaataaa agtatgtttt ctttgaaaag tttaagatttt tttatgagat       240 g                                                                        241

<210> SEQ ID NO 10
<211> LENGTH: 241
<212> TYPE: DNA
<213> ORGANISM: Nicotiana tabacum

<400> SEQUENCE: 10
tacctcggga gtgccgttgt tgatattttc ctattagtgt acttgtcttg attgttttat        60
ttttccttta atatgtaaat tcctgttgt cttccgtgat gtattattcg cccttactct        120
aagcagttaa attctgacat actgcttact tgattcactc tcattgttat tattttatta       180
ttattattat tattattatt attattatta tattattata tattattatt attatatatt       240
a                                                                        241

<210> SEQ ID NO 11
<211> LENGTH: 241
<212> TYPE: DNA
<213> ORGANISM: Nicotiana tabacum

<400> SEQUENCE: 11
gtcaagcagt ttttgaacaa gttctaccca cccaataaga ttgccaagta agttgatcag         60
atattgagct tcagggagaa tccaactgaa acactacaag aaacgtaaga gaggttcaaa        120
gggatactgg ttaagtgtcc acatcatggt attccagatt agatgttggg gcaaatgttc        180
tacatgggat tgacagacag cttgaaggcc aatgttgatg cttcagcaag tggagcattt       240
t                                                                        241

<210> SEQ ID NO 12
<211> LENGTH: 241
<212> TYPE: DNA
<213> ORGANISM: Nicotiana tabacum

<400> SEQUENCE: 12
cttcttctac gcgttcacaa ggtgctggtc acgttcgcga aggtatgagc tggtaaagct         60
ttgcattcgc gaagccgtgg tcgcatttgc gaagggtaag aattgtaaag tttcacgttc        120
gcgaaggatt aaattgtggg caatcgagtt gtgcttcgca aacgcaaggg acctgtcgtg        180
ttcgcgaaga agagaggtca ggacagaagg tttaagttca gaaaatggga cttcgtccca       240
t                                                                        241

<210> SEQ ID NO 13
<211> LENGTH: 201
```

<212> TYPE: DNA
<213> ORGANISM: Nicotiana tabacum

<400> SEQUENCE: 13

```
gagagcttcg tgctttaagt atggtatcgt ctttgttaga aagtgtttca cgttatatta      60
tggagttgtg caaatctgaa tttagtcggg gcccaatacg agacaccag gtgggacact      120
aaaaaagaaa agaaaaaaga ggagaaacaa agtccgaagt ctactagata caaatgcata    180
cgtctctatt aataaatttg t                                                201
```

<210> SEQ ID NO 14
<211> LENGTH: 241
<212> TYPE: DNA
<213> ORGANISM: Nicotiana tabacum

<400> SEQUENCE: 14

```
aatagtacaa gatgagagca atttcatata gtcactctca actaattagg aaatatgagg      60
cgcttgactg attgaagttt gtatgttgaa tatactagaa cttctgatgt agacatgtag    120
tattctgtat atttttagagc acatcactta taagcagccc aagaatatta ctgtatctaa    180
gacataattt agtaaataaa aagtatgttt tctttgaaag tttaagattt tttatgagat    240
g                                                                        241
```

<210> SEQ ID NO 15
<211> LENGTH: 241
<212> TYPE: DNA
<213> ORGANISM: Nicotiana tabacum

<400> SEQUENCE: 15

```
tacctcggga gtgccgttgt tgatattttc ctattagtgt acttgtcttg attgttttat      60
ttttccttta atatgtaaat tcctgtttgt cttccgtgat gtattattcg cccttactct    120
gagcagttaa attctgacat actgcttact tgattcactc tcattgttat tattttatta    180
ttattattat tattattatt attattatta tattattata tattattatt attatatatt    240
a                                                                        241
```

<210> SEQ ID NO 16
<211> LENGTH: 1822
<212> TYPE: DNA
<213> ORGANISM: Nicotiana tabacum

<400> SEQUENCE: 16

```
atgcaaacca gagttggtag tagattggtc actgaacagt atcacgatga agaagtacgg      60
ccatatattc aacaattaat gaatgctcag aattgctctc cagcccaaac ttatgataat    120
caatctaata ttttgaacaa ttctgttggt actggagctg agcagaacaa tgaatcaggt    180
tctatttttga gttttagta ttgagtccac tattttctta gtattgcttt gcactagctg    240
taggttctgc taaaacaagg agttaattct ccagctcaag actatttttct ttgtgaattt    300
gcttgcacta gatcatggac ctttgaatct gtttcaggtc cttcagaggt aagaaaagtt    360
tgtgggccta cactactaaa agatgtttgg aatctaccat caaggaagac aattgatgtg    420
caatagaata gtcgtaatca agctattgga aaaaagggtc gaaagcttgc tagctttcta    480
agtatcattg ctagaacccc agagctgaca ccgttaaata taaatgattg gcgagtattt    540
gacaaagaag aaaagaagaa attggtggag tttgtgaggg tatgcaattt ttattcttaa    600
gacaaagaag aaaagaagaa attggtggag tttgtgaggg tatgcaattt ttattcttaa    600
taagtatcat tctttttata catgatattt tcttgtaaac tcgtgcttta tttttagaa    660
```

```
aaagttctcg attccagtat gtagagaaga gtttataaaa aagtcaatag ggaaaaaatg      720
gaaggactat aaatgtgatt tgaagactat gtatgtgacc aagtataaga gcaaagatgc      780
cttgatgaaa aatagaccaa gtcacatacc aagggatcaa tggactggtc tcgtcttgta      840
ttggctttct gataaagcaa aggtgagtaa gttttgtgt tgaatctaca ttttataact       900
ctctgtcctg ttttcttct ttgaaccttt ttgtgtttat tcaaagaaca tatatttaat      960
aagaatgttt acttggtctt taccagttac atttcaccca cattatacca accaaaatat     1020
ttttagaaag tgctgcaaac gttgtggcag gtggttcaga atatgaattt tgccttttaa     1080
atatagcccc ttgagcacaa tagatgattt ggttattagt ttatcttata tgattaagta    1140
ttgttagtga gtatttttgt gttgcaataa cagaagcgca gtcaagcaaa tagaatcagt     1200
agggctaaac aaaagatgcc tcacacagga ggatccaaaa gcatagcaac cttgatgaat     1260
gaaaaggtat taatgtataa attacatacc ataagattct ataattcttt tctatgatat    1320
ctaattgttt ggcatcaatt taactttatt aggctataga tggaatagag cctacacgtg    1380
ctcaagttta catattaact catacaaagc gtaaggatgg tagaccattg gatgaggaat     1440
cttcaaatac agttgtaaga tttcttataa gttgtatttt ttaagattaa acatatgtac    1500
tagctcatgt ctaatgcatc ataatttgta gaggctttaa atgattgact gatccttaaa     1560
cttttatgtc tcttcttccg gctatttctt ttccatttcc atgtctaata tatttccttg     1620
cattaattgc tgatgttaat acaagttatg taagaaactg ccttaacttt gttaactaac     1680
attgactttt tcatatgtgc aaatgctggc tagtttggtt tcacaatatc tcatcttatt    1740
gttagttcgt cctccactgt attgtgtcat aaattgttat ctcaattact gtcaggacat   1800
tgatgaaaga gaagttgagt aa                                              1822

<210> SEQ ID NO 17
<211> LENGTH: 911
<212> TYPE: DNA
<213> ORGANISM: Nicotiana tabacum

<400> SEQUENCE: 17
atggtagacc attggatgag gaatcttcaa atacagttgt aagatttctt ataagttgta     60
ttttttaaga ttaaacatat gtactagctc atgtctaatg catcataatt tgtagaggct    120
ttaaatgatt gactgatcct taaactttta tgtctcttct tccggctatt tcttttccat    180
ttccatgtct aatatatttc cttgcattaa ttgctgatgt taatacaagt tatgtaagaa    240
actgccttaa ctttgttaac taacattgac ttttcatat gtgcaaatgc tggctagttt     300
ggtttcacaa tatctcatct tattgttagt tcgtcctcca ctgtattgtg tcataaattg    360
ttatctcaat tactgtcagg acattgatga aagagaagtt gagtaatggc gagacatctc    420
atgaacaacc tcatggcagt gttgcttggg aaggagatgt gtattctcaa gtgttgggaa    480
atgaaaaaag tggtaatgtc cgtggtttag gacttggtcc aaccccttct ctattatggg    540
gcggtaaatc ttccttacaa aatattaccg atgatggttt atctaatgag gctgcacata    600
agttagaaca agagataaag gagttaaagg acttgaacaa aaacaggat gaagaaatag    660 ctttgatgaa aaaaaatcaa gatatgctag tttcagaatt aacatggatg aggcaagtca    720
tgtggaaata tgttcccacc aaattatgtg gccctcaaaa ctatggaagc actactagac    780
aggttattca atttcaaagt tttaaacttt tcttcttaaa attaagcttt ataagaaaat    840
tatgtgatct aatatgtctt gatatatact aggttcctga tgccaatagt ggcaatgagc    900
aagcaaccta a                                                         911
```

<210> SEQ ID NO 18
<211> LENGTH: 5963
<212> TYPE: DNA
<213> ORGANISM: Nicotiana tabacum

<400> SEQUENCE: 18

```
atggaggtac cggtgctagc tcggtgtacg aatactccga cgacgtcgtt tctaggatgt      60
aaagtgagtt tatttgattt tccgattaga agaaagctaa ataagaggaa ttataaggcg     120
aagttttcag tgttaagagt taaagctatg gcggagagga cgagtactga ggcatcagcg     180
gatgctagag agagagaaag tggagggtac acgggaacta cgatggaggt gacaacattt     240
aatcagagct ttagtgatgc gcaattgcca gtttgggaaa agattggtgc tgtcgtcaga     300
ctcagttatg gaatcggtga gttctcaact cgttttgcgt ttacttaatt agtctgtttt     360
tttttttttt gttttttttcg gtttgaattc tggtttcctt tttcaacgct attttgggga    420
aagaagacaa ggaatatgca tattagttga atagattcaa tgaattcaga attttatttt     480
gtggcttttg gtttcctatt ttttggtcaa acatttggta tctgaaccca ctaacctgac     540
taattttgat tcgcgcctta gaaaacttac tgtgggagat ttaagtgttc tttacaaaga     600
ggattcaaac tcgaaacctt tgattacgtg taaaagaatt tttatcattc aacatacca      660
ttcaagggcg gatgtatcgt ttagcttatg agcttatttg aacccaattt tgactcggac     720
catatatatg tgttaaaaat acacaaatat aaataaatac atagattttg aacatagtaa     780
attaaatgga tatgtgatag aatcccaaaa ctctgaacct ataatgttca aatctttact     840
ttagtttttg gtggactttt tggttgttat gattagtcta tattgtgtgc gatttaatct     900
tagtagttac agtgtgagca gtgtaatact gttctcggtt tgatttatat agagcaacaa     960
ttgttaaaat ataagcttaa ttttggttct aatgattagg taatcctgcc catttacttc    1020
gaattaattt gctatttact gtagtttttt ttattagaac agagttattt tgttattttc    1080
cttccccaaa actatctcca taaaagcctt tctttttttt cttaaatttc gtgtccagtc    1140
aaataggttc atataaattg aaacagaaag aatattaaat agcatagtat aaatggattt    1200
cgaaattatt atagtagtat atacttatag tttaactttt aagttttaat aataacaagt    1260
attcggtaga acaatggagg tgcaaaatgc atttccgtat ttattcattt gcatgtaaag    1320
actagagtta gatgaaatgg gaatgtgtaa cgagaactta gtgctagaaa gaatagtaat    1380
taatgagaga aagtgaattt acaagtgatt cttggagttg caagtaaagg gaaaggaaaa    1440
gctaaatttg ctttctgtat atgtcattaa agtgcttcta aaaatggaaa agctaaggtt    1500
tttcttcttt ctaacttta ggttttatag ttggtaggac aacaaatgcc aaaaataaaa     1560
aaacactgca atattttgc agtcaattta atcatgtttc caatcacatg ttaagtggta    1620
ctttgtttcc taagtaagaa atataagcaa ttgtcaggaa taggattgta tttatataaa    1680
caattgtaga taaaattgaa tactttatt gttttttgctc atacttggct attgaggaaa    1740
acagaattgt agttaggcaa tttgtcagaa tgcattagaa gaagtgtaga tgcattttag    1800
aatgacagaa aatacaaatt tatttacatt tttaagaata gtataaaata agtgatttta    1860
taaatattta gaacatgata atagaagaaa ataggcgaa aattaaaaaa gaataaattt     1920
ggagccgaaa ttgatcattc taatgcttgt gtgctaacgt tgaatagctt taaatttagc    1980
aacttgttgg taattttta aatttgtaga aatattttgt ttttttgttt tctttttta     2040
ataaccaat tttatttgtt aacgcaacta catgcttcta tagaattaca tttggaaaag     2100
```

```
cttttttagcc caaatactgc caaaaataat taaatgctaa aaacaaaata aacaaataat    2160
aactccatcc cgtgccactt aattagaagt agaattgtac ttaccggagt aatttgaact    2220
ttggcaatag ttgttaaaat atgttctagc ctaactagct gtactaaggt ctcaaaaact    2280
ttgaaatctt gaatctaatc ttcctcaaag aagaatagaa tttaatcatt gtactcgagt    2340
aaattgaaca ttgcaattat tatcatagta catttcccca aaatgtagta tgtccattgt    2400
aatactacat attcattttt tttattactt ttttaatacg gtgttatctt ccactaatat    2460
atatcgggta actctgacac catacataaa tatgacctag tgttttttaat tccggtgtat    2520 ttatttgttt gttgcatgta tttccatccc attaaatttt ttggatatct ttacagaaga    2580
aaaagaaatt aaagtccttc aatcattctc tgatgttcag tttgttttttt gcactcaggc    2640 atatatggag caatggcttt agcaggaaag ttcatatgct caatgacagg aattgactgc    2700
acaggagggt tcagtccatc attagatgcc attgttgaag gactaggata tgcagctcca    2760
ccaattatgg ctcttctatt tatactagat gtacgttcaa gattccctgt ttttctttat    2820
gcacataaca attaagtgtc ccaaatcagc cgacgaaatg agttgttatc ttcttatata    2880
gtcttagata attctcacat catgagattg tgtcggagcc aaactcctct cttggtttac    2940
acaatgttgg gctcctatgt tttgttgtac acgcaccata tgtccaatct ggggcgggcg    3000
agggtgttaa gctagttgag gaaatgaact gttatctttt tatatgatct tggacgattt    3060
tcatctcata agctaacttt tgggactgaa ttaggttcga ggttcttttt cgttacaata    3120
tttaactgca ctcttggctt cttcaacttg aattaaattc ttctatctac atatggcttt    3180
actaactctg aagtacaaaa atgcaagaat attagcctta tgtattgcag ctatactacc    3240
tttgtccata tgacattctt ggatcatata atggatgttt tataataatt tgcggtgttt    3300
ataggatgaa gttgtgaagc tgtcgcctca tgctcgagct atcagagatg tagaggatga    3360
agagctacgg aatttctttt atggaatgtc accttggcag gtaaaaattt ctcaatatga    3420
gcatcaataa ttatgttaca atacagggaa gattgatact taacggattt tgatgcaatg    3480
gtgtagttca ttctgattgt ggctgctagc tctgttggag aagagctttt ctaccgcgct    3540
gctgtccagg taagatgtat atcatccatt tatggtatac aatcgcgaat tcatttgtac    3600
atttgcagcc ttgtgttttt tccatattgt ttttcctatt tataatggta acaacagata    3660
cctggaaatc ctttttggtga attttttttt ttgtgcttca gttttccaat gcatatattt    3720
gcttattaaa agaaattaat atagaaagaa aaagaatat tagaaaaaca tggaaaatag     3780
aaagaggctt aaggcgtgta gaacatagtt atctaaaagt aattgctgtt gttttttgtc    3840
tgatttaatt cacttctgaa gagccaacaa cagccaacga cgttcttatt catacaacag    3900
aatctcagaa agtgtgaaat cttttcagaa tagacatgtc ttttgttgat aaccactttc    3960
atattacaaa ctatccaaca atattatcaa cagcgtaatt attttaact tccataaaaa     4020 atgcatgtca aaaaggttat ttttctctaa gttatgtgat tctttcctcc tctctgatta    4080
tctttgtaat tacagggagc tttagctgac attttcttaa ggggcagtgg ttttgtgact    4140
gatgctagag gaatggcatc attggtacgt cggattctat ttctaaacat ccttctccaa    4200
gttacattat ccaaaaattt tccattgctc tgacacattc tgtttcctca aaatgtagac    4260
tggtgttttg ccaccgtatg tcccatttgc tcaagcgttt gcagctgtaa ttacggcagc    4320
tctcacgggt tctctatatt atatggctgc ctctccaaaa ggtaagtttc acaggctgca    4380
gtttatatta tatatctgcc tttcattgtc ctctactcta acatgcttaa tcacttagct    4440
atttgttgtt tcacttttca gatcctacct atgttgttgc accagtgctg aagtcgcatt    4500
```

```
caggtcgtga agatcttaaa aaactatttg caggtttgac atctcttcta tgctcatgac    4560
ataagcaaga tagctctcac ttggtgatca tttgagtcta aacttaatta acataatgat    4620
atgaatctgg ggatttgggg tccaactaat aatgctaatg ggatatgaag aattagtatg    4680
gctgattgca actaagaata gaagagctga agcacgttcc ttagcctagt ctacatccaa    4740
agttgacaga cttaaaatac aacagtctcg acctactttg aatcaaaaga aaggcgaaag    4800
gtttggcaac aagcgaatcg cttttcatca tagttgcaag gattccaaac ctgctccctg    4860
gtcgttgctc cactgcatct ggtcatctct agtcaccttt ggaaggcagg aagtgtgaca    4920
atatgcatgt tttctttact ccatcgggcc ttctcaggcc tttccttgta ggagtagctt    4980
cttaaactat tttaaataat atgagaccac caaggcaggc actcgttctg tcaaaagcaa    5040
cggacttact tctggttcta ggtgttagcg tgtacgaaag attccccggc tctctgtata    5100
cttaaggtgg tctcttcaca agtgtcacca gcagtggcag agccaggatt ttcaccaaga    5160
ggattcaaaa tataaagagg tgaacacttg gagaagccaa ggggactcaa cctctactat    5220
atatacatac aaatattttt ggtcttgtat acatagtgta attttccgtc gaagggagtt    5280
cggatgaacc cccttccacc accctagttc tgcccacggt caccagagag agcgagcaca    5340
gattggatta agaaaaatt ggtttctact gagcttatcg aaccaactca tatcgttaag    5400
atatgataag ttttatatta tttgatgtaa ccacctgtat cttatctcca tttcaaacct    5460
aacaaatcct actccctcta cataaacctg tacactacaa aatatcagaa gcaagtaaac    5520
aaagcatttc tgctctccaa cgtgtgatcc tttagttgaa acagataagt gcatgatatg    5580
ttaattattt catctgcctg aatgttttgc agcttggtac gagaggcgac agatgaagaa    5640
gatatactct cctttactag aagccatgtt agcccttttac cttgggtttg aatggatcca    5700
ggtaacatga atttcacatt gtatttattt ctgatactta aaaggttatg tctacatgaa    5760
attttggtca ctaaagctaa tttgaacttc taccccttgct aatgcaacag acaaacaaca    5820
tttttgcacc gataatcaca catgggatat actctgctgt tattctggga catggacttt    5880
ggaaaatcca cgatcatcgg agaagactac atcaagaat ccaacaactt aaacaagaag    5940
gtaacaattc aagaaacttg taa                                            5963

<210> SEQ ID NO 19
<211> LENGTH: 2193
<212> TYPE: DNA
<213> ORGANISM: Nicotiana tabacum

<400> SEQUENCE: 19
atggtaaatt tcaacaaccc ccaaaactcc tttaattctt tttattaaaa attttcatca      60
atttgattgc tttcaactct cttttttgttc atttatttta aaattgtgtc tcttttttgg    120
tattagggag ctggaatacc tgatgaagag gaaataatt ggccactatg gttaaagcca     180
ttgcttaaag aaaaattctt tggccattgc aaattacatg ctgattctca caagagtgaa    240
tgcaatatgt attgtcttga ttgtataaat ggccctcttt gttctctttg tttagcacat    300
cacaaggacc atattgctat tcaggtatct cattttttcct tcatagaaaa atggtctttt    360
tatgtcaatt tgtaacaaat ttttcctttta gttcttcctg tttagcagca actaatgctt    420
gtattagggt agtctgttta tgtcacatca catccctagg ggtgcggcac ttttttcggat    480 tccgagtgaa tatgaaatct cttgtgcatc ggcaggcctt tggtataca gtgtatacaa     540 tggcgaagtt agaaattta acgagggtct atagctacac attctatatg gtgacgaaag    600
```

```
ccagaaattc taacaacggg gttcaagaaa atgctaaagt gtcacaccta aagtttgatc    660
atgttatttt aagcaatttt taacctgcct ttgccactat actaaaatct tttttatgt    720
aaaaaatttt caaaatgcaa aaaagttat ttttgaccta cttttgagta taatttttcg    780
atgaaagtga ttcaattgaa cccctaaatt gtcattttac atggtgtata gctttgatat    840
gccaaagaag aagtcttgaa attatgaatg attgattttg agtgatctgt ttttgtttgg    900
ttggacagat aaggaggtca tcataccatg atgtgataag ggtgaatgaa attcaaaagt    960
atttggacat tcttcagtc caaacataca ttatcaacag tgctaaggtt gtctttttga   1020
atgaaaggcc acaacctagg ccaggcaaag gtgtaacaaa tacttgtcaa gtttgtgaaa   1080
ggagccttct tgattccttc aaattctgct ctcttggttg caaggtacaa tactgtttac   1140
ttttccaagt ctgatatata ttaattatac acggttataa acatattata tagattatgc   1200
atatgttata catacggagg ctatttttaa tttaaacagt tgagtggatt gctatttaag   1260
ttaattgttc taaagaaaaa ttcccttcta gagttttcatt aaattgttcc attttttca   1320
tcttgaccaa attttcttgc attaattttg acttttactg gcattgaatt gaattaggcg   1380
tgtccaaata tattgaattg cgtatatttc aaggtatatt ttggtttaat ggtcgttgat   1440
agtgtggttt gacaaatgtg aagcaattaa atggggcgtg gaaattgcac tcatatttac   1500
tagtctattg ataggaaaac tttggcataa tcaactttt ttaattggaa atttcaaagt   1560
tgttagacat tgtaattatc aatgactctt tcttgcagtt attgtgtacc ccaaatggaa   1620
atgatattca aatctttgat tattagcaat ctttgatata caataaatat tatgtgaatt   1680
attgaattgg tccgaataga gcagaattct atgttttgtg ttgatggtat atattgtctt   1740
tttcgtctttt ttcgtttttct tgagccgagg gtctattgga aacctcacct ctactctatc   1800
ggggtagggg taaggtccgt gcacacacta ccctccctag actccttacc tgcgggatt    1860
tactgggttg ttatccgaac agaacagaat gaatataggt gatttatata gtcgattcta   1920
ccttgatcat tgcaggttgt cgggtcctca aagaacttcg ttaagaaacc gaagcaatta   1980
tccgcgaaaa ggcggcggtc gatggtggcg gcatcggact ccgatgactc ttacagcagc   2040
agcagccatg gtaggtacaa gagccacagc aacaaggtcc aaagttttac tccgtcgacg   2100
ccccctccaa cttcagttaa ttacaaaacg gccaagcgaa gaaagggaat tccacataga   2160
tccccaatgg gaggactact catagaatat taa                                2193
```

<210> SEQ ID NO 20
<211> LENGTH: 8752
<212> TYPE: DNA
<213> ORGANISM: Nicotiana tabacum

<400> SEQUENCE: 20

```
atgtcttccg ataacttcac cgacaaaaac gccgtcttcc gcaagctcaa agccaagccg     60
gacaacaagg tttgcatctt aattcatcga attttgtttt tgatttgatc gaaaaattat    120
gtttttttgaa ttttttatcta ttttctcgcg tgttttttcg tttgaatcga ttgaaaattg    180
cgagatctga tttagatcta gtgtttgtgc tgagtagatt gtagtttctg agcgatctaa    240
gtcagctttt acctttttt tttttttgaa ttttatcaga tgtgttttga ttgcaatgcg    300
aagaatccta cgtgggcgtc ggttacgtat gggatcttct tgtgtattga ttgttcggcg    360
acgcatcgta gccttggtgt tcacatcagt tttgttaggt acgatttaaa gtttgatttt    420
ttactcgtct tcgttttttgg attcatgagc tgattttag cttgataatt tgttttcatg    480
atgagtggat tttgttcgga gttctataag gcatggtttt tggttttata aatatatcga    540
```

```
aaaaatgatt agaaatgttg aaatcaatag aatcaacagg ttcgaagccg tgacttctgc    600
cttataaata agtggctgat ttaaaatgtg gactgaggta agttcggacc cgctgtcttg    660
agtaggggca gatgtactgt tcggggtacg ggtttggtag aactcagaag ttttggccta    720
agccatgtat gtttcctaag aatttcactt aatatgaata gattattaat ttagaaccca    780
ttaactcata attgcctaaa ccccgcacct ttaaacttca aatcatggat ccgcctatgg    840
tcttgaactc aagttatatg ttgttgaaat ttatttaaaa atatgtagtt ataataggag    900
tagtggggtg caatggtatt ctacttgatt ctaaatcctg aattcgtctc tgtttattgg    960
acgctgaaat tttaattttt tgctgcgttc cttacgaggt gctttaggca atggtctttg   1020
atacaaggga acagattcta tactgtgaaa agaattatgc taatgatgaa agcattttaa   1080
agatctaatt atgtggcatg gtcccgggcc ctaaactcct cctaattgta gaatatgtgg   1140
acgttgagcg cgccattggg ctagatgcag tgaaatccat tggtttctca actatcttgc   1200
tttgttttct ctccttgata tgtggttttt agggttacgt gtggtccaag ttttggtgg    1260 tagttgatag atatgtattg ctcctattgc tcaatattgc aattacagtc agacctctct   1320
ataacatccc tatataacaa cacttcacta taaaagccaa gcttttccgg aatgttatgt   1380
tataatatat gttctatata acaacactta gttataacat ccaaaaatat tcggaacaaa   1440
cgaggctgtt atagagaggt ttgactcctg agcacgtatc aaaagattgc atcttttgat   1500
gaatatgtgt ccgacaatct tgattatgga ttaagcttaa tcttatgctc cgtattcgat   1560
cattgatgca aacgataaat tttgaacaag aaatggtcaa caccacatga tttccttta    1620 tggcggatat tggtgcgcat accccttttc gagaaagact attgatatat gacctcttcg   1680
aagctacaac cagtatgcga atatggacga tctagtatga atcccatatg tgtttcttat   1740
acaataccat tcccgcagtt tctggttcga aaccattatc ttcatcccat atgtgccaca   1800
acagcttcat tttgcccaac aattggtatg accaccttaa gagactttat gtgtttgcac   1860
caagggcttt ggtttagcgg taagagcgca atgtttgatg tgtggattag gcgcatgcca   1920
caggttttga atcctgtagc ggaaaaaagt ttggtgttta agtggagaag ggtagaaggt   1980 ggcccccttta tctaccgagt tccgaaccgt gcaccattgg cacttgtgaa tttttttgatt  2040 attagagaaa tggagagatt tttcttgtgt tacttgcagt gtcctaccta attacctatc   2100
atggttaaca aaaccgacaa agtgagccat cataatctgg ctactttat tcttaacaca    2160 ttttcttcca tctcattgaa aaatccatat tctttctttg gaggagggtg tgaatgaagc   2220
cttctctttt catccactac tagttcttca cattttttcc gatgacggtg gtgtcggggc   2280
cagtttgaat gctccttaat tattctaccg ggtacctggt tacctcccac tagcacatgt   2340
accaggtgga ctctgtctac ctaggcttgg gcgtatgtga agaaatcacc tattggtttt   2400
ttggcttcac taggatttga atatgagact tcatgattct cttcctactt cattgacccc   2460
taggtcacac cctgggtgc atgctagttc ttcatattat ataatgtcac tgctattttt    2520
ttcaaatgac actgccaatg ggatgaatct aagagaggaa gaacagaaaa gtaagccgag   2580
gaagaacgga aaaggacgag gaagaataga aaaggagaag ttctaaatgg ccatgtcaga   2640
cttcttggct gacatgcgtt ctttttataa caaccggcat gaccactgca tcacactttg   2700
ggcctcgtca gttccattgt tgctcatctc acctcaccat ggtagctgga ccttcctacc   2760
tctaacaatc agcatgtcag tatgttagtc aagcgaagac aataatagca ttttattacc   2820
ttatgaaaaa atgatgacaa caatggcatg gttagtgatt aatctataca ttgttaaacc   2880
```

```
taacctgatc atttgattga ttatgagaac aattggccat cggagattat ggaaggccat    2940
gaaggctaga ttttgaggta tttttgtggg tcggcttgct tcaaaagaga aagagggtg    3000 ggtgggggtt ggggggtggg tttgaaaggc agaagtggaa tgtagagttt gaatgcatgt    3060
atctgttagt atgtgttaga gatagagagg ggtgataata ttgctttgca tttcctttat    3120
catggttgag atgttcatta tgggccgaga gttatcttct gacccacccc cttttcgttt    3180
gtaatgtttt gaggtgggaa tgggtatggc caaccggaaa caaataaatt ctgcattttc    3240
tttgttattt tggcattact aactgtcagt tctctgatga attgattctt gcagatcgac    3300
aaatttagat tcatggtctc cagagcagtt aaagatgatg tactttggtg gaaacaaccg    3360
tgctcaagtt ttttttcaagc agcactgatg gacggatggc ggcaaggttg aagccaagta    3420
tacctccagg gctgctgaat tgtataaaca attactatca aaagaagttg ctaaaagtaa    3480
agcagaggat gcaggtttgc cagcatcgcc ttttgcctct caggctgtgc agagtacgaa    3540
tggattttct gatgttaaga ctagtgaagc tccaaaagaa acctcatcat ttaaggaaga    3600
aactcctgct tcgcccaaag catcacaatc agttgttact acttcaatta ggaaacctat    3660
aggtgcaaag aaatctggga agccaggtgg tggacttgga gctcggaaac ttactaaaaa    3720
ggtattctta gtcttatgag ctagagaaat gattgcaggg tataaattgc atattctgaa    3780
atgaagactt atatgtgcgg tttagagtaa gctgtttaac aaatttgctc caccaatttg    3840
gaatttatta attgattaag catcttttac cggtgtacag ccaagtgaaa gtctctacga    3900
ccagaagcct gaagaaccgc ctgttcaagt ttcttcctcc aattctacaa gtaatgcatc    3960
aactgttggt tcatcattcg catctcgctt tgagtacaca gacaatgtcc aacccgctga    4020
gatgagttct ggaggccctc gtgttcttaa ccatgtatcc cctccaatgt cctccagctt    4080
tttttcggac tacggaatgg acagcggttt cacaaagaag acaagttcaa attcgtcaaa    4140
agttcaagtg agtttgtatt ctagttttgt tttcaatcat atgaggattc taatgaactg    4200
ttacagttga acttaaatgt tgacatgatt atatgtgaga tatgaagaaa gtggtgtcgg    4260
acttagttac aaggtaaaga tataagcttc attttttcacc ttaatatcac caggaatatt    4320
agttccttgg tacgactata ccttttttcac gtcctattac ctagtataca catttgatct    4380
atctgaagca ggcttgagtt tttctgaacc tgcataagtg ctatatccaa gatgagcaat    4440
ttaatgtata caattaaaaa aagggcagca tgttgcacta agctcctgct atgcttgggt    4500
caggaaagga ccggaccaca ttgggtctga tgtacgcagt cgccttacct tgcatttata    4560
caaaaggctg ttttccatggt ttgaacccat gaggtcatgg cagcaacatt tattgttgcg    4620
cggaggtttc ccttccattg agcttctgaa agattggggg tagtgatttg tgaaagattt    4680
actgctttat gatcctattc cagcatcctg cactgtgaat aattacaagg attgtcactg    4740
aattgaaaaa aaattgtttc ccttggatct ttggatgctt ctcgacggtc tatttgcttt    4800 tcttttttttc tttttaaatg aaactaccca ttaccactct tgaaatactt attgccccac    4860
tcccttcccc actgaagaaa cattttcatt aggttaaccc aaatcgctag tgtctctacc    4920
tttttagtca ttcaagaaaa agtaaatgtt catcctaaac attaccagtg caagtttcaa    4980
gtgtctgctt actaatgaaa aagaaaaaga aacaactttt ggatgttttc tttttgaaat    5040
ataggttgcc tggaatattc tttgttgttt ttaaacctca tcttgtgctg gatttgtcct    5100
ttaatttgtg atttactgct ctcactcagt tcttcttttg ctcctgatag acgagttgac    5160
tgctttgcct aagttatttc tgtagtcttc aagttttctt ttctctcttc tcctttatca    5220
tcttcactgg ccgtgtttat ttcactgtaa ctcacatcct attttaatca gattgaggaa    5280
```

```
actgatgaag caaggaagaa gttttctaat gcaaaagcca tttcatctgc ccaattcttt    5340
ggtgataaga gcaaagctga aatggaagcc tcagtttctc tgcagaagtt ctcggtatgc    5400
ttgcttattg tagttaacat gcccatattt ttaggggcct tgctggtttt tcagtcagca    5460
tgcaaacaat gaaaaaccct ctcccttccc tcattcatta tgatagttag ggtcttgtcc    5520
tactaattag aaataactat tatcgcaaca acattatgcc ccatgttctc ctttttctt    5580
cccattccct tttgtccttt aatgcactgt acttcttccc atgctatcat tttgctgggt    5640
tttttttttt tgatgaagta agagaatttc attaaaggca tcaagaagat gcatagcaaa    5700
agagagtaca agtaaataga gtgtgtctgc tcataaacat aacaaaaaga aacctatgtt    5760
aaaactaagg agcagacaca gtccaaaaaa tgatcacaac tagatacagg tgcctgatta    5820
agccaagtaa aaaggttaaa taaacattta gctttaagag catgatttgg atttgatatc    5880
ccatcaaaac atctgctatt cctttcagtc catatacacc agaaaataga agcggggacc    5940
aaaagtcaag ttttttttgat ggatttgcca actctccaag agcaccagct ttcgtaggcc    6000
tctttaatac tattaggcat gacccaggct agtccaaaaa ttgagaagaa catactccac    6060
aaatctgctg caactgcaca atggagaaaa agatgcctca cactctctgc cttcatctga    6120
cacgtagcac ctattcacaa tgtagatgtt cctccgactt agattatctt gagtgagaca    6180
tgcttcatat aaggttatcc aagtgaagcc aattacttta ggtggaagtt tatagttctc    6240
cagatgagtt tccatggcca gttgtcaatc tactccttgt ttgagcacaa atgtacataa    6300
cctttcttga cagtgaatat cccatcatgt tggccattcc ataatagtct gtctctcctg    6360
aggtttgata gtgacccctg ctagcttaga ttgaagctcc agatagtcat ttagctccca    6420
gtcctgtaag tttctccctg tctgtaggtc ccatgagttg ttgtgccata tttgacccac    6480
tgtggagttt tgattgctag ctatgagata taaatttggg tagtcttctt tcagagtctg    6540
gttccctaac cacttatcct tctagaatga tacatgcgct ccattcccta actttattga    6600
acaattgagc tggaattcac cccataggct tgagatatgc ttccagggac cagtgccatg    6660
tggtaatctg ctctgtttgg tgcaccattg actcagcacc ccatactttg ccatgatcac    6720
atctttccac atcccaatgt tctccatgtt gtacctccaa tgccacttaa ttagcatgct    6780
cttgttgtgc aattttaagt cttttatgcc caaccctcca tgctcctttg gcaaaatcac    6840
tcttggccat ttcaccagat gaaatttgtt gttttgacta tttcctcccc acagaaagtt    6900
tctattaatt ttgtctaacc ttttctgcac cctggctggt ataggaaata gggacatgaa    6960
gtatgttggt atgctgtcca ggacactgtt aatgggtgtt gttctgcccc caagtgaaag    7020
atactgcatt tgccaagttt caagctttgt ttcaaatttc tctactatcc cattccagat    7080
atctggtgac ttgactttgg ctccaagtgg tagacccaaa tatgttgtgg aaaaagatcc    7140
cacattgcaa cccattagct ctgctagctc ctccatattt ggtaaatagt gctcttaaat    7200
ctgttcatgt ggaggccgga tatagcttca aaaatcatga gtgtgaggtt aagatagagc    7260
acctgcgacc tatcagctcc acagaaaata agtgtgtcat atgcatacaa gagatgggag    7320
acactaattc agctcccaac agaactttcc accttgaaac cctccaacca gtgtatttgg    7380
tttgctttgt caagcatttc gctaaggcct tacattgcca aaatgaacaa aaaggatgag    7440
aggattccgt tgacaagaac tgaatacttc acagtggtta cacaaaactt gatccacctg    7500
atccaacctg caccaaaccc catcttccta attatattga ataggtaaga ccagtttagc    7560
tggtcaaagg ccttttcaat agcaagtttg aaaaggagac ctggctgccc tgatttctgc    7620
```

```
ctccagtcta gtacctcatt agcaattagt gcagcatcag tgatttgtct tgttttgatg      7680
aatgcatttt gatgccctga gacaagcttc ccaatcactc ttttcagtct ttctgccagg      7740
attttggagg caatcttgta acttaaaaag agactgttca acagttactg tgagagcctt      7800
ctacaatgga acttattaat taccagtact tgggttgcag aaccacattt atctgtatgt      7860
tgaagatacc ttatcgatgc tgtttactga ggcgtagatt gaaggatata tacgatggat      7920 aattttttgaa attccattca tggagataat ggtgaagacc atttgccata acttgagata      7980
atggtgtcta gctgacctct tgtttgttcg cttcataatt gcttatgttc atttgcataa      8040
caagttatct actggtccga cgtactgtgg aatagtttac ccctcaggtg ttttttaatac     8100 ttaatctcat tttgaaggag cttgtaatag ctacttcagc aaatgaatat gatttgtaag      8160
ctaaaatgat ccgcacagct gatagcatta gtcctaatct gattatttac ctgttacatt      8220
tgcctgtcgg gttgcttccg ctagtgctta ttgtatattt acttcgtcaa aaaaaacttt      8280
gtgcttattt tgtatttttgt ctgacccatg tctgaagaat cctttagtgt caatttctaa     8340
acgagtgcaa ctatattact tgagcttgac ctgaaaagcg ataagttcac ctagaaatgt      8400
atgagtccaa ctcgtgctcc taaaaatgtg ttctgctatc tattcctcag ggttcaagtg      8460
ccatttcaag tgcagacctt tttggtaacg atgatagagc agatttggac ctcactgctg      8520
gtgatctcat taaccggctc tcttttccagg tatagaagca ataataacac aaatgtaaac     8580
gcttttcaat tcccataagc aaattttgaa cggattgctc tttcgtttgt ctctatgttt      8640
tcaggcacag caggacatct cctctctgaa aaatattgct ggagaaactg gaaagaaact      8700
tggctccttg gcagcaacct taatgtccga ctttcaagac agaatcctgt ga              8752
```

<210> SEQ ID NO 21
<211> LENGTH: 471
<212> TYPE: DNA
<213> ORGANISM: Nicotiana tabacum

<400> SEQUENCE: 21

```
atggcatctc tctcatggtg aatcctgct cctgccacga ctgcaatggc agcttgttct       60
ccaactccaa catcctgtaa aacctctaac tcattagcac tgccgcgctc tgtgtttgtc     120
agcaagcaag caaagttaat gaaacaagcc aatggtcttt tggttataac acagcaacag    180
tcaaagaaga agaatcattc attcaccaat tccagaagga ataccagcat tcagtgtctc    240
tcacaggaac agaaatggac tcatgaaggt tccattaccg aatcgctccc caatggcatg    300
tttagggtca aattggataa tgcagatgtc gttctgggat acatttctgg gaagatacga    360
aagaatttca tacggttgtt gccaggcgac agagtcaaaa ttgaagtaag tcggtatgat    420
tccactaaag gacgcatcat ttatcgtctc cgcggtggcc gagaaggcta g              471
```

<210> SEQ ID NO 22
<211> LENGTH: 768
<212> TYPE: DNA
<213> ORGANISM: Nicotiana tabacum

<400> SEQUENCE: 22

```
atgcaaacca gagttggtag tagattggtc actgaacagt atcacgatga agaagtacgg       60
ccatatattc aacaattaat gaatgctcag aattgctctc cagcccaaac ttatgataat      120
caatctaata ttttgaacaa ttctgttggt actggagctg agcagaacaa tgaatcaggt     180
ccttcagaga atagtcgtaa tcaagctatt ggaaaaaagg gtcgaaagct tgctagcttt     240
ctaagtatca ttgctagaac cccagagctg acaccgttaa atataaatga ttggcgagta     300
```

| | |
|---|---:|
| tttgacaaag aagaaaagaa gaaattggtg gagtttgtga ggaaaaagtt ctcgattcca | 360 |
| gtatgtagag aagagtttat aaaaaagtca atagggaaaa aatggaagga ctataaatgt | 420 |
| gatttgaaga ctatgtatgt gaccaagtat aagagcaaag atgccttgat gaaaaataga | 480 |
| ccaagtcaca taccaaggga tcaatggact ggtctcgtct tgtattggct ttctgataaa | 540 |
| gcaaagaagc gcagtcaagc aaatagaatc agtagggcta acaaaagat gcctcacaca | 600 |
| ggaggatcca aaagcatagc aaccttgatg aatgaaaagg ctatagatgg aatagagcct | 660 |
| acacgtgctc aagtttacat attaactcat acaaagcgta aggatggtag accattggat | 720 |
| gaggaatctt caaatacagt tgacattgat gaaagagaag ttgagtaa | 768 |

<210> SEQ ID NO 23
<211> LENGTH: 480
<212> TYPE: DNA
<213> ORGANISM: Nicotiana tabacum

<400> SEQUENCE: 23

| | |
|---|---:|
| atggtagacc attggatgag gaatcttcaa atacagttga cattgatgaa agagaagttg | 60 |
| agtaatggcg agacatctca tgaacaacct catggcagtg ttgcttggga aggagatgtg | 120 |
| tattctcaag tgttgggaaa tgaaaaaagt ggtaatgtcc gtggtttagg acttggtcca | 180 |
| acccottctc tattatgggg cggtaaatct tccttacaaa atattaccga tgatggttta | 240 |
| tctaatgagg ctgcacataa gttagaacaa gagataaagg agttaaagga cttgaacaaa | 300 |
| aaacaggatg aagaaatagc tttgatgaaa aaaaatcaag atatgctagt ttcagaatta | 360 |
| acatggatga ggcaagtcat gtggaaatat gttcccacca aattatgtgg ccctcaaaac | 420 |
| tatggaagca ctactagaca ggttcctgat gccaatagtg gcaatgagca agcaacctaa | 480 |

<210> SEQ ID NO 24
<211> LENGTH: 1113
<212> TYPE: DNA
<213> ORGANISM: Nicotiana tabacum

<400> SEQUENCE: 24

| | |
|---|---:|
| atggaggtac cggtgctagc tcggtgtacg aatactccga cgacgtcgtt tctaggatgt | 60 |
| aaagtgagtt tatttgattt tccgattaga agaaagctaa ataagaggaa ttataaggcg | 120 |
| aagttttcag tgttaagagt taagctatg gcggagagga cgagtactga ggcatcagcg | 180 |
| gatgctagag agagagaaag tggagggtac acgggaacta cgatggaggt gacaacattt | 240 |
| aatcagagct ttagtgatgc gcaattgcca gtttgggaaa agattggtgc tgtcgtcaga | 300 |
| ctcagttatg gaatcggcat atatggagca atggctttag caggaaagtt catatgctca | 360 |
| atgacaggaa ttgactgcac aggagggttc agtccatcat tagatgccat tgttgaagga | 420 |
| ctaggatatg cagctccacc aattatggct cttctattta tactagatga tgaagttgtg | 480 |
| aagctgtcgc ctcatgctcg agctatcaga gatgtagagg atgaagagct acggaatttc | 540 |
| ttttatggaa tgtcaccttg gcagttcatt ctgattgtgg ctgctagctc tgttggagaa | 600 |
| gagcttttct accgcgctgc tgtccaggga gctttagctg acattttctt aaggggcagt | 660 |
| ggttttgtga ctgatgctag aggaatggca tcattgactg gtgttttgcc accgtatgtc | 720 |
| ccatttgctc aagcgtttgc agctgtaatt acggcagctc tcacgggttc tctatattat | 780 |
| atggctgcct ctccaaaaga tcctacctat gttgttgcac cagtgctgaa gtcgcattca | 840 |
| ggtcgtgaag atcttaaaaa actatttgca gcttggtacg agaggcgaca gatgaagaag | 900 |

```
atatactctc ctttactaga agccatgtta gcccttttacc ttgggtttga atggatccag    960
acaaacaaca tttttgcacc gataatcaca catgggatat actctgctgt tattctggga   1020
catggacttt ggaaaatcca cgatcatcgg agaagactac atcaaagaat ccaacaactt   1080
aaacaagaag gtaacaattc aagaaacttg taa                                1113
```

<210> SEQ ID NO 25
<211> LENGTH: 675
<212> TYPE: DNA
<213> ORGANISM: Nicotiana tabacum

<400> SEQUENCE: 25

```
atgggagctg gaatacctga tgaagaggaa ataattggc cactatggtt aaagccattg      60
cttaaagaaa aattctttgg ccattgcaaa ttacatgctg attctcacaa gagtgaatgc    120
aatatgtatt gtcttgattg tataaatggc cctctttgtt ctctttgttt agcacatcac    180
aaggaccata ttgctattca gataaggagg tcatcatacc atgatgtgat aagggtgaat    240
gaaattcaaa agtatttgga catttcttca gtccaaacat acattatcaa cagtgctaag    300
gttgtctttt tgaatgaaag gccacaacct aggccaggca aggtgtaac aaatacttgt    360 caagtttgtg aaaggagcct tcttgattcc ttcaaattct gctctcttgg ttgcaaggtt    420
gtcgggtcct caaagaactt cgttaagaaa ccgaagcaat tatccgcgaa aaggcggcgg    480
tcgatggtgg cggcatcgga ctccgatgac tcttacagca gcagcagcca tggtaggtac    540
aagagccaca gcaacaaggt ccaaagtttt actccgtcga cgccccctcc aacttcagtt    600
aattacaaaa cggccaagcg aagaaaggga attccacata gatccccaat gggaggacta    660
ctcatagaat attaa                                                     675
```

<210> SEQ ID NO 26
<211> LENGTH: 1359
<212> TYPE: DNA
<213> ORGANISM: Nicotiana tabacum

<400> SEQUENCE: 26

```
atgtcttccg ataacttcac cgacaaaaac gccgtcttcc gcaagctcaa agccaagccg     60
gacaacaaga tgtgttttga ttgcaatgcg aagaatccta cgtgggcgtc ggttacgtat    120
gggatcttct tgtgtattga ttgttcggcg acgcatcgta gccttggtgt tcacatcagt    180
tttgttaggg gcagatgtac tgttcggggt acgggtttgg tagaactcag aagttttggc    240
ctaagccatt ttctggttcg aaaccattat cttcatccca tatgtgccac aacagcttca    300
ttttgcccaa caattggtat gaccaccttca agagacttta tgtgtttgca ccaagggctt    360
tggtttagcg gtaagagcgc aatgtttgat gtgtggatta ggcgcatgcc acagatcgac    420
aaatttagat tcatggtctc cagagcagtt aaagatgatg tactttggtg gaaacaaccg    480
tgctcaagtt tttttcaagc agcactgatg gacggatggc ggcaagagga tgcaggtttg    540
ccagcatcgc ctttttgcctc tcaggctgtg cagagtacga atggattttc tgatgttaag    600
actagtgaag ctccaaaaga aacctcatca tttaaggaag aaactcctgc ttcgcccaaa    660
gcatcacaat cagttgttac tacttcaatt aggaaaccta taggtgcaaa gaaatctggg    720
aagccaggtg gtggacttgg agctcggaaa cttactaaaa agccaagtga aagtctctac    780
gaccagaagc ctgaagaacc gcctgttcaa gtttcttcct ccaattctac aagtaatgca    840
tcaactgttg gttcatcatt cgcatctcgc tttgagtaca cagacaatgt ccaacccgct    900
gagatgagtt ctggaggccc tcgtgttctt aaccatgtat cccctccaat gtcctccagc    960
```

```
tttttttcgg actacggaat ggacagcggt tcacaaaga agacaagttc aaattcgtca   1020
aaagttcaaa ttgaggaaac tgatgaagca aggaagaagt tttctaatgc aaaagccatt   1080
tcatctgccc aattctttgg tgataagagc aaagctgaaa tggaagcctc agtttctctg   1140
cagaagttct cgggttcaag tgccatttca agtgcagacc tttttggtaa cgatgataga   1200
gcagatttgg acctcactgc tggtgatctc attaaccggc tctctttcca ggcacagcag   1260
gacatctcct ctctgaaaaa tattgctgga gaaactggaa agaaacttgg ctccttggca   1320
gcaaccttaa tgtccgactt caagacaga atcctgtga                          1359

<210> SEQ ID NO 27
<211> LENGTH: 471
<212> TYPE: DNA
<213> ORGANISM: Nicotiana tabacum

<400> SEQUENCE: 27
atggcatctc tctcatggtg gaatcctgct cctgccacga ctgcaatggc agcttgttct   60
ccaactccaa catcctgtaa aacctctaac tcattagcac tgccgcgctc tgtgtttgtc   120
agcaagcaag caaagttaat gaaacaagcc aatggtcttt tggttataac acagcaacag   180
tcaaagaaga agaatcattc attcaccaat tccagaagga ataccagcat tcagtgtctc   240
tcacaggaac agaaatggac tcatgaaggt tccattaccg aatcgctccc caatggcatg   300
tttagggtca aattggataa tgcagatgtc gttctgggat acatttctgg gaagatacga   360
aagaatttca tacggttgtt gccaggcgac agagtcaaaa ttgaagtaag tcggtatgat   420
tccactaaag gacgcatcat ttatcgtctc cgcggtggcc gagaaggcta g            471

<210> SEQ ID NO 28
<211> LENGTH: 255
<212> TYPE: PRT
<213> ORGANISM: Nicotiana tabacum

<400> SEQUENCE: 28

Met Gln Thr Arg Val Gly Ser Arg Leu Val Thr Glu Gln Tyr His Asp
1               5                   10                  15

Glu Glu Val Arg Pro Tyr Ile Gln Gln Leu Met Asn Ala Gln Asn Cys
            20                  25                  30

Ser Pro Ala Gln Thr Tyr Asp Asn Gln Ser Asn Ile Leu Asn Asn Ser
        35                  40                  45

Val Gly Thr Gly Ala Glu Gln Asn Asn Glu Ser Gly Pro Ser Glu Asn
    50                  55                  60

Ser Arg Asn Gln Ala Ile Gly Lys Lys Gly Arg Lys Leu Ala Ser Phe
65                  70                  75                  80

Leu Ser Ile Ile Ala Arg Thr Pro Glu Leu Thr Pro Leu Asn Ile Asn
                85                  90                  95

Asp Trp Arg Val Phe Asp Lys Glu Glu Lys Lys Leu Val Glu Phe
            100                 105                 110

Val Arg Lys Lys Phe Ser Ile Pro Val Cys Arg Glu Glu Phe Ile Lys
        115                 120                 125

Lys Ser Ile Gly Lys Lys Trp Lys Asp Tyr Lys Cys Asp Leu Lys Thr
    130                 135                 140

Met Tyr Val Thr Lys Tyr Lys Ser Lys Asp Ala Leu Met Lys Asn Arg
145                 150                 155                 160

Pro Ser His Ile Pro Arg Asp Gln Trp Thr Gly Leu Val Leu Tyr Trp
                165                 170                 175
```

```
Leu Ser Asp Lys Ala Lys Lys Arg Ser Gln Ala Asn Arg Ile Ser Arg
            180                 185                 190

Ala Lys Gln Lys Met Pro His Thr Gly Gly Ser Lys Ser Ile Ala Thr
            195                 200                 205

Leu Met Asn Glu Lys Ala Ile Asp Gly Ile Glu Pro Thr Arg Ala Gln
            210                 215                 220

Val Tyr Ile Leu Thr His Thr Lys Arg Lys Asp Gly Arg Pro Leu Asp
225                 230                 235                 240

Glu Glu Ser Ser Asn Thr Val Asp Ile Asp Glu Arg Glu Val Glu
                245                 250                 255

<210> SEQ ID NO 29
<211> LENGTH: 159
<212> TYPE: PRT
<213> ORGANISM: Nicotiana tabacum

<400> SEQUENCE: 29

Met Val Asp His Trp Met Arg Asn Leu Gln Ile Gln Leu Thr Leu Met
1               5                   10                  15

Lys Glu Lys Leu Ser Asn Gly Glu Thr Ser His Glu Gln Pro His Gly
            20                  25                  30

Ser Val Ala Trp Glu Gly Asp Val Tyr Ser Gln Val Leu Gly Asn Glu
        35                  40                  45

Lys Ser Gly Asn Val Arg Gly Leu Gly Leu Gly Pro Thr Pro Ser Leu
    50                  55                  60

Leu Trp Gly Gly Lys Ser Ser Leu Gln Asn Ile Thr Asp Asp Gly Leu
65                  70                  75                  80

Ser Asn Glu Ala Ala His Lys Leu Glu Gln Glu Ile Lys Glu Leu Lys
                85                  90                  95

Asp Leu Asn Lys Lys Gln Asp Glu Glu Ile Ala Leu Met Lys Lys Asn
            100                 105                 110

Gln Asp Met Leu Val Ser Glu Leu Thr Trp Met Arg Gln Val Met Trp
        115                 120                 125

Lys Tyr Val Pro Thr Lys Leu Cys Gly Pro Gln Asn Tyr Gly Ser Thr
    130                 135                 140

Thr Arg Gln Val Pro Asp Ala Asn Ser Gly Asn Glu Gln Ala Thr
145                 150                 155

<210> SEQ ID NO 30
<211> LENGTH: 370
<212> TYPE: PRT
<213> ORGANISM: Nicotiana tabacum

<400> SEQUENCE: 30

Met Glu Val Pro Val Leu Ala Arg Cys Thr Asn Thr Pro Thr Thr Ser
1               5                   10                  15

Phe Leu Gly Cys Lys Val Ser Leu Phe Asp Phe Pro Ile Arg Arg Lys
            20                  25                  30

Leu Asn Lys Arg Asn Tyr Lys Ala Lys Phe Ser Val Leu Arg Val Lys
            35                  40                  45

Ala Met Ala Glu Arg Thr Ser Thr Glu Ala Ser Asp Ala Arg Glu
    50                  55                  60

Arg Glu Ser Gly Gly Tyr Thr Gly Thr Thr Met Glu Val Thr Thr Phe
65                  70                  75                  80

Asn Gln Ser Phe Ser Asp Ala Gln Leu Pro Val Trp Glu Lys Ile Gly
                85                  90                  95
```

```
Ala Val Val Arg Leu Ser Tyr Gly Ile Gly Ile Tyr Gly Ala Met Ala
                100                 105                 110

Leu Ala Gly Lys Phe Ile Cys Ser Met Thr Gly Ile Asp Cys Thr Gly
            115                 120                 125

Gly Phe Ser Pro Ser Leu Asp Ala Ile Val Glu Gly Leu Gly Tyr Ala
    130                 135                 140

Ala Pro Pro Ile Met Ala Leu Leu Phe Ile Leu Asp Asp Glu Val Val
145                 150                 155                 160

Lys Leu Ser Pro His Ala Arg Ala Ile Arg Asp Val Glu Asp Glu Glu
                165                 170                 175

Leu Arg Asn Phe Phe Tyr Gly Met Ser Pro Trp Gln Phe Ile Leu Ile
            180                 185                 190

Val Ala Ala Ser Ser Val Gly Glu Glu Leu Phe Tyr Arg Ala Ala Val
        195                 200                 205

Gln Gly Ala Leu Ala Asp Ile Phe Leu Arg Gly Ser Gly Phe Val Thr
    210                 215                 220

Asp Ala Arg Gly Met Ala Ser Leu Thr Gly Val Leu Pro Pro Tyr Val
225                 230                 235                 240

Pro Phe Ala Gln Ala Phe Ala Ala Val Ile Thr Ala Ala Leu Thr Gly
                245                 250                 255

Ser Leu Tyr Tyr Met Ala Ala Ser Pro Lys Asp Pro Thr Tyr Val Val
            260                 265                 270

Ala Pro Val Leu Lys Ser His Ser Gly Arg Glu Asp Leu Lys Lys Leu
        275                 280                 285

Phe Ala Ala Trp Tyr Glu Arg Arg Gln Met Lys Lys Ile Tyr Ser Pro
    290                 295                 300

Leu Leu Glu Ala Met Leu Ala Leu Tyr Leu Gly Phe Glu Trp Ile Gln
305                 310                 315                 320

Thr Asn Asn Ile Phe Ala Pro Ile Ile Thr His Gly Ile Tyr Ser Ala
                325                 330                 335

Val Ile Leu Gly His Gly Leu Trp Lys Ile His Asp His Arg Arg Arg
            340                 345                 350

Leu His Gln Arg Ile Gln Gln Leu Lys Gln Gly Asn Asn Ser Arg
        355                 360                 365

Asn Leu
    370

<210> SEQ ID NO 31
<211> LENGTH: 224
<212> TYPE: PRT
<213> ORGANISM: Nicotiana tabacum

<400> SEQUENCE: 31

Met Gly Ala Gly Ile Pro Asp Glu Glu Glu Asn Asn Trp Pro Leu Trp
1               5                   10                  15

Leu Lys Pro Leu Leu Lys Glu Lys Phe Phe Gly His Cys Lys Leu His
            20                  25                  30

Ala Asp Ser His Lys Ser Glu Cys Asn Met Tyr Cys Leu Asp Cys Ile
        35                  40                  45

Asn Gly Pro Leu Cys Ser Leu Cys Leu Ala His His Lys Asp His Ile
    50                  55                  60

Ala Ile Gln Ile Arg Arg Ser Ser Tyr His Asp Val Ile Arg Val Asn
65                  70                  75                  80

Glu Ile Gln Lys Tyr Leu Asp Ile Ser Ser Val Gln Thr Tyr Ile Ile
```

```
                 85                  90                  95
Asn Ser Ala Lys Val Val Phe Leu Asn Glu Arg Pro Gln Pro Arg Pro
            100                 105                 110

Gly Lys Gly Val Thr Asn Thr Cys Gln Val Cys Glu Arg Ser Leu Leu
            115                 120                 125

Asp Ser Phe Lys Phe Cys Ser Leu Gly Cys Lys Val Val Gly Ser Ser
130                 135                 140

Lys Asn Phe Val Lys Lys Pro Lys Gln Leu Ser Ala Lys Arg Arg Arg
145                 150                 155                 160

Ser Met Val Ala Ala Ser Asp Ser Asp Asp Ser Tyr Ser Ser Ser Ser
            165                 170                 175

His Gly Arg Tyr Lys Ser His Ser Asn Lys Val Gln Ser Phe Thr Pro
            180                 185                 190

Ser Thr Pro Pro Thr Ser Val Asn Tyr Lys Thr Ala Lys Arg Arg
            195                 200                 205

Lys Gly Ile Pro His Arg Ser Pro Met Gly Gly Leu Leu Ile Glu Tyr
210                 215                 220

<210> SEQ ID NO 32
<211> LENGTH: 452
<212> TYPE: PRT
<213> ORGANISM: Nicotiana tabacum

<400> SEQUENCE: 32

Met Ser Ser Asp Asn Phe Thr Asp Lys Asn Ala Val Phe Arg Lys Leu
1               5                   10                  15

Lys Ala Lys Pro Asp Asn Lys Met Cys Phe Asp Cys Asn Ala Lys Asn
            20                  25                  30

Pro Thr Trp Ala Ser Val Thr Tyr Gly Ile Phe Leu Cys Ile Asp Cys
            35                  40                  45

Ser Ala Thr His Arg Ser Leu Gly Val His Ile Ser Phe Val Arg Gly
        50                  55                  60

Arg Cys Thr Val Arg Gly Thr Gly Leu Val Glu Leu Arg Ser Phe Gly
65                  70                  75                  80

Leu Ser His Phe Leu Val Arg Asn His Tyr Leu His Pro Ile Cys Ala
                85                  90                  95

Thr Thr Ala Ser Phe Cys Pro Thr Ile Gly Met Thr Thr Leu Arg Asp
            100                 105                 110

Phe Met Cys Leu His Gln Gly Leu Trp Phe Ser Gly Lys Ser Ala Met
            115                 120                 125

Phe Asp Val Trp Ile Arg Arg Met Pro Gln Ile Asp Lys Phe Arg Phe
130                 135                 140

Met Val Ser Arg Ala Val Lys Asp Asp Val Leu Trp Trp Lys Gln Pro
145                 150                 155                 160

Cys Ser Ser Phe Phe Gln Ala Ala Leu Met Asp Gly Trp Arg Gln Glu
            165                 170                 175

Asp Ala Gly Leu Pro Ala Ser Pro Phe Ala Ser Gln Ala Val Gln Ser
            180                 185                 190

Thr Asn Gly Phe Ser Asp Val Lys Thr Ser Glu Ala Pro Lys Glu Thr
            195                 200                 205

Ser Ser Phe Lys Glu Glu Thr Pro Ala Ser Pro Lys Ala Ser Gln Ser
        210                 215                 220

Val Val Thr Thr Ser Ile Arg Lys Pro Ile Gly Ala Lys Lys Ser Gly
225                 230                 235                 240
```

```
Lys Pro Gly Gly Gly Leu Gly Ala Arg Lys Leu Thr Lys Lys Pro Ser
                245                 250                 255

Glu Ser Leu Tyr Asp Gln Lys Pro Glu Glu Pro Pro Val Gln Val Ser
            260                 265                 270

Ser Ser Asn Ser Thr Ser Asn Ala Ser Thr Val Gly Ser Ser Phe Ala
        275                 280                 285

Ser Arg Phe Glu Tyr Thr Asp Asn Val Gln Pro Ala Glu Met Ser Ser
    290                 295                 300

Gly Gly Pro Arg Val Leu Asn His Val Ser Pro Pro Met Ser Ser Ser
305                 310                 315                 320

Phe Phe Ser Asp Tyr Gly Met Asp Ser Gly Phe Thr Lys Lys Thr Ser
                325                 330                 335

Ser Asn Ser Ser Lys Val Gln Ile Glu Glu Thr Asp Glu Ala Arg Lys
            340                 345                 350

Lys Phe Ser Asn Ala Lys Ala Ile Ser Ser Ala Gln Phe Phe Gly Asp
        355                 360                 365

Lys Ser Lys Ala Glu Met Glu Ala Ser Val Ser Leu Gln Lys Phe Ser
    370                 375                 380

Gly Ser Ser Ala Ile Ser Ser Ala Asp Leu Phe Gly Asn Asp Asp Arg
385                 390                 395                 400

Ala Asp Leu Asp Leu Thr Ala Gly Asp Leu Ile Asn Arg Leu Ser Phe
                405                 410                 415

Gln Ala Gln Gln Asp Ile Ser Ser Leu Lys Asn Ile Ala Gly Glu Thr
            420                 425                 430

Gly Lys Lys Leu Gly Ser Leu Ala Ala Thr Leu Met Ser Asp Phe Gln
        435                 440                 445

Asp Arg Ile Leu
    450

<210> SEQ ID NO 33
<211> LENGTH: 156
<212> TYPE: PRT
<213> ORGANISM: Nicotiana tabacum

<400> SEQUENCE: 33

Met Ala Ser Leu Ser Trp Trp Asn Pro Ala Pro Ala Thr Thr Ala Met
1               5                   10                  15

Ala Ala Cys Ser Pro Thr Pro Ser Cys Lys Thr Ser Asn Ser Leu
            20                  25                  30

Ala Leu Pro Arg Ser Val Phe Val Ser Lys Gln Ala Lys Leu Met Lys
        35                  40                  45

Gln Ala Asn Gly Leu Leu Val Ile Thr Gln Gln Ser Lys Lys Lys
    50                  55                  60

Asn His Ser Phe Thr Asn Ser Arg Arg Asn Thr Ser Ile Gln Cys Leu
65                  70                  75                  80

Ser Gln Glu Gln Lys Trp Thr His Glu Gly Ser Ile Thr Glu Ser Leu
                85                  90                  95

Pro Asn Gly Met Phe Arg Val Lys Leu Asp Asn Ala Asp Val Val Leu
            100                 105                 110

Gly Tyr Ile Ser Gly Lys Ile Arg Lys Asn Phe Ile Arg Leu Leu Pro
        115                 120                 125

Gly Asp Arg Val Lys Ile Glu Val Ser Arg Tyr Asp Ser Thr Lys Gly
    130                 135                 140

Arg Ile Ile Tyr Arg Leu Arg Gly Gly Arg Glu Gly
145                 150                 155
```

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tgttagccct ttaccttggg ttt                                              23

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tgtgattatc ggtgcaaaaa tgt                                              23

<210> SEQ ID NO 36
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
aatggatcca gacaaac                                                     17

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cacagcaaca aggtccaaag ttt                                              23

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tggccgtttt gtaattaact gaag                                             24

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
actccgtcga cgccccctcc                                                  20

```
<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ggcatctctc tcatggtgga a                                                  21

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ggatgttgga gttggagaac aag                                                23

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
cctgctcctg ccacgactgc aa                                                 22

<210> SEQ ID NO 43
<211> LENGTH: 376
<212> TYPE: PRT
<213> ORGANISM: Solanum lycopersicum

<400> SEQUENCE: 43
```

Met Glu Phe Pro Leu Ile Ala Arg Cys Thr Asn Thr Pro Ser Thr Thr
1               5                   10                  15

Ser Phe Leu Gly Cys Lys Val Ser Leu Cys Asp Phe Pro Ile Arg Asn
            20                  25                  30

Asn Tyr Arg Asp Lys Arg Asn Tyr Asn Glu Lys Phe Ser Val Val Arg
        35                  40                  45

Ile Lys Ala Met Ala Glu Lys Ser Ser Thr Gly Glu Ala Ser Ser Val
    50                  55                  60

Glu Ile Arg Glu Gly Glu Asn Gly Gly Val Gly Phe Thr Gly Ser Thr
65                  70                  75                  80

Met Glu Val Thr Thr Phe Asn Gln Ser Phe Ser Asp Ala Gln Leu Pro
                85                  90                  95

Val Trp Glu Lys Ile Gly Ala Val Val Arg Leu Ser Tyr Gly Ile Gly
                100                 105                 110

Ile Tyr Gly Ala Met Ala Leu Ala Gly Lys Phe Ile Cys Ser Ile Ser
            115                 120                 125

Gly Ile Asp Cys Thr Gly Gly Phe Ser Pro Ser Leu Asp Ala Ile Val
        130                 135                 140

Glu Gly Leu Gly Tyr Ala Val Pro Pro Ile Met Ala Leu Leu Phe Ile
145                 150                 155                 160

Leu Asp Asp Glu Val Val Lys Leu Ser Pro His Ala Arg Ala Ile Arg
                165                 170                 175

```
Asp Val Glu Asp Glu Leu Arg Asn Phe Phe Tyr Gly Met Ser Pro
            180                 185                 190

Trp Gln Phe Ile Leu Ile Val Ala Ala Ser Ser Val Gly Glu Glu Leu
        195                 200                 205

Phe Tyr Arg Ala Ala Val Gln Gly Ala Leu Ala Asp Ile Phe Val Arg
    210                 215                 220

Ser Thr Asp Leu Val Ser Asp Ala Arg Gly Met Ala Ser Leu Thr Gly
225                 230                 235                 240

Val Leu Pro Pro Tyr Val Pro Phe Ala Gln Ala Phe Ala Ala Val Met
                245                 250                 255

Thr Ala Ala Leu Thr Gly Ser Leu Tyr Tyr Met Ala Ala Ser Pro Lys
            260                 265                 270

Asp Pro Thr Tyr Val Val Ala Pro Val Leu Lys Ser Arg Ser Gly Arg
        275                 280                 285

Glu Asp Leu Lys Lys Leu Phe Ala Ala Trp Tyr Glu Arg Arg Gln Met
    290                 295                 300

Lys Lys Ile Tyr Ser Pro Leu Leu Glu Ala Ile Leu Ala Leu Tyr Leu
305                 310                 315                 320

Gly Phe Glu Trp Ile Gln Thr Asn Asn Ile Leu Ala Pro Ile Ile Thr
                325                 330                 335

His Gly Ile Tyr Ser Ala Val Ile Leu Gly His Gly Leu Trp Lys Ile
            340                 345                 350

His Asp His Arg Arg Arg Leu His His Arg Ile Gln Gln Val Lys Gln
        355                 360                 365

Glu Gly Lys Asn Ser Ser Asn Leu
    370                 375

<210> SEQ ID NO 44
<211> LENGTH: 1113
<212> TYPE: DNA
<213> ORGANISM: Nicotiana tabacum

<400> SEQUENCE: 44
atggaggtac cggtgctagc tcggtgtacg aatactccga cgacgtcgtt tctaggatgt      60
aaagtgagtt tatttgattt ccgattaga agaaagctaa ataagaggaa ttataaggcg      120
aagttttcag tgttaagagt taaagctatg gcggagagga cgagtactga ggcatcagcg     180
gatgctagag agagagaaag tggagggtac acgggaacta cgatggaggt gacaacattt     240
aatcagagct ttagtgatgc gcaattgcca gtttgggaaa agattggtgc tgtcgtcaga     300
ctcagttatg gaatcggcat atatggagca atggctttag caggaaagtt catatgctca     360
atgacaggaa ttgactgcac aggagggttc agtccatcat tagatgccat tgttgaagga     420
ctaggatatg cagctccacc aattatggct cttctattta tactagatga tgaagttgtg     480
aagctgtcgc tcatgctcg agctatcaga gatgtagagg atgaagagct acggaatttc     540
ttttatggaa tgtcaccttg gcagttcatt ctgattgtgg ctgctagctc tgttggagaa     600
gagcttttct accgcgctgc tgtccaggga gctttagctg acatttctt aaggggcagt      660 ggttttgtga ctgatgctag aggaatggca tcattgactg gtgttttgcc accgtatgtc     720
ccatttgctc aagcgtttgc agctgtaatt acggcagctc tcacgggttc tctatattat     780
atggctgcct ctccaaaaga tcctacctat gttgttgcac cagtgctgaa gtcgcattca     840
ggtcgtgaaa tcttaaaaaa actatttgca gcttggtacg agaggcgaca gatgaagaag     900
atatactctc ctttactaga agccatgtta gccctttacc ttgggtttga atggatccag     960
```

```
acaaacaaca ttttgcacc gataatcaca catgggatat actctgctgt tattctggga    1020
catggacttt ggaaaatcca cgatcatcgg agaagactac atcaaagaat ccaacaactt   1080
aaacaagaag gtaacaattc aagaaacttg taa                                1113
```

<210> SEQ ID NO 45
<211> LENGTH: 1113
<212> TYPE: DNA
<213> ORGANISM: Nicotiana tabacum

<400> SEQUENCE: 45

```
atggaggtac cggtgctagc tcggtgtacg aatactccga cgacgtcgtt tctaggatgt      60
aaagtgagtt tatttgattt tccgattaga agaaagctaa ataagaggaa ttataaggcg    120
aagttttcag tgttaagagt taaagctatg gcggagagga cgagtactga ggcatcagcg    180
gatgctagag agagagaaag tggagggtac acgggaacta cgatggaggt gacaacattt    240
aatcagagct ttagtgatgc gcaattgcca gtttgggaaa agattggtgc tgtcgtcaga    300
ctcagttatg gaatcggcat atatggagca atggctttag caggaaagtt catatgctca    360
atgacaggaa ttgactgcac aggagggttc agtccatcat tagatgccat tgttgaagga    420
ctaggatatg cagctccacc aattatggct cttctatttta tactagatga tgaagttgtg    480
aagctgtcgc ctcatgctcg agctatcaga gatgtagagg atgaagagct acggaatttc    540
ttttatggaa tgtcaccttg gcagttcatt ctgattgtgg ctgctagctc tgttggagaa    600
gagcttttct accgcgctgc tgtccaggga gctttagctg acatttctt aaggggcagt    660 ggttttgtga ctgatgctag aggaatggca tcattgactg gtgttttgcc accgtatgtc    720
ccatttgctc aagcgtttgc agctgtaatt acggcagctc tcacgggttc tctatattat    780
atggctgcct ctccaaaaga tcctacctat gttgttgcac cagtgctgaa gtcgcattca    840
ggtcgtgaag atcttaaaaa actatttgca gcttggtacg agaggcgaca gatgaagaag    900
atatactctc ctttactaga agccatgtta gccctttacc ttgggtttga atggatccag    960
acaaacaaca ttttgcacc gataatcaca catgggatat actctgctgt tattctggga   1020
catggacttt ggaaaatcca cgatcatcgg agaagactac atcaaagaat ccaacaactt  1080
aaacaagaag gtaacaattc aagaaacttg taa                              1113
```

<210> SEQ ID NO 46
<211> LENGTH: 370
<212> TYPE: PRT
<213> ORGANISM: Nicotiana tabacum

<400> SEQUENCE: 46

```
Met Glu Val Pro Val Leu Ala Arg Cys Thr Asn Thr Pro Thr Thr Ser
1               5                   10                  15

Phe Leu Gly Cys Lys Val Ser Leu Phe Asp Phe Pro Ile Arg Arg Lys
            20                  25                  30

Leu Asn Lys Arg Asn Tyr Lys Ala Lys Phe Ser Val Leu Arg Val Lys
        35                  40                  45

Ala Met Ala Glu Arg Thr Ser Thr Glu Ala Ser Ala Asp Ala Arg Glu
    50                  55                  60

Arg Glu Ser Gly Gly Tyr Thr Gly Thr Thr Met Glu Val Thr Thr Phe
65                  70                  75                  80

Asn Gln Ser Phe Ser Asp Ala Gln Leu Pro Val Trp Glu Lys Ile Gly
                85                  90                  95
```

```
Ala Val Val Arg Leu Ser Tyr Gly Ile Gly Ile Tyr Gly Ala Met Ala
            100                 105                 110

Leu Ala Gly Lys Phe Ile Cys Ser Met Thr Gly Ile Asp Cys Thr Gly
        115                 120                 125

Gly Phe Ser Pro Ser Leu Asp Ala Ile Val Glu Gly Leu Gly Tyr Ala
    130                 135                 140

Ala Pro Pro Ile Met Ala Leu Leu Phe Ile Leu Asp Asp Glu Val Val
145                 150                 155                 160

Lys Leu Ser Pro His Ala Arg Ala Ile Arg Asp Val Glu Asp Glu Glu
                165                 170                 175

Leu Arg Asn Phe Phe Tyr Gly Met Ser Pro Trp Gln Phe Ile Leu Ile
            180                 185                 190

Val Ala Ala Ser Ser Val Gly Glu Glu Leu Phe Tyr Arg Ala Ala Val
        195                 200                 205

Gln Gly Ala Leu Ala Asp Ile Phe Leu Arg Gly Ser Gly Phe Val Thr
    210                 215                 220

Asp Ala Arg Gly Met Ala Ser Leu Thr Gly Val Leu Pro Pro Tyr Val
225                 230                 235                 240

Pro Phe Ala Gln Ala Phe Ala Ala Val Ile Thr Ala Ala Leu Thr Gly
                245                 250                 255

Ser Leu Tyr Tyr Met Ala Ala Ser Pro Lys Asp Pro Thr Tyr Val Val
            260                 265                 270

Ala Pro Val Leu Lys Ser His Ser Gly Arg Glu Asp Leu Lys Lys Leu
        275                 280                 285

Phe Ala Ala Trp Tyr Glu Arg Arg Gln Met Lys Lys Ile Tyr Ser Pro
    290                 295                 300

Leu Leu Glu Ala Met Leu Ala Leu Tyr Leu Gly Phe Glu Trp Ile Gln
305                 310                 315                 320

Thr Asn Asn Ile Phe Ala Pro Ile Ile Thr His Gly Ile Tyr Ser Ala
                325                 330                 335

Val Ile Leu Gly His Gly Leu Trp Lys Ile His Asp His Arg Arg Arg
            340                 345                 350

Leu His Gln Arg Ile Gln Gln Leu Lys Gln Glu Gly Asn Asn Ser Arg
        355                 360                 365

Asn Leu
    370

<210> SEQ ID NO 47
<211> LENGTH: 370
<212> TYPE: PRT
<213> ORGANISM: Nicotiana tabacum

<400> SEQUENCE: 47

Met Glu Val Pro Val Leu Ala Arg Cys Thr Asn Thr Pro Thr Thr Ser
1               5                   10                  15

Phe Leu Gly Cys Lys Val Ser Leu Phe Asp Phe Pro Ile Arg Arg Lys
            20                  25                  30

Leu Asn Lys Arg Asn Tyr Lys Ala Lys Phe Ser Val Leu Arg Val Lys
        35                  40                  45

Ala Met Ala Glu Arg Thr Ser Thr Glu Ala Ser Ala Asp Ala Arg Glu
    50                  55                  60

Arg Glu Ser Gly Gly Tyr Thr Gly Thr Thr Met Glu Val Thr Thr Phe
65                  70                  75                  80

Asn Gln Ser Phe Ser Asp Ala Gln Leu Pro Val Trp Glu Lys Ile Gly
                85                  90                  95
```

Ala Val Val Arg Leu Ser Tyr Gly Ile Gly Ile Tyr Gly Ala Met Ala
            100                 105                 110

Leu Ala Gly Lys Phe Ile Cys Ser Met Thr Gly Ile Asp Cys Thr Gly
            115                 120                 125

Gly Phe Ser Pro Ser Leu Asp Ala Ile Val Glu Gly Leu Gly Tyr Ala
130                 135                 140

Ala Pro Pro Ile Met Ala Leu Leu Phe Ile Leu Asp Asp Glu Val Val
145                 150                 155                 160

Lys Leu Ser Pro His Ala Arg Ala Ile Arg Asp Val Glu Asp Glu Glu
                165                 170                 175

Leu Arg Asn Phe Phe Tyr Gly Met Ser Pro Trp Gln Phe Ile Leu Ile
            180                 185                 190

Val Ala Ala Ser Ser Val Gly Glu Glu Leu Phe Tyr Arg Ala Ala Val
            195                 200                 205

Gln Gly Ala Leu Ala Asp Ile Phe Leu Arg Gly Ser Gly Phe Val Thr
            210                 215                 220

Asp Ala Arg Gly Met Ala Ser Leu Thr Gly Val Leu Pro Pro Tyr Val
225                 230                 235                 240

Pro Phe Ala Gln Ala Phe Ala Ala Val Ile Thr Ala Ala Leu Thr Gly
                245                 250                 255

Ser Leu Tyr Tyr Met Ala Ala Ser Pro Lys Asp Pro Thr Tyr Val Val
            260                 265                 270

Ala Pro Val Leu Lys Ser His Ser Gly Arg Glu Asp Leu Lys Lys Leu
            275                 280                 285

Phe Ala Ala Trp Tyr Glu Arg Arg Gln Met Lys Lys Ile Tyr Ser Pro
            290                 295                 300

Leu Leu Glu Ala Met Leu Ala Leu Tyr Leu Gly Phe Glu Trp Ile Gln
305                 310                 315                 320

Thr Asn Asn Ile Phe Ala Pro Ile Ile Thr His Gly Ile Tyr Ser Ala
                325                 330                 335

Val Ile Leu Gly His Gly Leu Trp Lys Ile His Asp His Arg Arg Arg
            340                 345                 350

Leu His Gln Arg Ile Gln Gln Leu Lys Gln Glu Gly Asn Asn Ser Arg
            355                 360                 365

Asn Leu
    370

<210> SEQ ID NO 48
<211> LENGTH: 6554
<212> TYPE: DNA
<213> ORGANISM: Nicotiana tabacum

<400> SEQUENCE: 48
atggaggtac cggtgctagc tcggtgtacg aatactccga cgacgtcgtt tatgggatgt      60
aaagtgagtc aatttgattt tccgattagg agaaagctaa ataagaggaa ttataaggcg     120
aagttttcag tgttaagagt taaagctatg gcggagaggt cgagtagtgg tgaggcatca     180
gtggatgcta gagagagaga aagtggaggt tacacgggaa ctactatgga ggtaacaaca     240
tttaatcaga gctttagtga tacgcaattg cctgtttggg agaagattgg tgctgtcgtc     300
agactcagtt atggaatcgg tgagttctca actcgttttg cattttctta atttttttt      360 tttttttttt ctgtttgagt tctgttttcc tttttgaaga ctattttggg aaaaaagcc      420 aaggaatatt catataagtt gaatagattc aatgaattca gaattttatt ttatggcttt     480

```
tggtttccta ttctttggtc aaacatttgg tatatgaacc cactaacccg actaattttg    540
attcgcgtct taaaatctta ctgtggaaga tttaagtgtt ctttacaaag aggacttcat    600
tgtcataatt cgaacttgaa acttttgatt acgatgtaaa agaattttta tcattccaac    660
tagggcggtt cggtttggat cgattttttcc ttaaaagaa accaaatcaa gtaagttggt    720
ttttcaaata ttagaaccaa accaaaccaa ttaagtcggt tttttctcga ttcggtttat    780
gtcggatttt atcggttttt catgttttt ttggttattt gtcggttttt tcttaaatat    840
aagacataca ctaccaaaca tatattccgg cgaccacatt ttcaacgtaa cactatcaaa    900
tcaattgccc tttgagaaat ttattattta ctaaaatata ttgatgataa ttgaatcaaa    960
tagtgatgag taatttaacg actcaattta aaaatatttt ttttttaacat aaaatggatt   1020 cttacactta acaaaagaaa actaccaatc aaactagaat ataaaggtaa agaactgtac   1080
taaaagtgca aacaattaac atttaccata aattttttgaa attttctata aaaatataca   1140
tatatatagg tgtaataata aatttgaaat agctactcct atagtcggtt tggttcggtt   1200
tttttcggtt atttttttat taaaatcaaa accaaaccaa atttgatcgg ttttttaaaat   1260 tcaaaaccaa aatcaaacca aaccaaacca aaaagtatcg atttttttga tcggtttggt   1320
tctgattttt cgggtttatg agatagtgaa tttacaagtg attcttggaa ttgcaagtaa   1380
agggaaaggg ttttttgtcct tgtcaaaagg gaaagggttg ttgcatatct tcttttttgct  1440 ttctgtatat gtcattaaag tgcttctaaa agtggaaaag ctaaggtttt tcttcttcct   1500 aactttttagg ttttattgtt ggttggacaa caaatgccaa aaataaatac actgcaataa  1560
ttttgcagtc aatttaatca ttttttccaat cacatgttaa gtggtacttt gtttcctaag   1620
taagaaatat aagcaattgt caggaatagg attgtattta tatcctataa caacaataaa   1680
atttctccag tggggtctgg ggaggggaggc tgtgtccgag agaccctcag ctcaagaaga   1740
cgaaaataga caataaaatg tatttatatc ctactataaa taaaattatt aatgaaacaa   1800
ttttagataa aattgaatac tttcgttgtt tttgctcata cttggctatt gaggaaaaca   1860
gaattgtcgt taggcaattg ttagtatgca ttagaacaag tgtagatgta ttttagaatg   1920
atagaacata caaattttatt tacttttta agaacagtat aaataaatga agtgattta   1980 aaattattaa gaacatgata atagaagaaa ataggcgaa aattaaaaaa agaataaaag   2040
tggagccgaa attgatcatt ctaatgcatg tgggctaact ttgaatagct ttaaacttag   2100
caacttattg gtaattttta ttttatagaa atctttttgtt cttttcttttt ccttttttta   2160 ataaaccaat tttatttgtt aactcaacta catgcttctg tagaattaca tttagaaaag   2220 cttttttagtc caaacactac caaaaagagt taaatgctaa atacaaaata aacaaataat   2280
aactccatcc cgtgccactt aattagaagt agaattgtac ttacaggagt aatttgaact   2340
ttggcaatag ttgttaaaat atgttctagc ctaactagca gtactaaggt ctcaaaatct   2400
ttgatatctt gattctaatc ttcctctaaa aaaaaaaaa gaaagtagtc cctatgcgcg   2460
ggtccgaaaa gggctatttt atgcaatctt acccctgtatt tctgcaagag gctgtttcta   2520
cggtttgaac ccgtagcctc gtggtaacaa gacaacaatc ttcctcaaag aagaatagaa   2580
tttaatcatt atacttgagt aaattgaaca ttgcaattat tatcatagta catatccca   2640 aaatgtagga tgttgattgt aatactacat attcattttt ttcttccaat gtatttattt   2700
tttatcctta ctttttttaat acggtgttat cttccactaa tatatatcgg ataactgtga   2760
caccacagat aaatatcacc tagtgttttt aatcctgtgt atttgtttgt ttgttacatt   2820
gtttattgca tgtatttctt ccagccttgt atgagtccca tcccattaaa ttttttggat   2880
```

```
atctttagag aagaaaaaga aagaccttca atcattctct gatgttcagt ttgttttttgg    2940 gatttttaca caaatagccg ctcggtttta cgtttacttt ttctagccgg tatacataaa    3000
ttatacactg atttaacatt attttatata tataatttaa gtaactgagt gggctgctat    3060
ttaggttatt tcttctatgt ttttttttga actcaggcat atacggagca atggcttag     3120 caggaaagtt tatatgctca atgacaggaa ttgactgcac aggagggttc agtccatcat    3180
tagatgccat tgttgaagga ctaggatatg cagctccccc gattatggct cttctattta    3240
tactagatgt atgttcaact attcccattt cttccctgcc acaaactgta acagtccagc    3300
cattggtgat gttatctgct tgtgtggctt taaaacacat tactagggtc gtctggaact    3360
tgctttctta tatgtcaagc atccctctcg tgttttgtcg atgtgaaatt tgcctaagag    3420
tgttacaaaa atatatttaa cagcattctt ggtttactta acttgcatta ttttctttca    3480
tccacatatg gcttcactaa ctcttagaaa agatgcaaca atgttaacct tatactccct    3540
ccgttccagt ttatgtgaac ctatttcctt tttggtccgt tccaaagaga atggtccttt    3600
ctaatttagc ttaaattttc aattctacca ttaatgagaa gcttttataa ccacacaaat    3660
attctggacc ccattctgac atgtttaaga ccacaaattc caaagttttt tattttttct    3720
taaatttcgt gctcagtcaa acaggttcac ataaattgac acggggagta ttgtagccat    3780
tctagctttg tccatctgac attcttggat tatataaccg atgttttata ataaattgcg    3840
gtgtttatag gatgaagttg tgaagctatc acctcatgct cgagctatta gggatgttga    3900
ggatgaagag ctgcggaatt tcttttatgg aatgtcacct tggcaggtaa aagatttctc    3960
aatttcagca tcaatagtta tgtcacaata cagtgaaagg ttgatactta atggattttg    4020
atgcaaattt gtagttcatt ctgattgtgg ctgctagctc tgttggagag gaacttttct    4080
accgtgctgc tgtccaggta agatatatat catccatata tagcctgcaa ttatgaattc    4140
gttagtccag ttgcagcctt attttttgga tcaataatac tccatttcac tactttcctt    4200
cacgtgactt aaactcccac ccggtgtcaa tattggtacc gtgcttaccc tttcatgtga    4260
atcagacatc taacctagtg gttggaggtg aaggcagctc accaactaat caagcttctc    4320
tcttcagcca tctatgttaa attgtacaaa ccttgcattt cctacagttt taactaataa    4380
tacatactct gaaaccatt tggtgaaatt ttctgcactt cagttttcca atgtatacat     4440
ttattttgtt aaaagaaata atagagaaag aagaagaat atagaaaaac gtagaaacca     4500
gaaaaaggct tgaggtgtgt agaacacttt atcaaaagat tggttatctg gctcgaggga    4560
tagtgatctt cgggaataca aaccacactt atttgaatgt gatgattgtt gtcttttgcc    4620
tgatctaatt cactttcgga agagccaact actttcttat ttattggaaa taatctcaaa    4680
aaggttgaaa tcttttcaga atagacatat cttttgttaa taaccacttt catattacaa    4740
tctgtccaac aatattatca acagactaat tattttttaac ctgtcaaact taatggaaat   4800
gcatggcaaa aaagttatgt ttctcataag ttatgtgatt cttcctcct tgctcctctc     4860 tgattatctt ttaattacag ggagctttag ctgacatttt cttaagggc agtgattttg     4920 tgactgatgc tagaggaatg gcgtcattgg tacgtcggat tctatttcta gacatccttc    4980
tccaagttaa atatccaaaa aaattccatt gctctgacac attctgtttc ctcaaaatgt    5040
agactggtgt tttgccacct tatgtcccgt ttgctcaagc atttgcagct gtaattacag    5100
cagctctcac tggttcttta tattatatgg cagcctctcc aaaaggtcag tttcataggg    5160
tgcagtttca aatccttcgt tgtactctgc tcgaacatgc ttaatcagtt ggctatttgc    5220
```

```
tgtttcacttt tcagatccta cctatgttgt tgcacccgtg ttgaagtcgc attcaggccg    5280
tgaagatcta aaaaaactct ttgcaggttt gacctctctc tttgctcatg acaaaagcaa    5340
gacagctacc acttgtgatg atttgagtcc aagccttgtt aacataatgt aataaatctg    5400
gggattcagg atcaaggcaa atagatatat ttctacagct gactgactaa aataagagat    5460
aaagtctgtc ccttagtcta gtttatatcc acagctgact aaataaaata caactgttgt    5520
gacctgcttt gtatcaaaag aaaagcaaag ggtttacggc tttacacaac aagcaaaacg    5580
gctttctatc atagttgcaa gggccaaaca cactcctgat catcgttcta ctgcatctgg    5640
cctgtcctct aggcaccttt tatagaaggc agggagcgtg ataatatacc cgcttctttt    5700
gctccattag accttctcaa gctttttcat gtaagaatag ctttctaaac tattttaaat    5760
aatatgagac caccaagcct ataggctaga ctctcctgtc aaaacaacg tacctacttc     5820 tcattctagg tgttagcatg tagtgaagac tgaagagtcc cctttctgt atattgaact     5880 atgttgcccg aactctcaaa aaatgtagct aggtgtgcat cggatcatcc gtacaggtgc    5940
ggcagcattt tggagagtcc atgcgacata gaatattgaa gggggttgct tcacaagtgt    6000
caccggagag acggaggaga gattggatca aagaaaaatt agtttgagtt gagcttattg    6060
aggcagaatt gattgatacg agttttttt tttttttttt ggggggggg ggggagggt     6120 aaccaatatc atgaatagtt agtagtggaa acgtccagct catattttc atgtgtgtta    6180 attttatcat ctacctgaaa tgtttgcag cttggtacga gaggcgacag atgaagaaga    6240
tatactctcc gttactagaa gccatgttag cgctttacct tgggtttgaa tggatacagg    6300
taacatagat tttcgtttta tttattggta ctagtcatca aaggttgtgt cgacatgaat    6360
tttatgtcag tatagcttat ttgttcttac aaatgcaaca gacaaacaat attcttgcac    6420
ctataatcac acatgggata tactctgctg ttattctggg acatggactt tggaaaatcc    6480
acgatcatcg gagaagacta catcagagaa tccaaacact taaacaagaa ggtaataatt    6540
caagaaactt gtaa                                                       6554

<210> SEQ ID NO 49
<211> LENGTH: 1116
<212> TYPE: DNA
<213> ORGANISM: Nicotiana tabacum

<400> SEQUENCE: 49
atggaggtac cggtgctagc tcggtgtacg aatactccga cgacgtcgtt tatgggatgt      60
aaagtgagtc aatttgattt tccgattagg agaaagctaa ataagaggaa ttataaggcg     120
aagttttcag tgttaagagt taaagctatg gcggagaggt cgagtagtgg tgaggcatca     180
gtggatgcta gagagagaga aagtggaggt tacacgggaa ctactatgga ggtaacaaca     240
tttaatcaga gctttagtga tacgcaattg cctgtttggg agaagattgg tgctgtcgtc     300
agactcagtt atggaatcgg catatacgga gcaatggctt tagcaggaaa gtttatatgc     360
tcaatgacag gaattgactg cacaggaggg ttcagtccat cattagatgc cattgttgaa     420
ggactaggat atgcagctcc cccgattatg gctcttctat ttatactaga tgatgaagtt     480
gtgaagctat cacctcatgc tcgagctatt agggatgttg aggatgaaga gctgcggaat     540
ttcttttatg gaatgtcacc ttggcagttc attctgattg tggctgctag ctctgttgga     600
gaggaacttt tctaccgtgc tgctgtccag ggagctttag ctgacatttt cttaaggggc     660
agtgattttg tgactgatgc tagaggaatg gcgtcattga ctggtgtttt gccaccttat     720
gtcccgtttg ctcaagcatt tgcagctgta attacagcag ctctcactgg ttctttatat     780
```

```
tatatggcag cctctccaaa agatcctacc tatgttgttg cacccgtgtt gaagtcgcat    840
tcaggccgtg aagatctaaa aaaactcttt gcagcttggt acgagaggcg acagatgaag    900
aagatatact ctccgttact agaagccatg ttagcgcttt accttgggtt tgaatggata    960
cagacaaaca atattcttgc acctataatc acacatggga tatactctgc tgttattctg    1020
ggacatggac tttggaaaat ccacgatcat cggagaagac tacatcagag aatccaaaca    1080
cttaaacaag aaggtaataa ttcaagaaac ttgtaa                              1116
```

<210> SEQ ID NO 50
<211> LENGTH: 371
<212> TYPE: PRT
<213> ORGANISM: Nicotiana tabacum

<400> SEQUENCE: 50

```
Met Glu Val Pro Val Leu Ala Arg Cys Thr Asn Thr Pro Thr Thr Ser
1               5                   10                  15

Phe Met Gly Cys Lys Val Ser Gln Phe Asp Phe Pro Ile Arg Arg Lys
            20                  25                  30

Leu Asn Lys Arg Asn Tyr Lys Ala Lys Phe Ser Val Leu Arg Val Lys
        35                  40                  45

Ala Met Ala Glu Arg Ser Ser Ser Gly Glu Ala Ser Val Asp Ala Arg
    50                  55                  60

Glu Arg Glu Ser Gly Gly Tyr Thr Gly Thr Thr Met Glu Val Thr Thr
65                  70                  75                  80

Phe Asn Gln Ser Phe Ser Asp Thr Gln Leu Pro Val Trp Glu Lys Ile
                85                  90                  95

Gly Ala Val Val Arg Leu Ser Tyr Gly Ile Gly Ile Tyr Gly Ala Met
            100                 105                 110

Ala Leu Ala Gly Lys Phe Ile Cys Ser Met Thr Gly Ile Asp Cys Thr
        115                 120                 125

Gly Gly Phe Ser Pro Ser Leu Asp Ala Ile Val Glu Gly Leu Gly Tyr
    130                 135                 140

Ala Ala Pro Pro Ile Met Ala Leu Leu Phe Ile Leu Asp Asp Glu Val
145                 150                 155                 160

Val Lys Leu Ser Pro His Ala Arg Ala Ile Arg Asp Val Glu Asp Glu
                165                 170                 175

Glu Leu Arg Asn Phe Phe Tyr Gly Met Ser Pro Trp Gln Phe Ile Leu
            180                 185                 190

Ile Val Ala Ala Ser Ser Val Gly Glu Glu Leu Phe Tyr Arg Ala Ala
        195                 200                 205

Val Gln Gly Ala Leu Ala Asp Ile Phe Leu Arg Gly Ser Asp Phe Val
    210                 215                 220

Thr Asp Ala Arg Gly Met Ala Ser Leu Thr Gly Val Leu Pro Pro Tyr
225                 230                 235                 240

Val Pro Phe Ala Gln Ala Phe Ala Ala Val Ile Thr Ala Ala Leu Thr
                245                 250                 255

Gly Ser Leu Tyr Tyr Met Ala Ala Ser Pro Lys Asp Pro Thr Tyr Val
            260                 265                 270

Val Ala Pro Val Leu Lys Ser His Ser Gly Arg Glu Asp Leu Lys Lys
        275                 280                 285

Leu Phe Ala Ala Trp Tyr Glu Arg Arg Gln Met Lys Lys Ile Tyr Ser
    290                 295                 300

Pro Leu Leu Glu Ala Met Leu Ala Leu Tyr Leu Gly Phe Glu Trp Ile
```

Gln Thr Asn Asn Ile Leu Ala Pro Ile Ile Thr His Gly Ile Tyr Ser
305                 310                 315                 320

Ala Val Ile Leu Gly His Gly Leu Trp Lys Ile His Asp His Arg Arg
            325                 330                 335

Arg Leu His Gln Arg Ile Gln Thr Leu Lys Gln Glu Gly Asn Asn Ser
        340                 345                 350

Arg Asn Leu
    355                 360                 365

370

<210> SEQ ID NO 51
<211> LENGTH: 737
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gactggtgtt ttgccacctt atgtcccgtt tgctcaagca tttgcagctg taattacagc      60
agctctcact ggttctttat attatatggc agcctctcca aaagatccta cctatgttgt     120
tgcacccgtg ttgaagtcgc attcaggccg tgaagatcta aaaaaactct tgcagcttg     180 gtacgagagg cgacagatga agaagatata ctctccgtta ctagaagcca tgttagcgct     240
ttaccttggg tttgaatgga tacagacaaa caatattctt gcacctataa tctaataaga    300
tcttcaacac ctacaccatt tttttaatca ctactaccca ttgcattgaa caaacttcca    360
agttcttctt agcttcagat taagaaagta ccctttcttg ctttgttga tgtggtacca    420 ttgtccattg tcttgtgtgt ttccagatta taggtgcaag aatattgttt gtctgtatcc    480
attcaaaccc aaggtaaagc gctaacatgg cttctagtaa cggagagtat atcttcttca    540
tctgtcgcct ctcgtaccaa gctgcaaaga gttttttag atcttcacgg cctgaatgcg    600
acttcaacac gggtgcaaca acataggtag gatcttttgg agaggctgcc atataatata    660
aagaaccagt gagagctgct gtaattacag ctgcaaatgc ttgagcaaac gggacataag    720
gtggcaaaac accagtc                                                   737

<210> SEQ ID NO 52
<211> LENGTH: 737
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
gactggtgtt ttgccaccgt atgtcccatt tgctcaagcg tttgcagctg taattacggc      60
agctctcacg ggttctctat attatatggc tgcctctcca aaagatccta cctatgttgt     120
tgcaccagtg ctgaagtcgc attcaggtcg tgaagatctt aaaaaactat ttgcagcttg     180
gtacgagagg cgacagatga agaagatata ctctccttta ctagaagcca tgttagccct     240
ttaccttggg tttgaatgga tccagacaaa caacattttt gcaccgataa tctaataaga    300
tcttcaacac ctacaccatt tttttaatca ctactaccca ttgcattgaa caaacttcca    360
agttcttctt agcttcagat taagaaagta ccctttcttg ctttgttga tgtggtacca    420 ttgtccattg tcttgtgtgt ttccagatta tcggtgcaaa aatgttgttt gtctggatcc    480
attcaaaccc aaggtaaagg gctaacatgg cttctagtaa aggagagtat atcttcttca    540

```
tctgtcgcct ctcgtaccaa gctgcaaata gttttttaag atcttcacga cctgaatgcg      600
acttcagcac tggtgcaaca acataggtag gatcttttgg agaggcagcc atataatata      660
gagaacccgt gagagctgcc gtaattacag ctgcaaacgc ttgagcaaat gggacatacg      720
gtggcaaaac accagtc                                                     737
```

<210> SEQ ID NO 53
<211> LENGTH: 1116
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 53

```
atggaggtac cggtgctagc tcggtgtacg aatactccga cgacgtcgtt tatgggatgt       60
aaagtgagtc aatttgattt tccgattagg agaaagctaa ataagaggaa ttataaggcg      120
aagttttcag tgttaagagt taaagctatg gcggagaggt cgagtagtgg tgaggcatca      180
gtggatgcta gagagagaga aagtggaggt tacacgggaa ctactatgga ggtaacaaca      240
tttaatcaga gctttagtga tacgcaattg cctgtttggg agaagattgg tgctgtcgtc      300
agactcagtt atggaatcgg catatacgga gcaatggctt tagcaggaaa gtttatatgc      360
tcaatgacag gaattgactg cacaggaggg ttcagtccat cattagatgc cattgttgaa      420
ggactaggat atgcagctcc cccgattatg gctcttctat ttatactaga tgatgaagtt      480
gtgaagctat cacctcatgc tcgagctatt agggatgttg aggatgaaga gctgcggaat      540
ttcttttatg gaatgtcacc ttggcagttc attctgattg tggctgctag ctctgttgga      600
gaggaacttt tctaccgtgc tgctgtccag ggagctttag ctgacatttt cttaaggggc      660
agtgattttg tgactgatgc tagaggaatg gcgtcattga ctggtgtttt gccaccttat      720
gtcccgtttg ctcaagcatt tgcagctgta attacagcag ctctcactgg ttctttatat      780
tatatggcag cctctccaaa agatcctacc tatgttgttg cacccgtgtt gaagtcgcat      840
tcaggccgtg aagatctaaa aaaactcttt gcagcttggt acgagaggcg acagatgaag      900
aagatatact ctccgttact agaagccatg ttagcgcttt accttgggtt tgaatggata      960
cagacaaaca atattcttgc acctataatc acacatggga tatactctgc tgttattctg     1020
ggacatggac tttggaaaat ccacgatcat cggagaagac tacatcagag aatccaaaca     1080
cttaaacaag aaggtaataa ttcaagaaac ttgtaa                               1116
```

<210> SEQ ID NO 54
<211> LENGTH: 1113
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 54

```
atggaggtac cggtgctagc tcggtgtacg aatactccga cgacgtcgtt tctaggatgt       60
aaagtgagtt tatttgattt tccgattaga agaaagctaa ataagaggaa ttataaggcg      120
aagttttcag tgttaagagt taaagctatg gcggagagga cgagtactga ggcatcagcg      180
gatgctagag agagagaaag tggagggtac acgggaacta cgatggaggt gacaacattt      240
aatcagagct ttagtgatgc gcaattgcca gtttgggaaa agattggtgc tgtcgtcaga      300
```

-continued

```
ctcagttatg gaatcggcat atatggagca atggctttag caggaaagtt catatgctca      360
atgacaggaa ttgactgcac aggagggttc agtccatcat tagatgccat tgttgaagga      420
ctaggatatg cagctccacc aattatggct cttctattta tactagatga tgaagttgtg      480
aagctgtcgc ctcatgctcg agctatcaga gatgtagagg atgaagagct acggaatttc      540
ttttatggaa tgtcaccttg gcagttcatt ctgattgtgg ctgctagctc tgttggagaa      600
gagcttttct accgcgctgc tgtccaggga gctttagctg acattttctt aaggggcagt      660
ggttttgtga ctgatgctag aggaatggca tcattgactg gtgttttgcc accgtatgtc      720
ccatttgctc aagcgtttgc agctgtaatt acggcagctc tcacgggttc tctatattat      780
atggctgcct ctccaaaaga tcctacctat gttgttgcac cagtgctgaa gtcgcattca      840
ggtcgtgaag atcttaaaaa actatttgca gcttggtacg agaggcgaca gatgaagaag      900
atatactctc ctttactaga agccatgtta gcccttacc ttgggtttga atggatccag       960
acaaacaaca tttttgcacc gataatcaca catgggatat actctgctgt tattctggga     1020
catggacttt ggaaaatcca cgatcatcgg agaagactac atcaaagaat ccaacaactt     1080
aaacaagaag gtaacaattc aagaaacttg taa                                  1113
```

<210> SEQ ID NO 55
<211> LENGTH: 382
<212> TYPE: PRT
<213> ORGANISM: Arabidopsis thaliana

<400> SEQUENCE: 55

```
Met Glu Leu Pro Leu Leu Ser Tyr Ala Ser Ala Ser Phe Ser Arg
1               5                   10                  15

Thr Gly Leu Cys Ser Ser Ser Ser Ser Ser Thr Ser Ile Tyr Glu
            20                  25                  30

Phe Pro Glu Arg Arg Arg Ser Leu Lys Leu Arg Phe Asn Gly Gly Glu
        35                  40                  45

Arg Ser Arg Ser Val Ile Ala Ser Ala Glu Arg Ser Glu Gly Ile
    50                  55                  60

Glu Lys Thr Thr Asp Thr Val Gly Gly Gly Gly Gly Gly Ala Gly
65                  70                  75                  80

Arg Phe Ala Gly Thr Ala Met Glu Val Thr Thr Leu Asp Arg Gly Phe
                85                  90                  95

Ala Asn Ser Thr Thr Val Asp Phe Pro Ile Trp Asp Lys Ile Gly Ala
            100                 105                 110

Val Val Arg Leu Thr Tyr Gly Ile Gly Ile Tyr Gly Ala Met Ala Val
        115                 120                 125

Ala Gly Arg Phe Ile Cys Ser Val Thr Gly Ile Asp Ser Ser Gly Gly
    130                 135                 140

Phe Asp Pro Ser Leu Asp Ala Leu Leu Ala Gly Leu Gly Tyr Ala Thr
145                 150                 155                 160

Pro Pro Ile Met Ala Leu Leu Phe Ile Leu Asp Asp Glu Val Val Lys
                165                 170                 175

Leu Ser Pro His Ala Arg Ala Ile Arg Asp Val Glu Asp Glu Glu Leu
            180                 185                 190

Arg Ser Phe Phe Phe Gly Met Ser Pro Trp Gln Phe Ile Leu Ile Val
        195                 200                 205

Ala Ala Ser Ser Ile Gly Glu Glu Leu Phe Tyr Arg Val Ala Val Gln
    210                 215                 220

Gly Ala Leu Ser Asp Ile Phe Leu Lys Gly Thr Gln Leu Met Thr Asp
```

```
                225                 230                 235                 240
Ser Arg Gly Met Ala Ser Leu Thr Gly Val Phe Pro Pro Phe Val Pro
                245                 250                 255

Phe Ala Glu Val Phe Ala Ala Val Ile Thr Ala Thr Leu Thr Gly Ser
                260                 265                 270

Leu Tyr Phe Leu Ala Ala Ser Pro Lys Asp Pro Thr Tyr Ile Val Ala
                275                 280                 285

Pro Val Leu Arg Ser Arg Arg Asp Asp Phe Lys Lys Leu Leu Ser Ala
                290                 295                 300

Trp Tyr Glu Lys Arg Gln Met Lys Lys Ile Tyr Ser Pro Leu Leu Glu
305                 310                 315                 320

Gly Leu Leu Ala Leu Tyr Leu Gly Ile Glu Trp Val Gln Thr Asp Asn
                325                 330                 335

Ile Leu Ala Pro Met Met Thr His Gly Ile Tyr Ser Ala Val Ile Leu
                340                 345                 350

Gly His Gly Leu Trp Lys Ile His Asp His Arg Arg Arg Leu Arg Arg
                355                 360                 365

Arg Ile Glu His Ile Arg Ser Glu Ala Thr Asp Lys Leu Ile
                370                 375                 380

<210> SEQ ID NO 56
<211> LENGTH: 422
<212> TYPE: PRT
<213> ORGANISM: Arabidopsis thaliana

<400> SEQUENCE: 56

Met Gly Leu Pro Leu Leu Ser Cys Ser Ser Thr Arg Val Thr Leu Ser
1               5                   10                  15

Ser Ser Ser Ser Ser Trp Cys Ser Ser Gly Ser Gly Gly Phe Arg
                20                  25                  30

Ser Ser Ser Lys Leu Phe Asp Ser Pro Ala Cys Ser Arg Ser Asp Leu
                35                  40                  45

Lys Lys Arg Ser Gly Lys Arg Asn Ser Arg Leu Asn Gly Leu Ser Leu
50                  55                  60

Glu Lys Leu Arg Ser Ile Lys Ala Ser Ser Ser Ala Gly Gln Ser
65                  70                  75                  80

Ser Ser Glu Val Ile Asp Asp Gly Asp Ala Ala Ala Arg Gly Leu Ala
                85                  90                  95

Val Thr Ser Gly Asp Val Thr Ser Val Gly Ser Phe Ser Ser Gly Glu
                100                 105                 110

Phe Val Gly Ala Gly Ser Gly Gly Leu Ala Gly Pro Ser Gly Glu Val
                115                 120                 125

Thr Ser Val Gly Glu Phe Val Gly Gly Ser Gly Gly Asp Phe Lys Asp
                130                 135                 140

Trp Asp Lys Ile Gly Ala Ile Val Arg Leu Ser Tyr Gly Ile Gly Ile
145                 150                 155                 160

Tyr Cys Gly Met Ala Val Ala Gly Arg Phe Ile Cys Glu Val Ala Gly
                165                 170                 175

Ile Asp Tyr Thr Gly Gly Phe Asn Ala Ser Leu Asp Thr Ile Ile Ala
                180                 185                 190

Gly Leu Gly Tyr Ala Ser Pro Pro Ile Met Ala Leu Leu Phe Ile Leu
                195                 200                 205

Asp Asp Glu Val Val Lys Leu Ser Pro His Ala Arg Ala Ile Arg Asp
                210                 215                 220
```

-continued

```
Val Glu Asp Asp Glu Leu Arg Gly Phe Phe Gln Gly Met Ser Ala Trp
225                 230                 235                 240

Gln Phe Ile Leu Val Val Thr Ala Ser Ser Val Gly Glu Glu Leu Phe
            245                 250                 255

Tyr Arg Ala Ala Phe Gln Gly Ala Leu Ala Asp Ile Phe Leu Arg Gly
        260                 265                 270

Thr Asp Leu Ile Ser Asp Ser Arg Gly Met Val Ala Leu Thr Gly Leu
    275                 280                 285

Leu Pro Pro Phe Val Pro Phe Ala Gln Val Phe Ala Ala Thr Ile Thr
290                 295                 300

Ala Ala Leu Thr Gly Ser Leu Tyr Tyr Ile Ala Ala Ser Pro Lys Asp
305                 310                 315                 320

Pro Thr Tyr Ile Met Ala Pro Val Leu Lys Thr Arg Ser Ala Arg Asp
            325                 330                 335

Glu Leu Lys Lys Leu Phe Ala Ala Trp Tyr Glu Arg Arg Gln Met Lys
        340                 345                 350

Lys Ile Tyr Ser Pro Leu Leu Glu Gly Leu Leu Gly Tyr Leu Gly
    355                 360                 365

Phe Glu Trp Ile Gln Thr Asn Asn Leu Leu Ala Pro Ile Ile Thr His
370                 375                 380

Gly Ile Tyr Ser Ala Val Val Leu Gly Asn Gly Leu Trp Lys Leu His
385                 390                 395                 400

His His Gln Gln Arg Leu Arg Leu Arg Val Gln Lys Leu Glu Thr Glu
            405                 410                 415

Gly Asp Asn Asn Ser Arg
            420

<210> SEQ ID NO 57
<211> LENGTH: 340
<212> TYPE: PRT
<213> ORGANISM: Nicotiana tabacum

<400> SEQUENCE: 57

Met Glu Val Pro Val Leu Ala Arg Cys Thr Asn Thr Pro Thr Thr Ser
1               5                   10                  15

Phe Leu Gly Cys Lys Val Ser Leu Phe Asp Phe Pro Ile Arg Arg Lys
            20                  25                  30

Leu Asn Lys Arg Asn Tyr Lys Ala Lys Phe Ser Val Leu Arg Val Lys
        35                  40                  45

Ala Met Ala Glu Arg Thr Ser Thr Glu Ala Ser Ala Asp Ala Arg Glu
    50                  55                  60

Arg Glu Ser Gly Gly Tyr Thr Gly Asn Gly Asn Gly Ile Tyr Gly Ala
65                  70                  75                  80

Met Ala Leu Ala Gly Lys Phe Ile Cys Ser Met Thr Gly Ile Asp Cys
                85                  90                  95

Thr Gly Gly Phe Ser Pro Ser Leu Asp Ala Ile Val Glu Gly Leu Gly
            100                 105                 110

Tyr Ala Ala Pro Pro Ile Met Ala Leu Leu Phe Ile Leu Asp Asp Glu
        115                 120                 125

Val Val Lys Leu Ser Pro His Ala Arg Ala Ile Arg Asp Val Glu Asp
    130                 135                 140

Glu Glu Leu Arg Asn Phe Phe Tyr Gly Met Ser Pro Trp Gln Phe Ile
145                 150                 155                 160

Leu Ile Val Ala Ala Ser Ser Val Gly Glu Glu Leu Phe Tyr Arg Ala
                165                 170                 175
```

Ala Val Gln Gly Ala Leu Ala Asp Ile Phe Leu Arg Gly Ser Gly Phe
                180                 185                 190

Val Thr Asp Ala Arg Gly Met Ala Ser Leu Thr Gly Val Leu Pro Pro
            195                 200                 205

Tyr Val Pro Phe Ala Gln Ala Phe Ala Ala Val Ile Thr Ala Ala Leu
        210                 215                 220

Thr Gly Ser Leu Tyr Tyr Met Ala Ala Ser Pro Lys Asp Pro Thr Tyr
225                 230                 235                 240

Val Val Ala Pro Val Leu Lys Ser His Ser Gly Arg Glu Asp Leu Lys
                245                 250                 255

Lys Leu Phe Ala Ala Trp Tyr Glu Arg Arg Gln Met Lys Lys Ile Tyr
            260                 265                 270

Ser Pro Leu Leu Glu Ala Met Leu Ala Leu Tyr Leu Gly Phe Glu Trp
        275                 280                 285

Ile Gln Thr Asn Asn Ile Phe Ala Pro Ile Ile Thr His Gly Ile Tyr
    290                 295                 300

Ser Ala Val Ile Leu Gly His Gly Leu Trp Lys Ile His Asp His Arg
305                 310                 315                 320

Arg Arg Leu His Gln Arg Ile Gln Gln Leu Lys Gln Glu Gly Asn Asn
                325                 330                 335

Ser Arg Asn Leu
            340

<210> SEQ ID NO 58
<211> LENGTH: 370
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Glu Val Pro Val Leu Ala Arg Cys Thr Asn Thr Pro Thr Thr Ser
1               5                   10                  15

Phe Leu Gly Cys Lys Val Ser Leu Phe Asp Phe Pro Ile Arg Arg Lys
            20                  25                  30

Leu Asn Lys Arg Asn Tyr Lys Ala Lys Phe Ser Val Leu Arg Val Lys
        35                  40                  45

Ala Met Ala Glu Arg Thr Ser Thr Glu Ala Ser Ala Asp Ala Arg Glu
    50                  55                  60

Arg Glu Ser Gly Gly Tyr Thr Gly Thr Thr Met Glu Val Thr Thr Phe
65                  70                  75                  80

Asn Gln Ser Phe Ser Asp Ala Gln Leu Pro Val Trp Glu Lys Ile Gly
                85                  90                  95

Ala Val Val Arg Leu Ser Tyr Gly Ile Gly Ile Tyr Gly Ala Met Ala
            100                 105                 110

Leu Ala Gly Lys Phe Ile Cys Ser Met Thr Gly Ile Asp Cys Thr Gly
        115                 120                 125

Gly Phe Ser Pro Ser Leu Asp Ala Ile Val Glu Gly Leu Gly Tyr Ala
    130                 135                 140

Ala Pro Pro Ile Met Ala Leu Leu Phe Ile Leu Asp Asp Glu Val Val
145                 150                 155                 160

Lys Leu Ser Pro His Ala Arg Ala Ile Arg Asp Val Glu Asp Glu Glu
                165                 170                 175

Leu Arg Asn Phe Phe Tyr Gly Met Ser Pro Trp Gln Phe Ile Leu Ile

-continued

```
            180                 185                 190
Val Ala Ala Ser Ser Val Gly Glu Glu Leu Phe Tyr Arg Ala Ala Val
        195                 200                 205

Gln Gly Ala Leu Ala Asp Ile Phe Leu Arg Gly Ser Gly Phe Val Thr
        210                 215                 220

Asp Ala Arg Gly Met Ala Ser Leu Thr Gly Val Leu Pro Pro Tyr Val
225                 230                 235                 240

Pro Phe Ala Gln Ala Phe Ala Ala Val Ile Thr Ala Ala Leu Thr Gly
                245                 250                 255

Ser Leu Tyr Tyr Met Ala Ala Ser Pro Lys Asp Pro Thr Tyr Val Val
        260                 265                 270

Ala Pro Val Leu Lys Ser His Ser Gly Arg Glu Asp Leu Lys Lys Leu
        275                 280                 285

Phe Ala Ala Trp Tyr Glu Arg Arg Gln Met Lys Lys Ile Tyr Ser Pro
        290                 295                 300

Leu Leu Glu Ala Met Leu Ala Leu Tyr Leu Gly Phe Glu Trp Ile Gln
305                 310                 315                 320

Thr Asn Asn Ile Phe Ala Pro Ile Ile Thr His Gly Ile Tyr Ser Ala
                325                 330                 335

Val Ile Leu Gly His Gly Leu Trp Lys Ile His Asp His Arg Arg Arg
        340                 345                 350

Leu His Gln Arg Ile Gln Gln Leu Lys Gln Glu Gly Asn Asn Ser Arg
        355                 360                 365

Asn Leu
370
```

PALE YELLOW LOCUS AND ITS APPLICATIONS IN TOBACCO

CROSS-REFERENCE TO RELATED APPLICATIONS AND INCORPORATION OF SEQUENCE LISTING

This application claims the benefit of U.S. Provisional Application No. 62/913,313, filed Oct. 10, 2019; and U.S. Provisional Application No. 62/913,414, filed Oct. 10, 2019, both of which are incorporated by reference in their entireties herein. A sequence listing contained in the file "P34737US01_SL.txt" which is 101,588 bytes (measured in MS-Windows®) and created on Oct. 9, 2020, is filed electronically herewith and incorporated by reference in its entirety.

FIELD

The present disclosure relates to tobacco plants, tobacco seeds, compositions, and methods related to the identification and introgression of the Pale Yellow (PY) locus in tobacco. It also relates to generating novel mutations within the PY locus in tobacco.

SEQUENCES

A listing of nucleic acid sequences and amino acid sequences is provided in Table 1.

TABLE 1

Nucleic acid sequences and amino acid sequences

| SEQ ID NO. | Sequence Description | Sequence Type | Sequence |
|---|---|---|---|
| 1 | PY_SNP2 | Nucleic Acid | GTCAAGCAGTTTTTGAACAAGTTCTACCCACCCAATAAG ATTGCCAAGTAAGTTGATCAGATATTGAGCTTCAGGGAG AATCCAACTGAAACACTACAAGAAACGTAAGAGAGGTTC AAANGGATACTGGTTAAGTGTCCACATCATGGTATTCCA GATTAGATGTTGGGGCAAATGTTCTACATGGGATTGACA GACAGCTTGAAGGCCAATGTTGATGCTTCAGCAAGTGGA GCATTTT |
| 2 | PY_SNP3 | Nucleic Acid | CTTCTTCTACGCGTTCACAAGGTGCTGGTCACGTTCGCG AAGGTATGAGCTGGTAAAGCTTTGCATTCGCGAAGCCGT GGTCGCATTTGCGAAGGGTAAGAATTGTAAAGTTTCACG TTCNCGAAGGATTAAATTGTGGGCAATCGAGTTGTGCTT CGCAAACGCAAGGGACCTGTCGTGTTCGCGAAGAAGAGA GGTCAGGACAGAAGGTTTAAGTTCAGAAAATGGGACTTC GTCCCAT |
| 3 | PY_SNP4 | Nucleic Acid | GAGAGCTTCGTGCTTTAAGTATGGTATCGTCTTTGTTAG AAAGTGTTTCACGTTATATTATGGAGTTGTGCAAATCTG AATTTAGTCGGGGCCCAATACGNAGACACCAGGTGGGAC ACTAAAAAAGAAAAGAAAAAAGAGGAGAAACAAAGTCCG AAGTCTACTAGATACAAATGCATACGTCTCTATTAATAA ATTTGT |
| 4 | PY_SNP5 | Nucleic Acid | AATAGTACAAGATGAGAGCAATTTCATATAGTCACTCTC AACTAATTAGGAAATATGAGGCGCTTGACTGATTGAAGT TTGTATGTTGAATATACTAGAACTTCTGATGTAGACATG TAGNATTCTGTATATTTTAGAGCACATCACTTATAAGCA GCCCAAGAATATTACTGTATCTAAGACATAATTTAGTAA ATAAAAAGTATGTTTTCTTTGAAAGTTTAAGATTTTTTA TGAGATG |
| 5 | PY_SNP6 | Nucleic Acid | TACCTCGGGAGTGCCGTTGTTGATATTTTCCTATTAGTG TACTTGTCTTGATTGTTTTATTTTTCCTTTAATATGTAA ATTCCTGTTTGTCTTCCGTGATGTATTATTCGCCCTTAC TCTNAGCAGTTAAATTCTGACATACTGCTTACTTGATTC ACTCTCATTGTTATTATTTTATTATTATTATTATTATTA TTATTATTATTATTATATTATTATATATTATTATTATTA TATATTA |
| 6 | PY_SNP2 Non-PY Associated Sequence | Nucleic Acid | GTCAAGCAGTTTTTGAACAAGTTCTACCCACCCAATAAG ATTGCCAAGTAAGTTGATCAGATATTGAGCTTCAGGGAG AATCCAACTGAAACACTACAAGAAACGTAAGAGAGGTTC AAAAGGATACTGGTTAAGTGTCCACATCATGGTATTCCA GATTAGATGTTGGGGCAAATGTTCTACATGGGATTGACA GACAGCTTGAAGGCCAATGTTGATGCTTCAGCAAGTGGA GCATTTT |
| 7 | PY_SNP3 Non-PY Associated Sequence | Nucleic Acid | CTTCTTCTACGCGTTCACAAGGTGCTGGTCACGTTCGCG AAGGTATGAGCTGGTAAAGCTTTGCATTCGCGAAGCCGT GGTCGCATTTGCGAAGGGTAAGAATTGTAAAGTTTCACG TTCACGAAGGATTAAATTGTGGGCAATCGAGTTGTGCTT CGCAAACGCAAGGGACCTGTCGTGTTCGCGAAGAAGAGA GGTCAGGACAGAAGGTTTAAGTTCAGAAAATGGGACTTC GTCCCAT |

TABLE 1-continued

Nucleic acid sequences and amino acid sequences

| SEQ ID NO. | Sequence Description | Sequence Type | Sequence |
|---|---|---|---|
| 8 | PY_SNP4 Non-PY Associated Sequence | Nucleic Acid | GAGAGCTTCGTGCTTTAAGTATGGTATCGTCTTTGTTAG AAAGTGTTTCACGTTATATTATGGAGTTGTGCAAATCTG AATTTAGTCGGGGCCCAATACGAAGACACCAGGTGGGAC ACTAAAAAGAAAAGAAAAAAGAGGAGAAACAAAGTCCG AAGTCTACTAGATACAAATGCATACGTCTCTATTAATAA ATTTGT |
| 9 | PY_SNP5 Non-PY Associated Sequence | Nucleic Acid | AATAGTACAAGATGAGAGCAATTTCATATAGTCACTCTC AACTAATTAGGAAATATGAGGCGCTTGACTGATTGAAGT TTGTATGTTGAATATACTAGAACTTCTGATGTAGACATG TAGAATTCTGTATATTTTAGAGCACATCACTTATAAGCA GCCCAAGAATATTACTGTATCTAAGACATAATTTAGTAA ATAAAAAGTATGTTTTCTTTGAAAGTTTAAGATTTTTTA TGAGATG |
| 10 | PY_SNP6 Non-PY Associated Sequence | Nucleic Acid | TACCTCGGGAGTGCCGTTGTTGATATTTTCCTATTAGTG TACTTGTCTTGATTGTTTTATTTTTCCTTTAATATGTAA ATTCCTGTTTGTCTTCCGTGATGTATTATTCGCCCTTAC TCTAAGCAGTTAAATTCTGACATACTGCTTACTTGATTC ACTCTCATTGTTATTATTTTATTATTATTATTATTATTA TTATTATTATTATTATATTATTATATATTATTATTATTA TATATTA |
| 11 | PY_SNP2 PY Associated Sequence | Nucleic Acid | GTCAAGCAGTTTTTGAACAAGTTCTACCCACCCAATAAG ATTGCCAAGTAAGTTGATCAGATATTGAGCTTCAGGGAG AATCCAACTGAAACACTACAAGAAACGTAAGAGAGGTTC AAAGGGATACTGGTTAAGTGTCCACATCATGGTATTCCA GATTAGATGTTGGGGCAAATGTTCTACATGGGATTGACA GACAGCTTGAAGGCCAATGTTGATGCTTCAGCAAGTGGA GCATTTT |
| 12 | PY_SNP3PY Associated Sequence | Nucleic Acid | CTTCTTCTACGCGTTCACAAGGTGCTGGTCACGTTCGCG AAGGTATGAGCTGGTAAAGCTTTGCATTCGCGAAGCCGT GGTCGCATTTGCGAAGGGTAAGAATTGTAAAGTTTCACG TTCGCGAAGGATTAAATTGTGGGCAATCGAGTTGTGCTT CGCAAACGCAAGGGACCTGTCGTGTTCGCGAAGAAGAGA GGTCAGGACAGAAGGTTTAAGTTCAGAAAATGGGACTTC GTCCCAT |
| 13 | PY_SNP4PY Associated Sequence | Nucleic Acid | GAGAGCTTCGTGCTTTAAGTATGGTATCGTCTTTGTTAG AAAGTGTTTCACGTTATATTATGGAGTTGTGCAAATCTG AATTTAGTCGGGGCCCAATACGGAGACACCAGGTGGGAC ACTAAAAAGAAAAGAAAAAAGAGGAGAAACAAAGTCCG AAGTCTACTAGATACAAATGCATACGTCTCTATTAATAA ATTTGT |
| 14 | PY_SNP5PY Associated Sequence | Nucleic Acid | AATAGTACAAGATGAGAGCAATTTCATATAGTCACTCTC AACTAATTAGGAAATATGAGGCGCTTGACTGATTGAAGT TTGTATGTTGAATATACTAGAACTTCTGATGTAGACATG TAGTATTCTGTATATTTTAGAGCACATCACTTATAAGCA GCCCAAGAATATTACTGTATCTAAGACATAATTTAGTAA ATAAAAAGTATGTTTTCTTTGAAAGTTTAAGATTTTTTA TGAGATG |
| 15 | PY_SNP6PY Associated Sequence | Nucleic Acid | TACCTCGGGAGTGCCGTTGTTGATATTTTCCTATTAGTG TACTTGTCTTGATTGTTTTATTTTTCCTTTAATATGTAA ATTCCTGTTTGTCTTCCGTGATGTATTATTCGCCCTTAC TCTGAGCAGTTAAATTCTGACATACTGCTTACTTGATTC ACTCTCATTGTTATTATTTTATTATTATTATTATTATTA TTATTATTATTATATATTATTATATATTATTATTATTA TATATTA |
| 16 | G58887 genomic sequence | Nucleic Acid | ATGCAAACCAGAGTTGGTAGTAGATTGGTCACTGAACAG TATCACGATGAAGAAGTACGGCCATATATTCAACAATTA ATGAATGCTCAGAATTGCTCTCCAGCCCAAACTTATGAT AATCAATCTAATATTTTGAACAATTCTGTTGGTACTGGA GCTGAGCAGAACAATGAATCAGGTTCTATTTTGAAGTTT TAGTATTGAGTCCACTATTTTCTTAGTATTGCTTTGCAC TAGCTGTAGGTTCTGCTAAAACAAGGAGTTAATTCTCCA GCTCAAGACTATTTTCTTTGTGAATTTGCTTGCACTAGA TCATGGACCTTTGAATCTGTTTCAGGTCCTTCAGAGGTA AGAAAAGTTTGTGGGCCTACACTACTAAAAGATGTTTGG AATCTACCATCAAGGAAGACAATTGATGTGCAATAGAAT AGTCGTAATCAAGCTATTGGAAAAAAGGGTCGAAAGCTT |

TABLE 1-continued

Nucleic acid sequences and amino acid sequences

| SEQ ID NO. | Sequence Description | Sequence Type | Sequence |
|---|---|---|---|
|  |  |  | GCTAGCTTTCTAAGTATCATTGCTAGAACCCCAGAGCTG ACACCGTTAAATATAAATGATTGGCGAGTATTTGACAAA GAAGAAAAGAAGAAATTGGTGGAGTTTGTGAGGGTATGC AATTTTTATTCTTAATAAGTATCATTCTTTTTATACATG ATATTTTCTTGTAAACTCGTGCTTTATTTTTTAGAAAAA GTTCTCGATTCCAGTATGTAGAGAAGAGTTTATAAAAAA GTCAATAGGGAAAAAATGGAAGGACTATAAATGTGATTT GAAGACTATGTATGTGACCAAGTATAAGAGCAAAGATGC CTTGATGAAAAATAGACCAAGTCACATACCAAGGGATCA ATGGACTGGTCTCGTCTTGTATTGGCTTTCTGATAAAGC AAAGGTGAGTAAGTTTTTGTGTTGAATCTACATTTTATA ACTCTCTGTCCTGTTTTTCTTCTTTGAACCTTTTTGTGT TTATTCAAAGAACATATATTTAATAAGAATGTTTACTTG GTCTTTACCAGTTACATTTCACCCACATTATACCAACCA AAATATTTTAGAAAGTGCTGCAAACGTTGTGGCAGGTG GTTCAGAATATGAATTTTGCCTTTTAAATATAGCCCCTT GAGCACAATAGATGATTTGGTTATTAGTTTATCTTATAT GATTAAGTATTGTTAGTGAGTATTTTTGTGTTGCAATAA CAGAAGCGCAGTCAAGCAAATAGAATCAGTAGGGCTAAA CAAAAGATGCCTCACACAGGAGGATCCAAAAGCATAGCA ACCTTGATGAATGAAAAGGTATTAATGTATAAATTACAT ACCATAAGATTCTATAATTCTTTTCTATGATATCTAATT GTTTGGCATCAATTTAACTTTATTAGGCTATAGATGGAA TAGAGCCTACACGTGCTCAAGTTTACATATTAACTCATA CAAAGCGTAAGGATGGTAGACCATTGGATGAGGAATCTT CAAATACAGTTGTAAGATTCTTATAAGTTGTATTTTTT AAGATTAAACATATGTACTAGCTCATGTCTAATGCATCA TAATTTGTAGAGGCTTTAAATGATTGACTGATCCTTAAA CTTTTATGTCTCTTCTTCCGGCTATTTCTTTTCCATTTC CATGTCTAATATATTTCCTTGCATTAATTGCTGATGTTA ATACAAGTTATGTAAGAAACTGCCTTAACTTTGTTAACT AACATTGACTTTTTCATATGTGCAAATGCTGGCTAGTTT GGTTTCACAATATCTCATCTTATTGTTAGTTCGTCCTCC ACTGTATTGTGTCATAAATTGTTATCTCAATTACTGTCA GGACATTGATGAAAGAGAAGTTGAGTA |
| 17 | g58888 genomic sequence | Nucleic Acid | ATGGTAGACCATTGGATGAGGAATCTTCAAATACAGTTG TAAGATTTCTTATAAGTTGTATTTTTTAAGATTAAACAT ATGTACTAGCTCATGTCTAATGCATCATAATTTGTAGAG GCTTTAAATGATTGACTGATCCTTAAACTTTTATGTCTC TTCTTCCGGCTATTTCTTTTCCATTTCCATGTCTAATAT ATTTCCTTGCATTAATTGCTGATGTTAATACAAGTTATG TAAGAAACTGCCTTAACTTTGTTAACTAACATTGACTTT TTCATATGTGCAAATGCTGGCTAGTTTGGTTTCACAATA TCTCATCTTATTGTTAGTTCGTCCTCCACTGTATTGTGT CATAAATTGTTATCTCAATTACTGTCAGGACATTGATGA AGAGAAGTTGAGTAATGGCGAGACATCTCATGAACAAC CTCATGGCAGTGTTGCTTGGGAAGGAGATGTGTATTCTC AAGTGTTGGGAAATGAAAAAAGTGGTAATGTCCGTGGTT TAGGACTTGGTCCAACCCCTTCTCTATTATGGGGCGGTA AATCTTCCTTACAAAATATTACCGATGATGGTTTATCTA ATGAGGCTGCACATAAGTTAGAACAAGAGATAAAGGAGT TAAAGGACTTGAACAAAAAACAGGATGAAGAAATAGCTT TGATGAAAAAAAATCAAGATATGCTAGTTTCAGAATTAA CATGGATGAGGCAAGTCATGTGGAAATATGTTCCCACCA AATTATGTGGCCCTCAAAACTATGGAAGCACTACTAGAC AGGTTATTCAATTTCAAAGTTTTAAACTTTTCTTCTTAA AATTAAGCTTTATAAGAAAATTATGTGATCTAATATGTC TTGATATATACTAGGTTCCTGATGCCAATAGTGGCAATG AGCAAGCAACCTAA |
| 18 | g58899 genomic sequence | Nucleic Acid | ATGGAGGTACCGGTGCTAGCTCGGTGTACGAATACTCCG ACGACGTCGTTTCTAGGATGTAAAGTGAGTTTATTTGAT TTTCCGATTAGAAGAAAGCTAAATAAGAGGAATTATAAG GCGAAGTTTTCAGTGTTAAGAGTTAAAGCTATGGCGGAG AGGACGAGTACTGAGGCATCAGCGGATGCTAGAGAGAGA GAAAGTGGAGGGTACACGGGAACTACGATGGAGGTGACA ACATTTAATCAGAGCTTTAGTGATGCGCAATTGCCAGTT TGGGAAAAGATTGGTGCTGTCGTCAGACTCAGTTATGGA ATCGGTGAGTTCTCAACTCGTTTTGCGTTTACTTAATTA GTCTGTTTTTTTTTTTTTGTTTTTTTCGGTTTGAATTC TGGTTTCCTTTTTCAACGCTATTTTTGGGAAGAAGACA AGGAATATGCATATTAGTTGAATAGATTCAATGAATTCA GAATTTATTTTGTGGCTTTTGGTTCCTATTTTTTGGT CAAACATTTGGTATCTGAACCCACTAACCTGACTAATTT |

TABLE 1-continued

Nucleic acid sequences and amino acid sequences

| SEQ ID NO. | Sequence Description | Sequence Type | Sequence |
|---|---|---|---|
| | | | TGATTCGCGCCTTAGAAAACTTACTGTGGGAGATTTAAG
TGTTCTTTACAAAGAGGATTCAAACTCGAAACCTTTGAT
TACGTGTAAAAGAATTTTTATCATTCCAACATACCATTC
AAGGGCGGATGTATCGTTTAGCTTATGAGCTTATTTGAA
CCCAATTTTGACTCGGACCATATATATGTGTTAAAAATA
CACAAATATAAATAAATACATAGATTTTGAACATAGTAA
ATTAAATGGATATGTGATAGAATCCCAAAACTCTGAACC
TATAATGTTCAAATCTTTACTTTAGTTTTTGGTGGACTT
TTTGGTTGTTATGATTAGTCTATATTGTGTGCGATTTAA
TCTTAGTAGTTACAGTGTGAGCAGTGTAATACTGTTCTC
GGTTTGATTTATATAGAGCAACAATTGTTAAAATATAAG
CTTAATTTTGGTTCTAATGATTAGGTAATCCTGCCCATT
TACTTCGAATTAATTTGCTATTTACTGTAGTTTTTTTTA
TTAGAACAGAGTTATTTTGTTATTTTCCTTCCCCAAAAC
TATCTCCATAAAAGCCTTTCTTTTTTTTCTTAAATTTCG
TGTCCAGTCAAATAGGTTCATATAAATTGAAACAGAAAG
AATATTAAATAGCATAGTATAAATGGATTTCGAAATTAT
TATAGTAGTATATACTTATAGTTTAACTTTTAAGTTTTA
ATAATAACAAGTATTCGGTAGAACAATGGAGGTGCAAAA
TGCATTTCCGTATTTATTCATTTGCATGTAAAGACTAGA
GTTAGATGAAATGGGAATGTGTAACGAGAACTTAGTGCT
AGAAAGAATAGTAATTAATGAGAGAAAGTGAATTTACAA
GTGATTCTTGGAGTTGCAAGTAAAGGGAAAGGAAAAGCT
AAATTTGCTTTCTGTATATGTCATTAAAGTGCTTCTAAA
AATGGAAAAGCTAAGGTTTTTCTTCTTTCTAACTTTTAG
GTTTTATAGTTGGTAGGACAACAAATGCCAAAATAAAA
AAACACTGCAATATTTTTGCAGTCAATTTAATCATGTTT
CCAATCACATGTTAAGTGGTACTTTGTTTCCTAAGTAAG
AAATATAAGCAATTGTCAGGAATAGGATTGTATTTATAT
AAACAATTGTAGATAAAATTGAATACTTTTATTGTTTTT
GCTCATACTTGGCTATTGAGGAAAACAGAATTGTAGTTA
GGCAATTTGTCAGAATGCATTAGAAGAAGTGTAGATGCA
TTTTAGAATGACAGAAAATACAAATTTATTTACATTTTT
AAGAATAGTATAAAATAAGTGATTTTATAAATATTTAGA
ACATGATAATAGAAGAAAAATAGGCGAAAATTAAAAAAG
AATAAATTTGGAGCCGAAATTGATCATTCTAATGCTTGT
GTGCTAACGTTGAATAGCTTTAAATTTAGCAACTTGTTG
GTAATTTTTAAATTTGTAGAAATATTTTGTTTTTTGTT
TTTTCTTTTTAATAAACCAATTTTATTTGTTAACGCAA
CTACATGCTTCTATAGAATTACATTTGGAAAAGCTTTTT
AGCCCAAATACTGCCAAAAATAATTAAATGCTAAAACA
AAATAAACAAATAATAACTCCATCCCGTGCCACTTAATT
AGAAGTAGAATTGTACTTACCGGAGTAATTTGAACTTTG
GCAATAGTTGTTAAAATATGTTCTAGCCTAACTAGCTGT
ACTAAGGTCTCAAAAACTTTGAAATCTTGAATCTAATCT
TCCTCAAAGAAGAATAGAATTTAATCATTGTACTCGAGT
AAATTGAACATTGCAATTATTATCATAGTACATTTCCCC
AAAATGTAGTATGTCCATTGTAATACTACATATTCATTT
TTTTTATTACTTTTTTAATACGGTGTTATCTTCCACTAA
TATATATCGGGTAACTCTGACACCATACATAAATATGAC
CTAGTGTTTTTAATTCCGGTGTATTTATTTGTTTGTTGC
ATGTATTTCCATCCCATTAAATTTTTTGGATATCTTTAC
AGAAGAAAAAGAAATTAAAGTCCTTCAATCATTCTCTGA
TGTTCAGTTTGTTTTTTGCACTCAGGCATATATGGAGCA
ATGGCTTTAGCAGGAAAGTTCATATGCTCAATGACAGGA
ATTGACTGCACAGGAGGGTTCAGTCCATCATTAGATGCC
ATTGTTGAAGGACTAGGATATGCAGCTCCACCAATTATG
GCTCTTCTATTTATACTAGATGTACGTTCAAGATTCCCT
GTTTTTCTTTATGCACATAACAATTAAGTGTCCCAAATC
AGCCGACGAAATGAGTTGTTATCTTCTTATATAGTCTTA
GATAATTCTCACATCATGAGATTGTGTCGGAGCCAAACT
CCTCTCTTGGTTTACACAATGTTGGGCTCCTATGTTTTG
TTGTACACGCACCATATGTCCAATCTTGGGCGGGCGAGG
GTGTTAAGCTAGTTGAGGAAATGAACTGTTATCTTTTTA
TATGATCTTGGACGATTTTCATCTCATAAGCTAACTTTT
GGGACTGAATTAGGTTCGAGGTTCTTTTTCGTTACAATA
TTTAACTGCACTCTTGGCTTCTTCAACTTGAATTAAATT
CTTCTATCTACATATGGCTTTACTAACTCTGAAGTACAA
AAATGCAAGAATATTAGCCTTATGTATTGCAGCTATACT
ACCTTTGTCCATATGACATTCTTGGATCATATAATGGAT
GTTTTATAATAATTTGCGGTGTTTATAGGATGAAGTTGT
GAAGCTGTCGCCTCATGCTCGAGCTATCAGAGATGTAGA
GGATGAAGAGCTACGGAATTTCTTTTATGGAATGTCACC
TTGGCAGGTAAAAATTTCTCAATATGAGCATCAATAATT
ATGTTACAATACAGGGAAGATTGATACTTAACGGATTTT |

TABLE 1-continued

Nucleic acid sequences and amino acid sequences

| SEQ ID NO. | Sequence Description | Sequence Type | Sequence |
|---|---|---|---|
| | | | GATGCAATGGTGTAGTTCATTCTGATTGTGGCTGCTAGC TCTGTTGGAGAAGAGCTTTTCTACCGCGCTGCTGTCCAG GTAAGATGTATATCATCCATTTATGGTATACAATCGCGA ATTCATTTGTACATTTGCAGCCTTGTGTTTTTCCATAT TGTTTTTCCTATTTATAATGGTAACAACAGATACCTGGA AATCCTTTTGGTGAATTTTTTTTTTGTGCTTCAGTTTT CCAATGCATATATTTGCTTATTAAAAGAAATTAATATAG AAAGAAAAAAGAATATTAGAAAAACATGGAAAATAGAAA GAGGCTTAAGGCGTGTAGAACATAGTTATCTAAAAGTAA TTGCTGTTGTTTTTTGTCTGATTTAATTCACTTCTGAAG AGCCAACAACAGCCAACGACGTTCTTATTCATACAACAG AATCTCAGAAAGTGTGAAATCTTTTCAGAATAGACATGT CTTTTGTTGATAACCACTTTCATATTACAAACTATCCAA CAATATTATCAACAGCGTAATTATTTTTAACTTCCATAA AAAATGCATGTCAAAAAGGTTATTTTTCTCTAAGTTATG TGATTCTTTCCTCCTCTGATTATCTTTGTAATTACAG GGAGCTTTAGCTGACATTTTCTTAAGGGGCAGTGGTTTT GTGACTGATGCTAGAGGAATGGCATCATTGGTACGTCGG ATTCTATTTCTAAACATCCTTCTCCAAGTTACATTATCC AAAAATTTTCCATTGCTCTGACACATTCTGTTTCCTCAA AATGTAGACTGGTGTTTTGCCACCGTATGTCCCATTTGC TCAAGCGTTTGCAGCTGTAATTACGGCAGCTCTCACGGG TTCTCTATATTATATGGCTGCCTCTCCAAAAGGTAAGTT TCACAGGCTGCAGTTTATATTATATATCTGCCTTTCATT GTCCTCTACTCTAACATGCTTAATCACTTAGCTATTTGT TGTTTCACTTTTCAGATCCTACCTATGTTGTTGCACCAG TGCTGAAGTCGCATTCAGGTCGTGAAGATCTTAAAAAAC TATTTGCAGGTTTGACATCTCTTCTATGCTCATGACATA AGCAAGATAGCTCTCACTTGGTGATCATTTGAGTCTAAA CTTAATTAACATAATGATATGAATCTGGGGATTTGGGGT CCAACTAATAATGCTAATGGGATATGAAGAATTAGTATG GCTGATTGCAACTAAGAATAGAAGAGCTGAAGCACGTTC CTTAGCCTAGTCTACATCCAAAGTTGACAGACTTAAAAT ACAACAGTCTCGACCTACTTTGAATCAAAAGAAAGGCGA AAGGTTTGGCAACAAGCGAATCGCTTTTCATCATAGTTG CAAGGATTCCAAACCTGCTCCCTGGTCGTTGCTCCACTG CATCTGGTCATCTCTAGTCACCTTTGGAAGGCAGGAAGT GTGACAATATGCATGTTTTCTTTACTCCATCGGGCCTTC TCAGGCCTTTCCTTGTAGGAGTAGCTTCTTAAACTATTT TAAATAATATGAGACCACCAAGGCAGGCACTCGTTCTGT CAAAAGCAACGGACTTACTTCTGGTTCTAGGTGTTAGCG TGTACGAAAGATTCCCCGGCTCTCTGTATACTTAAGGTG GTCTCTTCACAAGTGTCACCAGCAGTGGCAGAGCCAGGA TTTTCACCAAGAGGATTCAAAATATAAAGAGGTGAACAC TTGGAGAAGCCAAGGGGACTCAACCTCTACTATATATAC ATACAAATATTTTTGGTCTTGTATACATAGTGTAATTTT CCGTCGAAGGGAGTTCGGATGAACCCCCTTCCACCACCC TAGTTCTGCCCACGGTCACCAGAGAGAGCGAGCACAGAT TGGATTAAAGAAAAATTGGTTTCTACTGAGCTTATCGAA CCAACTCATATCGTTAAGATATGATAAGTTTTATATTAT TTGATGTAACCACCTGTATCTTATCTCCATTTCAAACCT AACAAATCCTACTCCCTCTACATAAACCTGTACACTACA AAATATCAGAAGCAAGTAAACAAAGCATTTCTGCTCTCC AACGTGTGATCCTTTAGTTGAAACAGATAAGTGCATGAT ATGTTAATTATTTCATCTGCCTGAATGTTTTGCAGCTTG GTACGAGAGGCGACAGATGAAGAAGATATACTCTCCTTT ACTAGAAGCCATGTTAGCCCTTTACCTTGGGTTTGAATG GATCCAGGTAACATGAATTTCACATTGTATTTATTTCTG ATACTTAAAAGGTTATGTCTACATGAAATTTTGGTCACT AAAGCTAATTTGAACTTCTACCCTTGCTAATGCAACAGA CAAACAACATTTTTGCACCGATAATCACACATGGGATAT ACTCTGCTGTTATTCTGGGACATGGACTTTGGAAAATCC ACGATCATCGGAGAAGACTACATCAAAGAATCCAACAAC TTAAACAAGAAGGTAACAATTCAAGAAACTTGTAA |
| 19 | g58917 genomic sequence | Nucleic Acid | ATGGTAAATTTCAACAACCCCCAAAACTCCTTTAATTCT TTTTATTAAAAATTTTCATCAATTTGATTGCTTTCAACT CTCTTTTTGTTCATTTATTTTAAAATTGTGTCTCTTTTT TGGTATTAGGGAGCTGGAATACCTGATGAAGAGGAAAAT AATTGGCCACTATGGTTAAAGCCATTGCTTAAAGAAAAA TTCTTTGGCCATTGCAAATTACATGCTGATTCTCACAAG AGTGAATGCAATATGTATTGTCTTGATTGTATAAATGGC CCTCTTTGTTCTCTTTGTTTAGCACATCACAAGGACCAT ATTGCTATTCAGGTATCTCATTTTTCCTTCATAGAAAAA TGGTCTTTTTATGTCAATTTGTAACAAATTTTTCCTTTA |

TABLE 1-continued

Nucleic acid sequences and amino acid sequences

| SEQ ID NO. | Sequence Description | Sequence Type | Sequence |
|---|---|---|---|
| | | | GTTCTTCCTGTTTAGCAGCAACTAATGCTTGTATTAGGG
TAGTCTGTTTATGTCACATCACATCCCTAGGGGTGCGGC
ACTTTTTCGGATTCCGAGTGAATATGAAATCTCTTGTGC
ATCGGCAGGCCTTTTGGTATACAGTGTATACAATGGCGA
AGTTAGAAATTTTAACGAGGGTCTATAGCTACACATTCT
ATATGGTGACGAAAGCCAGAAATTCTAACAACGGGGTTC
AAGAAAATGCTAAAGTGTCACACCTAAAGTTTGATCATG
TTATTTTAAGCAATTTTTAACCTGCCTTTGCCACTATAC
TAAAATCTTTTTTTATGTAAAAAATTTTCAAAATGCAAA
AAAGTTTATTTTTGACCTACTTTTGAGTATAATTTTTCG
ATGAAAGTGATTCAATTGAACCCCTAAATTGTCATTTTA
CATGGTGTATAGCTTTGATATGCCAAAGAAGAAGTCTTG
AAATTATGAATGATTGATTTTGAGTGATCTGTTTTTGTT
TGGTTGGACAGATAAGGAGGTCATCATACCATGATGTGA
TAAGGGTGAATGAAATTCAAAAGTATTTGGACATTTCTT
CAGTCCAAACATACATTATCAACAGTGCTAAGGTTGTCT
TTTTGAATGAAAGGCCACAACCTAGGCCAGGCAAAGGTG
TAACAAATACTTGTCAAGTTTGTGAAAGGAGCCTTCTTG
ATTCCTTCAAATTCTGCTCTCTTGGTTGCAAGGTACAAT
ACTGTTTACTTTTTCAAGTCTGATATATATTAATTATAC
ACGGTTATAAACATATTATATAGATTATGCATATGTTAT
ACATACGGAGGCTATTTTTAATTTAAACAGTTGAGTGGA
TTGCTATTTAAGTTAATTGTTCTAAAAGAAAATTCCCTT
CTAGAGTTTCATTAAATTGTTCCATTTTTTTCATCTTGA
CCAAATTTTCTTGCATTAATTTTGACTTTTACTGGCATT
GAATTGAATTAGGCGTGTCCAAATATATTGAATTGCGTA
TATTTCAAGGTATATTTTGGTTTAATGGTCGTTGATAGT
GTGGTTTGACAAATGTGAAGCAATTAAATGGGGCGTGGA
AATTGCACTCATATTTACTAGTCTATTGATAGGAAAACT
TTGGCATAATCAACTTTTTTTAATTGGAAATTTCAAAGT
TGTTAGACATTGTAATTATCAATGACTCTTTCTTGCAGT
TATTGTGTACCCCAAATGGAAATGATATTCAAATCTTTG
ATTATTAGCAATCTTTGATATACAATAAATATTATGTGA
ATTATTGAATTGGTCCGAATAGAGCAGAATTCTATGTTT
TGTGTTGATGGTATATATTGTCTTTTTCGTCTTTTTCGT
TTTCTTGAGCCGAGGGTCTATTGGAAACCTCACCTCTAC
TCTATCGGGGTAGGGGTAAGGTCCGTGCACACACTACCC
TCCCTAGACTCCTTACCTGCGGGATTTTACTGGGTTGTT
ATCCGAACAGAACAGAATGAATATAGGTGATTTATATAG
TCGATTCTACCTTGATCATTGCAGGTTGTCGGGTCCTCA
AAGAACTTCGTTAAGAAACCGAAGCAATTATCCGCGAAA
AGGCGGCGGTCGATGGTGGCGGCATCGGACTCCGATGAC
TCTTACAGCAGCAGCAGCCATGGTAGGTACAAGAGCCAC
AGCAACAAGGTCCAAAGTTTTACTCCGTCGACGCCCCCT
CCAACTTCAGTTAATTACAAAACGGCCAAGCGAAGAAAG
GGAATTCCACATAGATCCCCAATGGGAGGACTACTCATA
GAATATTAA |
| 20 | g58905 genomic sequence | Nucleic Acid | ATGTCTTCCGATAACTTCACCGACAAAAACGCCGTCTTC
CGCAAGCTCAAAGCCAAGCCGGACAACAAGGTTTGCATC
TTAATTCATCGAATTTGTTTTTGATTTGATCGAAAAT
TATGTTTTTTGAATTTTATCTATTTTCTCGCGTGTTTT
TTCGTTTGAATCGATTGAAAATTGCGAGATCTGATTTGA
ATCTAGTGTTTGTGCTGAGTAGATTGTAGTTTCTGAGCG
ATCTAAGTCAGCTTTTACCTTTTTTTTTTTTTGAATTT
TATCAGATGTGTTTTGATTGCAATGCGAAGAATCCTACG
TGGGCGTCGGTTACGTATGGGATCTTCTTGTGTATTGAT
TGTTCGGCGACGCATCGTAGCCTTGGTGTTCACATCAGT
TTTGTTAGGTACGATTTAAAGTTTGATTTTTTACTCGTC
TTCGTTTTTGGATTCATGAGCTGATTTTTAGCTTGATAA
TTTGTTTTCATGATGAGTGGATTTTGTTCGGAGTTCTAT
AAGGCATGGTTTTTGGTTTTATAAATATATCGAAAAAAT
GATTAGAAATGTTGAAATCAATAGAATCAACAGGTTCGA
AGCCGTGACTTCTGCCTTATAAATAAGTGGCTGATTTAA
AATGTGGACTGAGGTAAGTTCGGACCCGCTGTCTTGAGT
AGGGGCAGATGTACTGTTCGGGGTACGGGTTTGGTAGAA
CTCAGAAGTTTTGGCCTAAGCCATGTATGTTTCCTAAGA
ATTTCACTTAATATGAATAGATTATTAATTTAGAACCCA
TTAACTCATAATTGCCTAAACCCCGCACCTTTAAACTTC
AAATCATGGATCCGCCTATGGTCTTGAACTCAAGTTATA
TGTTGTTGAAATTTATTTAAAAATATGTAGTTATAATAG
GAGTAGTGGGGTGCAATGGTATTCTACTTGATTCTAAAT
CCTGAATTCGTCTCTGTTTATTGGACGCTGAAATTTTAA
TTTTTTGCTGCGTTCCTTACGAGGTGCTTTAGGCAATGG
TCTTTGATACAAGGGAACAGATTCTATACTGTGAAAAGA |

TABLE 1-continued

Nucleic acid sequences and amino acid sequences

| SEQ ID NO. | Sequence Description | Sequence Type | Sequence |
|---|---|---|---|
| | | | ATTATGCTAATGATGAAAGCATTTTAAAGATCTAATTAT
GTGGCATGGTCCCGGGCCCTAAACTCCTCCTAATTGTAG
AATATGTGGACGTTGAGCGCGCCATTGGGCTAGATGCAG
TGAAATCCATTGGTTTCTCAACTATCTTGCTTTGTTTTC
TCTCCTTGATATGTGGTTTTTAGGGTTACATGTGGTCCA
AGTTTTTGGTGGTAGTTGATAGATATGTATTGCTCCTAT
TGCTCAATATTGCAATTACAGTCAGACCTCTCTATAACA
TCCCTATATAACAACACTTCACTATAAAAGCCAAGCTTT
TCCGGAATGTTATGTTATAATATATGTTCTATATAACAA
CACTTAGTTATAACATCCAAAATATTCGGAACAAACGA
GGCTGTTATAGAGAGGTTTGACTCCTGAGCACGTATCAA
AAGATTGCATCTTTTGATGAATATGTGTCCGACAATCTT
GATTATGGATTAAGCTTAATCTTATGCTCCGTATTCGAT
CATTGATGCAAACGATAAATTTTGAACAAGAAATGGTCA
ACACCACATGATTTCCTTTTATGGCGGATATTGGTGCGC
ATACCCCTTTTCGAGAAAGACTATTGATATATGACCTCT
TCGAAGCTACAACCAGTATGCGAATATGGACGATCTAGT
ATGAATCCCATATGTGTTTCTTATACAATACCATTCCCG
CAGTTTCTGGTTCGAAACCATTATCTTCATCCCATATGT
GCCACAACAGCTTCATTTTGCCCAACAATTGGTATGACC
ACCTTAAGAGACTTTATGTGTTTGCACCAAGGGCTTTGG
TTTAGCGGTAAGAGCGCAATGTTTGATGTGTGGATTAGG
CGCATGCCACAGGTTTTGAATCCTGTAGCGGAAAAAAGT
TTGGTGTTTAAGTGGAGAAGGGTAGAAGGTGGCCCCTTT
ATCTACCGAGTTCCGAACCGTGCACCATTGGCACTTGTG
AATTTTTTGATTATTAGAGAAATGGAGAGATTTTTCTTG
TGTTACTTGCAGTGTCCTACCTAATTACCTATCATGGTT
AACAAAACCGACAAAGTGAGCCATCATAATCTGGCTACT
TTTATTCTTAACACATTTTCTTCCATCTCATTGAAAAAT
CCATATTCTTTCTTTGGAGGAGGGTGTGAATGAAGCCTT
CTCTTTTCATCCACTACTAGTTCTTCACATTTTTTCCGA
TGACGGTGGTGTCGGGGCCAGTTTGAATGCTCCTTAATT
ATTCTACCGGGTACCTGGTTACCTCCCACTAGCACATGT
ACCAGGTGGACTCTGTCTACCTAGGCTTGGGCGTATGTG
AAGAAATCACCTATTGGTTTTTTGGCTTCACTAGGATTT
GAATATGAGACTTCATGATTCTCTTCCTACTTCATTGAC
CCCTAGGTCACACCCTTGGGTGCATGCTAGTTCTTCATA
TTATATAATGTCACTGCTATTTTTTTCAAATGACACTGC
CAATGGGATGAATCTAAGAGAGGAAGAACAGAAAAGTAA
GCCGAGGAAGAACGGAAAAGGACGAGGAAGAATAGAAAA
GGAGAAGTTCTAAATGGCCATGTCAGACTTCTTGGCTGA
CATGCGTTCTTTTTATAACAACCGGCATGACCACTGCAT
CACACTTTGGGCCTCGTCAGTTCCATTGTTGCTCATCTC
ACCTCACCATGGTAGCTGGACCTTCCTACCTCTAACAAT
CAGCATGTCAGTATGTTAGTCAAGCGAAGACAATAATAG
CATTTTATTACCTTATGAAAAAATGATGACAACAATGGC
ATGGTTAGTGATTAATCTATACATTGTTAAACCTAACCT
GATCATTTGATTGATTATGAGAACAATTGGCCATCGGAG
ATTATGGAAGGCCATGAAGGCTAGATTTTGAGGTATTTT
TGTGGGTCGGCTTGCTTCAAAAGAGAAAAGAGGGTGGGT
GGGGGTTGGGGGTGGGGTTTGAAAGGCAGAAGTGGAATG
TAGAGTTTGAATGCATGTATCTGTTAGTATGTGTTAGAG
ATAGAGAGGGTGATAATATTGCTTTGCATTTCCTTTAT
CATGGTTGAGATGTTCATTATGGGCCGAGAGTTATCTTC
TGACCCACCCCTTTTCGTTTGTAATGTTTTGAGGTGGG
AATGGGTATGGCCAACCGGAAACAAATAAATTCTGCATT
TTCTTTGTTATTTTGGCATTACTAACTGTCAGTTCTCTG
ATGAATTGATTCTTGCAGATCGACAAATTTAGATTCATG
GTCTCCAGAGCAGTTAAAGATGATGTACTTTGGTGGAAA
CAACCGTGCTCAAGTTTTTTTCAAGCAGCACTGATGGAC
GGATGGCGGCAAGGTTGAAGCCAAGTATACCTCCAGGGC
TGCTGAATTGTATAAACAATTACTATCAAAAGAAGTTGC
TAAAAGTAAAGCAGAGGATGCAGGTTTGCCAGCATCGCC
TTTTGCCTCTCAGGCTGTGCAGAGTACGAATGGATTTTC
TGATGTTAAGACTAGTGAAGCTCCAAAAGAAACCTCATC
ATTTAAGGAAGAAACTCCTGCTTCGCCCAAAGCATCACA
ATCAGTTGTTACTACTTCAATTAGGAAACCTATAGGTGC
AAAGAAATCTGGGAAGCCAGGTGGTGGACTTGGAGCTCG
GAAACTTACTAAAAAGGTATTCTTAGTCTTATGAGCTAG
AGAAATGATTGCAGGGTATAAATTGCATATTCTGAAATG
AAGACTTATATGTGCGGTTTAGAGTAAGCTGTTTAACAA
ATTTGCTCCACCAATTTGGAATTTATTAATTGATTAAGC
ATCTTTTACCGGTGTACAGCCAAGTGAAAGTCTCTACGA
CCAGAAGCCTGAAGAACCGCCTGTTCAAGTTTCTTCCTC
CAATTCTACAAGTAATGCATCAACTGTTGGTTCATCATT |

TABLE 1-continued

Nucleic acid sequences and amino acid sequences

| SEQ ID NO. | Sequence Description | Sequence Type | Sequence |
|---|---|---|---|
| | | | CGCATCTCGCTTTGAGTACACAGACAATGTCCAACCCGC
TGAGATGAGTTCTGGAGGCCCTCGTGTTCTTAACCATGT
ATCCCCTCCAATGTCCTCCAGCTTTTTTTCGGACTACGG
AATGGACAGCGGTTTCACAAAGAAGACAAGTTCAAATTC
GTCAAAAGTTCAAGTGAGTTTGTATTCTAGTTTTGTTTT
CAATCATATGAGGATTCTAATGAACTGTTACAGTTGAAC
TTAAATGTTGACATGATTATATGTGAGATATGAAGAAAG
TGGTGTCGGACTTAGTTACAAGGTAAAGATATAAGCTTC
ATTTTTCACCTTAATATCACCAGGAATATTAGTTCCTTG
GTACGACTATACCTTTTTCACGTCCTATTACCTAGTATA
CACATTTGATCTATCTGAAGCAGGCTTGAGTTTTTCTGA
ACCTGCATAAGTGCTATATCCAAGATGAGCAATTTAATG
TATACAATTAAAAAAAGGGCAGCATGTTGCACTAAGCTC
CTGCTATGCTTGGGTCAGGAAAGGACCGGACCACATTGG
GTCTGATGTACGCAGTCGCCTTACCTTGCATTTATACAA
AAGGCTGTTTCCATGGTTTGAACCCATGAGGTCATGGCA
GCAACATTTATTGTTGCGCGGAGGTTTCCCTTCCATTGA
GCTTCTGAAAGATTGGGGGTAGTGATTTGTGAAAGATTT
ACTGCTTTATGATCCTATTCCAGCATCCTGCACTGTGAA
TAATTACAAGGATTGTCACTGAATTGAAAAAAAATTGTT
TCCCTTGGATCTTTGGATGCTTCTCGACGGTCTATTTGC
TTTTCTTTTTTCTTTTAAATGAAACTACCCATTACCA
CTCTTGAAATACTTATTGCCCCACTCCCTTCCCCACTGA
AGAAACATTTTCATTAGGTTAACCCAAATCGCTAGTGTC
TCTACCTTTTTAGTCATTCAAGAAAAAGTAAATGTTCAT
CCTAAACATTACCAGTGCAAGTTTCAAGTGTCTGCTTAC
TAATGAAAAGAAAAGAAACAACTTTTGGATGTTTTCT
TTTTGAAATATAGGTTGCCTGGAATATTCTTTGTTGTTT
TTAAACCTCATCTTGTGCTGGATTTGTCCTTTAATTTGT
GATTTACTGCTCTCACTCAGTTCTTCTTTTGCTCCTGAT
AGACGAGTTGACTGCTTTGCCTAAGTTATTTCTGTAGTC
TTCAAGTTTTCTTTTCTCTCTTCTCCTTTATCATCTTCA
CTGGCCGTGTTTATTTCACTGTAACTCACATCCTATTTT
AATCAGATTGAGGAAACTGATGAAGCAAGGAAGAAGTTT
TCTAATGCAAAAGCCATTTCATCTGCCCAATTCTTTGGT
GATAAGAGCAAAGCTGAAATGGAAGCCTCAGTTTCTCTG
CAGAAGTTCTCGGTATGCTTGCTTATTGTAGTTAACATG
CCCATATTTTTAGGGGCCTTGCTGGTTTTTCAGTCAGCA
TGCAAACAATGAAAAACCCTCTCCCTTCCCTCATTCATT
ATGATAGTTAGGGTCTTGTCCTACTAATTAGAAATAACT
ATTATCGCAACAACATTATGCCCCATGTTCTCCTTTTTT
CTTCCCATTCCCTTTTGTCCTTTAATGCACTGTACTTCT
TCCCATGCTATCATTTTGCTGGGTTTTTTTTTTTTGATG
AAGTAAGAGAATTTCATTAAAGGCATCAAGAAGATGCAT
AGCAAAAGAGAGTACAAGTAAATAGAGTGTGTCTGCTCA
TAAACATAACAAAAAGAAACCTATGTTAAAACTAAGGAG
CAGACACAGTCCAAAAAATGATCACAACTAGATACAGGT
GCCTGATTAAGCCAAGTAAAAAGGTTAAATAAACATTTA
GCTTTAAGAGCATGATTTGGATTTGATATCCCATCAAAA
CATCTGCTATTCCTTTCAGTCCATATACACCAGAAAATA
GAAGCGGGGACCAAAAGTCAAGTTTTTTTGATGGATTTG
CCAACTCTCCAAGAGCACCAGCTTTCGTAGGCCTCTTTA
ATACTATTAGGCATGACCCAGGCTAGTCCAAAAATTGAG
AAGAACATACTCCACAAATCTGCTGCAACTGCACAATGG
AGAAAAAGATGCCTCACACTCTCTGCCTTCATCTGACAC
GTAGCACCTATTCACAATGTAGATGTTCCTCCGACTTAG
ATTATCTTGAGTGAGACATGCTTCATATAAGGTTATCCA
AGTGAAGCCAATTACTTTAGGTGGAAGTTTATAGTTCTC
CAGATGAGTTTCCATGGCCAGTTGTCAATCTACTCCTTG
TTTGAGCACAAATGTACATAACCTTTCTTGACAGTGAAT
ATCCCATCATGTTGGCCATTCCATAATAGTCTGTCTCTC
CTGAGGTTTGATAGTGACCCCTGCTAGCTTAGATTGAAG
CTCCAGATAGTCATTTAGCTCCCAGTCCTGTAAGTTTCT
CCCTGTCTGTAGGTCCCATGAGTTGTTGTGCCATATTTG
ACCCACTGTGGAGTTTTGATTGCTAGCTATGAGATATAA
ATTTGGGTAGTCTTCTTTCAGAGTCTGGTTCCCTAACCA
CTTATCCTTCTAGAATGATACATGCGCTCCATTCCCTAA
CTTTATTGAACAATTGAGCTGGAATTCACCCCATAGGCT
TGAGATATGCTTCCAGGGACCAGTGCCATGTGGTAATCT
GCTCTGTTTGGTGCACCATTGACTCAGCACCCCATACTT
TGCCATGATCACATCTTTCCACATCCCAATGTTCTCCAT
GTTGTACCTCCAATGCCACTTATTAGCATGCTCTTGTT
GTGCAATTTTAAGTCTTTTATGCCCAACCCTCCATGCTC
CTTTGGCAAAATCACTCTTGGCCATTTCACCAGATGAAA
TTTGTTGTTTTGACTATTTCCTCCCCACAGAAAGTTTCT |

TABLE 1-continued

Nucleic acid sequences and amino acid sequences

| SEQ ID NO. | Sequence Description | Sequence Type | Sequence |
|---|---|---|---|
| | | | ATTAATTTTGTCTAACCTTTTCTGCACCCTGGCTGGTAT<br>AGGAAATAGGGACATGAAGTATGTTGGTATGCTGTCCAG<br>GACACTGTTAATGGGTGTTGTTCTGCCCCCAAGTGAAAG<br>ATACTGCATTTGCCAAGTTTCAAGCTTTGTTTCAAATTT<br>CTCTACTATCCCATTCCAGATATCTGGTGACTTGACTTT<br>GGCTCCAAGTGGTAGACCCAAATATGTTGTGGAAAAAGA<br>TCCCACATTGCAACCCATTAGCTCTGCTAGCTCCTCCAT<br>ATTTGGTAAATAGTGCTCTTAAATCTGTTCATGTGGAGG<br>CCGGATATAGCTTCAAAAATCATGAGTGTGAGGTTAAGA<br>TAGAGCACCTGCGACCTATCAGCTCCACAGAAAATAAGT<br>GTGTCATATGCATACAAGAGATGGGAGACACTAATTCAG<br>CTCCCAACAGAACTTTCCACCTTGAAACCCTCCAACCAG<br>TGTATTTGGTTTGCTTTGTCAAGCATTTCGCTAAGGCCT<br>TACATTGCCAAAATGAACAAAAGGATGAGAGGATTCCG<br>TTGACAAGAACTGAATACTTCACAGTGGTTACACAAAAC<br>TTGATCCACCTGATCCAACCTGCACCAAACCCCATCTTC<br>CTAATTATATTGAATAGGTAAGACCAGTTTAGCTGGTCA<br>AAGGCCTTTTCAATAGCAAGTTTGAAAAGGAGACCTGGC<br>TGCCCTGATTTCTGCCTCCAGTCTAGTACCTCATTAGCA<br>ATTAGTGCAGCATCAGTGATTTGTCTTGTTTTGATGAAT<br>GCATTTTGATGCCCTGAGACAAGCTTCCCAATCACTCTT<br>TTCAGTCTTTCTGCCAGGATTTTGGAGGCAATCTTGTAA<br>CTTAAAAAGAGACTGTTCAACAGTTACTGTGAGAGCCTT<br>CTACAATGGAACTTATTAATTACCAGTACTTGGGTTGCA<br>GAACCACATTTATCTGTATGTTGAAGATACCTTATCGAT<br>GCTGTTTACTGAGGCGTAGATTGAAGGATATATACGATG<br>GATAATTTTTGAAATTCCATTCATGGAGATAATGGTGAA<br>GACCATTTGCCATAACTTGAGATAATGGTGTCTAGCTGA<br>CCTCTTGTTTGTTCGCTTCATAATTGCTTATGTTCATTT<br>GCATAACAAGTTATCTACTGGTCCGACGTACTGTGGAAT<br>AGTTTACCCCTCAGGTGTTTTTAATACTTAATCTCATTT<br>TGAAGGAGCTTGTAATAGCTACTTCAGCAAATGAATATG<br>ATTTGTAAGCTAAAATGATCCGCACAGCTGATAGCATTA<br>GTCCTAATCTGATTATTTACCTGTTACATTTGCCTGTCG<br>GGTTGCTTCCGCTAGTGCTTATTGTATATTTACTTCGTC<br>AAAAAAAACTTTGTGCTTATTTTGTATTTTGTCTGACCC<br>ATGTCTGAAGAATCCTTTAGTGTCAATTTCTAAACGAGT<br>GCAACTATATTACTTGAGCTTGACCTGAAAAGCGATAAG<br>TTCACCTAGAAATGTATGAGTCCAACTCGTGCTCCTAAA<br>AATGTGTTCTGCTATCTATTCCTCAGGGTTCAAGTGCCA<br>TTTCAAGTGCAGACCTTTTTGGTAACGATGATAGAGCAG<br>ATTTGGACCTCACTGCTGGTGATCTCATTAACCGGCTCT<br>CTTTTCCAGGTATAGAAGCAATAATAACACAAATGTAAAC<br>GCTTTTCAATTCCCATAAGCAAATTTTGAACGGATTGCT<br>CTTTCGTTTGTCTCTATGTTTTCAGGCACAGCAGGACAT<br>CTCCTCTCTGAAAAATATTGCTGGAGAAACTGGAAAGAA<br>ACTTGGCTCCTTGGCAGCAACCTTAATGTCCGACTTTCA<br>AGACAGAATCCTGTGA |
| 21 | g61524 genomic sequence | Nucleic Acid | ATGGCATCTCTCTCATGGTGGAATCCTGCTCCTGCCACG<br>ACTGCAATGGCAGCTTGTTCTCCAACTCCAACATCCTGT<br>AAAACCTCTAACTCATTAGCACTGCCGCGCTCTGTGTTT<br>GTCAGCAAGCAAGCAAAGTTAATGAAACAAGCCAATGGT<br>CTTTTGGTTATAACACAGCAACAGTCAAAGAAGAAGAAT<br>CATTCATTCACCAATTCCAGAAGGAATACCAGCATTCAG<br>TGTCTCTCACAGGAACAGAAATGGACTCATGAAGGTTCC<br>ATTACCGAATCGCTCCCCAATGGCATGTTTAGGGTCAAA<br>TTGGATAATGCAGATGTCGTTCTGGGATACATTTCTGGG<br>AAGATACGAAAGAATTTCATACGGTTGTTGCCAGGCGAC<br>AGAGTCAAAATTGAAGTAAGTCGGTATGATTCCACTAAA<br>GGACGCATCATTTATCGTCTCCGCGGTGGCCGAGAAGGC<br>TAG |
| 22 | G58887 cDNA sequence | Nucleic Acid | ATGCAAACCAGAGTTGGTAGTAGATTGGTCACTGAACAG<br>TATCACGATGAAGAAGTACGGCCATATATTCAACAATTA<br>ATGAATGCTCAGAATTGCTCTCCAGCCCAAACTTATGAT<br>AATCAATCTAATATTTTGAACAATTCTGTTGGTACTGGA<br>GCTGAGCAGAACAATGAATCAGGTCCTTCAGAGAATAGT<br>CGTAATCAAGCTATTGGAAAAAGGGTCGAAAGCTTGCT<br>AGCTTTCTAAGTATCATTGCTAGAACCCCAGAGCTGACA<br>CCGTTAAATATAAATGATTGGCGAGTATTTGACAAAGAA<br>GAAAAGAAGAAATTGGTGGAGTTTGTGAGGAAAAAGTTC<br>TCGATTCCAGTATGTAGAGAAGAGTTTATAAAAAAGTCA<br>ATAGGGAAAAATGGAAGGACTATAAATGTGATTTGAAG<br>ACTATGTATGTGACCAAGTATAAGAGCAAAGATGCCTTG |

TABLE 1-continued

Nucleic acid sequences and amino acid sequences

| SEQ ID NO. | Sequence Description | Sequence Type | Sequence |
|---|---|---|---|
|  |  |  | ATGAAAAATAGACCAAGTCACATACCAAGGGATCAATGG ACTGGTCTCGTCTTGTATTGGCTTTCTGATAAAGCAAAG AAGCGCAGTCAAGCAAATAGAATCAGTAGGGCTAAACAA AAGATGCCTCACACAGGAGGATCCAAAAGCATAGCAACC TTGATGAATGAAAAGGCTATAGATGGAATAGAGCCTACA CGTGCTCAAGTTTACATATTAACTCATACAAAGCGTAAG GATGGTAGACCATTGGATGAGGAATCTTCAAATACAGTT GACATTGATGAAAGAGAAGTTGAGTAA |
| 23 | g58888 cDNA sequence | Nucleic Acid | ATGGTAGACCATTGGATGAGGAATCTTCAAATACAGTTG ACATTGATGAAAGAGAAGTTGAGTAATGGCGAGACATCT CATGAACAACCTCATGGCAGTGTTGCTTGGGAAGGAGAT GTGTATTCTCAAGTGTTGGGAAATGAAAAAAGTGGTAAT GTCCGTGGTTTAGGACTTGGTCCAACCCCTTCTCTATTA TGGGGCGGTAAATCTTCCTTACAAAATATTACCGATGAT GGTTTATCTAATGAGGCTGCACATAAGTTAGAACAAGAG ATAAAGGAGTTAAAGGACTTGAACAAAAAACAGGATGAA GAAATAGCTTTGATGAAAAAAAATCAAGATATGCTAGTT TCAGAATTAACATGGATGAGGCAAGTCATGTGGAAATAT GTTCCCACCAAATTATGTGGCCCTCAAAACTATGGAAGC ACTACTAGACAGGTTCCTGATGCCAATAGTGGCAATGAG CAAGCAACCTAA |
| 24 | g58899 cDNA sequence | Nucleic Acid | ATGGAGGTACCGGTGCTAGCTCGGTGTACGAATACTCCG ACGACGTCGTTTCTAGGATGTAAAGTGAGTTTATTTGAT TTTCCGATTAGAAGAAAGCTAAATAAGAGGAATTATAAG GCGAAGTTTTCAGTGTTAAGAGTTAAAGCTATGGCGGAG AGGACGAGTACTGAGGCATCAGCGGATGCTAGAGAGAGA GAAAGTGGAGGGTACACGGGAACTACGATGGAGGTGACA ACATTTAATCAGAGCTTTAGTGATGCGCAATTGCCAGTT TGGGAAAAGATTGGTGCTGTCGTCAGACTCAGTTATGGA ATCGGCATATATGGAGCAATGGCTTTAGCAGGAAAGTTC ATATGCTCAATGACAGGAATTGACTGCACAGGAGGGTTC AGTCCATCATTAGATGCCATTGTTGAAGGACTAGGATAT GCAGCTCCACCAATTATGGCTCTTCTATTTATACTAGAT GATGAAGTTGTGAAGCTGTCGCCTCATGCTCGAGCTATC AGAGATGTAGAGGATGAAGAGCTACGGAATTTCTTTTAT GGAATGTCACCTTGGCAGTTCATTCTGATTGTGGCTGCT AGCTCTGTTGGAGAAGAGCTTTTCTACCGCGCTGCTGTC CAGGGAGCTTTAGCTGACATTTTCTTAAGGGGCAGTGGT TTTGTGACTGATGCTAGAGGAATGGCATCATTGACTGGT GTTTTGCCACCGTATGTCCCATTTGCTCAAGCGTTTGCA GCTGTAATTACGGCAGCTCTCACGGGTTCTCTATATTAT ATGGCTGCCTCTCCAAAAGATCCTACCTATGTTGTTGCA CCAGTGCTGAAGTCGCATTCAGGTCGTGAAGATCTTAAA AAACTATTTGCAGCTTGGTACGAGAGGCGACAGATGAAG AAGATATACTCTCCTTTACTAGAAGCCATGTTAGCCCTT TACCTTGGGTTTGAATGGATCCAGACAAACAACATTTTT GCACCGATAATCACACATGGGATATACTCTGCTGTTATT CTGGGACATGGACTTTGGAAAATCCACGATCATCGGAGA AGACTACATCAAAGAATCCAACAACTTAAACAAGAAGGT AACAATTCAAGAAACTTGTAA |
| 25 | g58917 cDNA sequence | Nucleic Acid | ATGGGAGCTGGAATACCTGATGAAGAGGAAAATAATTGG CCACTATGGTTAAAGCCATTGCTTAAAGAAAAATTCTTT GGCCATTGCAAATTACATGCTGATTCTCACAAGAGTGAA TGCAATATGTATTGTCTTGATTGTATAAATGGCCCTCTT TGTTCTCTTTGTTTAGCACATCACAAGGACCATATTGCT ATTCAGATAAGGAGGTCATCATACCATGATGTGATAAGG GTGAATGAAATTCAAAAGTATTTGGACATTTCTTCAGTC CAAACATACATTATCAACAGTGCTAAGGTTGTCTTTTTG AATGAAAGGCCACAACCTAGGCCAGGCAAAGGTGTAACA AATACTTGTCAAGTTTGTGAAAGGAGCCTTCTTGATTCC TTCAAATTCTGCTCTCTTGGTTGCAAGGTTGTCGGGTCC TCAAAGAACTTCGTTAAGAAACCGAAGCAATTATCCGCG AAAAGGCGGCGGTCGATGGTGGCGGCATCGGACTCCGAT GACTCTTACAGCAGCAGCAGCCATGGTAGGTACAAGAGC CACAGCAACAAGGTCCAAAGTTTTACTCCGTCGACGCCC CCTCCAACTTCAGTTAATTACAAAACGGCCAAGCGAAGA AAGGGAATTCCACATAGATCCCCAATGGGAGGACTACTC ATAGAATATTAA |

TABLE 1-continued

Nucleic acid sequences and amino acid sequences

| SEQ ID NO. | Sequence Description | Sequence Type | Sequence |
|---|---|---|---|
| 26 | g58905 cDNA sequence | Nucleic Acid | ATGTCTTCCGATAACTTCACCGACAAAAACGCCGTCTTC CGCAAGCTCAAAGCCAAGCCGGACAACAAGATGTGTTTT GATTGCAATGCGAAGAATCCTACGTGGGCGTCGGTTACG TATGGGATCTTCTTGTGTATTGATTGTTCGGCGACGCAT CGTAGCCTTGGTGTTCACATCAGTTTTGTTAGGGGCAGA TGTACTGTTCGGGGTACGGGTTTGGTAGAACTCAGAAGT TTTGGCCTAAGCCATTTTCTGGTTCGAAACCATTATCTT CATCCCATATGTGCCACAACAGCTTCATTTTGCCCAACA ATTGGTATGACCACCTTAAGAGACTTTATGTGTTTGCAC CAAGGGCTTTGGTTTAGCGGTAAGAGCGCAATGTTTGAT GTGTGGATTAGGCGCATGCCACAGATCGACAAATTTAGA TTCATGGTCTCCAGAGCAGTTAAAGATGATGTACTTTGG TGGAAACAACCGTGCTCAAGTTTTTTTCAAGCAGCACTG ATGGACGGATGGCGGCAAGAGGATGCAGGTTTGCCAGCA TCGCCTTTTGCCTCTCAGGCTGTGCAGAGTACGAATGGA TTTTCTGATGTTAAGACTAGTGAAGCTCCAAAAGAAACC TCATCATTTAAGGAAGAAACTCCTGCTTCGCCCAAAGCA TCACAATCAGTTGTTACTACTTCAATTAGGAAACCTATA GGTGCAAAGAAATCTGGGAAGCCAGGTGGTGGACTTGGA GCTCGGAAACTTACTAAAAAGCCAAGTGAAAGTCTCTAC GACCAGAAGCCTGAAGAACCGCCTGTTCAAGTTTCTTCC TCCAATTCTACAAGTAATGCATCAACTGTTGGTTCATCA TTCGCATCTCGCTTTGAGTACACAGACAATGTCCAACCC GCTGAGATGAGTTCTGGAGGCCCTCGTGTTCTTAACCAT GTATCCCCTCCAATGTCCTCCAGCTTTTTTTCGGACTAC GGAATGGACAGCGGTTTCACAAAGAAGACAAGTTCAAAT TCGTCAAAAGTTCAAATTGAGGAAACTGATGAAGCAAGG AAGAAGTTTTCTAATGCAAAAGCCATTTCATCTGCCCAA TTCTTTGGTGATAAGAGCAAAGCTGAAATGGAAGCCTCA GTTTCTCTGCAGAAGTTCTCGGGTTCAAGTGCCATTTCA AGTGCAGACCTTTTTGGTAACGATGATAGAGCAGATTTG GACCTCACTGCTGGTGATCTCATTAACCGGCTCTCTTTC CAGGCACAGCAGGACATCTCCTCTCTGAAAAATATTGCT GGAGAAACTGGAAAGAAACTTGGCTCCTTGGCAGCAACC TTATGTCCGACTTTCAAGACAGAATCCTGTGA |
| 27 | g61524 cDNA sequence | Nucleic Acid | ATGGCATCTCTCTCATGGTGGAATCCTGCTCCTGCCACG ACTGCAATGGCAGCTTGTTCTCCAACTCCAACATCCTGT AAAACCTCTAACTCATTAGCACTGCCGCGCTCTGTGTTT GTCAGCAAGCAAGCAAAGTTAATGAAACAAGCCAATGGT CTTTTGGTTATAACACAGCAACAGTCAAAGAAGAAGAAT CATTCATTCACCAATTCCAGAAGGAATACCAGCATTCAG TGTCTCTCACAGGAACAGAAATGGACTCATGAAGGTTCC ATTACCGAATCGCTCCCCAATGGCATGTTTAGGGTCAAA TTGGATAATGCAGATGTCGTTCTGGGATACATTTCTGGG AAGATACGAAAGAATTTCATACGGTTGTTGCCAGGCGAC AGAGTCAAAATTGAAGTAAGTCGGTATGATTCCACTAAA GGACGCATCATTTATCGTCTCCGCGGTGGCCGAGAAGGC TAG |
| 28 | G58887 protein sequence | Amino Acid | MQTRVGSRLVTEQYHDEEVRPYIQQLMNAQNCSPAQTYD NQSNILNNSVGTGAEQNNESGPSENSRNQAIGKKGRKLA SFLSIIARTPELTPLNINDWRVFDKEEKKKLVEFVRKKF SIPVCREEFIKKSIGKKWKDYKCDLKTMYVTKYKSKDAL MKNRPSHIPRDQWTGLVLYWLSDKAKKRSQANRISRAKQ KMPHTGGSKSIATLMNEKAIDGIEPTRAQVYILTHTKRK DGRPLDEESSNTVDIDEREVE |
| 29 | g58888 protein sequence | Amino Acid | MVDHWMRNLQIQLTLMKEKLSNGETSHEQPHGSVAWEGD VYSQVLGNEKSGNVRGLGLGPTPSLLWGGKSSLQNITDD GLSNEAAHKLEQEIKELKDLNKKQDEEIALMKKNQDMLV SELTWMRQVMWKYVPTKLCGPQNYGSTTRQVPDANSGNE QAT |
| 30 | g58899 protein sequence | Amino Acid | MEVPVLARCTNTPITSFLGCKVSLFDFPIRRKLNKRNYK AKFSVLRVKAMAERTSTEASADARERESGGYTGTTMEVT TFNQSFSDAQLPVWEKIGAVVRLSYGIGIYGAMALAGKF ICSMTGIDCTGGFSPSLDAIVEGLGYAAPPIMALLFILD DEVVKLSPHARAIRDVEDEELRNFFYGMSPWQFILIVAA SSVGEELFYRAAVQGALADIFLRGSGFVTDARGMASLTG VLPPYVPFAQAFAAVITAALTGSLYYMAASPKDPTYVVA PVLKSHSGREDLKKLFAAWYERRQMKKIYSPLLEAMLAL YLGFEWIQTNNIFAPIITHGIYSAVILGHGLWKIHDHRR RLHQRIQQLKQEGNNSRNL |

TABLE 1-continued

Nucleic acid sequences and amino acid sequences

| SEQ ID NO. | Sequence Description | Sequence Type | Sequence |
|---|---|---|---|
| 31 | g58917 protein sequence | Amino Acid | MGAGIPDEEENNWPLWLKPLLKEKFFGHCKLHADSHKSE CNMYCLDCINGPLCSLCLAHHKDHIAIQIRRSSYHDVIR VNEIQKYLDISSVQTYIINSAKVVFLNERPQPRPGKGVT NTCQVCERSLLDSFKFCSLGCKVVGSSKNFVKKPKQLSA KRRRSMVAASDSDDSYSSSSHGRYKSHSNKVQSFTPSTP PPTSVNYKTAKRRKGIPHRSPMGGLLIEY |
| 32 | g58905 protein sequence | Amino Acid | MSSDNFTDKNAVFRKLKAKPDNKMCFDCNAKNPTWASVT YGIFLCIDCSATHRSLGVHISFVRGRCTVRGTGLVELRS FGLSHFLVRNHYLHPICATTASFCPTIGMTTLRDFMCLH QGLWFSGKSAMFDVWIRRMPQIDKFRFMVSRAVKDDVLW WKQPCSSFFQAALMDGWRQEDAGLPASPFASQAVQSTNG FSDVKTSEAPKETSSFKEETPASPKASQSVVTTSIRKPI GAKKSGKPGGGLGARKLTKKPSESLYDQKPEEPPVQVSS SNSTSNASTVGSSFASRFEYTDNVQPAEMSSGGPRVLNH VSPPMSSSFFSDYGMDSGFTKKTSSNSSKVQIEETDEAR KKFSNAKAISSAQFFGDKSKAEMEASVSLQKFSGSSAIS SADLFGNDDRADLDLTAGDLINRLSFQAQQDISSLKNIA GETGKKLGSLAATLMSDFQDRIL |
| 33 | g61524 protein sequence | Amino Acid | MASLSWWNPAPATTAMAACSPTPTSCKTSNSLALPRSVF VSKQAKLMKQANGLLVITQQQSKKKNHSFTNSRRNTSIQ CLSQEQKWTHEGSITESLPNGMFRVKLDNADVVLGYISG KIRKNFIRLLPGDRVKIEVSRYDSTKGRIIYRLRGGREG |
| 34 | g58899 forward primer | Nucleic Acid | TGTTAGCCCTTTACCTTGGGTTT |
| 35 | g58899 reverse primer | Nucleic Acid | TGTGATTATCGGTGCAAAAATGT |
| 36 | g58899 probe | Nucleic Acid | AATGGATCCAGACAAAC |
| 37 | g58917 forward primer | Nucleic Acid | CACAGCAACAAGGTCCAAAGTTT |
| 38 | g58917 reverse primer | Nucleic Acid | TGGCCGTTTTGTAATTAACTGAAG |
| 39 | g58917 probe | Nucleic Acid | ACTCCGTCGACGCCCCCTCC |
| 40 | g61524 forward primer | Nucleic Acid | GGCATCTCTCTCATGGTGGAA |
| 41 | g61524 reverse primer | Nucleic Acid | GGATGTTGGAGTTGGAGAACAAG |
| 42 | g61524 probe | Nucleic Acid | CCTGCTCCTGCCACGACTGCAA |
| 43 | *Solanum lycopersicum* STAY-GREEN | Amino Acid | MEFPLIARCTNTPSTTSFLGCKVSLCDFPIRNNYRDKRN YNEKFSVVRIKAMAEKSSTGEASSVEIREGENGGVGFTG STMEVTTFNQSFSDAQLPVWEKIGAVVRLSYGIGIYGAM ALAGKFICSISGIDCTGGFSPSLDAIVEGLGYAVPPIMA LLFILDDEVVKLSPHARAIRDVEDEELRNFFYGMSPWQF ILIVAASSVGEELFYRAAVQGALADIFVRSTDLVSDARG MASLTGVLPPYVPFAQAFAAVMTAALTGSLYYMAASPKD PTYVVAPVLKSRSGREDLKKLFAAWYERRQMKKIYSPLL EAILALYLGFEWIQTNNILAPIITHGIYSAVILGHGLWK IHDHRRRLHHRIQQVKQEGKNSSNL |

TABLE 1-continued

Nucleic acid sequences and amino acid sequences

| SEQ ID NO. | Sequence Description | Sequence Type | Sequence |
|---|---|---|---|
| 44 | g58899 cDNA sequence from Narrow Leaf Madole | Nucleic Acid | ATGGAGGTACCGGTGCTAGCTCGGTGTACGAATACTCCG ACGACGTCGTTTCTAGGATGTAAAGTGAGTTTATTTGAT TTTCCGATTAGAAGAAAGCTAAATAAGAGGAATTATAAG GCGAAGTTTTCAGTGTTAAGAGTTAAAGCTATGGCGGAG AGGACGAGTACTGAGGCATCAGCGGATGCTAGAGAGAGA GAAAGTGGAGGGTACACGGGAACTACGATGGAGGTGACA ACATTTAATCAGAGCTTTAGTGATGCGCAATTGCCAGTT TGGGAAAAGATTGGTGCTGTCGTCAGACTCAGTTATGGA ATCGGCATATATGGAGCAATGGCTTTAGCAGGAAAGTTC ATATGCTCAATGACAGGAATTGACTGCACAGGAGGGTTC AGTCCATCATTAGATGCCATTGTTGAAGGACTAGGATAT GCAGCTCCACCAATTATGGCTCTTCTATTTATACTAGAT GATGAAGTTGTGAAGCTGTCGCCTCATGCTCGAGCTATC AGAGATGTAGAGGATGAAGAGCTACGGAATTTCTTTTAT GGAATGTCACCTTGGCAGTTCATTCTGATTGTGGCTGCT AGCTCTGTTGGAGAAGAGCTTTTCTACCGCGCTGCTGTC CAGGGAGCTTTAGCTGACATTTTCTTAAGGGGCAGTGGT TTTGTGACTGATGCTAGAGGAATGGCATCATTGACTGGT GTTTTGCCACCGTATGTCCCATTTGCTCAAGCGTTTGCA GCTGTAATTACGGCAGCTCTCACGGGTTCTCTATATTAT ATGGCTGCCTCTCCAAAAGATCCTACCTATGTTGTTGCA CCAGTGCTGAAGTCGCATTCAGGTCGTGAAGATCTTAAA AAACTATTTGCAGCTTGGTACGAGAGGCGACAGATGAAG AAGATATACTCTCCTTTACTAGAAGCCATGTTAGCCCTT TACCTTGGGTTTGAATGGATCCAGACAAACAACATTTTT GCACCGATAATCACACATGGGATATACTCTGCTGTTATT CTGGGACATGGACTTTGGAAAATCCACGATCATCGGAGA AGACTACATCAAAGAATCCAACAACTTAAACAAGAAGGT AACAATTCAAGAAACTTGTAA |
| 45 | g58899 cDNA sequence from TI1372 | Nucleic Acid | ATGGAGGTACCGGTGCTAGCTCGGTGTACGAATACTCCG ACGACGTCGTTTCTAGGATGTAAAGTGAGTTTATTTGAT TTTCCGATTAGAAGAAAGCTAAATAAGAGGAATTATAAG GCGAAGTTTTCAGTGTTAAGAGTTAAAGCTATGGCGGAG AGGACGAGTACTGAGGCATCAGCGGATGCTAGAGAGAGA GAAAGTGGAGGGTACACGGGAACTACGATGGAGGTGACA ACATTTAATCAGAGCTTTAGTGATGCGCAATTGCCAGTT TGGGAAAAGATTGGTGCTGTCGTCAGACTCAGTTATGGA ATCGGCATATATGGAGCAATGGCTTTAGCAGGAAAGTTC ATATGCTCAATGACAGGAATTGACTGCACAGGAGGGTTC AGTCCATCATTAGATGCCATTGTTGAAGGACTAGGATAT GCAGCTCCACCAATTATGGCTCTTCTATTTATACTAGAT GATGAAGTTGTGAAGCTGTCGCCTCATGCTCGAGCTATC AGAGATGTAGAGGATGAAGAGCTACGGAATTTCTTTTAT GGAATGTCACCTTGGCAGTTCATTCTGATTGTGGCTGCT AGCTCTGTTGGAGAAGAGCTTTTCTACCGCGCTGCTGTC CAGGGAGCTTTAGCTGACATTTTCTTAAGGGGCAGTGGT TTTGTGACTGATGCTAGAGGAATGGCATCATTGACTGGT GTTTTGCCACCGTATGTCCCATTTGCTCAAGCGTTTGCA GCTGTAATTACGGCAGCTCTCACGGGTTCTCTATATTAT ATGGCTGCCTCTCCAAAAGATCCTACCTATGTTGTTGCA CCAGTGCTGAAGTCGCATTCAGGTCGTGAAGATCTTAAA AAACTATTTGCAGCTTGGTACGAGAGGCGACAGATGAAG AAGATATACTCTCCTTTACTAGAAGCCATGTTAGCCCTT TACCTTGGGTTTGAATGGATCCAGACAAACAACATTTTT GCACCGATAATCACACATGGGATATACTCTGCTGTTATT CTGGGACATGGACTTTGGAAAATCCACGATCATCGGAGA AGACTACATCAAAGAATCCAACAACTTAAACAAGAAGGT AACAATTCAAGAAACTTGTAA |
| 46 | g58899 protein sequence from Narrow Leaf Madole | Amino Acid | MEVPVLARCTNTPITSFLGCKVSLFDFPIRRKLNKRNYK AKFSVLRVKAMAERTSTEASADARERESGGYTGTTMEVT TFNQSFSDAQLPVWEKIGAVVRLSYGIGIYGAMALAGKF ICSMTGIDCTGGFSPSLDAIVEGLGYAAPPIMALLFILD DEVVKLSPHARAIRDVEDEELRNFFYGMSPWQFILIVAA SSVGEELFYRAAVQGALADIFLRGSGFVTDARGMASLTG VLPPYVPFAQAFAAVITAALTGSLYYMAASPKDPTYVVA PVLKSHSGREDLKKLFAAWYERRQMKKIYSPLLEAMLAL YLGFEWIQTNNIFAPIITHGIYSAVILGHGLWKIHDHRR RLHQRIQQLKQEGNNSRNL |

TABLE 1-continued

Nucleic acid sequences and amino acid sequences

| SEQ ID NO. | Sequence Description | Sequence Type | Sequence |
|---|---|---|---|
| 47 | g58899 protein sequence from TI1372 | Amino Acid | MEVPVLARCTNTPITSFLGCKVSLFDFPIRRKLNKRNYK AKFSVLRVKAMAERTSTEASADARERESGGYTGTTMEVT TFNQSFSDAQLPVWEKIGAVVRLSYGIGIYGAMALAGKF ICSMTGIDCTGGFSPSLDAIVEGLGYAAPPIMALLFILD DEVVKLSPHARAIRDVEDEELRNFFYGMSPWQFILIVAA SSVGEELFYRAAVQGALADIFLRGSGFVTDARGMASLTG VLPPYVPFAQAFAAVITAALTGSLYYMAASPKDPTYVVA PVLKSHSGREDLKKLFAAWYERRQMKKIYSPLLEAMLAL YLGFEWIQTNNIFAPIITHGIYSAVILGHGLWKIHDHRR RLHQRIQQLKQEGNNSRNL |
| 48 | g20337 genomic DNA | Nucleic Acid | ATGGAGGTACCGGTGCTAGCTCGGTGTACGAATACTCCG ACGACGTCGTTTATGGGATGTAAAGTGAGTCAATTTGAT TTTCCGATTAGGAGAAAGCTAAATAAGAGGAATTATAAG GCGAAGTTTTCAGTGTTAAGAGTTAAAGCTATGGCGGAG AGGTCGAGTAGTGGTGAGGCATCAGTGGATGCTAGAGAG AGAGAAAGTGGAGGTTACACGGGAACTACTATGGAGGTA ACAACATTTAATCAGAGCTTTAGTGATACGCAATTGCCT GTTTGGGAGAAGATTGGTGCTGTCGTCAGACTCAGTTAT GGAATCGGTGAGTTCTCAACTCGTTTTGCATTTTCTTAA TTTTTTTTTTTTTTTTTTCTGTTTGAGTTCTGGTTTCC TTTTTGAAGACTATTTTTGGGAAAAAAGCCAAGGAATAT TCATATAAGTTGAATAGATTCAATGAATTCAGAATTTTA TTTTATGGCTTTTGGTTTCCTATTCTTTGGTCAAACATT TGGTATATGAACCCACTAACCCGACTAATTTTGATTCGC GTCTTAAAATCTTACTGTGGAAGATTTAAGTGTTCTTTA CAAAGAGGACTTCATTGTCATAATTCGAACTTGAAACTT TTGATTACGATGTAAAAGAATTTTTATCATTCCAACTAG GGCGGTTCGGTTTGGATCGATTTTTCCTTAAAAAGAAAC CAAATCAAGTAAGTTGGTTTTTCAAATATTAGAACCAAA CCAAACCAATTAAGTCGGTTTTTTCTCGATTCGGTTTAT GTCGGATTTTATCGGTTTTTCATGTTTTTTTTGGTTATT TGTCGGTTTTTTCTTAAATATAAGACATACACTACCAAA CATATATTCCGGCGACCACATTTTCAACGTAACACTATC AAATCAATTGCCCTTTGAGAAATTTATTATTTACTAAAA TATATTGATGATAATTGAATCAAATAGTGATGAGTAATT TAACGACTCAATTTAAAAAATATTTTTTTAACATAAAA TGGATTCTTACACTTAACAAAAGAAAACTACCAATCAAA CTAGAATATAAAGGTAAAGAACTGTACTAAAAGTGCAAA CAATTAACATTTACCATAAATTTTTGAAATTTTCTATAA AAATATACATATATATAGGTGTAATAATAAATTTGAAAT AGCTACTCCTATAGTCGGTTTGGTTCGGTTTTTTTCGGT TATTTTTTTATTAAAATCAAAACCAAACCAAATTTGATC GGTTTTTAAAATTCAAAACCAAAATCAAACCAAACCAAA CCAAAAAGTATCGATTTTTTTGATCGGTTTGGTTCTGAT TTTTCGGGTTTATGAGATAGTGAATTTACAAGTGATTCT TGGAATTGCAAGTAAAGGGAAAGGGTTTTGTCCTTGTC AAAAGGGAAAGGGTTGTTGCATATCTTCTTTTTGCTTTC TGTATATGTCATTAAAGTGCTTCTAAAAGTGGAAAAGCT AAGGTTTTTCTTCTTCCTAACTTTTAGGTTTTATTGTTG GTTGGACAACAAATGCCAAAATAAATACACTGCAATAA TTTTGCAGTCAATTTAATCATTTTTCCAATCACATGTTA AGTGGTACTTTGTTTCCTAAGTAAGAAATATAAGCAATT GTCAGGAATAGGATTGTATTTATATCCTATAACAACAAT AAAATTTCTCCAGTGGGGTCTGGGGAGGGAGGCTGTGTC CGAGAGACCCTCAGCTCAAGAAGACGAAAATAGACAATA AAATGTATTTATATCCTACTATAAATAAAATTATTAATG AAACAATTTTAGATAAAATTGAATACTTTCGTTGTTTTT GCTCATACTTGGCTATTGAGGAAAACAGAATTGTCGTTA GGCAATTGTTAGTATGCATTAGAACAAGTGTAGATGTAT TTTAGAATGATAGAACATACAAATTTATTTACTTTTTTA AGAACAGTATAAATAAATGAAGTGATTTTAAAATTATTA AGAACATGATAATAGAAGAAAAATAGGCGAAATTAAAA AAAGAATAAAAGTGGAGCCGAAATTGATCATTCTAATGC ATGTGGGCTAACTTTGAATAGCTTTAAACTTAGCAACTT ATTGGTAATTTTTATTTTATAGAAATCTTTTGTTCTTTC TTTTTCCTTTTTTAATAAACCAATTTTATTTGTTAACT CAACTACATGCTTCTGTAGAATTACATTTAGAAAAGCTT TTTAGTCCAAACACTACCAAAAAGAGTTAAATGCTAAAT ACAAATAAACAAATAATAACTCCATCCCGTGCCACTTA ATTAGAAGTAGAATTGTACTTACAGGAGTAATTTGAACT TTGGCAATAGTTGTTAAAATATGTTCTAGCCTAACTAGC AGTACTAAGGTCTCAAAATCTTTGATATCTTGATTCTAA TCTTCCTCTAAAAAAAAAAAAAGAAAGTAGTCCCTATGC |

TABLE 1-continued

Nucleic acid sequences and amino acid sequences

| SEQ ID NO. | Sequence Description | Sequence Type | Sequence |
|---|---|---|---|
| | | | GCGGGTCCGAAAAGGGCTATTTTATGCAATCTTACCCTG<br>TATTTCTGCAAGAGGCTGTTTCTACGGTTTGAACCCGTA<br>GCCTCGTGGTAACAAGACAACAATCTTCCTCAAAGAAGA<br>ATAGAATTTAATCATTATACTTGAGTAAATTGAACATTG<br>CAATTATTATCATAGTACATATCCCCAAAATGTAGGATG<br>TTGATTGTAATACTACATATTCATTTTTTTCTTCCAATG<br>TATTTATTTTTTATCCTTACTTTTTTAATACGGTGTTAT<br>CTTCCACTAATATATATCGGATAACTGTGACACCACAGA<br>TAAATATCACCTAGTGTTTTTAATCCTGTGTATTTGTTT<br>GTTTGTTACATTGTTTATTGCATGTATTTCTTCCAGCCT<br>TGTATGAGTCCCATCCCATTAAATTTTTTGGATATCTTT<br>AGAGAAGAAAAAGAAAGACCTTCAATCATTCTCTGATGT<br>TCAGTTTGTTTTTGGGATTTTTACACAAATAGCCGCTCG<br>GTTTTACGTTTACTTTTTCTAGCCGGTATACATAAATTA<br>TACACTGATTTAACATTATTTTATATATATAATTTAAGT<br>AACTGAGTGGGCTGCTATTTAGGTTATTTCTTCTATGTT<br>TTTTTTTGAACTCAGGCATATACGGAGCAATGGCTTTAG<br>CAGGAAAGTTTATATGCTCAATGACAGGAATTGACTGCA<br>CAGGAGGGTTCAGTCCATCATTAGATGCCATTGTTGAAG<br>GACTAGGATATGCAGCTCCCCCGATTATGGCTCTTCTAT<br>TTATACTAGATGTATGTTCAACTATTCCCATTTCTTTCC<br>TGCCACAAACTGTAACAGTCCAGCCATTGGTGATGTTAT<br>CTGCTTGTGTGGCTTTAAAACACATTACTAGGGTCGTCT<br>GGAACTTGCTTTCTTATATGTCAAGCATCCCTCTCGTGT<br>TTTGTCGATGTGAAATTTGCCTAAGAGTGTTACAAAAAT<br>ATATTTAACAGCATTCTTGGTTTACTTAACTTGCATTAT<br>TTTCTTTCATCCACATATGGCTTCACTAACTCTTAGAAA<br>AGATGCAACAATGTTAACCTTATACTCCCTCCGTTCCAG<br>TTTATGTGAACCTATTTCCTTTTTGGTCCGTTCCAAAGA<br>GAATGGTCCTTTCTAATTTAGCTTAAATTTTCAATTCTA<br>CCATTAATGAGAAGCTTTTATAACCACACAAATATTCTG<br>GACCCCATTCTGACATGTTTAAGACCACAAATTCCAAAA<br>GTTTTTATTTTTTCTTAAATTTCGTGCTCAGTCAAACAG<br>GTTCACATAAATTGACACGGGAGTATTGTAGCCATTCT<br>AGCTTTGTCCATCTGACATTCTTGGATTATATAACCGAT<br>GTTTTATAATAAATTGCGGTGTTTATAGGATGAAGTTGT<br>GAAGCTATCACCTCATGCTCGAGCTATTAGGGATGTTGA<br>GGATGAAGAGCTGCGGAATTTCTTTTATGGAATGTCACC<br>TTGGCAGGTAAAAGATTTCTCAATTTCAGCATCAATAGT<br>TATGTCACAATACAGTGAAAGGTTGATACTTAATGGATT<br>TTGATGCAAATTTGTAGTTCATTCTGATTGTGGCTGCTA<br>GCTCTGTTGGAGAGGAACTTTTCTACCGTGCTGCTGTCC<br>AGGTAAGATATATATCATCCATATATAGCCTGCAATTAT<br>GAATTCGTTAGTCCAGTTGCAGCCTTATTTTTTGGATCA<br>ATAATACTCCATTTCACTACTTTCCTTCACGTGACTTAA<br>ACTCCCACCCGGTGTCAATATTGGTACCGTGCTTACCCT<br>TTCATGTGAATCAGACATCTAACCTAGTGGTTGGAGGTG<br>AAGGCAGCTCACCAACTAATCAAGCTTCTCTCTTCAGCC<br>ATCTATGTTAAATTGTACAAACCTTGCATTTCCTACAGT<br>TTTAACTAATAATACATACTCTGAAAACCATTTGGTGAA<br>ATTTTCTGCACTTCAGTTTTCCAATGTATACATTTATTT<br>TGTTAAAAGAAATAATAGAGAAAGAAAGAAGAATATAGA<br>AAAACGTAGAAACCAGAAAAAGGCTTGAGGTGTGTAGAA<br>CACTTTATCAAAAGATTGGTTATCTGGCTCGAGGGATAG<br>TGATCTTCGGGAATACAAACCACACTTATTTGAATGTGA<br>TGATTGTTGTCTTTTGCCTGATCTAATTCACTTTCGGAA<br>GAGCCAACTACTTTCTTATTTATTGGAAATAATCTCAAA<br>AAGGTTGAAATCTTTTCAGAATAGACATATCTTTTGTTA<br>ATAACCACTTTCATATTACAATCTGTCCAACAATATTAT<br>CAACAGACTAATTATTTTTAACCTGTCAAACTTAATGGA<br>AATGCATGGCAAAAAAGTTATGTTTCTCATAAGTTATGT<br>GATTCTTTCCTCCTTGCTCCTCTCTGATTATCTTTTAAT<br>TACAGGGAGCTTTAGCTGACATTTTCTTAAGGGGCAGTG<br>ATTTTGTGACTGATGCTAGAGGAATGGCGTCATTGGTAC<br>GTCGGATTCTATTTCTAGACATCCTTCTCCAAGTTAAAT<br>ATCCAAAAAAATTCCATTGCTCTGACACATTCTGTTTCC<br>TCAAAATGTAGACTGGTGTTTTGCCACCTTATGTCCCGT<br>TTGCTCAAGCATTTGCAGCTGTAATTACAGCAGCTCTCA<br>CTGGTTCTTTATATTATATGGCAGCCTCTCCAAAAGGTC<br>AGTTTCATAGGGTGCAGTTTCAAATCCTTCGTTGTACTC<br>TGCTCGAACATGCTTAATCAGTTGGCTATTTGCTGTTTC<br>ACTTTCAGATCCTACCTATGTTGTTGCACCCGTGTTGAA<br>GTCGCATTCAGGCCGTGAAGATCTAAAAAAACTCTTTGC<br>AGGTTTGACCTCTCTCTTTGCTCATGACAAAAGCAAGAC<br>AGCTACCACTTGTGATGATTTGAGTCCAAGCCTTGTTAA |

TABLE 1-continued

Nucleic acid sequences and amino acid sequences

| SEQ ID NO. | Sequence Description | Sequence Type | Sequence |
|---|---|---|---|
| | | | CATAATGTAATAAATCTGGGGATTCAGGATCAAGGCAAA<br>TAGATATATTTCTACAGCTGACTGACTAAAATAAGAGAT<br>AAAGTCTGTCCCTTAGTCTAGTTTATATCCACAGCTGAC<br>TAAATAAAATACAACTGTTGTGACCTGCTTTGTATCAAA<br>AGAAAAGCAAAGGGTTTACGGCTTTACACAACAAGCAAA<br>ACGGCTTTCTATCATAGTTGCAAGGGCCAAACACACTCC<br>TGATCATCGTTCTACTGCATCTGGCCTGTCCTCTAGGCA<br>CCTTTTATAGAAGGCAGGGAGCGTGATAATATACCCGCT<br>TCTTTTGCTCCATTAGACCTTCTCAAGCTTTTTCATGTA<br>AGAATAGCTTTCTAAACTATTTTAAATAATATGAGACCA<br>CCAAGCCTATAGGCTAGACTCTCCTGTCAAAAACAACGT<br>ACCTACTTCTCATTCTAGGTGTTAGCATGTAGTGAAGAC<br>TGAAGAGTCCCCTTTTCTGTATATTGAACTATGTTGCCC<br>GAACTCTCAAAAAATGTAGCTAGGTGTGCATCGGATCAT<br>CCGTACAGGTGCGGCAGCATTTTGGAGAGTCCATGCGAC<br>ATAGAATATTGAAGGGGGTTGCTTCACAAGTGTCACCGG<br>AGAGACGGAGGAGAGATTGGATCAAAGAAAAATTAGTTT<br>GAGTTGAGCTTATTGAGGCAGAATTGATTGATACGAGTT<br>TTTTTTTTTTTTTTTGGGGGGGGGGGGGGAGGGTAAC<br>CAATATCATGAATAGTTAGTAGTGGAAACGTCCAGCTCA<br>TATTTTTCATGTGTGTTAATTTTATCATCTACCTGAAAT<br>GTTTTGCAGCTTGGTACAGAGGCGACAGATGAAGAAGA<br>TATACTCTCCGTTACTAGAAGCCATGTTAGCGCTTTACC<br>TTGGGTTTGAATGGATACAGGTAACATAGATTTTCGTTT<br>TATTTATTGGTACTAGTCATCAAAGGTTGTGTCGACATG<br>AATTTTATGTCAGTATAGCTTATTTGTTCTTACAAATGC<br>AACAGACAAACAATATTCTTGCACCTATAATCACACATG<br>GGATATACTCTGCTGTTATTCTGGGACATGGACTTTGGA<br>AAATCCACGATCATCGGAGAAGACTACATCAGAGAATCC<br>AAACACTTAAACAAGAAGGTAATAATTCAAGAAACTTGT<br>AA |
| 49 | g20337<br>cDNA | Nucleic<br>Acid | ATGGAGGTACCGGTGCTAGCTCGGTGTACGAATACTCCG<br>ACGACGTCGTTTATGGGATGTAAAGTGAGTCAATTTGAT<br>TTTCCGATTAGGAGAAAGCTAAATAAGAGGAATTATAAG<br>GCGAAGTTTTCAGTGTTAAGAGTTAAAGCTATGGCGGAG<br>AGGTCGAGTAGTGGTGAGGCATCAGTGGATGCTAGAGAG<br>AGAGAAAGTGGAGGTTACACGGGAACTACTATGGAGGTA<br>ACAACATTTAATCAGAGCTTTAGTGATACGCAATTGCCT<br>GTTTGGGAGAAGATTGGTGCTGTCGTCAGACTCAGTTAT<br>GGAATCGGCATATACGGAGCAATGGCTTTAGCAGGAAAG<br>TTTATATGCTCAATGACAGGAATTGACTGCACAGGAGGG<br>TTCAGTCCATCATTAGATGCCATTGTTGAAGGACTAGGA<br>TATGCAGCTCCCCCGATTATGGCTCTTCTATTTATACTA<br>GATGATGAAGTTGTGAAGCTATCACCTCATGCTCGAGCT<br>ATTAGGGATGTTGAGGATGAAGAGCTGCGGAATTTCTTT<br>TATGGAATGTCACCTTGGCAGTTCATTCTGATTGTGGCT<br>GCTAGCTCTGTTGGAGAGGAACTTTTCTACCGTGCTGCT<br>GTCCAGGGAGCTTTAGCTGACATTTTCTTAAGGGGCAGT<br>GATTTTGTGACTGATGCTAGAGGAATGGCGTCATTGACT<br>GGTGTTTTGCCACCTTATGTCCCGTTTGCTCAAGCATTT<br>GCAGCTGTAATTACAGCAGCTCTCACTGGTTCTTTATAT<br>TATATGGCAGCCTCTCCAAAAGATCCTACCTATGTTGTT<br>GCACCCGTGTTGAAGTCGCATTCAGGCCGTGAAGATCTA<br>AAAAAACTCTTTGCAGCTTGGTACGAGAGGCGACAGATG<br>AAGAAGATATACTCTCCGTTACTAGAAGCCATGTTAGCG<br>CTTTACCTTGGGTTTGAATGGATACAGACAAACAATATT<br>CTTGCACCTATAATCACACATGGGATATACTCTGCTGTT<br>ATTCTGGGACATGGACTTTGGAAAATCCACGATCATCGG<br>AGAAGACTACATCAGAGAATCCAAACACTTAAACAAGAA<br>GGTAATAATTCAAGAAACTTGTAA |
| 50 | g20337<br>protein | Amino<br>Acid | MEVPVLARCTNTPTTSFMGCKVSQFDFPIRRKLNKRNYK<br>AKFSVLRVKAMAERSSSGEASVDARERESGGYTGTTMEV<br>TTFNQSFSDTQLPVWEKIGAVVRLSYGIGIYGAMALAGK<br>FICSMTGIDCTGGFSPSLDAIVEGLGYAAPPIMALLFIL<br>DDEVVKLSPHARAIRDVEDEELRNFFYGMSPWQFILIVA<br>ASSVGEELFYRAAVQGALADIFLRGSDFVTDARGMASLT<br>GVLPPYVPFAQAFAAVITAALTGSLYYMAASPKDPTYVV<br>APVLKSHSGREDLKKLFAAWYERRQMKKIYSPLLEAMLA<br>LYLGFEWIQTNNILAPIITHGIYSAVILGHGLWKIHDHR<br>RRLHQRIQTLKQEGNNSRNL |

TABLE 1-continued

Nucleic acid sequences and amino acid sequences

| SEQ ID NO. | Sequence Description | Sequence Type | Sequence |
|---|---|---|---|
| 51 | g20337_RNAi | Nucleic acid | gactggtgttttgccaccttatgtcccgtttgctcaagc atttgcagctgtaattacagcagctctcactggttcttt atattatatggcagcctctccaaaagatcctacctatgt tgttgcacccgtgttgaagtcgcattcaggccgtgaaga tctaaaaaaactctttgcagcttggtacgagaggcgaca gatgaagaagatatactctccgttactagaagccatgtt agcgctttaccttgggtttgaatggatacagacaaacaa tattcttgcacctataatcTAATAAGATCTTCAACACCT CAACCATTTTTTAATCACTACTACCCATTGCATTGAAC AAACTTCCAAGTTCTTCTTAGCTTCAGATTAAGAAAGTA CCCTTTCTTGGCTTTGTTGATGTGGTACCATTGTCCATT GTCTTGTGTGTTTCCAgattataggtgcaagaatattgt ttgtctgtatccattcaaacccaaggtaaagcgctaaca tggcttctagtaacggagagtatatcttcttcatctgtc gcctctcgtaccaagctgcaaagagttttttagatctt cacggcctgaatgcgacttcaacacgggtgcaacaacat aggtaggatcttttggagaggctgccatataatataaag aaccagtgagagctgctgtaattacagctgcaaatgctt gagcaaacgggacataaggtggcaaaacaccagtc |
| 52 | G58899-Ntom-RNAi | Nucleic acid | GACTGGTGTTTTGCCACCGTATGTCCCATTTGCTCAAGC GTTTGCAGCTGTAATTACGGCAGCTCTCACGGGTTCTCT ATATTATATGGCTGCCTCTCCAAAAGATCCTACCTATGT TGTTGCACCAGTGCTGAAGTCGCATTCAGGTCGTGAAGA TCTTAAAAAACTATTTGCAGCTTGGTACGAGAGGCGACA GATGAAGAAGATATACTCTCCTTTACTAGAAGCCATGTT AGCCCTTTACCTTGGGTTTGAATGGATCCAGACAAACAA CATTTTTGCACCGATAATCTAATAAGATCTTCAACACCT ACACCATTTTTTAATCACTACTACCCATTGCATTGAAC AAACTTCCAAGTTCTTCTTAGCTTCAGATTAAGAAAGTA CCCTTTCTTGGCTTTGTTGATGTGGTACCATTGTCCATT GTCTTGTGTGTTTCCAGATTATCGGTGCAAAAATGTTGT TTGTCTGGATCCATTCAAACCCAAGGTAAAGGGCTAACA TGGCTTCTAGTAAAGGAGAGTATATCTTCTTCATCTGTC GCCTCTCGTACCAAGCTGCAAATAGTTTTTTAAGATCTT CACGACCTGAATGCGACTTCAGCACTGGTGCAACAACAT AGGTAGGATCTTTTGGAGAGGCAGCCATATAATATAGAG AACCCGTGAGAGCTGCCGTAATTACAGCTGCAAACGCTT GAGCAAATGGGACATACGGTGGCAAAACACCAGTC |
| 53 | G58899_Ns-OX | Nucleic acid | Atggaggtaccggtgctagctcggtgtacgaatactccg acgacgtcgtttatgggatgtaaagtgagtcaatttgat tttccgattaggagaaagctaaataagaggaattataag gcgaagttttcagtgttaagagttaaagctatggcggag aggtcgagtagtggtgaggcatcagtggatgctagagag agagaaagtggaggttacacgggaactactatggaggta acaacatttaatcagagctttagtgatacgcaattgcct gtttgggagaagattggtgctgtcgtcagactcagttat ggaatcggcatatacggagcaatggcttagcaggaaag tttatatgctcaatgacaggaattgactgcacaggaggg ttcagtccatcattagatgccattgttgaaggactagga tatgcagctcccccgattatggctcttctatttatacta gatgatgaagttgtgaagctatcacctcatgctcgagct attagggatgttgaggatgaagagctgcggaatttcttt tatgaatgtcaccttggcagttcattctgattgtggct gctagctctgttggagaggaacttttctaccgtgctgct gtccagggagcttagctgacattttcttaaggggcagt gattttgtgactgatgctagaggaatggcgtcattgact ggtgttttgccaccttatgtcccgtttgctcaagcattt gcagctgtaattacagcagctctcactggttctttatat tatatggcagcctctccaaaagatcctacctatgttgtt gcacccgtgttgaagtcgcattcaggccgtgaagatcta aaaaaactctttgcagcttggtacgagaggcgacagatg aagaagatatactctccgttactagaagccatgttagcg ctttaccttgggtttgaatggatacagacaaacaatatt cttgcacctataatcacacatgggatatactctgctgtt attctgggacatggactttggaaaatccacgatcatcgg agaagactacatcagagaatccaaacacttaaacaagaa ggtaataattcaagaaacttgtaa |
| 54 | G58899_Ntom-OX | Nucleic acid | ATGGAGGTACCGGTGCTAGCTCGGTGTACGAATACTCCG ACGACGTCGTTTCTAGGATGTAAAGTGAGTTTATTTGAT TTTCCGATTAGAAGAAAGCTAAATAAGAGGAATTATAAG GCGAAGTTTTCAGTGTTAAGAGTTAAAGCTATGGCGGAG |

TABLE 1-continued

Nucleic acid sequences and amino acid sequences

| SEQ ID NO. | Sequence Description | Sequence Type | Sequence |
|---|---|---|---|
| | | | AGGACGAGTACTGAGGCATCAGCGGATGCTAGAGAGAGA
GAAAGTGGAGGGTACACGGGAACTACGATGGAGGTGACA
ACATTTAATCAGAGCTTTAGTGATGCGCAATTGCCAGTT
TGGGAAAAGATTGGTGCTGTCGTCAGACTCAGTTATGGA
TACGGCATATATGGAGCAATGGCTTTAGCAGGAAAGTTC
ATATGCTCAATGACAGGAATTGACTGCACAGGAGGGTTC
AGTCCATCATTAGATGCCATTGTTGAAGGACTAGGATAT
GCAGCTCCACCAATTATGGCTCTTCTATTTATACTAGAT
GATGAAGTTGTGAAGCTGTCGCCTCATGCTCGAGCTATC
AGAGATGTAGAGGATGAAGAGCTACGGAATTTCTTTTAT
GGAATGTCACCTTGGCAGTTCATTCTGATTGTGGCTGCT
AGCTCTGTTGGAGAAGAGCTTTTCTACCGCGCTGCTGTC
CAGGGAGCTTTAGCTGACATTTTCTTAAGGGGCAGTGGT
TTTGTGACTGATGCTAGAGGAATGGCATCATTGACTGGT
GTTTTGCCACCGTATGTCCCATTTGCTCAAGCGTTTGCA
GCTGTAATTACGGCAGCTCTCACGGGTTCTCTATATTAT
ATGGCTGCCTCTCCAAAAGATCCTACCTATGTTGTTGCA
CCAGTGCTGAAGTCGCATTCAGGTCGTGAAGATCTTAAA
AAACTATTTGCAGCTTGGTACGAGAGGCGACAGATGAAG
AAGATATACTCTCCTTTACTAGAAGCCATGTTAGCCCTT
TACCTTGGGTTTGAATGGATCCAGACAAACAACATTTTT
GCACCGATAATCACACATGGGATATACTCTGCTGTTATT
CTGGGACATGGACTTTGGAAAATCCACGATCATCGGAGA
AGACTACATCAAGAATCCAACAACTTAAACAAGAAGGT
AACAATTCAAGAAACTTGTAA |
| 55 | BCM1 | Amino acid | MELPLLSYASSASFSRTGLCSSSSSSSTSIYEFPERRRS
LKLRFNGGERSRSVIASAERSSEGIEKTTDTVGGGGGGG
AGRFAGTAMEVTTLDRGFANSTTVDFPIWDKIGAVVRLT
YGIGIYGAMAVAGRFICSVTGIDSSGGFDPSLDALLAGL
GYATPPIMALLFILDDEVVKLSPHARAIRDVEDEELRSF
FFGMSPWQFILIVAASSIGEELFYRVAVQGALSDIFLKG
TQLMTDSRGMASLTGVFPPFVPFAEVFAAVITATLTGSL
YFLAASPKDPTYIVAPVLRSRRDDFKKLLSAWYEKRQMK
KIYSPLLEGLLALYLGIEWVQTDNILAPMMTHGIYSAVI
LGHGLWKIHDHRRRLRRRIEHIRSEATDKLI |
| 56 | BCM2 | Amino acid | MGLPLLSCSSTRVTLSSSSSSSWCSSGSGGFRSSSKLFD
SPACSRSDLKKRSGKRNSRLNGLSLEKLRSIKASSSSAG
QSSSEVIDDGDAAARGLAVTSGDVTSVGSFSSGEFVGAG
SGGLAGPSGEVTSVGEFVGGSGGDFKDWDKIGAIVRLSY
GIGIYCGMAVAGRFICEVAGIDYTGGFNASLDTIIAGLG
YASPPIMALLFILDDEVVKLSPHARAIRDVEDDELRGFF
QGMSAWQFILVVTASSVGEELFYRAAFQGALADIFLRGT
DLISDSRGMVALTGLLPPFVPFAQVFAATITAALTGSLY
YIAASPKDPTYIMAPVLKTRSARDELKKLFAAWYERRQM
KKIYSPLLEGLLGLYLGFEWIQTNNLLAPIITHGIYSAV
VLGNGLWKLHHHQQRLRLRVQKLETEGDNNSR |
| 57 | g58899 protein sequence from K326 | Amino acid | MEVPVLARCTNTPTTSFLGCKVSLFDFPIRRKLNKRNYK
AKFSVLRVKAMAERTSTEASADARERESGGYTGNGNGIY
GAMALAGKFICSMTGIDCTGGFSPSLDAIVEGLGYAAPP
IMALLFILDDEVVKLSPHARAIRDVEDEELRNFFYGMSP
WQFILIVAASSVGEELFYRAAVQGALADIFLRGSGFVTD
ARGMASLTGVLPPYVPFAQAFAAVITAALTGSLYYMAAS
PKDPTYVVAPVLKSHSGREDLKKLFAAWYERRQMKKIYS
PLLEAMLALYLGFEWIQTNNIFAPIITHGIYSAVILGHG
LWKIHDHRRRLHQRIQQLKQEGNNSRNL |
| 58 | G58899 consensus sequence | Amino acid | MEVPVLARCTNTPITSFLGCKVSLFDFPIRRKLNKRNYK
AKFSVLRVKAMAERTSTEASADARERESGGYTGTTMEVT
TFNQSFSDAQLPVWEKIGAVVRLSYGIGIYGAMALAGKF
ICSMTGIDCTGGFSPSLDAIVEGLGYAAPPIMALLFILD
DEVVKLSPHARAIRDVEDEELRNFFYGMSPWQFILIVAA
SSVGEELFYRAAVQGALADIFLRGSGFVTDARGMASLTG
VLPPYVPFAQAFAAVITAALTGSLYYMAASPKDPTYVVA
PVLKSHSGREDLKKLFAAWYERRQMKKIYSPLLEAMLAL
YLGFEWIQTNNIFAPIITHGIYSAVILGHGLWKIHDHRR
RLHQRIQQLKQEGNNSRNL |

BACKGROUND

In commercial tobacco (*Nicotiana tabacum*) varieties, accelerated senescence helps reduce levels of tobacco-specific nitrosamines (TSNA) that otherwise accumulate during the yellowing process associated with traditional varieties. Two loci, Yb1 and Yb2, are involved in controlling the rate of senescence in burley tobacco. A third locus, the pale yellow (PY) locus, is also known to be involved in controlling the rate of senescence in burley, flue-cured, and dark cultivars. Presence of the PY locus is also known to reduce TSNA levels.

The location and identify of the PY locus has remained unknown, requiring a time-consuming and subjective selection process to incorporate the PY locus into a desired tobacco variety. This disclosure provides the location of the PY locus within the tobacco genome. This disclosure also provides markers to facilitate accelerated breeding of the PY locus into different tobacco lines. Further, incorporating the PY locus into low-alkaloid tobacco lines produces significant improvements in leaf quality as measured by the USDA grade index.

SUMMARY

In one aspect, this disclosure provides a method of creating a population of tobacco plants exhibiting a pale yellow (PY) phenotype, the method comprising: (a) genotyping a first population of tobacco plants or tobacco seeds for the presence of one or more marker loci associated with a PY quantitative trait locus (QTL) and linked within 20 centimorgans (cM) of a locus selected from the group consisting of SEQ ID NOs: 1-5; (b) selecting one or more tobacco plants or tobacco seeds genotyped in step (a), where the one or more tobacco plants or seeds comprises the one or more marker loci and said PY QTL; and (c) producing from the one or more tobacco plants or tobacco seeds selected in step (b) a second population of tobacco plants or tobacco seeds comprising the PY QTL and the one or more marker loci, where the second population of tobacco plants or tobacco seeds comprises at least one tobacco plant or seed exhibiting said pale yellow phenotype.

In one aspect, this disclosure provides a method of creating a population of tobacco plants exhibiting a pale yellow (PY) phenotype, the method comprising: (a) genotyping a first population of tobacco plants or tobacco seeds for the presence of one or more marker loci associated with a PY quantitative trait locus (QTL) and positioned within 20,000,000 nucleotides of a locus selected from the group consisting of SEQ ID NOs: 1-5; (b) selecting one or more tobacco plants or tobacco seeds genotyped in step (a), where the one or more tobacco plants or seeds comprises the one or more marker loci and the PY QTL; and (c) producing from the one or more tobacco plants or tobacco seeds selected in step (b) a second population of tobacco plants or tobacco seeds comprising the PY QTL and the one or more marker loci, where the second population of tobacco plants or tobacco seeds comprises at least one tobacco plant or seed exhibiting said pale yellow phenotype.

In one aspect, this disclosure provides a method of introgressing a Pale Yellow (PY) QTL, the method comprising: (a) crossing a first tobacco plant comprising the PY quantitative trait locus (QTL) with a second tobacco plant of a different genotype to produce one or more progeny plants or seeds; and (b) selecting a progeny plant or seed produced in step (a) comprising at least one PY-associated single nucleotide polymorphism (SNP) selected from the group consisting of: (i) a guanine at nucleotide position 121 of SEQ ID NO: 1; (ii) a guanine at nucleotide position 121 of SEQ ID NO: 2; (iii) a guanine at nucleotide position 101 of SEQ ID NO: 3; (iv) a thymine at nucleotide position 121 of SEQ ID NO: 4; or (v) a guanine at nucleotide position 121 of SEQ ID NO: 5, where the selected progeny plant or seed comprises a pale yellow phenotype.

In one aspect, this disclosure provides a method of introgressing a Pale Yellow (PY) trait, said method comprising: (a) crossing a first tobacco plant comprising a non-natural mutation in a sequence selected from the group consisting of SEQ ID NOs: 16-21 and 48 with a second tobacco plant of a different genotype to produce one or more progeny plants or seeds; and (b) selecting a progeny plant or seed produced in step (a) comprising the non-natural mutation, where the progeny plant or seed comprises the PY trait.

In one aspect, this disclosure provides a modified tobacco plant, or part thereof, comprising a recombinant nucleic acid construct comprising a heterologous promoter operably linked to a polynucleotide that encodes a non-coding RNA molecule, where the non-coding RNA molecule is capable of binding to an RNA encoding an amino acid sequence having at least 80% sequence identity to an amino acid sequence selected from the group consisting of SEQ ID NOs: 28-33, 46, 47, and 50, where the non-coding RNA molecule suppresses the expression of the amino acid sequence, and where the modified tobacco plant comprises a pale yellow phenotype.

BRIEF DESCRIPTION OF THE DRAWINGS

FIG. 12 depicts an alignment of the g58899 amino acid sequence (SEQ ID NO: 30) with the *Arabidopsis* amino acid sequences for BCM1 (SEQ ID NO: 55) and BCM2 (SEQ ID NO: 56).

FIG. 13 also discloses the g58899 consensus sequence as SEQ ID NO: 58.

DETAILED DESCRIPTION

Figure 1:
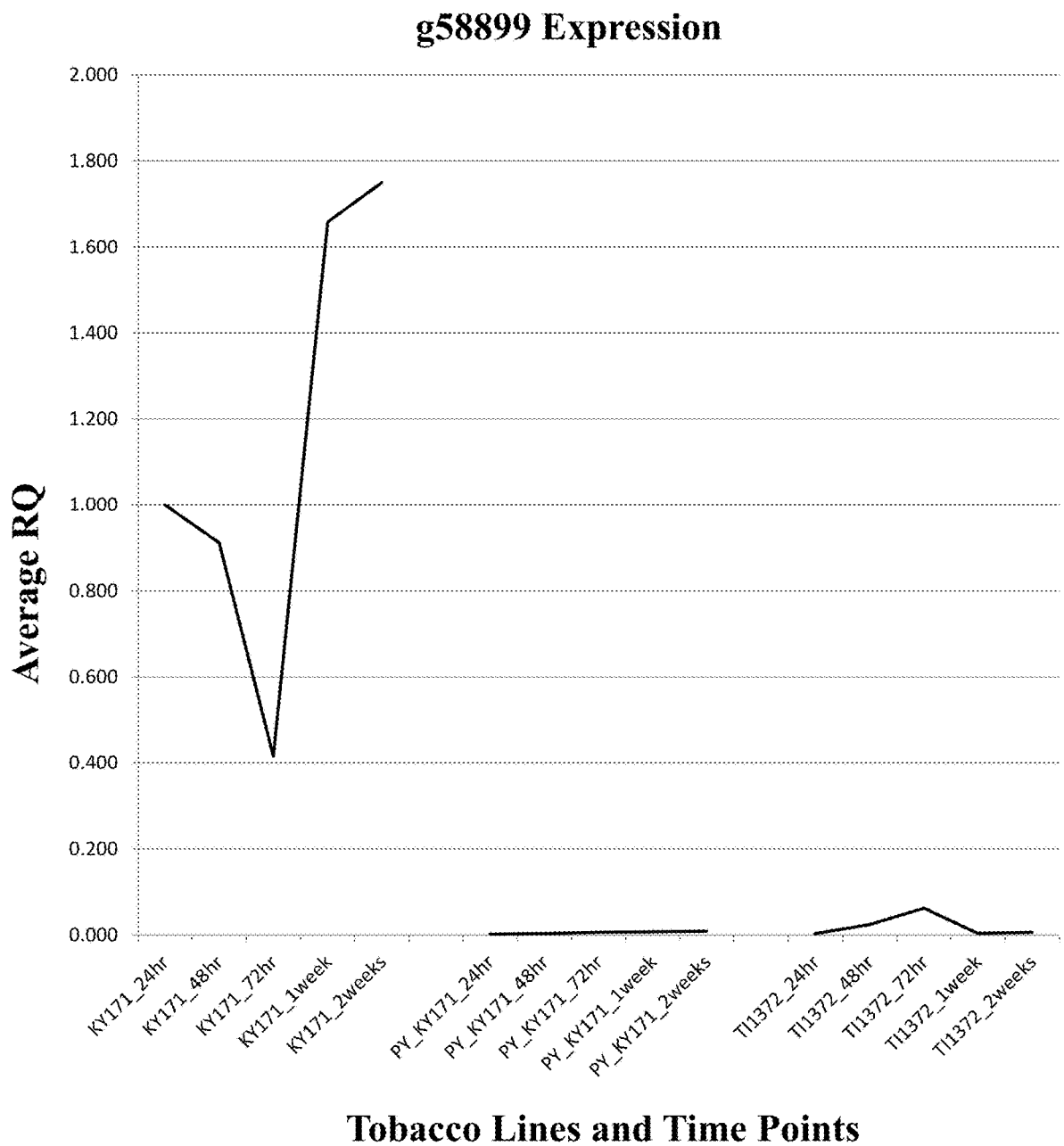
FIG. 1 depicts the expression of g58899 (SEQ ID NO: 24) as measured using quantitative RT-PCR. The average RQ (e.g., fold change) of g58899 as measured across three biological replicates is shown for tobacco varieties KY171, Pale Yellow KY171 (PY_KY171), and TI1372 at various timepoints after topping. Actin is used as a control.

Unless defined otherwise, all technical and scientific terms used have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York).

Any references cited herein, including, e.g., all patents, published patent applications, and non-patent publications, are incorporated herein by reference in their entirety.

When a grouping of alternatives is presented, any and all combinations of the members that make up that grouping of alternatives is specifically envisioned. For example, if an item is selected from a group consisting of A, B, C, and D, the inventors specifically envision each alternative individually (e.g., A alone, B alone, etc.), as well as combinations such as A, B, and D; A and C; B and C; etc. The term "and/or" when used in a list of two or more items means any one of the listed items by itself or in combination with any one or more of the other listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

When a range of numbers is provided herein, the range is understood to inclusive of the edges of the range as well as any number between the defined edges of the range. For example, "between 1 and 10" includes any number between 1 and 10, as well as the number 1 and the number 10.

When the term "about" is used, it is understood to mean plus or minus 10%. For example, "about 100" would include from 90 to 110.

As used herein, the singular form "a," "an," and "the" include plural references unless the context clearly dictates otherwise. For example, the term "a compound" or "at least one compound" may include a plurality of compounds, including mixtures thereof.

The presence of the dominant Pale Yellow (PY) locus in a tobacco plant accelerates leaf senescence. The accelerated senescence allows fewer tobacco-specific nitrosamines (TS-NAs) to accumulate in the leaves. Historically, the only way to introgress the PY locus into different tobacco lines or varieties is by subjectively scoring the phenotype of plants suspected of carrying the PY locus, crossing the suspected carriers to different tobacco plants, then growing and screening the progeny. However, crosses may need to be made prior to the onset of PY-associated phenotypes. To combat this, individual leaves can be treated with chemicals, such as ethephone, to speed senescence. This enables phenotypic scoring earlier in the life of the plant than would otherwise be possible while waiting for senescence to occur naturally. These requirements have made the process of introgressing the PY locus time-consuming and laborious When present, the PY locus produces what is termed the "pale yellow (PY) phenotype" or "PY trait." The PY phenotype accelerates the breakdown of chlorophyll and/or leaf maturation as compared to a control plant that lacks the dominant PY locus. The PY phenotype is manifested by an early onset of yellow coloration in the leaves, eventually resulting in an entirely yellow leaf. The yellowing occurs earlier than it appears in control tobacco plants of the same genetic background that lack the PY trait. Typically, the phenotype of the PY trait does not manifest until after a tobacco plant is topped.

In an aspect, a tobacco plant comprising the PY trait exhibits leaf yellowing of at least one green leaf after topping at least 1 day earlier than a control tobacco plant of the same variety lacking the PY trait when grown under the same environmental conditions. In another aspect, a tobacco plant comprising the PY trait exhibits leaf yellowing of at least one green leaf after topping at least 2 days earlier than a control tobacco plant of the same variety lacking the PY trait when grown under the same environmental conditions. In another aspect, a tobacco plant comprising the PY trait exhibits leaf yellowing of at least one green leaf after topping at least 3 days earlier than a control tobacco plant of the same variety lacking the PY trait when grown under the same environmental conditions. In another aspect, a tobacco plant comprising the PY trait exhibits leaf yellowing of at least one green leaf after topping at least 4 days earlier than a control tobacco plant of the same variety lacking the PY trait when grown under the same environmental conditions. In another aspect, a tobacco plant comprising the PY trait exhibits leaf yellowing of at least one green leaf after topping at least 5 days earlier than a control tobacco plant of the same variety lacking the PY trait when grown under the same environmental conditions. In another aspect, a tobacco plant comprising the PY trait exhibits leaf yellowing of at least one green leaf after topping at least 6 days earlier than a control tobacco plant of the same variety lacking the PY trait when grown under the same environmental conditions. In another aspect, a tobacco plant comprising the PY trait exhibits leaf yellowing of at least one green leaf after topping at least 7 days earlier than a control tobacco plant of the same variety lacking the PY trait when grown under the same environmental conditions. In another aspect, a tobacco plant comprising the PY trait exhibits leaf yellowing of at least one green leaf after topping at least 8 days earlier than a control tobacco plant of the same variety lacking the PY trait when grown under the same environmental conditions. In another aspect, a tobacco plant comprising the PY trait exhibits leaf yellowing of at least one green leaf after topping at least 9 days earlier than a control tobacco plant of the same variety lacking the PY trait when grown under the same environmental conditions. In another aspect, a tobacco plant comprising the PY trait exhibits leaf yellowing of at least one green leaf after topping at least 10 days earlier than a control tobacco plant of the same variety lacking the PY trait when grown under the same environmental conditions. In another aspect, a tobacco plant comprising the PY trait exhibits leaf yellowing of at least one green leaf after topping at least 14 days earlier than a control tobacco plant of the same variety lacking the PY trait when grown under the same environmental conditions. In another aspect, a tobacco plant comprising the PY trait exhibits leaf yellowing of at least one green leaf after topping at least 18 days earlier than a control tobacco plant of the same variety lacking the PY trait when grown under the same environmental conditions. In another aspect, a tobacco plant comprising the PY trait exhibits leaf yellowing of at least one green leaf after topping at least 21 days earlier than a control tobacco plant of the same variety lacking the PY trait when grown under the same environmental conditions.

In tobacco, new leaves are formed as the stalk grows. Therefore, the youngest leaf is the uppermost leaf on the stalk, and the oldest leaf is in the lowermost leaf on the stalk.

In an aspect, the youngest and oldest green leaves remaining on a tobacco plant comprising the PY trait after topping begin to turn yellow within 1 day of each other after the tobacco plant is topped. In another aspect, the youngest and oldest green leaves remaining on a tobacco plant comprising the PY trait after topping begin to turn yellow within 2 days of each other after the tobacco plant is topped. In another aspect, the youngest and oldest green leaves remaining on a tobacco plant comprising the PY trait after topping begin to turn yellow within 3 days of each other after the tobacco plant is topped. In another aspect, the youngest and oldest green leaves remaining on a tobacco plant comprising the PY trait after topping begin to turn yellow within 4 days of each other after the tobacco plant is topped. In another aspect, the youngest and oldest green leaves remaining on a tobacco plant comprising the PY trait after topping begin to turn yellow within 5 days of each other after the tobacco plant is topped. In another aspect, the youngest and oldest green leaves remaining on a tobacco plant comprising the PY trait after topping begin to turn yellow within 6 days of each other after the tobacco plant is topped. In another aspect, the youngest and oldest green leaves remaining on a tobacco plant comprising the PY trait after topping begin to turn yellow within 7 days of each other after the tobacco plant is topped.

It is appreciated in the art that the PY phenotype can manifest in slightly different ways depending on the tobacco variety. The PY phenotype is most easily observed in dark tobacco varieties because conventional dark tobacco varieties do not turn yellow during the ripening process. Typically, leaves of dark tobacco varieties continue to expand, thicken, and become more brittle after topping, but the leaves stay dark green in color. Occasionally, the leaves also develop age spots that are not green in color. When conventional dark tobacco varieties are harvested, approximately 5 to 7 weeks after topping, almost no yellowing is observed in the leaves or stalks. In contrast, when the PY trait has been introgressed into a dark tobacco variety the plants will begin to show yellowing of leaves within two weeks of topping. The plants will exhibit yellowing of all leaves, particularly in the leaf lamina (mid-ribs typically remain green). The plants will also exhibit yellow stalks.

In an aspect, a dark tobacco plant comprising the PY trait exhibits yellowing of at least one green leaf after topping.

Unlike dark tobacco varieties, conventional burley tobacco varieties yellow during the ripening process. When burley tobacco is topped, some of the lower (older) leaves may have begun to yellow already. Conventional burley tobacco will continue to yellow, from bottom to top, after topping. However, when the PY trait is present in burley tobacco the plant turns yellow at an accelerated pace, and all leaves begin to yellow at the same time, often within one week of topping.

As used herein, "yellowing" refers to the loss of chlorophyll in leaf or stalk tissue of tobacco, resulting in a yellow coloration.

This disclosure, for the first time, identifies the chromosomal position of the PY locus. This disclosure also provides markers suitable for tracking the PY locus in tobacco.

In an aspect, this disclosure provides a method of creating a population of tobacco plants exhibiting a pale yellow (PY) phenotype, the method comprising: (a) genotyping a first population of tobacco plants or tobacco seeds for the presence of one or more marker loci associated with a PY quantitative trait locus (QTL) and linked within 20 centimorgans of a locus selected from the group consisting of SEQ ID NOs: 1-5; (b) selecting one or more tobacco plants or tobacco seeds genotyped in step (a), where the one or more tobacco plants or tobacco seeds comprises the one or more marker loci and the PY QTL; and (c) producing from the one or more tobacco plants or tobacco seeds selected in step (b) a second population of tobacco plants or tobacco seeds comprising the PY QTL and the one or more marker loci, where the second population of tobacco plants or tobacco seeds comprises at least one tobacco plant or tobacco seed exhibiting the PY phenotype.

In another aspect, this disclosure provides a method of creating a population of tobacco plants exhibiting a pale yellow (PY) phenotype, the method comprising: (a) genotyping a first population of tobacco plants or tobacco seeds for the presence of one or more marker loci associated with a PY quantitative trait locus (QTL) and linked within 20,000,000 nucleotides of a locus selected from the group consisting of SEQ ID NOs: 1-5; (b) selecting one or more tobacco plants or tobacco seeds genotyped in step (a), where the one or more tobacco plants or tobacco seeds comprises the one or more marker loci and the PY QTL; and (c) producing from the one or more tobacco plants or tobacco seeds selected in step (b) a second population of tobacco plants or tobacco seeds comprising the PY QTL and the one or more marker loci, where the second population of tobacco plants or tobacco seeds comprises at least one tobacco plant or tobacco seed exhibiting the PY phenotype.

Markers

As used herein, the phrase "associated with" or "linked to" refers to a recognizable and/or assayable relationship between two entities. For example, the phrase "associated with PY trait" or "associated with PY QTL" refers to a trait, locus, gene, allele, marker, phenotype, etc., or the expression thereof, the presence or absence of which can influence an extent, degree, and/or rate at which a plant or a part of interest thereof that has a PY trait or PY QTL. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with PY trait" refers to a marker whose presence or absence can be used to predict whether and to what extent a plant will display a PY phenotype.

In an aspect, the PY QTL is positioned between the SSR markers PT51549 and PT55414 on chromosome 15 of the tobacco genome.

As used herein, a "locus" refers to a fixed position on a chromosome. In an aspect, a locus comprises a gene. In another aspect, a locus comprises a marker. A locus can represent a single nucleotide, a few nucleotides, or a large number of nucleotides in a genomic region. As used herein, a "marker," "molecular marker," or "marker locus" refers to a nucleic acid sequence that is sufficiently unique to characterize a specific locus on the genome. Any detectable polymorphic trait can be used as a marker so long as it is inherited differentially and exhibits linkage disequilibrium with a phenotypic trait of interest. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under environmental conditions where the trait can be expressed. It is appreciated in the art that markers can comprise more than two alleles, and more than one allele can be associated with a given trait.

As used herein, "allele" refers to an alternative nucleic acid sequence at a particular locus. The length of an allele can be as small as one nucleotide base. For example, a first allele can occur on one chromosome, while a second allele occurs on a second homologous chromosome, e.g., as occurs for different chromosomes of a heterozygous individual, or between different homozygous or heterozygous individuals in a population.

Genetic linkage refers to the tendency of DNA loci (e.g., genes, markers) to be inherited together during the meiosis phase of sexual reproduction. Loci that are physically near each other are more likely to be "linked" to each other genetically. Linkage can refer to either genetic linkage or physical linkage. Genetic linkage is typically measured using centimorgans, and physical linkage is typically measured in nucleotides.

As used herein, a "centimorgan" (cM) refers to the distance between chromosome positions (also termed loci or markers) for which the expected average number of intervening chromosomal crossovers in a single generation is 0.01. Two loci are typically considered unlinked genetically if the genetic distance between the two loci is greater than 50 cM.

In an aspect, one or more marker loci are within 20 cM of a locus selected from the group consisting of SEQ ID NOs: 1-5. In an aspect, one or more marker loci are within 17.5 cM of a locus selected from the group consisting of SEQ ID NOs: 1-5. In an aspect, one or more marker loci are within 15 cM of a locus selected from the group consisting of SEQ ID NOs: 1-5. In an aspect, one or more marker loci are within 14 cM of a locus selected from the group consisting of SEQ ID NOs: 1-5. In an aspect, one or more marker loci are within 13 cM of a locus selected from the group consisting of SEQ ID NOs: 1-5. In an aspect, one or more marker loci are within 12 cM of a locus selected from the group consisting of SEQ ID NOs: 1-5. In an aspect, one or more marker loci are within 11 cM of a locus selected from the group consisting of SEQ ID NOs: 1-5. In an aspect, one or more marker loci are within 10 cM of a locus selected from the group consisting of SEQ ID NOs: 1-5. In an aspect, one or more marker loci are within 9 cM of a locus selected from the group consisting of SEQ ID NOs: 1-5. In an aspect, one or more marker loci are within 8 cM of a locus selected from the group consisting of SEQ ID NOs: 1-5. In an aspect, one or more marker loci are within 7 cM of a locus selected from the group consisting of SEQ ID NOs: 1-5. In an aspect, one or more marker loci are within 6 cM of a locus selected from the group consisting of SEQ ID NOs: 1-5. In an aspect, one or more marker loci are within 5 cM of a locus selected from the group consisting of SEQ ID NOs: 1-5. In an aspect, one or more marker loci are within 4 cM of a locus selected from the group consisting of SEQ ID NOs: 1-5. In an aspect, one or more marker loci are within 3 cM of a locus selected from the group consisting of SEQ ID NOs: 1-5. In an aspect, one or more marker loci are within 2 cM of a locus selected from the group consisting of SEQ ID NOs: 1-5. In an aspect, one or more marker loci are within 1 cM of a locus selected from the group consisting of SEQ ID NOs: 1-5. In an aspect, one or more marker loci are within 0.5 cM of a locus selected from the group consisting of SEQ ID NOs: 1-5. In an aspect, one or more marker loci are within 0.25 cM of a locus selected from the group consisting of SEQ ID NOs: 1-5.

In an aspect, one or more marker loci are within between 0.01 cM and 20 cM of a locus selected from the group consisting of SEQ ID NOs: 1-5. In an aspect, one or more marker loci are within between 0.05 cM and 20 cM of a locus selected from the group consisting of SEQ ID NOs: 1-5. In an aspect, one or more marker loci are within between 0.1 cM and 20 cM of a locus selected from the group consisting of SEQ ID NOs: 1-5. In an aspect, one or more marker loci are within between 0.5 cM and 20 cM of a locus selected from the group consisting of SEQ ID NOs: 1-5. In an aspect, one or more marker loci are within between 1 cM and 20 cM of a locus selected from the group consisting of SEQ ID NOs: 1-5. In an aspect, one or more marker loci are within between 5 cM and 20 cM of a locus selected from the group consisting of SEQ ID NOs: 1-5. In an aspect, one or more marker loci are within between 10 cM and 20 cM of a locus selected from the group consisting of SEQ ID NOs: 1-5. In an aspect, one or more marker loci are within between 0.01 cM and 15 cM of a locus selected from the group consisting of SEQ ID NOs: 1-5. In an aspect, one or more marker loci are within between 0.01 cM and 10 cM of a locus selected from the group consisting of SEQ ID NOs: 1-5. In an aspect, one or more marker loci are within between 0.01 cM and 7.5 cM of a locus selected from the group consisting of SEQ ID NOs: 1-5. In an aspect, one or more marker loci are within between 0.01 cM and 5 cM of a locus selected from the group consisting of SEQ ID NOs: 1-5. In an aspect, one or more marker loci are within between 0.01 cM and 2.5 cM of a locus selected from the group consisting of SEQ ID NOs: 1-5. In an aspect, one or more marker loci are within between 0.01 cM and 1 cM of a locus selected from the group consisting of SEQ ID NOs: 1-5. In an aspect, one or more marker loci are within between 0.5 cM and 10 cM of a locus selected from the group consisting of SEQ ID NOs: 1-5. In an aspect, one or more marker loci are within between 0.5 cM and 5 cM of a locus selected from the group consisting of SEQ ID NOs: 1-5.

In an aspect, one or more marker loci are within 100,000,000 nucleotides of a locus selected from the group consisting of SEQ ID NOs: 1-5. In an aspect, one or more marker loci are within 75,000,000 nucleotides of a locus selected from the group consisting of SEQ ID NOs: 1-5. In an aspect, one or more marker loci are within 50,000,000 nucleotides of a locus selected from the group consisting of SEQ ID NOs: 1-5. In an aspect, one or more marker loci are within 40,000,000 nucleotides of a locus selected from the group consisting of SEQ ID NOs: 1-5. In an aspect, one or more marker loci are within 30,000,000 nucleotides of a locus selected from the group consisting of SEQ ID NOs: 1-5. In an aspect, one or more marker loci are within 25,000,000 nucleotides of a locus selected from the group consisting of SEQ ID NOs: 1-5. In an aspect, one or more marker loci are within 20,000,000 nucleotides of a locus selected from the group consisting of SEQ ID NOs: 1-5. In an aspect, one or more marker loci are within 17,500,000 nucleotides of a locus selected from the group consisting of SEQ ID NOs: 1-5. In an aspect, one or more marker loci are within 15,000,000 nucleotides of a locus selected from the group consisting of SEQ ID NOs: 1-5. In an aspect, one or more marker loci are within 12,500,000 nucleotides of a locus selected from the group consisting of SEQ ID NOs: 1-5. In an aspect, one or more marker loci are within 10,000,000 nucleotides of a locus selected from the group consisting of SEQ ID NOs: 1-5. In an aspect, one or more marker loci are within 9,000,000 nucleotides of a locus selected from the group consisting of SEQ ID NOs: 1-5. In an aspect, one or more marker loci are within 8,000,000 nucleotides of a locus selected from the group consisting of SEQ ID NOs: 1-5. In an aspect, one or more marker loci are within 7,000,000 nucleotides of a locus selected from the group consisting of SEQ ID NOs: 1-5. In an aspect, one or more marker loci are within 6,000,000 nucleotides of a locus selected from the group consisting of SEQ ID NOs: 1-5. In an aspect, one or more marker loci are within 5,000,000 nucleotides of a locus selected from the group consisting of SEQ ID NOs: 1-5. In an aspect, one or more marker loci are within 4,000,000 nucleotides of a locus selected from the group consisting of SEQ ID NOs: 1-5. In an aspect, one or more marker loci are within 3,000,000 nucleotides of a locus selected from the group consisting of SEQ ID NOs: 1-5. In an aspect, one or more marker loci are within 2,000,000 nucleotides of a locus selected from the group consisting of SEQ ID NOs: 1-5. In an aspect, one or more marker loci are within 1,000,000 nucleotides of a locus selected from the group consisting of SEQ ID NOs: 1-5. In an aspect, one or more marker loci are within 750,000 nucleotides of a locus selected from the group consisting of SEQ ID NOs: 1-5. In an aspect, one or more marker loci are within 500,000 nucleotides of a locus selected from the group consisting of SEQ ID NOs: 1-5. In an aspect, one or more marker loci are within 250,000 nucleotides of a locus selected from the group consisting of SEQ ID NOs: 1-5. In an aspect, one or more marker loci are within 100,000 nucleotides of a locus selected from the group consisting of SEQ ID NOs: 1-5. In an aspect, one or more marker loci are within 75,000 nucleotides of a locus selected from the group consisting of SEQ ID NOs: 1-5. In an aspect, one or more marker loci are within 50,000 nucleotides of a locus selected from the group consisting of SEQ ID NOs: 1-5. In an aspect, one or more marker loci are within 25,000 nucleotides of a locus selected from the group consisting of SEQ ID NOs: 1-5. In an aspect, one or more marker loci are within 10,000 nucleotides of a locus selected from the group consisting of SEQ ID NOs: 1-5. In an aspect, one or more marker loci are within 5,000 nucleotides of a locus selected from the group consisting of SEQ ID NOs: 1-5. In an aspect, one or more marker loci are within 2,500 nucleotides of a locus selected from the group consisting of SEQ ID NOs: 1-5. In an aspect, one or more marker loci are within 1,000 nucleotides of a locus selected from the group consisting of SEQ ID NOs: 1-5. In an aspect, one or more marker loci are within 750 nucleotides of a locus selected from the group consisting of SEQ ID NOs: 1-5. In an aspect, one or more marker loci are within 500 nucleotides of a locus selected from the group consisting of SEQ ID NOs: 1-5. In an aspect, one or more marker loci are within 250 nucleotides of a locus selected from the group consisting of SEQ ID NOs: 1-5. In an aspect, one or more marker loci are within 100 nucleotides of a locus selected from the group consisting of SEQ ID NOs: 1-5.

In an aspect, one or more marker loci are between 1 nucleotide and 100,000,000 nucleotides of a locus selected from the group consisting of SEQ ID NOs: 1-5. In an aspect, one or more marker loci are between 10 nucleotides and 100,000,000 nucleotides of a locus selected from the group consisting of SEQ ID NOs: 1-5. In an aspect, one or more marker loci are between 100 nucleotides and 100,000,000 nucleotides of a locus selected from the group consisting of SEQ ID NOs: 1-5. In an aspect, one or more marker loci are between 1,000 nucleotides and 100,000,000 nucleotides of a locus selected from the group consisting of SEQ ID NOs: 1-5. In an aspect, one or more marker loci are between 10,000 nucleotides and 100,000,000 nucleotides of a locus selected from the group consisting of SEQ ID NOs: 1-5. In an aspect, one or more marker loci are between 100,000 nucleotides and 100,000,000 nucleotides of a locus selected from the group consisting of SEQ ID NOs: 1-5. In an aspect, one or more marker loci are between 1,000,000 nucleotides and 100,000,000 nucleotides of a locus selected from the group consisting of SEQ ID NOs: 1-5. In an aspect, one or more marker loci are between 10,000,000 nucleotides and 100,000,000 nucleotides of a locus selected from the group consisting of SEQ ID NOs: 1-5. In an aspect, one or more marker loci are between 1 nucleotide and 50,000,000 nucleotides of a locus selected from the group consisting of SEQ ID NOs: 1-5. In an aspect, one or more marker loci are between 10 nucleotides and 50,000,000 nucleotides of a locus selected from the group consisting of SEQ ID NOs: 1-5. In an aspect, one or more marker loci are between 100 nucleotides and 50,000,000 nucleotides of a locus selected from the group consisting of SEQ ID NOs: 1-5. In an aspect, one or more marker loci are between 1,000 nucleotides and 50,000,000 nucleotides of a locus selected from the group consisting of SEQ ID NOs: 1-5. In an aspect, one or more marker loci are between 10,000 nucleotides and 50,000,000 nucleotides of a locus selected from the group consisting of SEQ ID NOs: 1-5. In an aspect, one or more marker loci are between 100,000 nucleotides and 50,000,000 nucleotides of a locus selected from the group consisting of SEQ ID NOs: 1-5. In an aspect, one or more marker loci are between 1,000,000 nucleotides and 50,000,000 nucleotides of a locus selected from the group consisting of SEQ ID NOs: 1-5. In an aspect, one or more marker loci are between 10,000,000 nucleotides and 50,000,000 nucleotides of a locus selected from the group consisting of SEQ ID NOs: 1-5. In an aspect, one or more marker loci are between 1 nucleotide and 20,000,000 nucleotides of a locus selected from the group consisting of SEQ ID NOs: 1-5. In an aspect, one or more marker loci are between 10 nucleotides and 20,000,000 nucleotides of a locus selected from the group consisting of SEQ ID NOs: 1-5. In an aspect, one or more marker loci are between 100 nucleotides and 20,000,000 nucleotides of a locus selected from the group consisting of SEQ ID NOs: 1-5. In an aspect, one or more marker loci are between 1,000 nucleotides and 20,000,000 nucleotides of a locus selected from the group consisting of SEQ ID NOs: 1-5. In an aspect, one or more marker loci are between 10,000 nucleotides and 20,000,000 nucleotides of a locus selected from the group consisting of SEQ ID NOs: 1-5. In an aspect, one or more marker loci are between 100,000 nucleotides and 20,000,000 nucleotides of a locus selected from the group consisting of SEQ ID NOs: 1-5. In an aspect, one or more marker loci are between 1,000,000 nucleotides and 20,000,000 nucleotides of a locus selected from the group consisting of SEQ ID NOs: 1-5. In an aspect, one or more marker loci are between 10,000,000 nucleotides and 20,000,000 nucleotides of a locus selected from the group consisting of SEQ ID NOs: 1-5. In an aspect, one or more marker loci are between 1 nucleotide and 10,000,000 nucleotides of a locus selected from the group consisting of SEQ ID NOs: 1-5. In an aspect, one or more marker loci are between 10 nucleotides and 10,000,000 nucleotides of a locus selected from the group consisting of SEQ ID NOs: 1-5. In an aspect, one or more marker loci are between 100 nucleotides and 10,000,000 nucleotides of a locus selected from the group consisting of SEQ ID NOs: 1-5. In an aspect, one or more marker loci are between 1,000 nucleotides and 10,000,000 nucleotides of a locus selected from the group consisting of SEQ ID NOs: 1-5. In an aspect, one or more marker loci are between 10,000 nucleotides and 10,000,000 nucleotides of a locus selected from the group consisting of SEQ ID NOs: 1-5. In an aspect, one or more marker loci are between 100,000 nucleotides and 10,000,000 nucleotides of a locus selected from the group consisting of SEQ ID NOs: 1-5. In an aspect, one or more marker loci are between 1,000,000 nucleotides and 10,000,000 nucleotides of a locus selected from the group consisting of SEQ ID NOs: 1-5.

In an aspect, a locus comprises SEQ ID NO: 1. In another aspect, a locus comprises SEQ ID NO: 2. In another aspect, a locus comprises SEQ ID NO: 3. In another aspect, a locus comprises SEQ ID NO: 4. In another aspect, a locus comprises SEQ ID NO: 5.

Any type of polymorphic marker is envisioned for use with the methods and compositions provided herein. In an aspect, a marker locus is selected from the group consisting of SEQ ID NOs: 1-5. In an aspect, a marker locus comprises SEQ ID NO: 1. In an aspect, a marker locus comprises SEQ ID NO: 2. In an aspect, a marker locus comprises SEQ ID NO: 3. In an aspect, a marker locus comprises SEQ ID NO: 4. In an aspect, a marker locus comprises SEQ ID NO: 5.

In an aspect, one or more marker loci comprise a single nucleotide polymorphism (SNP) selected from the group consisting of: (a) a guanine at position 121 of SEQ ID NO: 1; (b) a guanine at position 121 of SEQ ID NO: 2; (c) a guanine at position 101 of SEQ ID NO: 3; (d) a thymine at position 121 of SEQ ID NO: 4; and (e) a guanine at position 121 of SEQ ID NO: 5.

In an aspect, a marker locus comprises a guanine at position 121 of SEQ ID NO: 1. In another aspect, a marker locus comprises a guanine at position 121 of SEQ ID NO: 2. In another aspect, a marker locus comprises a guanine at position 101 of SEQ ID NO: 3. In another aspect, a marker locus comprises a thymine at position 121 of SEQ ID NO: 4. In another aspect, a marker locus comprises a guanine at position 121 of SEQ ID NO: 5.

In an aspect, a plant or seed is homozygous for a SNP. In another aspect, a plant or seed is heterozygous for a SNP.

In an aspect, a plant or seed is homozygous at a marker locus. In another aspect, a plant or seed is heterozygous at a marker locus.

In an aspect, a marker locus comprises one or more single nucleotide polymorphism markers. In another aspect, a marker locus comprises one or more insertion-deletion (INDEL) markers. In another aspect, a marker locus comprises one or more simple sequence repeat (SSR) markers. In another aspect, a marker locus comprises one or more restriction fragment length polymorphism (RFLP) markers. In another aspect, a marker locus comprises one or more random amplified polymorphic DNA (RAPD) markers. In another aspect, a marker locus comprises one or more amplified fragment length polymorphism (AFLP) markers. In an aspect, one or more marker loci are selected from the group consisting of one or more SNP markers, one or more INDEL markers, one or more SSR markers, one or more RFLP markers, one or more RAPD markers, and one or more AFLP markers.

It will be appreciated that genotyping must involve the determination of the genetic make-up of an individual plant or plant cell by examining the DNA sequence using molecular assays and comparing the sequence to a reference sequence. Genotyping is distinct from visual phenotyping, which is performed with no more than a visual inspection of the plant or plant cell. In an aspect, genotyping does not comprise visual phenotyping of a plant or plant cell.

In an aspect, genotyping comprises detecting one or more marker loci. In another aspect, genotype comprises detecting one or more alleles or one or more marker loci. Detecting the presence of a marker locus, or a particular allele of a marker locus can comprise any suitable method or technique or method known in the art. Non-limiting examples for detecting a marker or an allele of a marker include gel electrophoresis, DNA sequencing, RNA sequencing, Southern blot, and microarray technology.

In an aspect, genotyping comprises the use of an oligonucleotide probe. As used herein, As used herein, an "oligonucleotide probe" refers to an oligonucleotide (synthetic or occurring naturally) that is complementary (though not necessarily fully complementary) to a polynucleotide of interest and forms a duplex structure by hybridization with at least one strand of the polynucleotide of interest. In an aspect, an oligonucleotide probe comprises DNA. In another aspect, an oligonucleotide probe comprises RNA. In another aspect, an oligonucleotide probe is single-stranded. In another aspect, an oligonucleotide probe is partially double-stranded. In an aspect, an oligonucleotide probe can function as a primer for PCR.

Typically, oligonucleotide probes comprise between 10 nucleotides and 50 nucleotides in length, but longer or shorter sequences can be employed. In an aspect an oligonucleotide probe comprises between 15 nucleotides and 40 nucleotides. In an aspect an oligonucleotide probe comprises between 15 nucleotides and 35 nucleotides. In an aspect an oligonucleotide probe comprises between 15 nucleotides and 30 nucleotides. In an aspect an oligonucleotide probe comprises between 20 nucleotides and 40 nucleotides. In an aspect an oligonucleotide probe comprises between 20 nucleotides and 35 nucleotides. In an aspect an oligonucleotide probe comprises between 10 nucleotides and 100 nucleotides. In an aspect an oligonucleotide probe comprises between 10 nucleotides and 75 nucleotides. In an aspect an oligonucleotide probe comprises between 10 nucleotides and 50 nucleotides. In an aspect an oligonucleotide probe comprises between 10 nucleotides and 40 nucleotides. In an aspect an oligonucleotide probe comprises between 10 nucleotides and 30 nucleotides.

In an aspect, an oligonucleotide probe comprises at least 18 nucleotides. In an aspect, an oligonucleotide probe comprises at least 19 nucleotides. In an aspect, an oligonucleotide probe comprises at least 20 nucleotides. In an aspect, an oligonucleotide probe comprises at least 21 nucleotides. In an aspect, an oligonucleotide probe comprises at least 22 nucleotides. In an aspect, an oligonucleotide probe comprises at least 23 nucleotides. In an aspect, an oligonucleotide probe comprises at least 24 nucleotides. In an aspect, an oligonucleotide probe comprises at least 25 nucleotides. In an aspect, an oligonucleotide probe comprises at least 26 nucleotides. In an aspect, an oligonucleotide probe comprises at least 27 nucleotides. In an aspect, an oligonucleotide probe comprises at least 28 nucleotides. In an aspect, an oligonucleotide probe comprises at least 29 nucleotides. In an aspect, an oligonucleotide probe comprises at least 30 nucleotides. In an aspect, an oligonucleotide probe comprises at least 31 nucleotides. In an aspect, an oligonucleotide probe comprises at least 32 nucleotides. In an aspect, an oligonucleotide probe comprises at least 33 nucleotides. In an aspect, an oligonucleotide probe comprises at least 34 nucleotides. In an aspect, an oligonucleotide probe comprises at least 35 nucleotides.

A probe can further contain a detectable label. The detectable label can be on the 5'-end, the 3'-end, or internal to the oligonucleotide probe. Oligonucleotide probes can be designed to hybridize to specific markers or specific alleles of markers. Non-limiting examples of detectable labels include biotin, fluorophores (e.g., green fluorescence protein, Texas Red®, VIC™, JUN™, ABY™), and radioactive isotopes (e.g., phosphorus-32, sulfur-35, iodine-125).

In an aspect, an oligonucleotide probe is a TaqMan™ probe. TaqMan™ probes are often used to increase the specificity of quantitative PCR. TaqMan™ probes rely on the 5' to 3' exonuclease activity of Taq polymerase to cleave a dual-labeled probe during hybridization to the complementary target sequence and fluorophore-based detection. As in other quantitative PCR methods, the resulting fluorescence signal permits quantitative measurements of the accumulation of the product during the exponential stages of the PCR; however, the TaqMan™ probe significantly increases the specificity of the detection.

In an aspect, an oligonucleotide probe comprises at nucleic acid sequence at least 80% identical to a nucleic acid sequence selected from the group consisting of SEQ ID NOs: 34-42. In another aspect, an oligonucleotide probe comprises at nucleic acid sequence at least 85% identical to a nucleic acid sequence selected from the group consisting of SEQ ID NOs: 34-42. In another aspect, an oligonucleotide probe comprises at nucleic acid sequence at least 90% identical to a nucleic acid sequence selected from the group consisting of SEQ ID NOs: 34-42. In another aspect, an oligonucleotide probe comprises at nucleic acid sequence at least 95% identical to a nucleic acid sequence selected from the group consisting of SEQ ID NOs: 34-42. In another aspect, an oligonucleotide probe comprises at nucleic acid sequence at least 96% identical to a nucleic acid sequence selected from the group consisting of SEQ ID NOs: 34-42. In another aspect, an oligonucleotide probe comprises at nucleic acid sequence at least 97% identical to a nucleic acid sequence selected from the group consisting of SEQ ID NOs: 34-42. In another aspect, an oligonucleotide probe comprises at nucleic acid sequence at least 98% identical to a nucleic acid sequence selected from the group consisting of SEQ ID NOs: 34-42. In another aspect, an oligonucleotide probe comprises at nucleic acid sequence at least 99% identical to a nucleic acid sequence selected from the group consisting of SEQ ID NOs: 34-42. In another aspect, an oligonucleotide probe comprises at nucleic acid sequence at 100% identical to a nucleic acid sequence selected from the group consisting of SEQ ID NOs: 34-42.

In an aspect, an oligonucleotide probe is at least 80% identical to at least 18 contiguous nucleotides of a nucleic acid sequence selected from the group consisting of SEQ ID NOs: 16-21 and 48. In another aspect, an oligonucleotide probe is at least 85% identical to at least 18 contiguous nucleotides of a nucleic acid sequence selected from the group consisting of SEQ ID NOs: 16-21 and 48. In another aspect, an oligonucleotide probe is at least 90% identical to at least 18 contiguous nucleotides of a nucleic acid sequence selected from the group consisting of SEQ ID NOs: 16-21 and 48. In another aspect, an oligonucleotide probe is at least 91% identical to at least 18 contiguous nucleotides of a nucleic acid sequence selected from the group consisting of SEQ ID NOs: 16-21 and 48. In another aspect, an oligonucleotide probe is at least 92% identical to at least 18 contiguous nucleotides of a nucleic acid sequence selected from the group consisting of SEQ ID NOs: 16-21 and 48. In another aspect, an oligonucleotide probe is at least 93% identical to at least 18 contiguous nucleotides of a nucleic acid sequence selected from the group consisting of SEQ ID NOs: 16-21 and 48. In another aspect, an oligonucleotide probe is at least 94% identical to at least 18 contiguous nucleotides of a nucleic acid sequence selected from the group consisting of SEQ ID NOs: 16-21 and 48. In another aspect, an oligonucleotide probe is at least 95% identical to at least 18 contiguous nucleotides of a nucleic acid sequence selected from the group consisting of SEQ ID NOs: 16-21 and 48. In another aspect, an oligonucleotide probe is at least 96% identical to at least 18 contiguous nucleotides of a nucleic acid sequence selected from the group consisting of SEQ ID NOs: 16-21 and 48. In another aspect, an oligonucleotide probe is at least 97% identical to at least 18 contiguous nucleotides of a nucleic acid sequence selected from the group consisting of SEQ ID NOs: 16-21 and 48. In another aspect, an oligonucleotide probe is at least 98% identical to at least 18 contiguous nucleotides of a nucleic acid sequence selected from the group consisting of SEQ ID NOs: 16-21 and 48. In another aspect, an oligonucleotide probe is at least 99% identical to at least 18 contiguous nucleotides of a nucleic acid sequence selected from the group consisting of SEQ ID NOs: 16-21 and 48. In another aspect, an oligonucleotide probe is 100% identical to at least 18 contiguous nucleotides of a nucleic acid sequence selected from the group consisting of SEQ ID NOs: 16-21 and 48.

In an aspect, an oligonucleotide probe is at least 80% identical to at least 21 contiguous nucleotides of a nucleic acid sequence selected from the group consisting of SEQ ID NOs: 16-21 and 48. In another aspect, an oligonucleotide probe is at least 85% identical to at least 21 contiguous nucleotides of a nucleic acid sequence selected from the group consisting of SEQ ID NOs: 16-21 and 48. In another aspect, an oligonucleotide probe is at least 90% identical to at least 21 contiguous nucleotides of a nucleic acid sequence selected from the group consisting of SEQ ID NOs: 16-21 and 48. In another aspect, an oligonucleotide probe is at least 91% identical to at least 21 contiguous nucleotides of a nucleic acid sequence selected from the group consisting of SEQ ID NOs: 16-21 and 48. In another aspect, an oligonucleotide probe is at least 92% identical to at least 21 contiguous nucleotides of a nucleic acid sequence selected from the group consisting of SEQ ID NOs: 16-21 and 48. In another aspect, an oligonucleotide probe is at least 93% identical to at least 21 contiguous nucleotides of a nucleic acid sequence selected from the group consisting of SEQ ID NOs: 16-21 and 48. In another aspect, an oligonucleotide probe is at least 94% identical to at least 21 contiguous nucleotides of a nucleic acid sequence selected from the group consisting of SEQ ID NOs: 16-21 and 48. In another aspect, an oligonucleotide probe is at least 95% identical to at least 21 contiguous nucleotides of a nucleic acid sequence selected from the group consisting of SEQ ID NOs: 16-21 and 48. In another aspect, an oligonucleotide probe is at least 96% identical to at least 21 contiguous nucleotides of a nucleic acid sequence selected from the group consisting of SEQ ID NOs: 16-21 and 48. In another aspect, an oligonucleotide probe is at least 97% identical to at least 21 contiguous nucleotides of a nucleic acid sequence selected from the group consisting of SEQ ID NOs: 16-21 and 48. In another aspect, an oligonucleotide probe is at least 98% identical to at least 21 contiguous nucleotides of a nucleic acid sequence selected from the group consisting of SEQ ID NOs: 16-21 and 48. In another aspect, an oligonucleotide probe is at least 99% identical to at least 21 contiguous nucleotides of a nucleic acid sequence selected from the group consisting of SEQ ID NOs: 16-21 and 48. In another aspect, an oligonucleotide probe is 100% identical to at least 21 contiguous nucleotides of a nucleic acid sequence selected from the group consisting of SEQ ID NOs: 16-21 and 48.

In an aspect, an oligonucleotide probe is adjacent to a polymorphic nucleotide position of one or more marker loci. As used herein, "adjacent" refers to a distance of between 0 nucleotides to 50 nucleotides from the closest end (3' or 5') of the oligonucleotide probe and the polymorphic nucleotide position. As used herein, a "polymorphic nucleotide position" refers to a difference (e.g., insertion, deletion, substitution) between two or more alleles of a given marker locus. A polymorphic nucleotide position can be found by generating a pairwise comparison between allele sequences. For example, if a first allele comprises the nucleotide sequence ATTTG and a second allele comprises the nucleotide sequence TTTTG, the first nucleotide would be the "polymorphic nucleotide position."

In an aspect, genotyping comprises detecting a haplotype. As used herein, a "haplotype" refers to a group of two or more loci inherited from a single parent. The loci can contain genes, markers, or a combination of genes and markers. Typically, the genetic loci described by a haplotype are physically and genetically linked. A haplotype can also refer to a combination of SNPs positioned within a single locus.

In an aspect, detecting a haplotype comprises detecting at least two single nucleotide polymorphisms (SNPs) selected from the group consisting of a guanine at nucleotide position 121 of SEQ ID NO: 1, a guanine at nucleotide position 121 of SEQ ID NO: 2, a guanine at nucleotide position 101 of SEQ ID NO: 3, a thymine at nucleotide position 121 of SEQ ID NO: 4, and a guanine at nucleotide position 121 of SEQ ID NO: 5.

Introgression

In an aspect, this disclosure provides a method of introgressing a Pale Yellow (PY) quantitative trait locus (QTL), the method comprising: (a) crossing a first tobacco plant comprising the PY QTL with a second tobacco plant of a different genotype to produce one or more progeny plants or seeds; and (b) selecting a progeny plant or seed produced in step (a) comprising at least one PY-associated single nucleotide polymorphism selected from the group consisting of: (i) a guanine at nucleotide position 121 of SEQ ID NO: 1; (ii) a guanine at nucleotide position 121 of SEQ ID NO: 2; (iii) a guanine at nucleotide position 101 of SEQ ID NO: 3; (iv) a thymine at nucleotide position 121 of SEQ ID NO: 4; and (v) a guanine at nucleotide position 121 of SEQ ID NO: 5, where the selected progeny plant or seed comprises a PY phenotype.

As used herein, "introgression" refers to the transmission of a desired allele of a genetic locus from one genetic background (e.g., genotype) to another.

As used herein, a "PY-associated single nucleotide polymorphism" refers to a polymorphism that segregates with the PY QTL.

As used herein, a "genotype" refers to the genetic constitution of a plant or cell. Two tobacco plants from different tobacco lines or varieties would be understood to have different genotypes. Alternatively, plants of an inbred line typically comprise identical genotypes. However, without being limiting, if the PY QTL has been introgressed into a single TN 90 plant, the single TN 90 plant comprising the PY QTL would have a different genotype than all TN 90 plants lacking the PY QTL.

Mutations

In an aspect, this disclosure provides a method of introgressing a Pale Yellow (PY) trait, the method comprising: (a) crossing a first tobacco plant comprising a non-natural mutation in a nucleic acid selected from the group consisting of SEQ ID NOs: 16-21 and 48 with a second tobacco plant of a different genotype to produce one or more progeny plants or seeds; and (b) selecting a progeny plant or seed produced in step (a) comprising the non-natural mutation, where the progeny plant or seed comprises the PY trait.

In an aspect, this disclosure provides a modified tobacco plant, or part thereof, comprising a non-natural mutation in a nucleic acid sequence selected from the group consisting of SEQ ID NOs: 16-21 and 48, where the modified tobacco plant comprises a pale yellow phenotype, and where the mutation is as compared to a control tobacco plant of the same tobacco variety.

In another aspect, this disclosure provides a modified tobacco plant, or part thereof, comprising a non-natural mutation in a nucleic acid sequence encoding an amino acid sequence selected from the group consisting of SEQ ID NOs: 28-33, 46, 47, and 50, where the modified tobacco plant comprises a pale yellow phenotype, and where the mutation is as compared to a control tobacco plant of the same tobacco variety.

In an aspect, a plant or seed is homozygous for a non-natural mutation in a nucleic acid sequence selected from the group consisting of SEQ ID NOs: 16-21 and 48. In an aspect, a plant or seed is heterozygous for a non-natural mutation in a nucleic acid sequence selected from the group consisting of SEQ ID NOs: 16-21 and 48.

In an aspect, a plant or seed is homozygous for a non-natural mutation in a nucleic acid sequence encoding an amino acid selected from the group consisting of SEQ ID NOs: 28-33, 46, 47, and 50. In an aspect, a plant or seed is heterozygous for a non-natural mutation in a nucleic acid sequence encoding an amino acid selected from the group consisting of SEQ ID NOs: 28-33, 46, 47, and 50. As used herein, a "mutation" refers to an inheritable genetic modification introduced into a gene to alter the expression or activity of a product encoded by the gene. Such a modification can be in any sequence region of a gene, for example, in a promoter, 5' UTR, exon, intron, 3' UTR, or terminator region. In an aspect, a mutation reduces, inhibits, or eliminates the expression or activity of a gene product. In another aspect, a mutation increases, elevates, strengthens, or augments the expression or activity of a gene product.

In an aspect, a mutation is a "non-natural" or "non-naturally occurring" mutation. As used herein, a "non-natural" or "non-naturally occurring" mutation refers to a non-spontaneous mutation generated via human intervention, and does not correspond to a spontaneous mutation generated without human intervention. Non-limiting examples of human intervention include mutagenesis (e.g., chemical mutagenesis, ionizing radiation mutagenesis) and targeted genetic modifications (e.g., CRISPR-based methods, TALEN-based methods, zinc finger-based methods). Non-natural mutations and non-naturally occurring mutations do not include spontaneous mutations that arise naturally (e.g., via aberrant DNA replication in a germ line of a plant).

It will be appreciated that, when identifying a mutation, the reference DNA sequence should be from the same variety of tobacco. For example, if a modified tobacco plant comprising a mutation is from the variety TN90, then the endogenous reference sequence must be the endogenous TN90 sequence, not a homologous sequence from a different tobacco variety (e.g., K326). Similarly, if a modified tobacco cell comprising a mutation is a TN90 cell, then the endogenous reference sequence must be the endogenous TN90 sequence, not a homologous sequence from a tobacco cell from a different tobacco variety (e.g., K326).

In an aspect, an endogenous nucleic acid sequence comprising a non-natural mutation comprises a nucleic acid sequence at least 75% identical to a sequence selected from the group consisting of SEQ ID NOs: 16-21 and 48. In an aspect, an endogenous nucleic acid sequence comprising a non-natural mutation comprises a nucleic acid sequence at least 80% identical to a sequence selected from the group consisting of SEQ ID NOs: 16-21 and 48. In an aspect, an endogenous nucleic acid sequence comprising a non-natural mutation comprises a nucleic acid sequence at least 85% identical to a sequence selected from the group consisting of SEQ ID NOs: 16-21 and 48. In an aspect, an endogenous nucleic acid sequence comprising a non-natural mutation comprises a nucleic acid sequence at least 90% identical to a sequence selected from the group consisting of SEQ ID NOs: 16-21 and 48. In an aspect, an endogenous nucleic acid sequence comprising a non-natural mutation comprises a nucleic acid sequence at least 95% identical to a sequence selected from the group consisting of SEQ ID NOs: 16-21 and 48. In an aspect, an endogenous nucleic acid sequence comprising a non-natural mutation comprises a nucleic acid sequence at least 96% identical to a sequence selected from the group consisting of SEQ ID NOs: 16-21 and 48. In an aspect, an endogenous nucleic acid sequence comprising a non-natural mutation comprises a nucleic acid sequence at least 97% identical to a sequence selected from the group consisting of SEQ ID NOs: 16-21 and 48. In an aspect, an endogenous nucleic acid sequence comprising a non-natural mutation comprises a nucleic acid sequence at least 98% identical to a sequence selected from the group consisting of SEQ ID NOs: 16-21 and 48. In an aspect, an endogenous nucleic acid sequence comprising a non-natural mutation comprises a nucleic acid sequence at least 99% identical to a sequence selected from the group consisting of SEQ ID NOs: 16-21 and 48. In an aspect, an endogenous nucleic acid sequence comprising a non-natural mutation comprises a nucleic acid sequence 100% identical to a sequence selected from the group consisting of SEQ ID NOs: 16-21 and 48.

In an aspect, a mutation provided herein creates a dominant allele of the mutated locus. Dominant alleles are alleles that mask the contribution of a second allele at the same locus. A dominant allele can be a "dominant negative allele" or a "dominant positive allele." Dominant negative alleles, or antimorphs, are alleles that act in opposition to normal allelic function. A dominant negative allele typically does not function normally and either directly inhibits the activity of a wild-type protein (e.g., through dimerization) or inhibits the activity of a second protein that is required for the normal function of the wild-type protein (e.g., an activator or a downstream component of a pathway). For example, a dominant negative allele abrogates or reduces the normal function of an allele in a heterozygous or homozygous state. Dominant positive alleles can increase normal gene function (e.g., a hypermorph) or provide new functions for a gene (e.g., a neomorph). A semi-dominant allele occurs when penetrance of a linked phenotype in individuals heterozygous for the allele is less than that which is observed in individuals homozygous for the allele.

In an aspect, a mutation provided herein creates a dominant negative allele of the mutated locus. In another aspect, a mutation provided herein creates a dominant positive allele of a mutated locus.

As used herein, "inducing" a mutation refers to generating a mutation in a polynucleotide sequence via human intervention. Many suitable methods for inducing mutations in tobacco are known in the art. Non-limiting examples of such methods include use of chemical mutagens, use of radiation, and use of nucleases. In an aspect, inducing a mutation comprises the use of an agent selected from the group consisting of a chemical mutagen, irradiation, a transposon, *Agrobacterium*, and a nuclease.

In an aspect, inducing a mutation comprises the use of a chemical mutagen. In an aspect, a chemical mutagen comprises ethyl methanesulfonate (EMS).

In another aspect, inducing a mutation comprises the use of irradiation. In an aspect, irradiation comprises gamma rays, X-rays, or ionizing radiation. In another aspect, irradiation comprises the use of fast neutrons.

In an aspect, inducing a mutation comprises the use of a transposon. In another aspect, inducing a mutation comprises the use of *Agrobacterium*.

In a further aspect, inducing a mutation comprises the use of a nuclease. In an aspect, a nuclease is selected from the group consisting of a meganuclease, a zinc-finger nuclease, a transcription activator-like effector nuclease, a CRISPR/Cas9 nuclease, a CRISPR/Cpf1 nuclease, a CRISPR/CasX nuclease, a CRISPR/CasY nuclease, and a Csm1 nuclease. In an aspect, inducing a mutation comprises the use of a CRISPR/Cas9 nuclease. In an aspect, inducing a mutation comprises the use of a CRISPR/Cpf1 nuclease. In an aspect, inducing a mutation comprises the use of a CRISPR/CasX nuclease. In an aspect, inducing a mutation comprises the use of a CRISPR/CasY nuclease. In an aspect, inducing a mutation comprises the use of a Csm1 nuclease.

Several types of mutations are known in the art. In an aspect, a mutation comprises an insertion. An "insertion" refers to the addition of one or more nucleotides or amino acids to a given polynucleotide or amino acid sequence, respectively, as compared to an endogenous reference polynucleotide or amino acid sequence. In another aspect, a mutation comprises a deletion. A "deletion" refers to the removal of one or more nucleotides or amino acids to a given polynucleotide or amino acid sequence, respectively, as compared to an endogenous reference polynucleotide or amino acid sequence. In another aspect, a mutation comprises a substitution. A "substitution" refers to the replacement of one or more nucleotides or amino acids to a given polynucleotide or amino acid sequence, respectively, as compared to an endogenous reference polynucleotide or amino acid sequence. In another aspect, a mutation comprises an inversion. An "inversion" refers to when a segment of a polynucleotide or amino acid sequence is reversed end-to-end. In an aspect, a mutation provided herein comprises a mutation selected from the group consisting of an insertion, a deletion, a substitution, and an inversion.

In an aspect, a non-natural mutation comprises a mutation selected from the group consisting of a substitution, a deletion, an insertion, a duplication, and an inversion of one or more nucleotides relative to a wildtype nucleic acid sequence selected from the group consisting of SEQ ID NOs: 16-21 and 48.

In an aspect, a non-natural mutation comprises a mutation selected from the group consisting of a substitution, a deletion, an insertion, a duplication, and an inversion of one or more nucleotides relative to a wildtype nucleic acid sequence encoding an amino acid sequence selected from the group consisting of SEQ ID NOs: 28-33, 46, 47, and 50.

In an aspect, a non-natural mutation comprises one or more mutation types selected from the group consisting of a nonsense mutation, a missense mutation, a frameshift mutation, a splice-site mutation, and any combinations thereof. As used herein, a "nonsense mutation" refers to a mutation to a nucleic acid sequence that introduces a premature stop codon to an amino acid sequence by the nucleic acid sequence. As used herein, a "missense mutation" refers to a mutation to a nucleic acid sequence that causes a substitution within the amino acid sequence encoded by the nucleic acid sequence. As used herein, a "frameshift mutation" refers to an insertion or deletion to a nucleic acid sequence that shifts the frame for translating the nucleic acid sequence to an amino acid sequence. A "splice-site mutation" refers to a mutation in a nucleic acid sequence that causes an intron to be retained for protein translation, or, alternatively, for an exon to be excluded from protein translation. Splice-site mutations can cause nonsense, missense, or frameshift mutations.

Mutations in coding regions of genes (e.g., exonic mutations) can result in a truncated protein or polypeptide when a mutated messenger RNA (mRNA) is translated into a protein or polypeptide. In an aspect, this disclosure provides a mutation that results in the truncation of a protein or polypeptide. As used herein, a "truncated" protein or polypeptide comprises at least one fewer amino acid as compared to an endogenous control protein or polypeptide. For example, if endogenous Protein A comprises 100 amino acids, a truncated version of Protein A can comprise between 1 and 99 amino acids.

Without being limited by any scientific theory, one way to cause a protein or polypeptide truncation is by the introduction of a premature stop codon in an mRNA transcript of an endogenous gene. In an aspect, this disclosure provides a mutation that results in a premature stop codon in an mRNA transcript of an endogenous gene. As used herein, a "stop codon" refers to a nucleotide triplet within an mRNA transcript that signals a termination of protein translation. A "premature stop codon" refers to a stop codon positioned earlier (e.g., on the 5'-side) than the normal stop codon position in an endogenous mRNA transcript. Without being limiting, several stop codons are known in the art, including "UAG," "UAA," "UGA," "TAG," "TAA," and "TGA."

In an aspect, a mutation provided herein comprises a null mutation. As used herein, a "null mutation" refers to a mutation that confers a complete loss-of-function for a protein encoded by a gene comprising the mutation, or, alternatively, a mutation that confers a complete loss-of-function for a small RNA encoded by a genomic locus. A null mutation can cause lack of mRNA transcript production, a lack of small RNA transcript production, a lack of protein function, or a combination thereof.

A mutation provided herein can be positioned in any part of an endogenous gene. In an aspect, a mutation provided herein is positioned within an exon of an endogenous gene. In another aspect, a mutation provided herein is positioned within an intron of an endogenous gene. In a further aspect, a mutation provided herein is positioned within a 5'-untranslated region (UTR) of an endogenous gene. In still another aspect, a mutation provided herein is positioned within a 3'-UTR of an endogenous gene. In yet another aspect, a mutation provided herein is positioned within a promoter of an endogenous gene. In yet another aspect, a mutation provided herein is positioned within a terminator of an endogenous gene.

The screening and selection of mutagenized tobacco plants can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454) enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

In an aspect, a mutation in an endogenous gene results in a reduced level of expression as compared to the endogenous gene lacking the mutation. In another aspect, a mutation in an endogenous gene results in an increased level of expression as compared to the endogenous gene lacking the mutation.

In an aspect, a non-natural mutation results in a reduced level of expression as compared to expression of the gene in a control tobacco plant. In an aspect, a non-natural mutation results in an increased level of expression as compared to expression of the gene in a control tobacco plant.

In a further aspect, a mutation in an endogenous gene results in a reduced level of activity by a protein or polypeptide encoded by the endogenous gene having the mutation as compared to a protein or polypeptide encoded by the endogenous gene lacking the mutation. In a further aspect, a mutation in an endogenous gene results in an increased level of activity by a protein or polypeptide encoded by the endogenous gene having the mutation as compared to a protein or polypeptide encoded by the endogenous gene lacking the mutation.

In an aspect, a non-natural mutation results in a reduced level of activity by a protein or polypeptide encoded by the polynucleotide comprising the non-natural mutation as compared to a protein or polypeptide encoded by the polynucleotide lacking the non-natural mutation. In another aspect, a non-natural mutation results in an increased level of activity by a protein or polypeptide encoded by the polynucleotide comprising the non-natural mutation as compared to a protein or polypeptide encoded by the polynucleotide lacking the non-natural mutation.

In an aspect, a mutation in a genomic locus results in a reduced level of expression as compared to the genomic locus lacking the mutation. In another aspect, a mutation in a genomic locus results in an increased level of expression as compared to the genomic locus lacking the mutation. In a further aspect, a mutation in a genomic locus results in a reduced level of activity by a protein or polypeptide encoded by the genomic locus having the mutation as compared to a protein or polypeptide encoded by the genomic locus lacking the mutation. In a further aspect, a mutation in a genomic locus results in an increased level of activity by a protein or polypeptide encoded by the genomic locus having the mutation as compared to a protein or polypeptide encoded by the genomic locus lacking the mutation.

Levels of gene expression are routinely investigated in the art. As non-limiting examples, gene expression can be measured using quantitative reverse transcriptase PCR (qRT-PCR), RNA sequencing, or Northern blots. In an aspect, gene expression is measured using qRT-PCR. In another aspect, gene expression is measured using a Northern blot. In another aspect, gene expression is measured using RNA sequencing.

In an aspect, a method provided herein further comprises crossing a tobacco plant with a tobacco plant comprising a mutation or transgene directly suppressing or eliminating the expression or activity of one or more genes encoding a product selected from the group consisting of MPO, QPT, BBL, A622, aspartate oxidase, agmatine deiminase (AIC), arginase, diamine oxidase, ornithine decarboxylase, arginine decarboxylase, nicotine uptake permease (NUP), and MATE transporter.

As used herein, a "transgene" refers to exogenous DNA that has been stably integrated into the genome of a modified tobacco plant.

In an aspect, a tobacco plant comprising the PY trait further comprises a mutation or transgene directly suppressing or eliminating the expression or activity of one or more genes encoding a product selected from the group consisting of methylputrescine oxidase (MPO), quinolate phosphoribosyl transferase (QPT), quinolinate synthase (QS), BBL, A622, aspartate oxidase, agmatine deiminase (AIC), S-adenosyl-methionine synthetase (SAMS), arginase, diamine oxidase, ornithine decarboxylase (ODC), phosphoribosylanthranilate isomerase (PRAI), arginine decarboxylase (ADC), nicotine uptake permease (NUP), and MATE transporter.

In an aspect, a tobacco plant comprising the PY trait further comprises a mutation in an ERF gene of Nic2 locus. In an aspect, a tobacco plant comprising the PY trait further comprises one or more mutations in two or more, three or more, four or more, five or more, six or more, or all seven genes selected from the group consisting of ERF189, ERF115, ERF221, ERF104, ERF179, ERF17, and ERF168. See Shoji et al., *Plant Cell*, (10):3390-409 (2010); and Kajikawa et al., *Plant physiol.* 2017, 174:999-1011. In an aspect, a tobacco plant comprising the PY trait further comprises one or more mutations in ERF189, ERF115, or both.

In an aspect, a tobacco plant comprising the PY trait further comprises a mutation in an ERF gene of Nic1 locus (or Nic1b locus as in PCT/US2019/013345 filed on Jan. 11, 2019, published as WO/2019/140297). See also WO/2018/237107. In an aspect, a tobacco comprising the PY trait plant further comprises one or more mutations in two or more, three or more, four or more, five or more, six or more, or seven or more genes selected from the group consisting of ERF101, ERF110, ERFnew, ERF199, ERF19, ERF130, ERF16, ERF29, ERF210, and ERF91L2. See Kajikawa et al., *Plant physiol.* 2017, 174:999-1011. In an aspect, a tobacco plant comprising the PY trait further comprises one or more mutations in one or more, two or more, three or more, four or more, five or more, or all six genes selected from the group consisting of ERFnew, ERF199, ERF19, ERF29, ERF210, and ERF91L2.

In an aspect, a tobacco plant provided herein comprises a mutation or transgene conferring a reduced level of nicotine as compared to a tobacco plant lacking the mutation or transgene. In an aspect, a tobacco plant provided herein is a low-alkaloid tobacco plant.

A variety of factors affect tobacco alkaloid levels including genotype, environment, fertilization, and agronomic practices (for example, nicotine production is stimulated by topping, wounding, and herbivore damage). Low-alkaloid traits initially found in strains of Cuban cigar tobacco varieties were introduced into cigarette varieties through a series of backcrosses. Low-alkaloid tobacco germplasm was subsequently registered in the genetic background of cultivar Burley 21 (Legg et al., *Crop Science,* 10:212 (1970)). Genetic studies using the low alkaloid Burley 21 (LA BU21) lines indicated that two unlinked loci contribute to nicotine levels in the tobacco leaf. These two loci are referred to as Nic1 and Nic2. nic1 and nic2 (same as nicotine 1 and nicotine 2, respectively) mutations in LA BU21 are semi-dominant. They exhibit dose-dependent effects on nicotine levels, with the effects of nic1 about 2.4 times stronger than those of nic2. Molecular characterization of Nic2 locus has been reported. The nic2 mutation was shown to contain a deletion of a cluster of transcription factor genes from the ethylene responsive factor (ERF) family, e.g., ERF 189, ERF 115, ERF221, ERF 104, ERF 179, ERF 17, and ERF 168 (Shoji et al., *Plant Cell*, (10):3390-409 (2010)).

Reducing total alkaloid content in tobacco can have many benefits. It can increase the value of tobacco as a biomass resource. Increases in nicotinic alkaloid in tobacco plants may play an important role in protecting plants against insects and herbivores.

Consistent with alkaloids' role in insect defense, LA BU21 was reported to be extremely susceptible to insect damage (Legg et al., *Crop Science*, 10:212 (1970)). A further study comparing isogenic lines of flue-cured tobacco with low total alkaloids percentage (approximately 0.20%) with their "normal" recurring parents (total alkaloids 1.85 to 2.70%) reported that yield, grade index, total N, and reducing sugar content in the low alkaloid lines were lower than in the normal flue-cured cultivars (Chaplin and Weeks, *Crop Science*, 16(3):416-18 (1976)).

Without being limiting, low-alkaloid tobacco varieties include LA Burley 21, LAFC53, LN B&W, and LN KY171.

In an aspect, a mutation conferring a reduced level of nicotine comprises a nic1 mutation, a nic2 mutation, or both. In an aspect, a nic1 mutation, a nic2 mutation, or both are introgressed or derived from a variety selected from the group consisting of LA Burley 21, LAFC53, LN B&W, and LN KY171.

As used herein, a "low alkaloid variety" of tobacco refers to tobacco variety comprising one or more genetic modifications reducing the total alkaloids (measured via dry weight) to a level less than 25% of the total alkaloid level in a control tobacco variety of a substantially similar genetic background except for the one or more genetic modifications. As a non-limiting example, KY171 can serve as a control for the low-alkaloid variety LA KY171.

As used herein, a "genetic modification" refers to plants, seeds, plant parts, plant cells, and plant genomes that have been subjected to mutagenesis, genome editing, genetic transformation, or a combination thereof.

In an aspect, a mutation conferring a reduced level of nicotine comprises a mutation in a gene or locus encoding a protein selected from the group consisting of aspartate oxidase, agmatine deiminase (AIC), arginase, diamine oxidase, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), S-adenosyl-methionine synthetase (SAMS), A622, NBB1, BBL, MYC2, Nic1_ERF, Nic2_ERF, ethylene response factor (ERF) transcription factor, nicotine uptake permease (NUP), and MATE transporter. In another aspect, a mutation conferring a reduced level of nicotine comprises a mutation in a gene or locus encoding a protein selected from the group consisting of ERF101, ERF110, ERFnew, ERF199, ERF19, ERF130, ERF16, ERF29, ERF210, and ERF91L2. In another aspect, a mutation conferring a reduced level of nicotine comprises a mutation in a gene or locus encoding a protein selected from the group consisting of ERF32, ERF34, ERF39, ERF189, ERF115, ERF221, ERF104, ERF179, ERF17, and ERF168.

In an aspect, a transgene conferring a reduced level of nicotine comprises a transgene targeting and suppressing a gene encoding a protein selected from the group consisting of aspartate oxidase, agmatine deiminase (AIC), arginase, diamine oxidase, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), S-adenosyl-methionine synthetase (SAMS), A622, NBB1, BBL, MYC2, Nic1 ERF, Nic2 ERF, ethylene response factor (ERF) transcription factor, nicotine uptake permease (NUP), and MATE transporter. In another aspect, a transgene conferring a reduced level of nicotine comprises a transgene targeting and suppressing a gene encoding a protein selected from the group consisting of ERF101, ERF110, ERFnew, ERF199, ERF19, ERF130, ERF16, ERF29, ERF210, and ERF91L2. In another aspect, a transgene conferring a reduced level of nicotine comprises a transgene targeting and suppressing a gene encoding a protein selected from the group consisting of ERF32, ERF34, ERF39, ERF189, ERF115, ERF221, ERF104, ERF179, ERF17, and ERF168.

In an aspect, a tobacco plant, seed, or cell comprises a recombinant DNA construct comprising a heterologous promoter operably linked to a nucleic acid sequence at least 75% identical to a sequence selected from the group consisting of SEQ ID NOs: 22-27, 44, 45, and 49. In another aspect, a tobacco plant, seed, or cell comprises a recombinant DNA construct comprising a heterologous promoter operably linked to a nucleic acid sequence at least 80% identical to a sequence selected from the group consisting of SEQ ID NOs: 22-27, 44, 45, and 49. In another aspect, a tobacco plant, seed, or cell comprises a recombinant DNA construct comprising a heterologous promoter operably linked to a nucleic acid sequence at least 85% identical to a sequence selected from the group consisting of SEQ ID NOs: 22-27, 44, 45, and 49. In another aspect, a tobacco plant, seed, or cell comprises a recombinant DNA construct comprising a heterologous promoter operably linked to a nucleic acid sequence at least 90% identical to a sequence selected from the group consisting of SEQ ID NOs: 22-27, 44, 45, and 49. In another aspect, a tobacco plant, seed, or cell comprises a recombinant DNA construct comprising a heterologous promoter operably linked to a nucleic acid sequence at least 95% identical to a sequence selected from the group consisting of SEQ ID NOs: 22-27, 44, 45, and 49. In another aspect, a tobacco plant, seed, or cell comprises a recombinant DNA construct comprising a heterologous promoter operably linked to a nucleic acid sequence at least 96% identical to a sequence selected from the group consisting of SEQ ID NOs: 22-27, 44, 45, and 49. In another aspect, a tobacco plant, seed, or cell comprises a recombinant DNA construct comprising a heterologous promoter operably linked to a nucleic acid sequence at least 97% identical to a sequence selected from the group consisting of SEQ ID NOs: 22-27, 44, 45, and 49. In another aspect, a tobacco plant, seed, or cell comprises a recombinant DNA construct comprising a heterologous promoter operably linked to a nucleic acid sequence at least 98% identical to a sequence selected from the group consisting of SEQ ID NOs: 22-27, 44, 45, and 49. In another aspect, a tobacco plant, seed, or cell comprises a recombinant DNA construct comprising a heterologous promoter operably linked to a nucleic acid sequence at least 99% identical to a sequence selected from the group consisting of SEQ ID NOs: 22-27, 44, 45, and 49. In another aspect, a tobacco plant, seed, or cell comprises a recombinant DNA construct comprising a heterologous promoter operably linked to a nucleic acid sequence 100% identical to a sequence selected from the group consisting of SEQ ID NOs: 22-27, 44, 45, and 49.

In an aspect, a tobacco plant, seed, or cell comprises a recombinant DNA construct comprising a heterologous promoter operably linked to a nucleic acid that encodes an amino acid sequence at least 80% identical or similar to an amino acid sequence selected from the group consisting of SEQ ID NOs: 28-33, 46, 47, and 50. In an aspect, a tobacco plant, seed, or cell comprises a recombinant DNA construct comprising a heterologous promoter operably linked to a nucleic acid that encodes an amino acid sequence at least 85% identical or similar to an amino acid sequence selected from the group consisting of SEQ ID NOs: 28-33, 46, 47, and 50. In an aspect, a tobacco plant, seed, or cell comprises a recombinant DNA construct comprising a heterologous promoter operably linked to a nucleic acid that encodes an amino acid sequence at least 90% identical or similar to an amino acid sequence selected from the group consisting of SEQ ID NOs: 28-33, 46, 47, and 50. In an aspect, a tobacco plant, seed, or cell comprises a recombinant DNA construct comprising a heterologous promoter operably linked to a nucleic acid that encodes an amino acid sequence at least 95% identical or similar to an amino acid sequence selected from the group consisting of SEQ ID NOs: 28-33, 46, 47, and 50. In an aspect, a tobacco plant, seed, or cell comprises a recombinant DNA construct comprising a heterologous promoter operably linked to a nucleic acid that encodes an amino acid sequence at least 96% identical or similar to an amino acid sequence selected from the group consisting of SEQ ID NOs: 28-33, 46, 47, and 50. In an aspect, a tobacco plant, seed, or cell comprises a recombinant DNA construct comprising a heterologous promoter operably linked to a nucleic acid that encodes an amino acid sequence at least 97% identical or similar to an amino acid sequence selected from the group consisting of SEQ ID NOs: 28-33, 46, 47, and 50. In an aspect, a tobacco plant, seed, or cell comprises a recombinant DNA construct comprising a heterologous promoter operably linked to a nucleic acid that encodes an amino acid sequence at least 98% identical or similar to an amino acid sequence selected from the group consisting of SEQ ID NOs: 28-33, 46, 47, and 50. In an aspect, a tobacco plant, seed, or cell comprises a recombinant DNA construct comprising a heterologous promoter operably linked to a nucleic acid that encodes an amino acid sequence at least 99% identical or similar to an amino acid sequence selected from the group consisting of SEQ ID NOs: 28-33, 46, 47, and 50. In an aspect, a tobacco plant, seed, or cell comprises a recombinant DNA construct comprising a heterologous promoter operably linked to a nucleic acid that encodes an amino acid sequence 100% identical or similar to an amino acid sequence selected from the group consisting of SEQ ID NOs: 28-33, 46, 47, and 50.

In an aspect, a tobacco plant, seed, or cell comprises a heterologous promoter operably linked to a polynucleotide comprising a non-natural mutation in a nucleic acid sequence selected from the group consisting of SEQ ID NOs: 16-21 and 48.

In an aspect, a tobacco plant, seed, or cell comprises a non-natural mutation in an endogenous nucleic acid sequence encoding a g58899 protein, wherein the non-natural mutation comprises an insertion, deletion, or substitution of an amino acid residue at a position selected from the group consisting of positions 18, 24, 54, 56, 57, 60, 87, 221, and 325 as compared to SEQ ID NO: 46.

In an aspect, a tobacco plant, seed, or cell comprises a non-natural mutation in the promoter of an endogenous nucleic acid sequence encoding a g58899 protein, wherein the tobacco plant, seed, or cell, exhibits reduced expression of the endogenous nucleic acid as compared to a control tobacco plant, seed, or cell, lacking the non-natural mutation.

In an aspect, a tobacco plant, seed, or cell comprises a non-natural mutation in an endogenous nucleic acid sequence encoding a g58899 protein, wherein the non-natural mutation results in a premature stop codon in the g58899 protein as compared to an amino acid sequence selected from the group consisting of SEQ ID NOs: 30, 46, and 47. In an aspect, a tobacco plant, seed, or cell comprises a non-natural mutation in an endogenous nucleic acid sequence encoding a g58887 protein, wherein the non-natural mutation results in a premature stop codon in the g58887 protein as compared to SEQ ID NO: 28. In another aspect, a tobacco plant, seed, or cell comprises a non-natural mutation in an endogenous nucleic acid sequence encoding a g58888 protein, wherein the non-natural mutation results in a premature stop codon in the g58888 protein as compared to SEQ ID NO: 29. In another aspect, a tobacco plant, seed, or cell comprises a non-natural mutation in an endogenous nucleic acid sequence encoding a g58917 protein, wherein the non-natural mutation results in a premature stop codon in the g58917 protein as compared to SEQ ID NO: 31. In another aspect, a tobacco plant, seed, or cell comprises a non-natural mutation in an endogenous nucleic acid sequence encoding a g58905 protein, wherein the non-natural mutation results in a premature stop codon in the g58905 protein as compared to SEQ ID NO: 32. In another aspect, a tobacco plant, seed, or cell comprises a non-natural mutation in an endogenous nucleic acid sequence encoding a g61524 protein, wherein the non-natural mutation results in a premature stop codon in the g61524 protein as compared to SEQ ID NO: 33.

Artificial miRNAs

In an aspect, this disclosure provides a recombinant nucleic acid comprising a heterologous promoter operably linked to a polynucleotide that encodes a non-coding RNA molecule, where the non-coding RNA molecule is capable of binding to an RNA encoding an amino acid sequence having at least 80% sequence identity to an amino acid sequence selected from the group consisting of SEQ ID NOs: 28-33, 46, 47, and 50. In another aspect, this disclosure provides a recombinant nucleic acid comprising a heterologous promoter operably linked to a polynucleotide that encodes a non-coding RNA molecule, where the non-coding RNA molecule is capable of binding to an RNA encoding an amino acid sequence having at least 85% sequence identity to an amino acid sequence selected from the group consisting of SEQ ID NOs: 28-33, 46, 47, and 50. In another aspect, this disclosure provides a recombinant nucleic acid comprising a heterologous promoter operably linked to a polynucleotide that encodes a non-coding RNA molecule, where the non-coding RNA molecule is capable of binding to an RNA encoding an amino acid sequence having at least 90% sequence identity to an amino acid sequence selected from the group consisting of SEQ ID NOs: 28-33, 46, 47, and 50. In another aspect, this disclosure provides a recombinant nucleic acid comprising a heterologous promoter operably linked to a polynucleotide that encodes a non-coding RNA molecule, where the non-coding RNA molecule is capable of binding to an RNA encoding an amino acid sequence having at least 95% sequence identity to an amino acid sequence selected from the group consisting of SEQ ID NOs: 28-33, 46, 47, and 50. In another aspect, this disclosure provides a recombinant nucleic acid comprising a heterologous promoter operably linked to a polynucleotide that encodes a non-coding RNA molecule, where the non-coding RNA molecule is capable of binding to an RNA encoding an amino acid sequence having at least 96% sequence identity to an amino acid sequence selected from the group consisting of SEQ ID NOs: 28-33, 46, 47, and 50. In another aspect, this disclosure provides a recombinant nucleic acid comprising a heterologous promoter operably linked to a polynucleotide that encodes a non-coding RNA molecule, where the non-coding RNA molecule is capable of binding to an RNA encoding an amino acid sequence having at least 97% sequence identity to an amino acid sequence selected from the group consisting of SEQ ID NOs: 28-33, 46, 47, and 50. In another aspect, this disclosure provides a recombinant nucleic acid comprising a heterologous promoter operably linked to a polynucleotide that encodes a non-coding RNA molecule, where the non-coding RNA molecule is capable of binding to an RNA encoding an amino acid sequence having at least 98% sequence identity to an amino acid sequence selected from the group consisting of SEQ ID NOs: 28-33, 46, 47, and 50. In another aspect, this disclosure provides a recombinant nucleic acid comprising a heterologous promoter operably linked to a polynucleotide that encodes a non-coding RNA molecule, where the non-coding RNA molecule is capable of binding to an RNA encoding an amino acid sequence having at least 99% sequence identity to an amino acid sequence selected from the group consisting of SEQ ID NOs: 28-33, 46, 47, and 50. In another aspect, this disclosure provides a recombinant nucleic acid comprising a heterologous promoter operably linked to a polynucleotide that encodes a non-coding RNA molecule, where the non-coding RNA molecule is capable of binding to an RNA encoding an amino acid sequence having 100% sequence identity to an amino acid sequence selected from the group consisting of SEQ ID NOs: 28-33, 46, 47, and 50.

In an aspect, this disclosure provides a recombinant nucleic acid comprising a heterologous promoter operably linked to a polynucleotide that encodes a non-coding RNA molecule, where the non-coding RNA molecule is capable of binding to an RNA at least 80% identical to a nucleic acid sequence selected from the group consisting of SEQ ID NOs: 16-21 and 48. In another aspect, this disclosure provides a recombinant nucleic acid comprising a heterologous promoter operably linked to a polynucleotide that encodes a non-coding RNA molecule, where the non-coding RNA molecule is capable of binding to an RNA at least 85% identical to a nucleic acid sequence selected from the group consisting of SEQ ID NOs: 16-21 and 48. In another aspect, this disclosure provides a recombinant nucleic acid comprising a heterologous promoter operably linked to a polynucleotide that encodes a non-coding RNA molecule, where the non-coding RNA molecule is capable of binding to an RNA at least 90% identical to a nucleic acid sequence selected from the group consisting of SEQ ID NOs: 16-21 and 48. In another aspect, this disclosure provides a recombinant nucleic acid comprising a heterologous promoter operably linked to a polynucleotide that encodes a non-coding RNA molecule, where the non-coding RNA molecule is capable of binding to an RNA at least 95% identical to a nucleic acid sequence selected from the group consisting of SEQ ID NOs: 16-21 and 48. In another aspect, this disclosure provides a recombinant nucleic acid comprising a heterologous promoter operably linked to a polynucleotide that encodes a non-coding RNA molecule, where the non-coding RNA molecule is capable of binding to an RNA at least 96% identical to a nucleic acid sequence selected from the group consisting of SEQ ID NOs: 16-21 and 48. In another aspect, this disclosure provides a recombinant nucleic acid comprising a heterologous promoter operably linked to a polynucleotide that encodes a non-coding RNA molecule, where the non-coding RNA molecule is capable of binding to an RNA at least 97% identical to a nucleic acid sequence selected from the group consisting of SEQ ID NOs: 16-21 and 48. In another aspect, this disclosure provides a recombinant nucleic acid comprising a heterologous promoter operably linked to a polynucleotide that encodes a non-coding RNA molecule, where the non-coding RNA molecule is capable of binding to an RNA at least 98% identical to a nucleic acid sequence selected from the group consisting of SEQ ID NOs: 16-21 and 48. In another aspect, this disclosure provides a recombinant nucleic acid comprising a heterologous promoter operably linked to a polynucleotide that encodes a non-coding RNA molecule, where the non-coding RNA molecule is capable of binding to an RNA at least 99% identical to a nucleic acid sequence selected from the group consisting of SEQ ID NOs: 16-21 and 48. In another aspect, this disclosure provides a recombinant nucleic acid comprising a heterologous promoter operably linked to a polynucleotide that encodes a non-coding RNA molecule, where the non-coding RNA molecule is capable of binding to an RNA 100% identical to a nucleic acid sequence selected from the group consisting of SEQ ID NOs: 16-21 and 48.

In an aspect, a non-coding RNA molecule is selected from the group consisting of a microRNA (miRNA), a small interfering RNA (siRNA), a trans-acting siRNA (ta-siRNA), a transfer RNA (tRNA), a ribosomal RNA (rRNA), an intron, a hairpin RNA (hpRNA), and an intron-containing hairpin RNA (ihpRNA).

miRNAs are generally of between about 19 to about 25 nucleotides (commonly about 20-24 nucleotides in plants), that guide cleavage in trans of target transcripts, negatively regulating the expression of genes involved in various regulation and development pathways (Bartel (2004) Cell, 116:281-297). In some cases, miRNAs serve to guide in-phase processing of siRNA primary transcripts (see Allen et al. (2005) Cell, 121:207-221).

Many microRNA genes (MIR genes) have been identified and made publicly available in a database ("miRBase", available on line at microrna[dot]sanger[dot]ac[dot]uk/sequences; also see Griffiths-Jones et al. (2003) Nucleic Acids Res., 31:439-441). MIR genes have been reported to occur in intergenic regions, both isolated and in clusters in the genome, but can also be located entirely or partially within introns of other genes (both protein-coding and non-protein-coding). For a recent review of miRNA biogenesis, see Kim (2005) Nature Rev. Mol. Cell. Biol., 6:376-385. Transcription of MIR genes can be, at least in some cases, under promotional control of a MIR gene's own promoter. The primary transcript, termed a "pri-miRNA", can be quite large (several kilobases) and can be polycistronic, containing one or more pre-miRNAs (fold-back structures containing a stem-loop arrangement that is processed to the mature miRNA) as well as the usual 5' "cap" and polyadenylated tail of an mRNA. See, for example, FIG. 1 in Kim (2005) Nature Rev. Mol. Cell. Biol., 6:376-385.

Maturation of a mature miRNA from its corresponding precursors (pri-miRNAs and pre-miRNAs) differs significantly between animals and plants. For example, in plant cells, microRNA precursor molecules are believed to be largely processed to the mature miRNA entirely in the nucleus, whereas in animal cells, the pri-miRNA transcript is processed in the nucleus by the animal-specific enzyme Drosha, followed by export of the pre-miRNA to the cytoplasm where it is further processed to the mature miRNA. Mature miRNAs in plants are typically 21 nucleotides in length. For a recent review of miRNA biogenesis in both plants and animals, see Kim (2005) Nature Rev. Mol. Cell. Biol., 6:376-385. Additional reviews on miRNA biogenesis and function are found, for example, in Bartel (2004) Cell, 116:281-297; Murchison and Hannon (2004) Curr. Opin. Cell Biol., 16:223-229; and Dugas and Bartel (2004) Curr. Opin. Plant Biol., 7:512-520.

Transgenic expression of miRNAs (whether a naturally occurring sequence or an artificial sequence) can be employed to regulate expression of the miRNA's target gene or genes. Inclusion of a miRNA recognition site in a transgenically expressed transcript is also useful in regulating expression of the transcript; see, for example, Parizotto et al. (2004) Genes Dev., 18:2237-2242. Recognition sites of miRNAs have been validated in all regions of an mRNA, including the 5' untranslated region, coding region, and 3' untranslated region, indicating that the position of the miRNA target site relative to the coding sequence may not necessarily affect suppression (see, e.g., Jones-Rhoades and Bartel (2004). Mol. Cell, 14:787-799, Rhoades et al. (2002) Cell, 110:513-520, Allen et al. (2004) Nat. Genet., 36:1282-1290, Sunkar and Zhu (2004) Plant Cell, 16:2001-2019). Because miRNAs are important regulatory elements in eukaryotes, transgenic suppression of miRNAs is useful for manipulating biological pathways and responses. Finally, promoters of MIR genes can have very specific expression patterns (e.g., cell-specific, tissue-specific, temporally specific, or inducible), and thus are useful in recombinant constructs to induce such specific transcription of a DNA sequence to which they are operably linked. Various utilities of miRNAs, their precursors, their recognition sites, and their promoters are described in detail in U.S. Patent Application Publication 2006/0200878 A1, incorporated by reference herein. Non-limiting examples of these utilities include: (1) the expression of a native miRNA or miRNA precursor sequence to suppress a target gene; (2) the expression of an artificial miRNA or miRNA precursor sequence to suppress a target gene; (3) expression of a transgene with a miRNA recognition site, where the transgene is suppressed when the mature miRNA is expressed; (4) expression of a transgene driven by a miRNA promoter.

Designing an artificial miRNA sequence can be as simple as substituting sequence that is complementary to the intended target for nucleotides in the miRNA stem region of the miRNA precursor, as demonstrated by Zeng et al. (2002) Mol. Cell, 9:1327-1333. One non-limiting example of a general method for determining nucleotide changes in the native miRNA sequence to produce the engineered miRNA precursor includes the following steps: (a) Selecting a unique target sequence of at least 18 nucleotides specific to the target gene, e.g., by using sequence alignment tools such as BLAST (see, for example, Altschul et al. (1990) J. Mol. Biol., 215:403-410; Altschul et al. (1997) Nucleic Acids Res., 25:3389-3402), for example, of both tobacco cDNA and genomic DNA databases, to identify target transcript orthologues and any potential matches to unrelated genes, thereby avoiding unintentional silencing of non-target sequences; (b) Analyzing the target gene for undesirable sequences (e.g., matches to sequences from non-target species), and score each potential 19-mer segment for GC content, Reynolds score (see Reynolds et al. (2004) Nature Biotechnol., 22:326-330), and functional asymmetry characterized by a negative difference in free energy (".DELTA..DELTA.G" or "ΔΔG") (see Khvorova et al. (2003) Cell, 115:209-216). Preferably 19-mers are selected that have all or most of the following characteristics: (1) a Reynolds score>4, (2) a GC content between about 40% to about 60%, (3) a negative ΔΔG, (4) a terminal adenosine, (5) lack of a consecutive run of 4 or more of the same nucleotide; (6) a location near the 3' terminus of the target gene; (7) minimal differences from the miRNA precursor transcript. Positions at every third nucleotide in an siRNA have been reported to be especially important in influencing RNAi efficacy and an algorithm, "siExplorer" is publicly available at rna[dot]chem[dot]t[dot]u-tokyo[dot]ac[dot]jp/siexplorer.htm (see Katoh and Suzuki (2007) Nucleic Acids Res., 10.1093/nar/gkl1120); (c) Determining the reverse complement of the selected 19-mers to use in making a modified mature miRNA. The additional nucleotide at position 20 is preferably matched to the selected target sequence, and the nucleotide at position 21 is preferably chosen to either be unpaired to prevent spreading of silencing on the target transcript or paired to the target sequence to promote spreading of silencing on the target transcript; and (d) transforming the artificial miRNA into a plant.

In one aspect, an artificial miRNA provided herein is complementary to a polynucleotide having at least 80% sequence identity to a polynucleotide selected from the group consisting of SEQ ID NOs: 16-21 and 48. In one aspect, an artificial miRNA provided herein is complementary to a polynucleotide having at least 85% sequence identity to a polynucleotide selected from the group consisting of SEQ ID NOs: 16-21 and 48. In one aspect, an artificial miRNA provided herein is complementary to a polynucleotide having at least 90% sequence identity to a polynucleotide selected from the group consisting of SEQ ID NOs: 16-21 and 48. In one aspect, an artificial miRNA provided herein is complementary to a polynucleotide having at least 95% sequence identity to a polynucleotide selected from the group consisting of SEQ ID NOs: 16-21 and 48. In one aspect, an artificial miRNA provided herein is complementary to a polynucleotide having at least 96% sequence identity to a polynucleotide selected from the group consisting of SEQ ID NOs: 16-21 and 48. In one aspect, an artificial miRNA provided herein is complementary to a polynucleotide having at least 97% sequence identity to a polynucleotide selected from the group consisting of SEQ ID NOs: 16-21 and 48. In one aspect, an artificial miRNA provided herein is complementary to a polynucleotide having at least 98% sequence identity to a polynucleotide selected from the group consisting of SEQ ID NOs: 16-21 and 48. In one aspect, an artificial miRNA provided herein is complementary to a polynucleotide having at least 99% sequence identity to a polynucleotide selected from the group consisting of SEQ ID NOs: 16-21 and 48. In one aspect, an artificial miRNA provided herein is complementary to a polynucleotide having 100% sequence identity to a polynucleotide selected from the group consisting of SEQ ID NOs: 16-21 and 48.

In another aspect, an artificial miRNA provided herein is complementary to a polynucleotide encoding a polypeptide having at least 80% sequence identity or similarity to a polypeptide selected from the group consisting of SEQ ID NOs: 28-33, 46, 47, and 50. In another aspect, an artificial miRNA provided herein is complementary to a polynucleotide encoding a polypeptide having at least 85% sequence identity or similarity to a polypeptide selected from the group consisting of SEQ ID NOs: 28-33, 46, 47, and 50. In another aspect, an artificial miRNA provided herein is complementary to a polynucleotide encoding a polypeptide having at least 90% sequence identity or similarity to a polypeptide selected from the group consisting of SEQ ID NOs: 28-33, 46, 47, and 50. In another aspect, an artificial miRNA provided herein is complementary to a polynucleotide encoding a polypeptide having at least 95% sequence identity or similarity to a polypeptide selected from the group consisting of SEQ ID NOs: 28-33, 46, 47, and 50. In another aspect, an artificial miRNA provided herein is complementary to a polynucleotide encoding a polypeptide having at least 96% sequence identity or similarity to a polypeptide selected from the group consisting of SEQ ID NOs: 28-33, 46, 47, and 50. In another aspect, an artificial miRNA provided herein is complementary to a polynucleotide encoding a polypeptide having at least 97% sequence identity or similarity to a polypeptide selected from the group consisting of SEQ ID NOs: 28-33, 46, 47, and 50. In another aspect, an artificial miRNA provided herein is complementary to a polynucleotide encoding a polypeptide having at least 98% sequence identity or similarity to a polypeptide selected from the group consisting of SEQ ID NOs: 28-33, 46, 47, and 50. In another aspect, an artificial miRNA provided herein is complementary to a polynucleotide encoding a polypeptide having at least 99% sequence identity or similarity to a polypeptide selected from the group consisting of SEQ ID NOs: 28-33, 46, 47, and 50. In another aspect, an artificial miRNA provided herein is complementary to a polynucleotide encoding a polypeptide having 100% sequence identity or similarity to a polypeptide selected from the group consisting of SEQ ID NOs: 28-33, 46, 47, and 50.

In an aspect, an artificial miRNA comprises at least 15 contiguous nucleotides complementary to a nucleic acid sequence selected from the group consisting of SEQ ID NOs: 16-21 and 48. In another aspect, an artificial miRNA comprises at least 16 contiguous nucleotides complementary to a nucleic acid sequence selected from the group consisting of SEQ ID NOs: 16-21 and 48. In another aspect, an artificial miRNA comprises at least 17 contiguous nucleotides complementary to a nucleic acid sequence selected from the group consisting of SEQ ID NOs: 16-21 and 48. In another aspect, an artificial miRNA comprises at least 18 contiguous nucleotides complementary to a nucleic acid sequence selected from the group consisting of SEQ ID NOs: 16-21 and 48. In another aspect, an artificial miRNA comprises at least 19 contiguous nucleotides complementary to a nucleic acid sequence selected from the group consisting of SEQ ID NOs: 16-21 and 48. In another aspect, an artificial miRNA comprises at least 20 contiguous nucleotides complementary to a nucleic acid sequence selected from the group consisting of SEQ ID NOs: 16-21 and 48. In another aspect, an artificial miRNA comprises at least 21 contiguous nucleotides complementary to a nucleic acid sequence selected from the group consisting of SEQ ID NOs: 16-21 and 48.

In an aspect, an artificial miRNA provided herein reduces or eliminates RNA transcription or protein translation of a gene selected from the group consisting of G58887, g58888, g58899, g58917, g58905, g61524, and g20337.

In an aspect, a modified tobacco plant, or a part thereof, comprises any non-coding RNA molecule provided herein. In another aspect, a modified tobacco plant, or a part thereof, comprises any artificial miRNA provided herein. In another aspect, a modified tobacco plant, or a part thereof, comprises any recombinant nucleic acid provided herein.

When expressed in a tobacco plant, a non-coding RNA molecule provided herein reduces the expression or translation of a cognate target transcript (e.g., SEQ ID NOs: 16-21 and 48) as compared to a control tobacco plant that does not express the non-coding RNA molecule. Similarly, when expressed in a tobacco plant, an artificial miRNA provided herein reduces the expression or translation of a cognate target transcript (e.g., SEQ ID NOs: 16-21 and 48) as compared to a control tobacco plant that does not express the non-coding RNA molecule.

In an aspect, a modified tobacco plant provided herein exhibits a pale yellow phenotype.

In an aspect, an artificial miRNA is operably linked to a heterologous promoter.

As used herein, "capable of binding to" is synonymous with "capable of hybridizing to." In an aspect, a first nucleic acid molecule that is capable of binding to a second nucleic acid molecule binds to the second nucleic acid molecule. As used herein, a first nucleic acid molecule can "hybridize" a second nucleic acid molecule via non-covalent interactions (e.g., Watson-Crick base-pairing) in a sequence-specific, antiparallel manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine pairing with thymine, adenine pairing with uracil, and guanine (G) pairing with cytosine (C) [DNA, RNA]. In addition, it is also known in the art that for hybridization between two RNA molecules (e.g., dsRNA), guanine base pairs with uracil. For example, G/U base-pairing is partially responsible for the degeneracy (i.e., redundancy) of the genetic code in the context of tRNA anti-codon base-pairing with codons in mRNA. In the context of this disclosure, a guanine of a protein-binding segment (dsRNA duplex) of a subject DNA-targeting RNA molecule is considered complementary to an uracil, and vice versa. As such, when a G/U base-pair can be made at a given nucleotide position a protein-binding segment (dsRNA duplex) of a subject DNA-targeting RNA molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer nucleotides) the position of mismatches becomes important (see Sambrook et al.). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides). Furthermore, the skilled artisan will recognize that the temperature and wash solution salt concentration may be adjusted as necessary according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST® programs (basic local alignment search tools) and PowerBLAST programs known in the art (see Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

Promoters

As commonly understood in the art, the term "promoter" refers to a DNA sequence that contains an RNA polymerase binding site, transcription start site, and/or TATA box and assists or promotes the transcription and expression of an associated transcribable polynucleotide sequence and/or gene (or transgene). A promoter can be synthetically produced, varied, or derived from a known or naturally occurring promoter sequence or other promoter sequence. A promoter can also include a chimeric promoter comprising a combination of two or more heterologous sequences. A promoter of the present application can thus include variants of promoter sequences that are similar in composition, but not identical to, other promoter sequence(s) known or provided herein.

Promoters that drive expression in all or most tissues of the plant are referred to as "constitutive" promoters. A non-limiting example of a constitutive promoter is the Cauliflower Mosaic Virus (CaMV) 35S promoter. Promoters that drive expression during certain periods or stages of development are referred to as "developmental" promoters. Promoters that drive enhanced expression in certain tissues of an organism relative to other tissues of the organism are referred to as "tissue-preferred" promoters. Thus, a "tissue-preferred" promoter causes relatively higher or preferential expression in a specific tissue(s) of a plant, but with lower levels of expression in other tissue(s) of the plant. An "inducible" promoter is a promoter that initiates transcription in response to an environmental stimulus such as heat, cold, drought, light, or other stimuli, such as wounding or chemical application.

In an aspect, a promoter provided herein is a constitutive promoter. In another aspect, a promoter provided herein is an inducible promoter. In a further aspect, a promoter provided herein is a developmental promoter.

In an aspect, this disclosure provides a heterologous promoter. In another aspect, this disclosure provides a promoter that is operably linked to a heterologous polynucleotide. In another aspect, this disclosure provides a polynucleotide sequence that is operably linked to a heterologous promoter.

As used herein, "operably linked" refers to a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous. In an aspect, a promoter provided herein is operably linked to a heterologous nucleic acid molecule.

Plants

As used herein, "tobacco" refers to *Nicotiana tabacum*.

In an aspect, tobacco parts provided include, but are not limited to, a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In an aspect, tobacco part provided does not include seed. In an aspect, this disclosure provides tobacco plant cells, tissues, and organs that are not reproductive material and do not mediate the natural reproduction of the plant. In another aspect, this disclosure also provides tobacco plant cells, tissues, and organs that are reproductive material and mediate the natural reproduction of the plant. In another aspect, this disclosure provides tobacco plant cells, tissues, and organs that cannot maintain themselves via photosynthesis. In another aspect, this disclosure provides somatic tobacco plant cells. Somatic cells, contrary to germline cells, do not mediate plant reproduction.

Cells, tissues and organs can be from seed, fruit, leaf, cotyledon, hypocotyl, meristem, embryos, endosperm, root, shoot, stem, pod, flower, infloresence, stalk, pedicel, style, stigma, receptacle, petal, sepal, pollen, anther, filament, ovary, ovule, pericarp, phloem, vascular tissue. In another aspect, this disclosure provides a tobacco plant chloroplast. In a further aspect, this disclosure provides epidermal cells, stomata cell, leaf or root hairs, a storage root, or a tuber. In another aspect, this disclosure provides a tobacco protoplast.

Skilled artisans understand that tobacco plants naturally reproduce via seeds, not via asexual reproduction or vegetative propagation. In an aspect, this disclosure provides tobacco endosperm.

This disclosure provides cells from tobacco plants provided herein.

As used herein, a "progeny plant" can be from any filial generation, e.g., $F_1$, $F_2$, $F_3$, $F_4$, $F_5$, $F_6$, $F_7$, etc.

In an aspect, a tobacco plant is of a tobacco variety selected from the group consisting of a flue cured variety, a bright variety, a Burley variety, a Virginia variety, a Maryland variety, a dark variety, a Galpão variety, an Oriental variety, and a Turkish variety. In one aspect, a modified tobacco plant provided herein is of a tobacco variety selected from the group consisting of a flue cured variety, a bright variety, a Burley variety, a Virginia variety, a Maryland variety, a dark variety, a Galpão variety, an Oriental variety, and a Turkish variety.

In an aspect, a tobacco cell is of a tobacco variety selected from the group consisting of a flue cured variety, a bright variety, a Burley variety, a Virginia variety, a Maryland variety, a dark variety, a Galpão variety, an Oriental variety, and a Turkish variety. In an aspect, a modified tobacco cell is of a tobacco variety selected from the group consisting of a flue cured variety, a bright variety, a Burley variety, a Virginia variety, a Maryland variety, a dark variety, a Galpão variety, an Oriental variety, and a Turkish variety.

In an aspect, a tobacco leaf is of a tobacco variety selected from the group consisting of a flue cured variety, a bright variety, a Burley variety, a Virginia variety, a Maryland variety, a dark variety, a Galpão variety, an Oriental variety, and a Turkish variety.

In an aspect, a cured tobacco leaf or plant part is of a tobacco variety selected from the group consisting of a flue cured variety, a bright variety, a Burley variety, a Virginia variety, a Maryland variety, a dark variety, a Galpão variety, an Oriental variety, and a Turkish variety. Skilled artisans further understand that cured tobacco does not constitute a living organism and is not capable of growth or reproduction Flue-cured tobaccos (also called "Virginia" or "bright" tobaccos) amount to approximately 40% of world tobacco production. Flue-cured tobaccos are often also referred to as "bright tobacco" because of the golden-yellow to deeporange color it reaches during curing. Flue-cured tobaccos have a light, bright aroma and taste. Flue-cured tobaccos are generally high in sugar and low in oils. Major flue-cured tobacco growing countries are Argentina, Brazil, China, India, Tanzania and the United States of America. In one aspect, tobacco plants or seeds or modified tobacco plants or seeds provided herein are of a flue-cured tobacco variety selected from the group consisting of the varieties listed in Table 2, and any variety essentially derived from any one of the foregoing varieties. See WO 2004/041006 A1. In a further aspect, modified tobacco plants or seeds provided herein are in a flue-cured variety selected from the group consisting of K326, K346, and NC196.

TABLE 2

| Flue-cured Tobacco Varieties | | |
|---|---|---|
| 400 (TC 225) | K 346 | Reams 134 |
| 401 (TC 226) | K 346 (TC 569) | Reams 158 |
| 401 Cherry Red (TC 227) | K358 | Reams 713 |
| 401 Cherry Red Free (TC 228) | K 394 (TC 321) | Reams 744 |
| Cash (TC 250) | K 399 | Reams M1 |
| Cash (TI 278) | K 399 (TC 322) | RG 11 (TC 600) |
| CC 101 | K 730 | RG 13 (TC 601) |
| CC 1063 | Lonibow (TI 1573) | RG 17 (TC 627) |
| CC 13 | Lonibow (TI 1613) | RG 22 (TC 584) |
| CC 143 | McNair 10 (TC 330) | RG 8 (TC 585) |
| CC 200 | McNair 135 (TC 337) | RG 81 (TC 618) |
| CC 27 | McNair 30 (TC 334) | RG H51 |
| CC 301 | McNair 373 (TC 338) | RG4H 217 |
| CC 33 | McNair 944 (TC 339) | RGH 12 |
| CC 35 | MK94 (TI 1512) | RGH 4 |
| CC 37 | MS K 326 | RGH 51 |
| CC 400 | MS NC 71 | RGH 61 |
| CC 500 | MS NC 72 | SC 58 (TC 400) |
| CC 600 | NC 100 | SC 72 (TC 403) |
| CC 65 | NC 102 | Sp. G-168 |
| CC 67 | NC 1071 (TC 364) | SPEIGHT 168 |
| CC 700 | NC 1125-2 | Speight 168 (TC 633) |
| CC 800 | NC 12 (TC 346) | Speight 172 (TC 634) |
| CC 900 | NC 1226 | Speight 178 |
| Coker 139 (TC 259) | NC 196 | Speight 179 |
| Coker 139 yb1, yb2 | NC 2326 (TC 365) | Speight 190 |
| Coker 140 (TC 260) | NC 27 NF (TC 349) | Speight 196 |
| Coker 176 (TC 262) | NC 291 | SPEIGHT 220 |
| Coker 187 (TC 263) | NC 297 | SPEIGHT 225 |
| Coker 187-Hicks (TC 265) | NC 299 | SPEIGHT 227 |
| Coker 209 (TC 267) | NC 37 NF (TC 350) | SPEIGHT 236 |
| Coker 258 (TC 270) | NC 471 | Speight G-10 (TC 416) |
| Coker 298 (TC 272) | NC 55 | Speight G-102 |
| Coker 316 (TC 273) | NC 567 (TC 362) | Speight G-108 |
| Coker 319 (TC 274) | NC 60 (TC 352) | Speight G-111 |
| Coker 347 (TC 275) | NC 606 | Speight G-117 |
| Coker 371-Gold (TC 276) | NC 6140 | Speight G-126 |
| Coker 411 (TC 277) | NC 71 | Speight G-15 (TC 418) |
| Coker 48 (TC 253) | NC 72 | Speight G-23 |
| Coker 51 (TC 254) | NC 729 (TC 557) | Speight G-28 (TC 420) |
| Coker 86 (TC 256) | NC 810 (TC 659) | Speight G-33 |
| CU 263 (TC 619) | NC 82 (TC 356) | Speight G-41 |
| CU 561 | NC 8640 | Speight G-5 |
| DH95-1562-1 | NC 89 (TC 359) | Speight G-52 |
| Dixie Bright 101 (TC 290) | NC 92 | Speight G-58 |
| Dixie Bright 102 (TC 291) | NC 925 | Speight G-70 |
| Dixie Bright 244 (TC 292) | NC 95 (TC 360) | Speight G-70 (TC 426) |
| Dixie Bright 27 (TC 288) | NC 98 (TC 361) | Speight G-80 (TC 427) |
| Dixie Bright 28 (TC 289) | NC EX 24 | Speight NF3 (TC 629) |
| GF 157 | NC PY 10 (TC 367) | STNCB |
| GF 318 | NCTG61 | VA 182 |
| GL 26H | Oxford 1 (TC 369) | VA 45 (TC 559) |
| GL 338 | Oxford 1-181 (TC 370) | Vesta 30 (TC 439) |
| GL 350 | Oxford 2 (TC 371) | Vesta 33 (TC 440) |
| GL 368 | Oxford 207 (TC 632) | Vesta 5 (TC 438) |
| GL 395 | Oxford 26 (TC 373) | Vesta 62 (TC 441) |
| GL 600 | Oxford 3 (TC 372) | Virginia (TI 220) |
| GL 737 | Oxford 414 NF | Virginia (TI 273) |
| GL 939 | PD 611 (TC 387) | Virginia (TI 877) |
| GL 939 (TC 628) | PVH 03 | Virginia 115 (TC 444) |
| Hicks (TC 310) | PVH 09 | Virginia 21 (TC 443) |
| Hicks Broadleaf (TC 311) | PVH 1118 | Virginia Bright (TI 964) |
| K 149 (TC 568) | PVH 1452 | Virginia Bright Leaf (TC 446) |
| K 317 | PVH 1600 | Virginia Gold (TC 447) |
| K 326 | PVH 2110 | White Stem Orinoco (TC 451) |
| K 326 (TC 319) | PVH 2275 | |
| K 340 (TC 320) | R 83 (Line 256-1) (TI 1400) | |

Air-cured tobaccos include "Burley," "Maryland," and "dark" tobaccos. The common factor linking air-cured tobaccos is that curing occurs primarily without artificial sources of heat and humidity. Burley tobaccos are light to dark brown in color, high in oil, and low in sugar. Burley tobaccos are typically air-cured in barns. Major Burley growing countries include Argentina, Brazil, Italy, Malawi, and the United States of America.

Maryland tobaccos are extremely fluffy, have good burning properties, low nicotine and a neutral aroma. Major Maryland growing countries include the United States of America and Italy.

In one aspect, tobacco plants or seeds or modified tobacco plants or seeds provided herein are of a Burley tobacco variety selected from the group consisting of the tobacco varieties listed in Table 3, and any variety essentially derived from any one of the foregoing varieties. In a further aspect, modified tobacco plants or seeds provided herein are in a Burley variety selected from the group consisting of TN 90, KT 209, KT 206, KT212, and HB 4488.

TABLE 3

Burley Tobacco Varieties

| | | |
|---|---|---|
| 4407 LC | HB 4108P | KY 54 (TC 71) |
| AA-37-1 | HB 4151P | KY 56 (TC 72) |
| Burley 21 (TC 7) | HB 4192P | KY 56 (TC 72) |
| Burley 49 (TC 10) | HB 4194P | KY 57 (TC 73) |
| Burley 64 (TC 11) | HB 4196 | KY 58 (TC 74) |
| Burley Mammoth | HB 4488 | KY 8654 (TC 77) |
| KY 16 (TC 12) | | |
| Clay 402 | HB 4488P | KY 8959 |
| Clay 403 | HB04P | KY 9 (TC 54) |
| Clay 502 | HB 4488 LC | KY 907 LC |
| Clays 403 | HIB 21 | KY 908 (TC 630) |
| GR 10 (TC 19) | HPB 21 | NBH 98 (Screened) |
| GR 10 (TC 19) | HY 403 | NC 1206 |
| GR 10A (TC 20) | Hybrid 403 LC | NC 129 |
| GR 13 (TC 21) | Hybrid 404 LC | NC 2000 LC |
| GR 14 (TC 22) | Hybrid 501 LC | NC 2002 LC |
| GR 149 LC | KDH-959 (TC 576) | NC 3 LC |
| GR 153 | KDH-960 (TC 577) | NC 5 LC |
| GR 17 (TC 23) | KT 200 LC | NC 6 LC |
| GR 17B (TC 24) | KT 204 LC | NC 7 LC |
| GR 18 (TC 25) | KT 206 LC | NC BH 129 LC |
| GR 19 (TC 26) | KT 209 LC | NC03-42-2 |
| GR 2 (TC 15) | KT 210 LC | Newton 98 |
| GR 24 (TC 27) | KT 212 LC | R610 LC |
| GR 36 (TC 28) | KT 215 LC | R 630 LC |
| GR 38 (TC 29) | KY 1 (TC 52) | R7-11 |
| GR 38A (TC 30) | KY 10 (TC 55) | R7-12 LC |
| GR 40 (TC 31) | KY 12 (TC 56) | RG 17 |
| GR 42 (TC 32) | KY 14 (TC 57) | TKF 1801 LC |
| GR 42C (TC 33) | KY 14 x L8 LC | TKF 2002 LC |
| GR 43 (TC 34) | KY 15 (TC 58) | TKF 4024 LC |
| GR 44 (TC 35) | KY 16 (TC 59) | TKF 4028 LC |
| GR 45 (TC 36) | KY 17 (TC 60) | TKF 6400 LC |
| GR 46 (TC 37) | KY 19 (TC 61) | TKF 7002 LC |
| GR 48 (TC 38) | KY 21 (TC 62) | TKS 2002 LC |
| GR 5 (TC 16) | KY 22 (TC 63) | TN 86 (TC 82) |

TABLE 3-continued

Burley Tobacco Varieties

| | | |
|---|---|---|
| GR 53 (TC 39) | KY 24 (TC 64) | TN 90 LC |
| GR 6 (TC 17) | KY 26 (TC 65) | TN 97 Hybrid LC |
| GR 9 (TC 18) | KY 33 (TC 66) | TN 97 LC |
| GR139 NS | KY 34 (TC 67) | VA 116 |
| GR139 S | KY 35 (TC 68) | VA 119 |
| HB 04P | KY 41A (TC 69) | Virgin A Mutante (TI 1406) |
| HB 04P LC | KY 5 (TC 53) | Virginia 509 (TC 84) |
| HB 3307P LC | KY 52 (TC 70) | |

In another aspect, tobacco plants or seeds or modified tobacco plants or seeds provided herein are of a Maryland tobacco variety selected from the group consisting of the tobacco varieties listed in Table 4, and any variety essentially derived from any one of the foregoing varieties.

TABLE 4

Maryland Tobacco Varieties

Maryland 10 (TC 498)
Maryland 14 D2 (TC 499)
Maryland 201 (TC 503)
Maryland 21 (TC 500)
Maryland 341 (TC 504)
Maryland 40
Maryland 402
Maryland 59 (TC 501)
Maryland 601
Maryland 609 (TC 505)
Maryland 64 (TC 502)
Maryland 872 (TC 506)
Maryland Mammoth (TC 507)

Dark air-cured tobaccos are distinguished from other tobacco types primarily by its curing process, which gives dark air-cured tobacco its medium-brown to dark-brown color and a distinct aroma. Dark air-cured tobaccos are mainly used in the production of chewing tobacco and snuff. In one aspect, modified tobacco plants or seeds provided herein are of a dark air-cured tobacco variety selected from the group consisting of Sumatra, Jatim, Dominican Cubano, Besuki, One sucker, Green River, Va. sun-cured, and Paraguan Passado, and any variety essentially derived from any one of the foregoing varieties.

Dark fire-cured tobaccos are generally cured with low-burning wood fires on the floors of closed curing barns. Dark fire-cured tobaccos are typically used for making pipe blends, cigarettes, chewing tobacco, snuff, and strong-tasting cigars. Major growing regions for dark fire-cured tobaccos are Tennessee, Kentucky, and Virginia in the United States of America. In one aspect, tobacco plants or seeds or modified tobacco plants or seeds provided herein are of a dark fire-cured tobacco variety selected from the group consisting of the tobacco varieties listed in Table 5, and any variety essentially derived from any one of the foregoing varieties.

TABLE 5

Dark Fire-Cured Tobacco Varieties

| | | |
|---|---|---|
| Black Mammoth (TC 461) | KY 171 (TC 475) | PD 7309 LC |
| Black Mammoth Small Stalk (TC 641) | KY 171 LC | PD 7312 LC |
| Certified Madole (TC 463) | KY 171 NS | PD 7318 LC |
| D-534-A-1 (TC 464) | KY 180 (TC 573) | PD 7319 LC |
| DAC ULT 302 | KY 190 (TC 574) | Petico M PG04 |
| DAC ULT 303 | Little Crittenden | PY KY 160 (TC 612) |
| DAC ULT 306 | Little Crittenden (TC 476) | PY KY 171 (TC 613) |
| DAC ULT 308 | Little Crittenden LC (certified) | Shirey |

TABLE 5-continued

| Dark Fire-Cured Tobacco Varieties | | |
|---|---|---|
| DAC ULT 312 | Little Crittenden PhPh | TI 1372 |
| DF 300 (TC 465) | Lizard Tail Turtle Foot | TN D94 |
| DF 485 (TC 466) | Madole (TC 478) | TN D94 (TC 621) |
| DF 516 (TC 467) | Madole (TC 479) | TN D950 |
| DF 911 (TC 468) | MS KY 171 | TN D950 (PhPh) |
| DT 508 | MS NL Madole LC | TN D950 |
| DT 518 (Screened) | MS TN D950 LC | TN D950 (TC 622) |
| DT 538 LC | Nance (TC 616) | TR Madole (TC 486) |
| DT 592 | Narrow Leaf Madole LC (certified) | VA 309 |
| Improved Madole (TC 471) | Neal Smith Madole (TC 646) | VA 309 (TC 560) |
| Jernigan's Madole (TC 472) | Newtons VH Madole | VA 309 LC (certified) |
| KT 14LC | NL Madole | VA 310 (TC 487) |
| KT D17LC | NL Madole (PhPh) | VA 331 (TC 592) |
| KT D4 LC | NL Madole (TC 484) | VA 355 (TC 638) |
| KT D6 LC | NL Madole LC | VA 359 |
| KT D8 LC | NL Madole LC (PhPh) | VA 359 (Screened) |
| KY 153 (TC 216) | NL Madole NS | VA 359 (TC 639) |
| KY 157 (TC 217) | One Sucker (TC 224) | VA 359 LC (certified) |
| KY 160 | OS 400 | VA 403 (TC 580) |
| KY 160 (TC 218) | PD 302H | VA 405 (TC 581) |
| KY 163 (TC 219) | PD 312H | VA 409 (TC 562) |
| KY 165 (TC 220) | PD 318H | VA 510 (TC 572) |
| KY 170 (TC 474) | PD 7302 LC | |
| KY 171 (PhPh) | PD 7305 | |

Oriental tobaccos are also referred to as Greek, aroma and Turkish tobaccos due to the fact that they are typically grown in eastern Mediterranean regions such as Turkey, Greece, Bulgaria, Macedonia, Syria, Lebanon, Italy, and Romania. The small plant size, small leaf size, and unique aroma properties of Oriental tobacco varieties are a result of their adaptation to the poor soil and stressful climatic conditions in which they have been developed. In one aspect, tobacco plants or seeds or modified tobacco plants or seeds provided herein are of an Oriental tobacco variety selected from the group consisting of the tobacco varieties listed in Table 6, and any variety essentially derived from any one of the foregoing varieties.

TABLE 6

| Oriental Tobacco Varieties | | |
|---|---|---|
| Bafra (TI 1641) | Edirne (TI 1671) | Samsun (TC 536) |
| Bahce (TI 1730) | Ege (TI 1642) | Samsun 959 (TI 1570) |
| Bahia (TI 1416) | Ege-64 (TI 1672) | Samsun Evkaf (TI 1723) |
| Bahia (TI 1455) | Izmir (Akhisar) (TI 1729) | Samsun Holmes NN (TC 540) |
| Baiano (TI 128) | Izmir (Gavurkoy) (TI 1727) | Samsun Maden (TI 1647) |
| Basma | Izmir Ege 64 | Samsun NO 15 (TC 541) |
| Basma (TI 1666) | Izmir-Incekara (TI 1674) | Samsun-BLK SHK Tol (TC 542) |
| Basma Drama | Izmir-Ozbas (TI 1675) | Samsun-Canik (TI 1678) |
| Basma Hybrid (PhPh) | Jaka Dzebel (TI 1326) | Samsun-Maden (TI 1679) |
| Basma Zihna I | Kaba-Kulak | Saribaptar 407 - Izmir Region |
| Bitlis (TI 1667) | Kagoshima Maruba (TI 158) | Smyrna (TC 543) |
| Bitlis (TI 1725) | Katerini | Smyrna No. 23 (TC 545) |
| Bubalovac (TI 1282) | Katerini S53 | Smyrna No. 9 (TC 544) |
| Bursa (TI 1650) | Krumovgrad 58 | Smyrna-Blk Shk Tol (TC 546) |
| Bursa (TI 1668) | MS Basma | Trabzon (TI 1649) |
| Canik (TI 1644) | MS Katerini S53 | Trabzon (TI 1682) |
| Djebel 174 (TI 1492) | Nevrokop 1146 | Trapezund 161 (TI 1407) |
| Djebel 359 (TI 1493) | Ozbas (TI 1645) | Turkish (TC 548) |
| Djebel 81 | Perustitza (TI 980) | Turkish Angshit (TI 90) |
| Dubec 566 (TI 1409) | Prilep (TI 1291) | Turkish Samsum (TI 92) |
| Dubec 7 (TI 1410) | Prilep (TI 1325) | Turkish Tropizoid (TI 93) |
| Dubek 566 (TI 1567) | Prilep 12-2/1 | Turkish Varotic (TI 89) |
| Duzce (TI 1670) | Prilep 23 | Xanthi (TI 1662) |

In an aspect, tobacco plants or seeds or modified tobacco plants or seeds provided herein are of an cigar tobacco variety selected from the group consisting of the tobacco varieties listed in Table 7, and any variety essentially derived from any one of the foregoing varieties.

TABLE 7

Cigar Tobacco Varieties

| | | |
|---|---|---|
| Bahai (TI 62) | Castillo Negro, Blanco, Pina (TI 449) | Enshu (TI 1586) |
| Beinhart 1000 | Caujaro (TI 893) | Florida 301 |
| Beinhart 1000 (TI 1562) | Chocoa (TI 289) | Florida 301 (TC 195) |
| Beinhart 1000-1 (TI 1561) | Chocoa (TI 313) | PA Broadleaf (TC 119) |
| Bergerac C | Connecticut 15 (TC 183) | Pennsylvania Broadleaf |
| Bergerac C (TI 1529) | Connecticut Broadleaf | Pennsylvania Broadleaf (TC 119) |
| Big Cuban (TI 1565) | Connecticut Broadleaf (TC 186) | Petite Havana SR1 |
| Castillo Negro, Blanco, Pina (TI 448) | Connecticut Shade (TC 188) | Petite Havana SR1 (TC 105) |
| Castillo Negro, Blanco, Pina (TI 448A) | Criollo, Colorado (TI 1093) | |

In an aspect, tobacco plants or seeds or modified tobacco plants or seeds provided herein are of a tobacco variety selected from the group consisting of the tobacco varieties listed in Table 8, and any variety essentially derived from any one of the foregoing varieties.

TABLE 8

Other Tobacco Varieties

Chocoa (TI 319)
Hoja Parada (TI 1089)
Hoja Parado (Galpoa) (TI 1068)
Perique (St. James Parrish)
Perique (TC 556)
Perique (TI 1374)
Sylvestris (TI 984)
TI 179

In an aspect, a tobacco plant, seed, or cell is from a variety selected from the group consisting of the tobacco varieties listed in Table 2, Table 3, Table 4, Table 5, Table 6, Table 7, and Table 8.

All foregoing mentioned specific varieties of flue-cured, dark air-cured, Burley, Md., dark fire-cured, cigar, or Oriental type are listed only for exemplary purposes. Any additional flue-cured, dark air-cured, Burley, Md., dark fire-cured, cigar, or Oriental varieties are also contemplated in the present application.

In an aspect, a tobacco plant or variety provided herein is an inbred tobacco plant or variety. As used herein, an "inbred" tobacco variety is a variety that has been bred for genetic homogeneity.

In an aspect, a tobacco plant or variety provided herein is a hybrid tobacco plant or variety. As used herein, a "hybrid" is created by crossing two plants from different varieties or species, such that the progeny comprises genetic material from each parent. Skilled artisans recognize that higher order hybrids can be generated as well. For example, a first hybrid can be made by crossing Variety C with Variety D to create a C×D hybrid, and a second hybrid can be made by crossing Variety E with Variety F to create an E×F hybrid. The first and second hybrids can be further crossed to create the higher order hybrid (C×D)×(E×F) comprising genetic information from all four parent varieties. In an aspect, a modified tobacco plant provided herein is a hybrid tobacco plant. In another aspect, a modified tobacco seed provided herein is a hybrid tobacco seed.

As used herein, the term "crossing" refers to the deliberate mating of two plants. In an aspect, crossing comprises pollination and/or fertilization of a first tobacco plant by a second tobacco plant. The two tobacco plants being crossed can be distantly related, closely related, or identical. In an aspect, the two tobacco plants being crossed are both modified tobacco plants. In an aspect, the two tobacco plants being crossed are of the same tobacco variety. In an aspect, the two tobacco plants being crossed are of two different tobacco varieties. In an aspect, one of the two tobacco plants being crossed is male sterile. In an aspect, one of the two tobacco plants being crossed is female sterile. In an aspect, at least one of the two tobacco plants being crossed is a hybrid tobacco plant. In an aspect, at least one of the two tobacco plants being crossed is a modified tobacco plant.

In an aspect, a tobacco plant or variety provided herein is male sterile. In another aspect, a tobacco plant or variety provided herein is cytoplasmic male sterile (CMS). Male sterile tobacco plants can be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y. 761 pp.

In another aspect, a tobacco plant or variety provided herein is female sterile. As a non-limiting example, female sterile plants can be made by mutating the STIG1 gene. See, for example, Goldman et al. 1994, *EMBO Journal* 13:2976-2984. In an aspect, a modified tobacco plant provided herein is female sterile.

As used herein, a "population" of plants or seeds means a set comprising any number, including one, of individuals, objects, or data from which samples are taken for evaluation. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants or seeds. The population members need not be identical to the population members selected for use in subsequent cycles of analyses or those ultimately selected to obtain final progeny plants or seeds. Often, a plant or seed population is derived from a single biparental cross, but may also derive from two or more crosses between the same or different parents. Although a population of plants or seeds may comprise any number of individuals, those of skill in the art will recognize that plant breeders commonly use population sizes ranging from one or two hundred individuals to several thousand, and that the highest performing 5%-20% of a population is what is commonly selected to be used in subsequent crosses in order to improve the performance of subsequent generations of the population.

Numerous methods for introducing a recombinant DNA construct to a plant cell are known in the art, which can be used according to methods of the present application to produce a transgenic plant cell and plant. Any suitable method or technique for transformation of a plant cell known in the art can be used according to present methods. Effective methods for transformation of plants include bacterially mediated transformation, such as *Agrobacterium*-mediated or *Rhizobium*-mediated transformation and microprojectile bombardment-mediated transformation. A variety of methods are known in the art for transforming explants with a transformation vector via bacterially mediated transformation or microprojectile bombardment and then subsequently culturing, etc., those explants to regenerate or develop transgenic plants. Other methods for plant transformation, such as microinjection, electroporation, vacuum infiltration, pressure, sonication, silicon carbide fiber agitation, polyethylene glycol (PEG)-mediated transformation, etc., are also known in the art. Transgenic plants produced by these transformation methods can be chimeric or non-chimeric for the transformation event depending on the methods and explants used.

Methods of transforming plant cells are well known by persons of ordinary skill in the art. For instance, specific instructions for transforming plant cells by microprojectile bombardment with particles coated with recombinant DNA (e.g., biolistic transformation) are found in U.S. Pat. Nos. 5,550,318; 5,538,880 6,160,208; 6,399,861; and 6,153,812 and *Agrobacterium*-mediated transformation is described in U.S. Pat. Nos. 5,159,135; 5,824,877; 5,591,616; 6,384,301; 5,750,871; 5,463,174; and 5,188,958, all of which are incorporated herein by reference. Additional methods for transforming plants can be found in, for example, Compendium of Transgenic Crop Plants (2009) Blackwell Publishing. Any appropriate method known to those skilled in the art can be used to transform a tobacco cell with any of the nucleic acid molecules provided herein.

In an aspect, a method of providing a nucleic acid molecule to a tobacco cell comprises *Agrobacterium*-mediated transformation. In another aspect, a method of providing a nucleic acid molecule to a cell comprises PEG-mediated transformation. In another aspect, a method of providing a nucleic acid molecule to a cell comprises biolistic transformation. In another aspect, a method of providing a nucleic acid molecule to a cell comprises liposome-mediated transfection (lipofection). In another aspect, a method of providing a nucleic acid molecule to a cell comprises lentiviral transfection.

Lipofection is described in e.g., U.S. Pat. Nos. 5,049,386, 4,946,787; and 4,897,355) and lipofection reagents are sold commercially (e.g., Transfectam™ and Lipofectin™) Cationic and neutral lipids that are suitable for efficient receptor-recognition lipofection of polynucleotides include those of WO 91/17424 and WO 91/16024. Delivery can be to cells (e.g. in vitro or ex vivo administration) or target tissues (e.g. in vivo administration).

Any tobacco cell from which a fertile tobacco plant can be regenerated is contemplated as a useful recipient cell for practice of this disclosure. In an aspect, a recombinant DNA construct is introduced to a tobacco cell. In an aspect, a recombinant DNA construct is introduced to a tobacco protoplast cell. In another aspect, a recombinant DNA construct is introduced to a tobacco callus cell. In an aspect, a recombinant DNA construct is introduced to a tobacco cell selected from the group consisting of a seed cell, a fruit cell, a leaf cell, a cotyledon cell, a hypocotyl cell, a meristem cell, an embryo cell, an endosperm cell, a root cell, a shoot cell, a stem cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, and a phloem cell.

Callus can be initiated from various tissue sources, including, but not limited to, immature embryos or parts of embryos, seedling apical meristems, microspores, and the like. Those cells which are capable of proliferating as callus can serve as recipient cells for transformation. Practical transformation methods and materials for making transgenic plants of this disclosure (e.g., various media and recipient target cells, transformation of immature embryos, and subsequent regeneration of fertile transgenic plants) are disclosed, for example, in U.S. Pat. Nos. 6,194,636 and 6,232,526 and U. S. Patent Application Publication 2004/0216189, all of which are incorporated herein by reference.

TSNA Reduction

"Alkaloids" are complex, nitrogen-containing compounds that naturally occur in plants, and have pharmacological effects in humans and animals. "Nicotine" is the primary natural alkaloid in commercialized cigarette tobacco and accounts for about 90 percent of the alkaloid content in *Nicotiana tabacum*. Other major alkaloids in tobacco include cotinine, nornicotine, myosmine, nicotyrine, anabasine and anatabine. Minor tobacco alkaloids include nicotine-n-oxide, N-methyl anatabine, N-methyl anabasine, pseudooxynicotine, 2,3 dipyridyl and others.

Alkaloid levels can be assayed by methods known in the art, for example by quantification based on gas-liquid chromatography, high performance liquid chromatography, radio-immunoassays, and enzyme-linked immunosorbent assays. For example, nicotinic alkaloid levels can be measured by a GC-FID method based on CORESTA Recommended Method No. 7, 1987 and ISO Standards (ISO TC 126N 394 E. See also Hibi et al., *Plant Physiology* 100: 826-35 (1992) for a method using gas-liquid chromatography equipped with a capillary column and an FID detector.

Alternatively, tobacco total alkaloids can be measured using a segmented-flow colorimetric method developed for analysis of tobacco samples as adapted by Skalar Instrument Co. (West Chester, Pa.) and described by Collins et al., *Tobacco Science* 13:79-81 (1969). In short, samples of tobacco are dried, ground, and extracted prior to analysis of total alkaloids and reducing sugars. The method then employs an acetic acid/methanol/water extraction and charcoal for decolorization. Determination of total alkaloids was based on the reaction of cyanogen chloride with nicotine alkaloids in the presence of an aromatic amine to form a colored complex which is measured at 460 nm.

In an aspect, the level of total TSNAs or an individual TSNA is measured based on a freeze-dried cured leaf sample using liquid chromatography with tandem mass spectrometry (LC/MS/MS).

In another aspect, introgression of a PY QTL or a PY trait into a second tobacco variety reduces the level of at least one tobacco-specific nitrosamine (TSNA) as compared to the second tobacco variety lacking the PY QTL or PY trait. TSNAs include N-nitrosonornicotine (NNN) and 4-(methylnitrosamino)-1-(3-pyridyl)-1-butanone (NNK), N'-nitrosoanatabine (NAT), and N'-nitrosoanabasine (NAB).

In an aspect, a reduced level of at least one TSNA comprised reduced NNN. In an aspect, a reduced level of at least one TSNA comprised reduced NNK. In an aspect, a reduced level of at least one TSNA comprised reduced NAT. In an aspect, a reduced level of at least one TSNA comprised reduced NAB.

In an aspect, a reduced level of at least one TSNA comprises a reduction of NNN by at least 1% as compared to a control tobacco variety lacking a PY QTL or PY trait. In an aspect, a reduced level of at least one TSNA comprises a reduction of NNN by at least 2% as compared to a control tobacco variety lacking a PY QTL or PY trait. In an aspect, a reduced level of at least one TSNA comprises a reduction of NNN by at least 3% as compared to a control tobacco variety lacking a PY QTL or PY trait. In an aspect, a reduced level of at least one TSNA comprises a reduction of NNN by at least 4% as compared to a control tobacco variety lacking a PY QTL or PY trait. In an aspect, a reduced level of at least one TSNA comprises a reduction of NNN by at least 5% as compared to a control tobacco variety lacking a PY QTL or PY trait. In an aspect, a reduced level of at least one TSNA comprises a reduction of NNN by at least 10% as compared to a control tobacco variety lacking a PY QTL or PY trait. In an aspect, a reduced level of at least one TSNA comprises a reduction of NNN by at least 15% as compared to a control tobacco variety lacking a PY QTL or PY trait. In an aspect, a reduced level of at least one TSNA comprises a reduction of NNN by at least 20% as compared to a control tobacco variety lacking a PY QTL or PY trait. In an aspect, a reduced level of at least one TSNA comprises a reduction of NNN by at least 25% as compared to a control tobacco variety lacking a PY QTL or PY trait. In an aspect, a reduced level of at least one TSNA comprises a reduction of NNN by at least 50% as compared to a control tobacco variety lacking a PY QTL or PY trait. In an aspect, a reduced level of at least one TSNA comprises a reduction of NNN by at least 75% as compared to a control tobacco variety lacking a PY QTL or PY trait. In an aspect, a reduced level of at least one TSNA comprises a reduction of NNN by between 1% and 99% as compared to a control tobacco variety lacking a PY QTL or PY trait. In an aspect, a reduced level of at least one TSNA comprises a reduction of NNN by between 1% and 90% as compared to a control tobacco variety lacking a PY QTL or PY trait. In an aspect, a reduced level of at least one TSNA comprises a reduction of NNN by between 1% and 80% as compared to a control tobacco variety lacking a PY QTL or PY trait. In an aspect, a reduced level of at least one TSNA comprises a reduction of NNN by between 1% and 70% as compared to a control tobacco variety lacking a PY QTL or PY trait. In an aspect, a reduced level of at least one TSNA comprises a reduction of NNN by between 1% and 60% as compared to a control tobacco variety lacking a PY QTL or PY trait. In an aspect, a reduced level of at least one TSNA comprises a reduction of NNN by between 1% and 50% as compared to a control tobacco variety lacking a PY QTL or PY trait. In an aspect, a reduced level of at least one TSNA comprises a reduction of NNN by between 1% and 40% as compared to a control tobacco variety lacking a PY QTL or PY trait. In an aspect, a reduced level of at least one TSNA comprises a reduction of NNN by between 1% and 30% as compared to a control tobacco variety lacking a PY QTL or PY trait. In an aspect, a reduced level of at least one TSNA comprises a reduction of NNN by between 1% and 20% as compared to a control tobacco variety lacking a PY QTL or PY trait. In an aspect, a reduced level of at least one TSNA comprises a reduction of NNN by between 1% and 10% as compared to a control tobacco variety lacking a PY QTL or PY trait. In an aspect, a reduced level of at least one TSNA comprises a reduction of NNN by between 1% and 5% as compared to a control tobacco variety lacking a PY QTL or PY trait.

In an aspect, a reduced level of at least one TSNA comprises a reduction of NNK by at least 1% as compared to a control tobacco variety lacking a PY QTL or PY trait. In an aspect, a reduced level of at least one TSNA comprises a reduction of NNK by at least 2% as compared to a control tobacco variety lacking a PY QTL or PY trait. In an aspect, a reduced level of at least one TSNA comprises a reduction of NNK by at least 3% as compared to a control tobacco variety lacking a PY QTL or PY trait. In an aspect, a reduced level of at least one TSNA comprises a reduction of NNK by at least 4% as compared to a control tobacco variety lacking a PY QTL or PY trait. In an aspect, a reduced level of at least one TSNA comprises a reduction of NNK by at least 5% as compared to a control tobacco variety lacking a PY QTL or PY trait. In an aspect, a reduced level of at least one TSNA comprises a reduction of NNK by at least 10% as compared to a control tobacco variety lacking a PY QTL or PY trait. In an aspect, a reduced level of at least one TSNA comprises a reduction of NNK by at least 15% as compared to a control tobacco variety lacking a PY QTL or PY trait. In an aspect, a reduced level of at least one TSNA comprises a reduction of NNK by at least 20% as compared to a control tobacco variety lacking a PY QTL or PY trait. In an aspect, a reduced level of at least one TSNA comprises a reduction of NNK by at least 25% as compared to a control tobacco variety lacking a PY QTL or PY trait. In an aspect, a reduced level of at least one TSNA comprises a reduction of NNK by at least 50% as compared to a control tobacco variety lacking a PY QTL or PY trait. In an aspect, a reduced level of at least one TSNA comprises a reduction of NNK by at least 75% as compared to a control tobacco variety lacking a PY QTL or PY trait. In an aspect, a reduced level of at least one TSNA comprises a reduction of NNK by between 1% and 99% as compared to a control tobacco variety lacking a PY QTL or PY trait. In an aspect, a reduced level of at least one TSNA comprises a reduction of NNK by between 1% and 90% as compared to a control tobacco variety lacking a PY QTL or PY trait. In an aspect, a reduced level of at least one TSNA comprises a reduction of NNK by between 1% and 80% as compared to a control tobacco variety lacking a PY QTL or PY trait. In an aspect, a reduced level of at least one TSNA comprises a reduction of NNK by between 1% and 70% as compared to a control tobacco variety lacking a PY QTL or PY trait. In an aspect, a reduced level of at least one TSNA comprises a reduction of NNK by between 1% and 60% as compared to a control tobacco variety lacking a PY QTL or PY trait. In an aspect, a reduced level of at least one TSNA comprises a reduction of NNK by between 1% and 50% as compared to a control tobacco variety lacking a PY QTL or PY trait. In an aspect, a reduced level of at least one TSNA comprises a reduction of NNK by between 1% and 40% as compared to a control tobacco variety lacking a PY QTL or PY trait. In an aspect, a reduced level of at least one TSNA comprises a reduction of NNK by between 1% and 30% as compared to a control tobacco variety lacking a PY QTL or PY trait. In an aspect, a reduced level of at least one TSNA comprises a reduction of NNK by between 1% and 20% as compared to a control tobacco variety lacking a PY QTL or PY trait. In an aspect, a reduced level of at least one TSNA comprises a reduction of NNK by between 1% and 10% as compared to a control tobacco variety lacking a PY QTL or PY trait. In an aspect, a reduced level of at least one TSNA comprises a reduction of NNK by between 1% and 5% as compared to a control tobacco variety lacking a PY QTL or PY trait.

In an aspect, a reduced level of at least one TSNA comprises a reduction of NAT by at least 1% as compared to a control tobacco variety lacking a PY QTL or PY trait. In an aspect, a reduced level of at least one TSNA comprises a reduction of NAT by at least 2% as compared to a control tobacco variety lacking a PY QTL or PY trait. In an aspect, a reduced level of at least one TSNA comprises a reduction of NAT by at least 3% as compared to a control tobacco variety lacking a PY QTL or PY trait. In an aspect, a reduced level of at least one TSNA comprises a reduction of NAT by at least 4% as compared to a control tobacco variety lacking a PY QTL or PY trait. In an aspect, a reduced level of at least one TSNA comprises a reduction of NAT by at least 5% as compared to a control tobacco variety lacking a PY QTL or PY trait. In an aspect, a reduced level of at least one TSNA comprises a reduction of NAT by at least 10% as compared to a control tobacco variety lacking a PY QTL or PY trait. In an aspect, a reduced level of at least one TSNA comprises a reduction of NAT by at least 15% as compared to a control tobacco variety lacking a PY QTL or PY trait. In an aspect, a reduced level of at least one TSNA comprises a reduction of NAT by at least 20% as compared to a control tobacco variety lacking a PY QTL or PY trait. In an aspect, a reduced level of at least one TSNA comprises a reduction of NAT by at least 25% as compared to a control tobacco variety lacking a PY QTL or PY trait. In an aspect, a reduced level of at least one TSNA comprises a reduction of NAT by at least 50% as compared to a control tobacco variety lacking a PY QTL or PY trait. In an aspect, a reduced level of at least one TSNA comprises a reduction of NAT by at least 75% as compared to a control tobacco variety lacking a PY QTL or PY trait. In an aspect, a reduced level of at least one TSNA comprises a reduction of NAT by between 1% and 99% as compared to a control tobacco variety lacking a PY QTL or PY trait. In an aspect, a reduced level of at least one TSNA comprises a reduction of NAT by between 1% and 90% as compared to a control tobacco variety lacking a PY QTL or PY trait. In an aspect, a reduced level of at least one TSNA comprises a reduction of NAT by between 1% and 80% as compared to a control tobacco variety lacking a PY QTL or PY trait. In an aspect, a reduced level of at least one TSNA comprises a reduction of NAT by between 1% and 70% as compared to a control tobacco variety lacking a PY QTL or PY trait. In an aspect, a reduced level of at least one TSNA comprises a reduction of NAT by between 1% and 60% as compared to a control tobacco variety lacking a PY QTL or PY trait. In an aspect, a reduced level of at least one TSNA comprises a reduction of NAT by between 1% and 50% as compared to a control tobacco variety lacking a PY QTL or PY trait. In an aspect, a reduced level of at least one TSNA comprises a reduction of NAT by between 1% and 40% as compared to a control tobacco variety lacking a PY QTL or PY trait. In an aspect, a reduced level of at least one TSNA comprises a reduction of NAT by between 1% and 30% as compared to a control tobacco variety lacking a PY QTL or PY trait. In an aspect, a reduced level of at least one TSNA comprises a reduction of NAT by between 1% and 20% as compared to a control tobacco variety lacking a PY QTL or PY trait. In an aspect, a reduced level of at least one TSNA comprises a reduction of NAT by between 1% and 10% as compared to a control tobacco variety lacking a PY QTL or PY trait. In an aspect, a reduced level of at least one TSNA comprises a reduction of NAT by between 1% and 5% as compared to a control tobacco variety lacking a PY QTL or PY trait.

In an aspect, a reduced level of at least one TSNA comprises a reduction of NAB by at least 1% as compared to a control tobacco variety lacking a PY QTL or PY trait. In an aspect, a reduced level of at least one TSNA comprises a reduction of NAB by at least 2% as compared to a control tobacco variety lacking a PY QTL or PY trait. In an aspect, a reduced level of at least one TSNA comprises a reduction of NAB by at least 3% as compared to a control tobacco variety lacking a PY QTL or PY trait. In an aspect, a reduced level of at least one TSNA comprises a reduction of NAB by at least 4% as compared to a control tobacco variety lacking a PY QTL or PY trait. In an aspect, a reduced level of at least one TSNA comprises a reduction of NAB by at least 5% as compared to a control tobacco variety lacking a PY QTL or PY trait. In an aspect, a reduced level of at least one TSNA comprises a reduction of NAB by at least 10% as compared to a control tobacco variety lacking a PY QTL or PY trait. In an aspect, a reduced level of at least one TSNA comprises a reduction of NAB by at least 15% as compared to a control tobacco variety lacking a PY QTL or PY trait. In an aspect, a reduced level of at least one TSNA comprises a reduction of NAB by at least 20% as compared to a control tobacco variety lacking a PY QTL or PY trait. In an aspect, a reduced level of at least one TSNA comprises a reduction of NAB by at least 25% as compared to a control tobacco variety lacking a PY QTL or PY trait. In an aspect, a reduced level of at least one TSNA comprises a reduction of NAB by at least 50% as compared to a control tobacco variety lacking a PY QTL or PY trait. In an aspect, a reduced level of at least one TSNA comprises a reduction of NAB by at least 75% as compared to a control tobacco variety lacking a PY QTL or PY trait. In an aspect, a reduced level of at least one TSNA comprises a reduction of NAB by between 1% and 99% as compared to a control tobacco variety lacking a PY QTL or PY trait. In an aspect, a reduced level of at least one TSNA comprises a reduction of NAB by between 1% and 90% as compared to a control tobacco variety lacking a PY QTL or PY trait. In an aspect, a reduced level of at least one TSNA comprises a reduction of NAB by between 1% and 80% as compared to a control tobacco variety lacking a PY QTL or PY trait. In an aspect, a reduced level of at least one TSNA comprises a reduction of NAB by between 1% and 70% as compared to a control tobacco variety lacking a PY QTL or PY trait. In an aspect, a reduced level of at least one TSNA comprises a reduction of NAB by between 1% and 60% as compared to a control tobacco variety lacking a PY QTL or PY trait. In an aspect, a reduced level of at least one TSNA comprises a reduction of NAB by between 1% and 50% as compared to a control tobacco variety lacking a PY QTL or PY trait. In an aspect, a reduced level of at least one TSNA comprises a reduction of NAB by between 1% and 40% as compared to a control tobacco variety lacking a PY QTL or PY trait. In an aspect, a reduced level of at least one TSNA comprises a reduction of NAB by between 1% and 30% as compared to a control tobacco variety lacking a PY QTL or PY trait. In an aspect, a reduced level of at least one TSNA comprises a reduction of NAB by between 1% and 20% as compared to a control tobacco variety lacking a PY QTL or PY trait. In an aspect, a reduced level of at least one TSNA comprises a reduction of NAB by between 1% and 10% as compared to a control tobacco variety lacking a PY QTL or PY trait. In an aspect, a reduced level of at least one TSNA comprises a reduction of NAB by between 1% and 5% as compared to a control tobacco variety lacking a PY QTL or PY trait.

Leaf Grading

In an aspect, a introgression of a PY QTL or a PY trait into a low-alkaloid tobacco variety improves the USDA leaf grade index of the progeny plant as compared to a low-alkaloid tobacco variety lacking the PY QTL or PY trait.

In an aspect, introgression of a PY QTL or a PY trait into a low-alkaloid tobacco variety improves the USDA leaf grade index by at least 1% as compared to a low-alkaloid tobacco variety lacking the PY QTL or PY trait. In an aspect, introgression of a PY QTL or a PY trait into a low-alkaloid tobacco variety improves the USDA leaf grade index by at least 2% as compared to a low-alkaloid tobacco variety lacking the PY QTL or PY trait. In an aspect, introgression of a PY QTL or a PY trait into a low-alkaloid tobacco variety improves the USDA leaf grade index by at least 3% as compared to a low-alkaloid tobacco variety lacking the PY QTL or PY trait. In an aspect, introgression of a PY QTL or a PY trait into a low-alkaloid tobacco variety improves the USDA leaf grade index by at least 4% as compared to a low-alkaloid tobacco variety lacking the PY QTL or PY trait. In an aspect, introgression of a PY QTL or a PY trait into a low-alkaloid tobacco variety improves the USDA leaf grade index by at least 5% as compared to a low-alkaloid tobacco variety lacking the PY QTL or PY trait. In an aspect, introgression of a PY QTL or a PY trait into a low-alkaloid tobacco variety improves the USDA leaf grade index by at least 10% as compared to a low-alkaloid tobacco variety lacking the PY QTL or PY trait. In an aspect, introgression of a PY QTL or a PY trait into a low-alkaloid tobacco variety improves the USDA leaf grade index by at least 15% as compared to a low-alkaloid tobacco variety lacking the PY QTL or PY trait. In an aspect, introgression of a PY QTL or a PY trait into a low-alkaloid tobacco variety improves the USDA leaf grade index by at least 20% as compared to a low-alkaloid tobacco variety lacking the PY QTL or PY trait. In an aspect, introgression of a PY QTL or a PY trait into a low-alkaloid tobacco variety improves the USDA leaf grade index by at least 25% as compared to a low-alkaloid tobacco variety lacking the PY QTL or PY trait. In an aspect, introgression of a PY QTL or a PY trait into a low-alkaloid tobacco variety improves the USDA leaf grade index by at least 30% as compared to a low-alkaloid tobacco variety lacking the PY QTL or PY trait. In an aspect, introgression of a PY QTL or a PY trait into a low-alkaloid tobacco variety improves the USDA leaf grade index by at least 50% as compared to a low-alkaloid tobacco variety lacking the PY QTL or PY trait. In an aspect, introgression of a PY QTL or a PY trait into a low-alkaloid tobacco variety improves the USDA leaf grade index by at least 75% as compared to a low-alkaloid tobacco variety lacking the PY QTL or PY trait. In an aspect, introgression of a PY QTL or a PY trait into a low-alkaloid tobacco variety improves the USDA leaf grade index by at least 100% as compared to a low-alkaloid tobacco variety lacking the PY QTL or PY trait. In an aspect, introgression of a PY QTL or a PY trait into a low-alkaloid tobacco variety improves the USDA leaf grade index by at least 200% as compared to a low-alkaloid tobacco variety lacking the PY QTL or PY trait. In an aspect, introgression of a PY QTL or a PY trait into a low-alkaloid tobacco variety improves the USDA leaf grade index by between 1% and 20% as compared to a low-alkaloid tobacco variety lacking the PY QTL or PY trait. In an aspect, introgression of a PY QTL or a PY trait into a low-alkaloid tobacco variety improves the USDA leaf grade index by between 1% and 30% as compared to a low-alkaloid tobacco variety lacking the PY QTL or PY trait. In an aspect, introgression of a PY QTL or a PY trait into a low-alkaloid tobacco variety improves the USDA leaf grade index by between 1% and 40% as compared to a low-alkaloid tobacco variety lacking the PY QTL or PY trait. In an aspect, introgression of a PY QTL or a PY trait into a low-alkaloid tobacco variety improves the USDA leaf grade index by between 1% and 50% as compared to a low-alkaloid tobacco variety lacking the PY QTL or PY trait. In an aspect, introgression of a PY QTL or a PY trait into a low-alkaloid tobacco variety improves the USDA leaf grade index by between 1% and 60% as compared to a low-alkaloid tobacco variety lacking the PY QTL or PY trait. In an aspect, introgression of a PY QTL or a PY trait into a low-alkaloid tobacco variety improves the USDA leaf grade index by between 1% and 70% as compared to a low-alkaloid tobacco variety lacking the PY QTL or PY trait. In an aspect, introgression of a PY QTL or a PY trait into a low-alkaloid tobacco variety improves the USDA leaf grade index by between 1% and 80% as compared to a low-alkaloid tobacco variety lacking the PY QTL or PY trait. In an aspect, introgression of a PY QTL or a PY trait into a low-alkaloid tobacco variety improves the USDA leaf grade index by between 1% and 90% as compared to a low-alkaloid tobacco variety lacking the PY QTL or PY trait. In an aspect, introgression of a PY QTL or a PY trait into a low-alkaloid tobacco variety improves the USDA leaf grade index by between 1% and 100% as compared to a low-alkaloid tobacco variety lacking the PY QTL or PY trait. In an aspect, introgression of a PY QTL or a PY trait into a low-alkaloid tobacco variety improves the USDA leaf grade index by between 1% and 150% as compared to a low-alkaloid tobacco variety lacking the PY QTL or PY trait. In an aspect, introgression of a PY QTL or a PY trait into a low-alkaloid tobacco variety improves the USDA leaf grade index by between 1% and 200% as compared to a low-alkaloid tobacco variety lacking the PY QTL or PY trait. In an aspect, introgression of a PY QTL or a PY trait into a low-alkaloid tobacco variety improves the USDA leaf grade index by between 1% and 300% as compared to a low-alkaloid tobacco variety lacking the PY QTL or PY trait. In an aspect, introgression of a PY QTL or a PY trait into a low-alkaloid tobacco variety improves the USDA leaf grade index by between 10% and 50% as compared to a low-alkaloid tobacco variety lacking the PY QTL or PY trait. In an aspect, introgression of a PY QTL or a PY trait into a low-alkaloid tobacco variety improves the USDA leaf grade index by between 10% and 30% as compared to a low-alkaloid tobacco variety lacking the PY QTL or PY trait.

In an aspect, introgression of a PY QTL or a PY trait into a low-alkaloid tobacco variety improves the USDA leaf grade index by at least 1 as compared to a low-alkaloid tobacco variety lacking the PY QTL or PY trait. In an aspect, introgression of a PY QTL or a PY trait into a low-alkaloid tobacco variety improves the USDA leaf grade index by at least 2 as compared to a low-alkaloid tobacco variety lacking the PY QTL or PY trait. In an aspect, introgression of a PY QTL or a PY trait into a low-alkaloid tobacco variety improves the USDA leaf grade index by at least 3 as compared to a low-alkaloid tobacco variety lacking the PY QTL or PY trait. In an aspect, introgression of a PY QTL or a PY trait into a low-alkaloid tobacco variety improves the USDA leaf grade index by at least 4 as compared to a low-alkaloid tobacco variety lacking the PY QTL or PY trait. In an aspect, introgression of a PY QTL or a PY trait into a low-alkaloid tobacco variety improves the USDA leaf grade index by at least 5 as compared to a low-alkaloid tobacco variety lacking the PY QTL or PY trait. In an aspect, introgression of a PY QTL or a PY trait into a low-alkaloid tobacco variety improves the USDA leaf grade index by at least 6 as compared to a low-alkaloid tobacco variety lacking the PY QTL or PY trait. In an aspect, introgression of a PY QTL or a PY trait into a low-alkaloid tobacco variety improves the USDA leaf grade index by at least 7 as compared to a low-alkaloid tobacco variety lacking the PY QTL or PY trait. In an aspect, introgression of a PY QTL or a PY trait into a low-alkaloid tobacco variety improves the USDA leaf grade index by at least 8 as compared to a low-alkaloid tobacco variety lacking the PY QTL or PY trait. In an aspect, introgression of a PY QTL or a PY trait into a low-alkaloid tobacco variety improves the USDA leaf grade index by at least 9 as compared to a low-alkaloid tobacco variety lacking the PY QTL or PY trait. In an aspect, introgression of a PY QTL or a PY trait into a low-alkaloid tobacco variety improves the USDA leaf grade index by at least 10 as compared to a low-alkaloid tobacco variety lacking the PY QTL or PY trait. In an aspect, introgression of a PY QTL or a PY trait into a low-alkaloid tobacco variety improves the USDA leaf grade index by at least 11 as compared to a low-alkaloid tobacco variety lacking the PY QTL or PY trait. In an aspect, introgression of a PY QTL or a PY trait into a low-alkaloid tobacco variety improves the USDA leaf grade index by at least 12 as compared to a low-alkaloid tobacco variety lacking the PY QTL or PY trait. In an aspect, introgression of a PY QTL or a PY trait into a low-alkaloid tobacco variety improves the USDA leaf grade index by at least 13 as compared to a low-alkaloid tobacco variety lacking the PY QTL or PY trait. In an aspect, introgression of a PY QTL or a PY trait into a low-alkaloid tobacco variety improves the USDA leaf grade index by at least 14 as compared to a low-alkaloid tobacco variety lacking the PY QTL or PY trait. In an aspect, introgression of a PY QTL or a PY trait into a low-alkaloid tobacco variety improves the USDA leaf grade index by at least 15 as compared to a low-alkaloid tobacco variety lacking the PY QTL or PY trait. In an aspect, introgression of a PY QTL or a PY trait into a low-alkaloid tobacco variety improves the USDA leaf grade index by at least 16 as compared to a low-alkaloid tobacco variety lacking the PY QTL or PY trait. In an aspect, introgression of a PY QTL or a PY trait into a low-alkaloid tobacco variety improves the USDA leaf grade index by at least 17 as compared to a low-alkaloid tobacco variety lacking the PY QTL or PY trait. In an aspect, introgression of a PY QTL or a PY trait into a low-alkaloid tobacco variety improves the USDA leaf grade index by at least 18 as compared to a low-alkaloid tobacco variety lacking the PY QTL or PY trait. In an aspect, introgression of a PY QTL or a PY trait into a low-alkaloid tobacco variety improves the USDA leaf grade index by at least 19 as compared to a low-alkaloid tobacco variety lacking the PY QTL or PY trait. In an aspect, introgression of a PY QTL or a PY trait into a low-alkaloid tobacco variety improves the USDA leaf grade index by at least 20 as compared to a low-alkaloid tobacco variety lacking the PY QTL or PY trait. In an aspect, introgression of a PY QTL or a PY trait into a low-alkaloid tobacco variety improves the USDA leaf grade index by at least 25 as compared to a low-alkaloid tobacco variety lacking the PY QTL or PY trait. In an aspect, introgression of a PY QTL or a PY trait into a low-alkaloid tobacco variety improves the USDA leaf grade index by at least 30 as compared to a low-alkaloid tobacco variety lacking the PY QTL or PY trait. In an aspect, introgression of a PY QTL or a PY trait into a low-alkaloid tobacco variety improves the USDA leaf grade index by at least 40 as compared to a low-alkaloid tobacco variety lacking the PY QTL or PY trait. In an aspect, introgression of a PY QTL or a PY trait into a low-alkaloid tobacco variety improves the USDA leaf grade index by at least 50 as compared to a low-alkaloid tobacco variety lacking the PY QTL or PY trait. In an aspect, introgression of a PY QTL or a PY trait into a low-alkaloid tobacco variety improves the USDA leaf grade index by between 1 and 90 as compared to a low-alkaloid tobacco variety lacking the PY QTL or PY trait. In an aspect, introgression of a PY QTL or a PY trait into a low-alkaloid tobacco variety improves the USDA leaf grade index by between 1 and 80 as compared to a low-alkaloid tobacco variety lacking the PY QTL or PY trait. In an aspect, introgression of a PY QTL or a PY trait into a low-alkaloid tobacco variety improves the USDA leaf grade index by between 1 and 70 as compared to a low-alkaloid tobacco variety lacking the PY QTL or PY trait. In an aspect, introgression of a PY QTL or a PY trait into a low-alkaloid tobacco variety improves the USDA leaf grade index by between 1 and 60 as compared to a low-alkaloid tobacco variety lacking the PY QTL or PY trait. In an aspect, introgression of a PY QTL or a PY trait into a low-alkaloid tobacco variety improves the USDA leaf grade index by between 1 and 50 as compared to a low-alkaloid tobacco variety lacking the PY QTL or PY trait. In an aspect, introgression of a PY QTL or a PY trait into a low-alkaloid tobacco variety improves the USDA leaf grade index by between 1 and 40 as compared to a low-alkaloid tobacco variety lacking the PY QTL or PY trait. In an aspect, introgression of a PY QTL or a PY trait into a low-alkaloid tobacco variety improves the USDA leaf grade index by between 1 and 30 as compared to a low-alkaloid tobacco variety lacking the PY QTL or PY trait. In an aspect, introgression of a PY QTL or a PY trait into a low-alkaloid tobacco variety improves the USDA leaf grade index by between 1 and 20 as compared to a low-alkaloid tobacco variety lacking the PY QTL or PY trait. In an aspect, introgression of a PY QTL or a PY trait into a low-alkaloid tobacco variety improves the USDA leaf grade index by between 1 and 10 as compared to a low-alkaloid tobacco variety lacking the PY QTL or PY trait. In an aspect, introgression of a PY QTL or a PY trait into a low-alkaloid tobacco variety improves the USDA leaf grade index by between 1 and 5 as compared to a low-alkaloid tobacco variety lacking the PY QTL or PY trait. In an aspect, introgression of a PY QTL or a PY trait into a low-alkaloid tobacco variety improves the USDA leaf grade index by between 5 and 10 as compared to a low-alkaloid tobacco variety lacking the PY QTL or PY trait. In an aspect, introgression of a PY QTL or a PY trait into a low-alkaloid tobacco variety improves the USDA leaf grade index by between 5 and 15 as compared to a low-alkaloid tobacco variety lacking the PY QTL or PY trait. In an aspect, introgression of a PY QTL or a PY trait into a low-alkaloid tobacco variety improves the USDA leaf grade index by between 10 and 20 as compared to a low-alkaloid tobacco variety lacking the PY QTL or PY trait.

As used herein, a "low-alkaloid varieties" refers to tobacco varieties that comprise alkaloid levels equal to, less than, or no more than 20% higher than the alkaloid levels measured in known low-alkaloid lines such as CS15 and LN KY171.

As used herein, "USDA grade index", "grade index", or "numerical grade index" refers to a subdivision of a type according to group, quality, and color. In one aspect, a USDA grade quality score is quantified as a 0-100 numerical representation of the grade as determined by an official USDA grader and is a weighted average of all stalk positions. A higher grade index indicates higher quality. Alternatively, leaf grade can be determined via hyper-spectral imaging. See e.g., WO 2011/027315 (published on Mar. 10, 2011, and incorporated by reference in its entirety).

As used herein, a "certified tobacco leaf grader" refers to a person trained to grade tobacco leaves in accordance with USDA Official Standards Grades defined by the United States Department of Agriculture (USDA), Agricultural Marketing Systems as published in 7 CFR § 29. As used herein, an "official USDA grade" may be assigned by an employee, a past employee, or a person otherwise trained to grade tobacco leaves in accordance with USDA Official Standards Grades. Exemplary steps of a standard operation for commercial inspection service begins with a grower delivering tobacco to market after which the tobacco is arranged on flat baskets as lots. Each lot is weighed and then inspected by an official USDA grader. After examination, the grader assigns a grade to each lot which becomes a certificate of grade indicating group, quality, and color. The steps for grading experimental lots is similar; however, experimental tobacco is not taken to market or otherwise used for commercial purposes.

Tobacco grades are evaluated based on factors including, but not limited to, the leaf stalk position, leaf size, leaf color, leaf uniformity and integrity, ripeness, texture, elasticity, sheen (related with the intensity and the depth of coloration of the leaf as well as the shine), hygroscopicity (the faculty of the tobacco leaves to absorb and to retain the ambient moisture), and green nuance or cast. Leaf grade can be determined, for example, using an Official Standard Grade published by the Agricultural Marketing Service of the US Department of Agriculture (7 U.S.C. § 511). See, e.g., Official Standard Grades for Burley Tobacco (U.S. Type 31 and Foreign Type 93), effective Nov. 5, 1990 (55 F.R. 40645); Official Standard Grades for Flue-Cured Tobacco (U.S. Types 11, 12, 13, 14 and Foreign Type 92), effective Mar. 27, 1989 (54 F.R. 7925); Official Standard Grades for Pennsylvania Seedleaf Tobacco (U.S. Type 41), effective Jan. 8, 1965 (29 F.R. 16854); Official Standard Grades for Ohio Cigar-Leaf Tobacco (U.S. Types 42, 43, and 44), effective Dec. 8, 1963 (28 F.R. 11719 and 28 F.R. 11926); Official Standard Grades for Wisconsin Cigar-Binder Tobacco (U.S. Types 54 and 55), effective Nov. 20, 1969 (34 F.R. 17061); Official Standard Grades for Wisconsin Cigar-Binder Tobacco (U.S. Types 54 and 55), effective Nov. 20, 1969 (34 F.R. 17061); Official Standard Grades for Georgia and Florida Shade-Grown Cigar-Wrapper Tobacco (U.S. Type 62), Effective April 1971. A USDA grade index value can be determined according to an industry accepted grade index. See, e.g., Bowman et al, *Tobacco Science,* 32:39-40 (1988); Legacy Tobacco Document Library (Bates Document #523267826-523267833, Jul. 1, 1988, Memorandum on the Proposed Burley Tobacco Grade Index); and Miller et al., 1990, Tobacco Intern., 192:55-57 (all foregoing references are incorporated by reference in their entirety).

Unless specified otherwise, measurements of leaf grade index values, alkaloid, or nicotine levels mentioned herein for a tobacco plant, variety, cultivar, or line refer to average measurements, including, for example, an average of multiple leaves of a single plant or an average measurement from a population of tobacco plants from a single variety, cultivar, or line. A population of tobacco plants or a collection of tobacco leaves for determining an average measurement (e.g., leaf grading or alkaloid or nicotine level) can be of any size, for example, 5, 10, 15, 20, 25, 30, 35, 40, 50, or more. A population of at least 5 or more tobacco plants is used to determine standard deviation. Industry-accepted standard protocols are followed for determining average measurements or grade index values.

As used herein, "USDA graded leaf group", "leaf group", or "group" is a division of a type covering closely related grades based on certain characteristics which are related to stalk position, body, or general quality. Group is the first factor of a USDA grade. Group determination is part of the grading procedure and is assigned by an official USDA grader.

Unless specified otherwise, measurements of alkaloid or nicotine levels (or another leaf chemistry or property characterization) or leaf grade index values mentioned herein for a tobacco plant, variety, cultivar, or line refer to average measurements, including, for example, an average of multiple leaves of a single plant or an average measurement from a population of tobacco plants from a single variety, cultivar, or line.

Unless specified otherwise, the nicotine or alkaloid level (or another leaf chemistry or property characterization) of a tobacco plant is measured after topping in a pooled leaf sample collected from leaf number 3, 4, and 5 after topping. As used herein, whenever a comparison between leaves from two plants (e.g., a mutant plant versus a control plant) is mentioned, leaves from the same or comparable stalk position(s) and developmental stage(s) are intended so that the comparison can demonstrate effects due to genotype differences, not from other factors. As a non-limiting illustration, leaf 3 of a wild-type control plant is intended as a reference point for comparing with leaf 3 of a plant comprising the PY trait.

As used herein, leaf numbering is based on the leaf position on a tobacco stalk with leaf number 1 being the youngest leaf (at the top) after topping and the highest leaf number assigned to the oldest leaf (at the bottom).

Unless specified otherwise, all comparisons to control plants require similar growth conditions or comparable growth conditions for the two plants being compared. As used herein, "similar growth conditions" or "comparable growth conditions" refer to similar environmental conditions and/or agronomic practices for growing and making meaningful comparisons between two or more plant genotypes so that neither environmental conditions nor agronomic practices would contribute to or explain any difference observed between the two or more plant genotypes. Environmental conditions include, for example, light, temperature, water (humidity), and nutrition (e.g., nitrogen and phosphorus). Agronomic practices include, for example, seeding, clipping, undercutting, transplanting, topping, and suckering. See Chapters 4B and 4C of Tobacco, Production, Chemistry and Technology, Davis & Nielsen, eds., Blackwell Publishing, Oxford (1999), pp 70-103.

Curing/Products

"Curing" is the aging process that reduces moisture and brings about the destruction of chlorophyll giving tobacco leaves a golden color and by which starch is converted to sugar. Cured tobacco therefore has a higher reducing sugar content and a lower starch content compared to harvested green leaf. In one aspect, tobacco plants or plant components provided herein can be cured using conventional means, e.g., flue-cured, barn-cured, fire-cured, air-cured or sun-cured. See, for example, Tso (1999, Chapter 1 in Tobacco, Production, Chemistry and Technology, Davis & Nielsen, eds., Blackwell Publishing, Oxford) for a description of different types of curing methods. Cured tobacco is usually aged in a wooden drum (e.g., a hogshead) or cardboard cartons in compressed conditions for several years (e.g., two to five years), at a moisture content ranging from 10% to about 25%. See, U.S. Pat. Nos. 4,516,590 and 5,372,149. Cured and aged tobacco then can be further processed. Further processing includes conditioning the tobacco under vacuum with or without the introduction of steam at various temperatures, pasteurization, and fermentation.

Information regarding the harvesting of burley and dark tobacco varieties can be found in the 2019-2020 *Burley and Dark Tobacco Production Guide* (December 2018) published by the University of Kentucky, The University of Tennessee, Virginia Tech, and North Carolina State University, which is incorporated herein by reference in its entirety.

In an aspect, this disclosure provides cured tobacco material from any plant provided herein.

In an aspect, cured tobacco material comprises tobacco material selected from the group selected from leaf material, stem material, bud material, flower material, and root material.

In an aspect, cured tobacco leaf provided herein is selected from the group consisting of air-cured tobacco leaf, fire-cured tobacco leaf, sun-cured tobacco leaf, and flue-cured tobacco leaf. In another aspect, cured tobacco material provided herein is selected from the group consisting of air-cured tobacco material, fire-cured tobacco material, sun-cured tobacco material, and flue-cured tobacco material. In an aspect, cured tobacco leaf is from a tobacco variety selected from the group consisting of a flue-cured variety, a bright variety, a Burley variety, a Virginia variety, a Maryland variety, a dark variety, an Oriental variety, and a Turkish variety. In another aspect, cured tobacco material is from a tobacco variety selected from the group consisting of a flue-cured variety, a bright variety, a Burley variety, a Virginia variety, a Maryland variety, a dark variety, an Oriental variety, and a Turkish variety.

Fermentation typically is characterized by high initial moisture content, heat generation, and a 10 to 20% loss of dry weight. See, for example, U.S. Pat. Nos. 4,528,993, 4,660,577, 4,848,373, 5,372,149; U.S. Publication No. 2005/0178398; and Tso (1999, Chapter 1 in Tobacco, Production, Chemistry and Technology, Davis & Nielsen, eds., Blackwell Publishing, Oxford). Cured, aged, and fermented tobacco can be further processed (e.g., cut, shredded, expanded, or blended). See, for example, U.S. Pat. Nos. 4,528,993; 4,660,577; and 4,987,907. In one aspect, this disclosure provides fermented tobacco material from any tobacco plant provided herein.

Tobacco material obtained from the tobacco lines, varieties or hybrids of the present disclosure can be used to make tobacco products. As used herein, "tobacco product" is defined as any product made or derived from tobacco that is intended for human use or consumption. In an aspect, this disclosure provides a tobacco product comprising plant material from tobacco plant provided herein. In another aspect, this disclosure provides a tobacco product comprising cured tobacco material. In another aspect, this disclosure provides a tobacco product comprising fermented tobacco material.

Tobacco products provided include, without limitation, cigarette products (e.g., cigarettes and bidi cigarettes), cigar products (e.g., cigar wrapping tobacco and cigarillos), pipe tobacco products, products derived from tobacco, tobacco-derived nicotine products, smokeless tobacco products (e.g., moist snuff, dry snuff, and chewing tobacco), films, chewables, tabs, shaped parts, gels, consumable units, insoluble matrices, hollow shapes, reconstituted tobacco, expanded tobacco, and the like. See, e.g., U.S. Patent Publication No. US 2006/0191548.

As used herein, "cigarette" refers a tobacco product having a "rod" and "filler". The cigarette "rod" includes the cigarette paper, filter, plug wrap (used to contain filtration materials), tipping paper that holds the cigarette paper (including the filler) to the filter, and all glues that hold these components together. The "filler" includes (1) all tobaccos, including but not limited to reconstituted and expanded tobacco, (2) non-tobacco substitutes (including but not limited to herbs, non-tobacco plant materials and other spices that may accompany tobaccos rolled within the cigarette paper), (3) casings, (4) flavorings, and (5) all other additives (that are mixed into tobaccos and substitutes and rolled into the cigarette).

As used herein, "reconstituted tobacco" refers to a part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars. In an aspect, a tobacco product comprises reconstituted tobacco.

As used herein, "expanded tobacco" refers to a part of tobacco filler which is processed through expansion of suitable gases so that the tobacco is "puffed" resulting in reduced density and greater filling capacity. It reduces the weight of tobacco used in cigarettes. In an aspect, a tobacco product comprises expanded tobacco.

Tobacco products derived from plants of the present disclosure also include cigarettes and other smoking articles, particularly those smoking articles including filter elements, where the rod of smokable material includes cured tobacco within a tobacco blend. In an aspect, a tobacco product of the present disclosure is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, and cut tobacco. In another aspect, a tobacco product of the present disclosure is a smokeless tobacco product. Smokeless tobacco products are not combusted and include, but not limited to, chewing tobacco, moist smokeless tobacco, snus, and dry snuff. Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer's cheek and gum. Snus is a heat treated smokeless tobacco. Dry snuff is finely ground tobacco that is placed in the mouth or used nasally. In yet another aspect, a tobacco product of the present disclosure is selected from the group consisting of an electronically heated cigarette, an e-cigarette, an electronic vaporing device.

In an aspect, a smokeless tobacco product is selected from the group consisting of loose leaf chewing tobacco, plug chewing tobacco, moist snuff, nasal snuff, dry snuff, and snus.

In an aspect, a tobacco product of the present disclosure can be a blended tobacco product.

In another aspect, this disclosure provides a tobacco blend comprising cured tobacco material. A tobacco blend can comprise any combination of cured tobacco, uncured tobacco, fermented tobacco, unfermented tobacco, expanded tobacco, and reconstituted tobacco.

In an aspect, a tobacco blend comprises at least 5% cured tobacco by weight. In an aspect, a tobacco blend comprises at least 10% cured tobacco by weight. In an aspect, a tobacco blend comprises at least 15% cured tobacco by weight. In an aspect, a tobacco blend comprises at least 20% cured tobacco by weight. In an aspect, a tobacco blend comprises at least 25% cured tobacco by weight. In an aspect, a tobacco blend comprises at least 30% cured tobacco by weight. In an aspect, a tobacco blend comprises at least 35% cured tobacco by weight. In an aspect, a tobacco blend comprises at least 40% cured tobacco by weight. In an aspect, a tobacco blend comprises at least 45% cured tobacco by weight. In an aspect, a tobacco blend comprises at least 50% cured tobacco by weight. In an aspect, a tobacco blend comprises at least 55% cured tobacco by weight. In an aspect, a tobacco blend comprises at least 60% cured tobacco by weight. In an aspect, a tobacco blend comprises at least 65% cured tobacco by weight. In an aspect, a tobacco blend comprises at least 70% cured tobacco by weight. In an aspect, a tobacco blend comprises at least 75% cured tobacco by weight. In an aspect, a tobacco blend comprises at least 80% cured tobacco by weight. In an aspect, a tobacco blend comprises at least 85% cured tobacco by weight. In an aspect, a tobacco blend comprises at least 90% cured tobacco by weight. In an aspect, a tobacco blend comprises at least 95% cured tobacco by weight.

In an aspect, a tobacco blend comprises at least 5% cured tobacco by volume. In an aspect, a tobacco blend comprises at least 10% cured tobacco by volume. In an aspect, a tobacco blend comprises at least 15% cured tobacco by volume. In an aspect, a tobacco blend comprises at least 20% cured tobacco by volume. In an aspect, a tobacco blend comprises at least 25% cured tobacco by volume. In an aspect, a tobacco blend comprises at least 30% cured tobacco by volume. In an aspect, a tobacco blend comprises at least 35% cured tobacco by volume. In an aspect, a tobacco blend comprises at least 40% cured tobacco by volume. In an aspect, a tobacco blend comprises at least 45% cured tobacco by volume. In an aspect, a tobacco blend comprises at least 50% cured tobacco by volume. In an aspect, a tobacco blend comprises at least 55% cured tobacco by volume. In an aspect, a tobacco blend comprises at least 60% cured tobacco by volume. In an aspect, a tobacco blend comprises at least 65% cured tobacco by volume. In an aspect, a tobacco blend comprises at least 70% cured tobacco by volume. In an aspect, a tobacco blend comprises at least 75% cured tobacco by volume. In an aspect, a tobacco blend comprises at least 80% cured tobacco by volume. In an aspect, a tobacco blend comprises at least 85% cured tobacco by volume. In an aspect, a tobacco blend comprises at least 90% cured tobacco by volume. In an aspect, a tobacco blend comprises at least 95% cured tobacco by volume.

Sequences

The terms "percent identity" or "percent identical" as used herein in reference to two or more nucleotide or amino acid sequences is calculated by (i) comparing two optimally aligned sequences (nucleotide or amino acid) over a window of comparison (the "alignable" region or regions), (ii) determining the number of positions at which the identical nucleic acid base (for nucleotide sequences) or amino acid residue (for proteins and polypeptides) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, for purposes of the present application, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

When percentage of sequence identity is used in reference to amino acids it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity can be adjusted upwards to correct for the conservative nature of the substitution. Sequences that differ by such conservative substitutions are said to have "sequence similarity" or "similarity."

For optimal alignment of sequences to calculate their percent identity, various pair-wise or multiple sequence alignment algorithms and programs are known in the art, such as ClustalW or Basic Local Alignment Search Tool® (BLAST™), etc., that can be used to compare the sequence identity or similarity between two or more nucleotide or amino acid sequences. Although other alignment and comparison methods are known in the art, the alignment and percent identity between two sequences (including the percent identity ranges described above) can be as determined by the ClustalW algorithm, see, e.g., Chenna et al., "Multiple sequence alignment with the Clustal series of programs," *Nucleic Acids Research* 31: 3497-3500 (2003); Thompson et al., "Clustal W: Improving the sensitivity of progressive multiple sequence alignment through sequence weighting, position-specific gap penalties and weight matrix choice," *Nucleic Acids Research* 22: 4673-4680 (1994); Larkin M A et al., "Clustal W and Clustal X version 2.0," *Bioinformatics* 23: 2947-48 (2007); and Altschul et al. "Basic local alignment search tool." *J. Mol. Biol.* 215:403-410 (1990), the entire contents and disclosures of which are incorporated herein by reference.

The terms "percent complementarity" or "percent complementary" as used herein in reference to two nucleotide sequences is similar to the concept of percent identity but refers to the percentage of nucleotides of a query sequence that optimally base-pair or hybridize to nucleotides a subject sequence when the query and subject sequences are linearly arranged and optimally base paired without secondary folding structures, such as loops, stems or hairpins. Such a percent complementarity can be between two DNA strands, two RNA strands, or a DNA strand and a RNA strand. The "percent complementarity" can be calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences can be determined based on the known pairings of nucleotide bases, such as G-C, A-T, and A-U, through hydrogen binding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present application, when two sequences (query and subject) are optimally base-paired (with allowance for mismatches or non-base-paired nucleotides), the "percent complementarity" for the query sequence is equal to the number of base-paired positions between the two sequences divided by the total number of positions in the query sequence over its length, which is then multiplied by 100%.

The use of the term "polynucleotide" or "nucleic acid molecule" is not intended to limit the present disclosure to polynucleotides comprising deoxyribonucleic acid (DNA). For example, ribonucleic acid (RNA) molecules are also envisioned. Those of ordinary skill in the art will recognize that polynucleotides and nucleic acid molecules can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like. In an aspect, a nucleic acid molecule provided herein is a DNA molecule. In another aspect, a nucleic acid molecule provided herein is an RNA molecule. In an aspect, a nucleic acid molecule provided herein is single-stranded. In another aspect, a nucleic acid molecule provided herein is double-stranded. A nucleic acid molecule can encode a polypeptide or a small RNA.

As used herein, a "recombinant nucleic acid" refers to a nucleic acid molecule formed by laboratory methods of genetic recombination, such as, without being limiting, molecular cloning.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In one aspect, this disclosure provides methods of detecting recombinant nucleic acids and polypeptides in plant cells. Without being limiting, nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.).

In an aspect, a nucleic acid sequence provided herein is at least 70% identical to a sequence selected from the group consisting of SEQ ID NOs: 1-27, 34-42, 44, 45, 48, and 49. In an aspect, a nucleic acid sequence provided herein is at least 75% identical to a sequence selected from the group consisting of SEQ ID NOs: 1-27, 34-42, 44, 45, 48, and 49. In an aspect, a nucleic acid sequence provided herein is at least 80% identical to a sequence selected from the group consisting of SEQ ID NOs: 1-27, 34-42, 44, 45, 48, and 49. In an aspect, a nucleic acid sequence provided herein is at least 85% identical to a sequence selected from the group consisting of SEQ ID NOs: 1-27, 34-42, 44, 45, 48, and 49. In an aspect, a nucleic acid sequence provided herein is at least 90% identical to a sequence selected from the group consisting of SEQ ID NOs: 1-27, 34-42, 44, 45, 48, and 49. In an aspect, a nucleic acid sequence provided herein is at least 95% identical to a sequence selected from the group consisting of SEQ ID NOs: 1-27, 34-42, 44, 45, 48, and 49. In an aspect, a nucleic acid sequence provided herein is at least 96% identical to a sequence selected from the group consisting of SEQ ID NOs: 1-27, 34-42, 44, 45, 48, and 49. In an aspect, a nucleic acid sequence provided herein is at least 97% identical to a sequence selected from the group consisting of SEQ ID NOs: 1-27, 34-42, 44, 45, 48, and 49. In an aspect, a nucleic acid sequence provided herein is at least 98% identical to a sequence selected from the group consisting of SEQ ID NOs: 1-27, 34-42, 44, 45, 48, and 49. In an aspect, a nucleic acid sequence provided herein is at least 99% identical to a sequence selected from the group consisting of SEQ ID NOs: 1-27, 34-42, 44, 45, 48, and 49. In an aspect, a nucleic acid sequence provided herein is 100% identical to a sequence selected from the group consisting of SEQ ID NOs: 1-27, 34-42, 44, 45, 48, and 49.

As used herein, the term "polypeptide" refers to a chain of at least two covalently linked amino acids. Polypeptides can be encoded by polynucleotides provided herein. Proteins provided herein can be encoded by nucleic acid molecules provided herein. Proteins can comprise polypeptides provided herein. As used herein, a "protein" refers to a chain of amino acid residues that is capable of providing structure or enzymatic activity to a cell.

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

Detection (e.g., of an amplification product, of a hybridization complex, of a polypeptide) can be accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

In an aspect, an amino acid sequence provided herein is at least 70% identical or similar to a sequence selected from the group consisting of SEQ ID NOs: 28-33, 46, 47, and 50. In an aspect, an amino acid sequence provided herein is at least 75% identical or similar to a sequence selected from the group consisting of SEQ ID NOs: 28-33, 46, 47, and 50. In an aspect, an amino acid sequence provided herein is at least 80% identical or similar to a sequence selected from the group consisting of SEQ ID NOs: 28-33, 46, 47, and 50. In an aspect, an amino acid sequence provided herein is at least 85% identical or similar to a sequence selected from the group consisting of SEQ ID NOs: 28-33, 46, 47, and 50. In an aspect, an amino acid sequence provided herein is at least 90% identical or similar to a sequence selected from the group consisting of SEQ ID NOs: 28-33, 46, 47, and 50. In an aspect, an amino acid sequence provided herein is at least 95% identical or similar to a sequence selected from the group consisting of SEQ ID NOs: 28-33, 46, 47, and 50. In an aspect, an amino acid sequence provided herein is at least 96% identical or similar to a sequence selected from the group consisting of SEQ ID NOs: 28-33, 46, 47, and 50. In an aspect, an amino acid sequence provided herein is at least 97% identical or similar to a sequence selected from the group consisting of SEQ ID NOs: 28-33, 46, 47, and 50. In an aspect, an amino acid sequence provided herein is at least 98% identical or similar to a sequence selected from the group consisting of SEQ ID NOs: 28-33, 46, 47, and 50. In an aspect, an amino acid sequence provided herein is at least 99% identical or similar to a sequence selected from the group consisting of SEQ ID NOs: 28-33, 46, 47, and 50. In an aspect, an amino acid sequence provided herein is 100% identical or similar to a sequence selected from the group consisting of SEQ ID NOs: 28-33, 46, 47, and 50.

The following exemplary, non-limiting, embodiments are envisioned:

1. A modified tobacco plant, or part thereof, comprising a non-natural mutation in a polynucleotide having at least 70%, at least 80%, at least 90%, at least 95%, at least 97%, at least 99%, or 100% identity to a nucleic acid sequence selected from the group consisting of SEQ ID NOs: 18, 16, 17, 19-21 and 48, wherein said modified tobacco plant comprises a pale yellow phenotype, and wherein said mutation is as compared to a control tobacco plant of the same tobacco variety.
2. The modified tobacco plant, or part thereof, of embodiment 1, wherein said modified tobacco plant is of a tobacco variety selected from the group consisting of a flue-cured variety, a bright variety, a Burley variety, a Virginia variety, a Maryland variety, a dark variety, a Galpão variety, an Oriental variety, and a Turkish variety.
3. The modified tobacco plant, or part thereof, of embodiment 1 or 2, wherein said modified tobacco plant is of a variety selected from the group consisting of the tobacco varieties listed in Table 2, Table 3, Table 4, Table 5, Table 6, Table 7, and Table 8.
4. The modified tobacco plant, or part thereof, of any one of embodiments 1-3, wherein said tobacco plant, or part thereof, is heterozygous for said mutation.
5. The modified tobacco plant, or part thereof, of any one of embodiments 1-3, wherein said tobacco plant, or part thereof, is homozygous for said mutation.
6. The modified tobacco plant, or part thereof, of any one of embodiments 1-5, wherein said modified tobacco plant is a hybrid.
7. The modified tobacco plant, or part thereof, of any one of embodiments 1-6, wherein said modified tobacco plant is male sterile or cytoplasmically male sterile.
8. The modified tobacco plant, or part thereof, of any one of embodiments 1-7, wherein said non-natural mutation results in a reduced level of expression of said gene as compared to said control tobacco plant.
9. The modified tobacco plant, or part thereof, of any one of embodiments 1-8, wherein said non-natural mutation results in a reduced level of activity by a protein or polypeptide encoded by the polynucleotide comprising the non-natural mutation as compared to a protein or polypeptide encoded by the polynucleotide lacking the non-natural mutation.
10. The modified tobacco plant, or part thereof, of any one of embodiments 1-7, wherein said non-natural mutation results in an increased level of expression of said gene as compared to said control tobacco plant.
11. The modified tobacco plant, or part thereof, of any one of embodiments 1-7 or 10, wherein said non-natural mutation results in an increased level of activity by a protein or polypeptide encoded by the polynucleotide comprising the non-natural mutation as compared to a protein or polypeptide encoded by the polynucleotide lacking the non-natural mutation.
12. The modified tobacco plant, or part thereof, of any one of embodiments 1-11, wherein said non-natural mutation comprises a mutation in a sequence region selected from the group consisting of a promoter, a 5' UTR, an intron, an exon, a 3'UTR, a terminator, and any combination thereof
13. The modified tobacco plant, or part thereof, of any one of embodiments 1-12, wherein said non-natural mutation comprises one or more mutation types selected from the group consisting of a nonsense mutation, a missense mutation, a frameshift mutation, a splice-site mutation, and any combination thereof.
14. The modified tobacco plant, or part thereof, of any one of embodiments 1-13, wherein said non-natural mutation comprises a mutation selected from the group consisting of a substitution, a deletion, an insertion, a duplication, and an inversion of one or more nucleotides relative to a wild type gene selected from the group consisting of SEQ ID NOs: 18, 16, 17, 19-21 and 48.
15. The modified tobacco plant, or part thereof, of any one of embodiments 1-14, wherein said tobacco plant comprises a mutation or transgene conferring a reduced level of nicotine.
16. The modified tobacco plant, or part thereof, of embodiment 15, wherein said tobacco plant is a low-alkaloid tobacco plant.
17. The modified tobacco plant, or part thereof, of embodiment 15, wherein said mutation conferring a reduced level of nicotine comprises a nic1 mutation, a nic2 mutation, or both.
18. The modified tobacco plant, or part thereof, of embodiment 17, wherein said nic1 mutation, said nic2 mutation, or both are introgressed or derived from a variety selected from the group consisting of LA Burley 21, LAFC53, LN B&W, and LN KY171.
19. The modified tobacco plant, or part thereof, of embodiment 15, wherein said mutation conferring a reduced level of nicotine comprises a mutation in a gene or locus encoding a protein selected from the group consisting of aspartate oxidase, agmatine deiminase (AIC), arginase, diamine oxidase, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), S-adenosyl-methionine synthetase (SAMS), A622, NBB1, BBL, MYC2, Nic1_ERF, Nic2 ERF, ethylene response factor (ERF) transcription factor, nicotine uptake permease (NUP), and MATE transporter.

20. The modified tobacco plant, or part thereof, of embodiment 15, wherein said mutation conferring a reduced level of nicotine comprises a mutation in a gene or locus encoding a protein selected from the group consisting of ERF101, ERF110, ERFnew, ERF199, ERF19, ERF130, ERF16, ERF29, ERF210, and ERF91L2.

21. The modified tobacco plant, or part thereof, of embodiment 15, wherein said mutation conferring a reduced level of nicotine comprises a mutation in a gene or locus encoding a protein selected from the group consisting of ERF32, ERF34, ERF39, ERF189, ERF115, ERF221, ERF104, ERF179, ERF17, and ERF168.

22. The modified tobacco plant, or part thereof, of embodiment 15, wherein said transgene conferring a reduced level of nicotine comprises a transgene targeting and suppressing a gene encoding a protein selected from the group consisting of aspartate oxidase, agmatine deiminase (AIC), arginase, diamine oxidase, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), S-adenosyl-methionine synthetase (SAMS), A622, NBB1, BBL, MYC2, Nic1_ERF, Nic2 ERF, ethylene response factor (ERF) transcription factor, nicotine uptake permease (NUP), and MATE transporter.

23. The modified tobacco plant, or part thereof, of embodiment 15, wherein said transgene conferring a reduced level of nicotine comprises a transgene targeting and suppressing a gene encoding a protein selected from the group consisting of ERF101, ERF110, ERFnew, ERF199, ERF19, ERF130, ERF16, ERF29, ERF210, and ERF91L2.

24. The modified tobacco plant, or part thereof, of embodiment 15, wherein said transgene conferring a reduced level of nicotine comprises a transgene targeting and suppressing a gene encoding a protein selected from the group consisting of ERF32, ERF34, ERF39, ERF189, ERF115, ERF221, ERF104, ERF179, ERF17, and ERF168.

25. A modified tobacco plant, or part thereof, comprising a recombinant nucleic acid construct comprising a heterologous promoter operably linked to a polynucleotide that encodes a non-coding RNA molecule, wherein said non-coding RNA molecule is capable of binding to an RNA encoding an amino acid sequence having at least 80% sequence identity to an amino acid sequence selected from the group consisting of SEQ ID NOs: 28-33, 46, 47, and 50, wherein said non-coding RNA molecule suppresses the expression of the amino acid sequence, and wherein said modified tobacco plant comprises a pale yellow phenotype.

26. The modified tobacco plant or part thereof of embodiment 25, wherein the non-coding RNA molecule is a microRNA molecule.

27. Cured tobacco material from the tobacco plant of any one of embodiments 1-25.

28. The cured tobacco material of embodiment 27, wherein said cured tobacco material is made by a curing process selected from the group consisting of flue curing, air curing, fire curing, and sun curing.

29. A tobacco blend comprising said cured tobacco material of embodiment 27 or 28.

30. The tobacco blend of embodiment 29, wherein said cured tobacco material constitutes at least 10% of cured tobacco in said tobacco blend by weight.

31. The tobacco blend of embodiment 29, wherein said cured tobacco material constitutes at least 10% of cured tobacco in said tobacco blend by volume.

32. A tobacco product comprising the cured tobacco material of embodiment 27 or 28.

33. The tobacco product of embodiment 32, wherein said tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, and cut tobacco.

34. The tobacco product of embodiment 32, wherein said tobacco product is a smokeless tobacco product.

35. The tobacco product of embodiment 32, wherein said smokeless tobacco product is selected from the group consisting of loose leaf chewing tobacco, plug chewing tobacco, moist snuff, nasal snuff, dry snuff, and snus.

36. A reconstituted tobacco comprising the cured tobacco material of embodiment 27 or 28.

37. A method of creating a population of tobacco plants exhibiting a pale yellow (PY) phenotype, said method comprising:
    (a) genotyping a first population of tobacco plants or tobacco seeds for the presence of one or more marker loci associated with a PY quantitative trait locus (QTL) and linked within 20 centimorgans (cM) of a locus selected from the group consisting of SEQ ID NOs: 1-5;
    (b) selecting one or more tobacco plants or tobacco seeds genotyped in step (a), wherein the one or more tobacco plants or seeds comprises said one or more marker loci and said PY QTL; and
    (c) producing from said one or more tobacco plants or tobacco seeds selected in step (b) a second population of tobacco plants or tobacco seeds comprising said PY QTL and said one or more marker loci, wherein said second population of tobacco plants or tobacco seeds comprises at least one tobacco plant or seed exhibiting said pale yellow phenotype.

38. A method of creating a population of tobacco plants exhibiting a pale yellow (PY) phenotype, said method comprising:
    (a) genotyping a first population of tobacco plants or tobacco seeds for the presence of one or more marker loci associated with a PY quantitative trait locus (QTL) and positioned within 20,000,000 nucleotides of a locus selected from the group consisting of SEQ ID NOs: 1-5;
    (b) selecting one or more tobacco plants or tobacco seeds genotyped in step (a), wherein the one or more tobacco plants or seeds comprises said one or more marker loci and said PY QTL; and
    (c) producing from said one or more tobacco plants or tobacco seeds selected in step (b) a second population of tobacco plants or tobacco seeds comprising said PY QTL and said one or more marker loci, wherein said second population of tobacco plants or tobacco seeds comprises at least one tobacco plant or seed exhibiting said pale yellow phenotype.

39. The method of embodiments 37 or 38, wherein said method further comprises: crossing said one or more tobacco plants produced in step (c) with a tobacco plant comprising a mutation or transgene directly suppressing or eliminating the expression or activity of one or more genes encoding a product selected from the group consisting of methylputrescine oxidase (MPO), quinolate phosphoribosyl transferase (QPT), quinolinate synthase (QS), BBL, A622, aspartate oxidase, agmatine deiminase (AIC), S-adenosyl-methionine synthetase (SAMS), arginase, diamine oxidase, ornithine decarboxylase (ODC), phosphoribosylanthranilate isomerase (PRAI), arginine decarboxylase (ADC), nicotine uptake permease (NUP), and MATE transporter.

40. The method of embodiment 37, wherein said one or more marker loci are linked within 15 cM of a locus selected from the group consisting of SEQ ID NOs: 1-5.
41. The method of embodiment 37, wherein said tobacco plants or tobacco seeds of step (a) comprise a marker locus linked within 10 cM of a locus selected from the group consisting of SEQ ID NOs: 1-5.
42. The method of embodiment 37, wherein said tobacco plants or tobacco seeds of step (a) comprise a marker locus linked within 5 cM of a locus selected from the group consisting of SEQ ID NOs: 1-5.
43. The method of embodiment 37, wherein said tobacco plants or tobacco seeds of step (a) comprise a marker locus linked within 1 cM of a locus selected from the group consisting of SEQ ID NOs: 1-5.
44. The method of embodiment 37, wherein said tobacco plants or tobacco seeds of step (a) comprise a marker locus linked within 0.5 cM of a locus selected from the group consisting of SEQ ID NOs: 1-5.
45. The method of embodiment 38, wherein said one or more marker loci are positioned within 500,000 nucleotides of a locus selected from the group consisting of SEQ ID NOs: 1-5.
46. The method of embodiment 38, wherein said one or more marker loci are positioned within 250,000 nucleotides of a locus selected from the group consisting of SEQ ID NOs: 1-5.
47. The method of embodiment 38, wherein said one or more marker loci are positioned within 100,000 nucleotides of a locus selected from the group consisting of SEQ ID NOs: 1-5.
48. The method of embodiment 38, wherein said one or more marker loci are positioned within 50,000 nucleotides of a locus selected from the group consisting of SEQ ID NOs: 1-5
49. The method of embodiments 37 or 38, wherein said pale yellow phenotype comprises an average at least 80% yellowing of at least 25% of the leaves of the progeny plant.
50. The method of any one of embodiments 37-49, wherein said locus is SEQ ID NO: 1.
51. The method of any one of embodiments 37-49, wherein said locus is SEQ ID NO: 2.
52. The method of any one of embodiments 37-49, wherein said locus is SEQ ID NO: 3.
53. The method of any one of embodiments 37-49, wherein said locus is SEQ ID NO: 4.
54. The method of any one of embodiments 37-49, wherein said locus is SEQ ID NO: 5.
55. The method of any one of embodiments 37-49, wherein said genotyping of step (a) comprises detecting one or more marker loci.
56. The method of embodiment 55, wherein said one or more marker loci are selected from the group consisting of one or more single nucleotide polymorphism (SNP) markers, one or more insertion-deletion (INDEL) markers, one or more simple sequence repeat (SSR) markers, one or more restriction fragment length polymorphism (RFLP) markers, one or more random amplified polymorphic DNA (RAPD) markers, and one or more amplified fragment length polymorphism (AFLP) markers.
57. The method of embodiment 55, wherein said genotyping comprises the use of an oligonucleotide probe.
58. The method of embodiment 57, wherein said oligonucleotide probe comprises a nucleic acid sequence at least 80% identical to a nucleic acid sequence selected from the group consisting of SEQ ID NOs: 34-42.
59. The method of embodiment 57, wherein said oligonucleotide probe is adjacent to a polymorphic nucleotide position of said marker loci.
60. The method of any one of embodiments 37-49, wherein said genotyping of step (a) comprises detecting a haplotype.
61. The method of embodiment 60, wherein said haplotype comprises at least two SNPs selected from the group consisting of a guanine at nucleotide position 121 of SEQ ID NO: 1, a guanine at nucleotide position 121 of SEQ ID NO: 2, a guanine at nucleotide position 101 of SEQ ID NO: 3, a thymine at nucleotide position 121 of SEQ ID NO: 4, and a guanine at nucleotide position 121 of SEQ ID NO: 5.
62. The method of any one of embodiments 37-61, wherein said tobacco plant is of a tobacco variety selected from the group consisting of a flue-cured variety, a bright variety, a Burley variety, a Virginia variety, a Maryland variety, a dark variety, a Galpão variety, an Oriental variety, and a Turkish variety.
63. The method of any one of embodiments 37-61, wherein said tobacco plant is of a variety selected from the group consisting of the tobacco varieties listed in Table 2, Table 3, Table 4, Table 5, Table 6, Table 7, and Table 8.
64. The method of embodiment 37 or 38, wherein said one or more marker loci are selected from the group consisting of SEQ ID NOs: 1-5.
65. The method of embodiment 64, wherein said one or more marker loci comprise a single nucleotide polymorphism selected from the group consisting of:
    (a) a guanine at nucleotide position 121 of SEQ ID NO: 1;
    (b) a guanine at nucleotide position 121 of SEQ ID NO: 2;
    (c) a guanine at nucleotide position 101 of SEQ ID NO: 3;
    (d) a thymine at nucleotide position 121 of SEQ ID NO: 4; and
    (e) a guanine at nucleotide position 121 of SEQ ID NO: 5.
66. A method of introgressing a Pale Yellow (PY) QTL, said method comprising:
    (a) crossing a first tobacco plant comprising said PY quantitative trait locus (QTL) with a second tobacco plant of a different genotype to produce one or more progeny plants or seeds; and
    (b) selecting a progeny plant or seed produced in step (a) comprising at least one PY-associated single nucleotide polymorphism (SNP) selected from the group consisting of:

(i) a guanine at nucleotide position 121 of SEQ ID NO: 1;
(ii) a guanine at nucleotide position 121 of SEQ ID NO: 2;
(iii) a guanine at nucleotide position 101 of SEQ ID NO: 3;
(iv) a thymine at nucleotide position 121 of SEQ ID NO: 4; or
(v) a guanine at nucleotide position 121 of SEQ ID NO: 5,
wherein the selected progeny plant or seed comprises a pale yellow phenotype.

67. A method of introgressing a Pale Yellow (PY) trait, said method comprising:
(a) crossing a first tobacco plant comprising a non-natural mutation in a sequence selected from the group consisting of SEQ ID NOs: 16-21 and 48 with a second tobacco plant of a different genotype to produce one or more progeny plants or seeds; and
(b) selecting a progeny plant or seed produced in step (a) comprising the non-natural mutation, wherein the progeny plant or seed comprises said pale yellow trait.

68. The method of embodiment 66, wherein said progeny plant or seed of step (b) is heterozygous for said SNP.

69. The method of embodiment 66, wherein said progeny plant or seed of step (b) is homozygous for said SNP.

70. The method of any one of embodiments 66-69, wherein said progeny plant or seed of step (b) comprises at least two SNPs selected from the group consisting of a guanine at nucleotide position 121 of SEQ ID NO: 1, a guanine at nucleotide position 121 of SEQ ID NO: 2, a guanine at nucleotide position 101 of SEQ ID NO: 3, a thymine at nucleotide position 121 of SEQ ID NO: 4, and a guanine at nucleotide position 121 of SEQ ID NO: 5.

71. The method of any one of embodiments 66-69, wherein said single nucleotide polymorphism is a guanine at nucleotide position 121 of SEQ ID NO: 1.

72. The method of any one of embodiments 66-69, wherein said single nucleotide polymorphism is a guanine at nucleotide position 121 of SEQ ID NO: 2.

73. The method of any one of embodiments 66-69, wherein said single nucleotide polymorphism is a guanine at nucleotide position 101 of SEQ ID NO: 3.

74. The method of any one of embodiments 66-69, wherein said single nucleotide polymorphism is a thymine at nucleotide position 121 of SEQ ID NO: 4.

75. The method of any one of embodiments 66-69, wherein said single nucleotide polymorphism is a guanine at nucleotide position 121 of SEQ ID NO: 5.

76. The method of any one of embodiments 66-75, wherein said tobacco plant is of a tobacco variety selected from the group consisting of a flue-cured variety, a bright variety, a Burley variety, a Virginia variety, a Maryland variety, a dark variety, a Galpão variety, an Oriental variety, and a Turkish variety.

77. The method of any one of embodiments 66-75, wherein said tobacco plant is of a variety selected from the group of tobacco varieties listed in Table 2, Table 3, Table 4, Table 5, Table 6, Table 7, and Table 8.

78. The method of embodiment 67, wherein said progeny plant or seed is heterozygous for said non-natural mutation.

79. The method of embodiment 67, wherein said progeny plant or seed is homozygous for said non-natural mutation.

80. The method of embodiment 67, wherein said non-natural mutation results in a reduced level of expression of said gene as compared to said control tobacco plant.

81. The method of embodiment 67, wherein said non-natural mutation results in an increased level of expression of said gene as compared to said control tobacco plant.

82. The method of embodiment 67, wherein said non-natural mutation comprises a mutation in a sequence region selected from the group consisting of a promoter, a 5' UTR, an intron, an exon, a 3'UTR, a terminator, and any combination thereof.

83. The method of embodiment 67, wherein said non-natural mutation comprises one or more mutation types selected from the group consisting of a nonsense mutation, a missense mutation, a frameshift mutation, a splice-site mutation, and any combination thereof.

84. The method of embodiment 67, wherein said non-natural mutation comprises a mutation selected from the group consisting of a substitution, a deletion, an insertion, a duplication, and an inversion of one or more nucleotides relative to a wildtype nucleic acid sequence selected from the group consisting of SEQ ID NOs: 16-21 and 48.

85. The method of embodiment 66, wherein the progeny plant or seed comprises a reduced level of at least one tobacco-specific nitrosamine (TSNA) as compared to the second tobacco plant lacking the PY QTL.

86. The method of embodiment 85, wherein the at least one TSNA is selected from the group consisting of N-nitrosonornicotine and 4-(methylnitrosamino)-1-(3-pyridyl)-1-butanone, N'-nitrosoanatabine, and N'-nitrosoanabasine.

87. The method of embodiment 66, wherein the progeny plant or seed comprises an increased USDA leaf grade index as compared to the second tobacco plant lacking the PY QTL.

Having now generally described the disclosure, the same will be more readily understood through reference to the following examples that are provided by way of illustration, and are not intended to be limiting of the present disclosure, unless specified.

EXAMPLES

Example 1. Mapping the Pale Yellow (PY) Locus in Tobacco

The Pale Yellow (PY) locus is known to accelerate senescence in tobacco. However, the location of the PY locus within the tobacco genome is not known.

In order to determine the location of the PY locus, an $F_2$ mapping population is generated from a cross between Narrow Leaf Madole LC (NL Madole LC, lacking the PY trait) and TI1372 (the origin of the PY trait). $F_2$ individuals are phenotypically scored in a field by visual observation of the ripening process after topping, and by scoring by visual observation before and after treatment of a leaf of each plant with ethephon. See Tables 9-12. Leaves are removed from the plant and dipped in an ethephon treatment (1.2 g ai/L) so they are wetted thoroughly.

Leaves are screened on each of five consecutive days following ethephon treatment. Ethephon is converted into ethylene in plants, which induces ripening, with plants carrying the PY trait exhibiting faster or accelerated yellowing with application of ethephon.

TABLE 9

Phenotypic scoring scale for untreated tobacco leaves.

| Phenotypic Score | Description of Phenotype |
| --- | --- |
| Yes | Definitely pale yellow |
| No | Definitely not pale yellow |
| ? | Probably pale yellow, but not strong enough to be scored "Yes" |
| Diseased | No score determined due to presence of disease |

TABLE 10

Phenotypic scoring scale for ethephon-treated tobacco leaves.

| Phenotypic Score | Description of Phenotype |
| --- | --- |
| 0 | Leaf remains dark green in color |
| 1 | Leaf is turning pale green, or the leaf margins are turning yellow |
| 2 | Yellowing occurring throughout the leaf, but green mottling persists |
| 3 | Bright yellow color throughout the leaf |
| X | No score obtained |

TABLE 11

Phenotypic scoring of F2 mapping individuals. Tables 9 and 10 provide descriptions for the scoring used in this table.

| Plant Number | Untreated Score | Ethephon-treated Score | | | | |
| --- | --- | --- | --- | --- | --- | --- |
| | | Day 1 | Day 2 | Day 3 | Day 4 | Day 5 |
| 18G395-1 | Yes | 1 | 2 | 2 | 3 | 3 |
| 18G395-2 | Yes | 1 | 2 | 2 | 3 | 3 |
| 18G395-3 | Yes | 3 | 3 | 3 | 3 | 3 |
| 18G395-4 | Yes | 1 | 2 | 2 | 3 | 3 |
| 18G395-5 | Yes | 1 | 1 | 1 | 1 | 1 |
| 18G395-6 | Yes | 2 | 2 | 3 | 3 | 3 |
| 18G395-7 | No | 0 | 1 | 1 | 1 | 1 |
| 18G395-8 | Yes | 2 | 3 | 3 | 3 | 3 |
| 18G395-9 | Yes | 1 | 2 | 2 | 2 | 2 |
| 18G395-10 | Yes | 1 | 2 | 2 | 3 | 3 |
| 18G395-11 | Diseased | X | X | X | X | X |
| 18G395-12 | No | 0 | 1 | 1 | 1 | 1 |
| 18G395-13 | Yes | 1 | 1 | 1 | 2 | 2 |
| 18G395-14 | Yes | 1 | 2 | 2 | 3 | 3 |
| 18G395-15 | Yes | 1 | 1 | 1 | 1 | 1 |
| 18G395-16 | Yes | 2 | 3 | 3 | 3 | 3 |
| 18G395-17 | Yes | 1 | 2 | 3 | 3 | 3 |
| 18G395-18 | Yes | 1 | 1 | 2 | 3 | 3 |
| 18G395-19 | ? | 1 | 2 | 3 | 3 | 3 |
| 18G395-20 | Yes | 1 | 2 | 2 | 2 | 2 |
| 18G395-21 | Yes | 2 | 2 | 3 | 3 | 3 |
| 18G395-22 | No | 0 | 1 | 1 | 1 | 1 |
| 18G395-23 | Yes | 2 | 3 | 3 | 3 | 3 |
| 18G395-24 | ? | 1 | 1 | 1 | 1 | 1 |
| 18G395-25 | No | 0 | 1 | 1 | 1 | 1 |
| 18G395-26 | Yes | 1 | 2 | 2 | 2 | 2 |
| 18G395-27 | Yes | 1 | 1 | 2 | 2 | 3 |
| 18G395-28 | No | 0 | 0 | 1 | 1 | 1 |
| 18G395-29 | No | 0 | 0 | 0 | 0 | 0 |
| 18G395-30 | No | 0 | 0 | 0 | 0 | 0 |
| 18G395-31 | Yes | 1 | 2 | 3 | 3 | 3 |
| 18G395-32 | Yes | 1 | 2 | 3 | 3 | 3 |
| 18G395-33 | Yes | 0 | 1 | 2 | 2 | 2 |
| 18G395-34 | Yes | 2 | 3 | 3 | 3 | 3 |
| 18G395-35 | No | 0 | 0 | 0 | 0 | 0 |
| 18G395-36 | No | 0 | 1 | 1 | 1 | 1 |
| 18G395-37 | ? | 1 | 2 | 2 | 2 | 2 |
| 18G395-38 | No | 0 | 0 | 0 | 0 | 0 |
| 18G395-39 | Yes | 1 | 2 | 3 | 3 | 3 |
| 18G395-40 | Yes | 1 | 2 | 2 | 3 | 3 |
| 18G395-41 | Yes | 0 | 1 | 2 | 2 | 3 |
| 18G395-42 | Yes | 1 | 2 | 2 | 3 | 3 |
| 18G395-43 | No | 0 | 1 | 1 | 1 | 1 |
| 18G395-44 | Yes | 1 | 2 | 3 | 3 | 3 |
| 18G395-45 | Yes | 2 | 3 | 3 | 3 | 3 |
| 18G395-46 | No | 1 | 1 | 1 | 1 | 1 |
| 18G395-47 | Yes | 2 | 2 | 2 | 3 | 3 |
| 18G395-48 | Yes | 2 | 2 | 3 | 3 | 3 |
| 18G395-49 | Yes | 1 | 1 | 1 | 2 | 2 |
| 18G395-50 | No | 0 | 1 | 0 | 0 | 0 |
| 18G395-51 | Yes | 2 | 3 | 3 | 3 | 3 |
| 18G395-52 | Yes | 2 | 3 | 3 | 3 | 3 |
| 18G395-53 | No | 0 | 1 | 1 | 1 | 1 |
| 18G395-54 | Yes | 1 | 1 | 2 | 2 | 2 |
| 18G395-55 | No | 1 | 1 | 1 | 1 | 1 |

TABLE 11-continued

Phenotypic scoring of F2 mapping individuals. Tables 9 and 10 provide descriptions for the scoring used in this table.

| Plant Number | Untreated Score | Ethephon-treated Score | | | | |
|---|---|---|---|---|---|---|
| | | Day 1 | Day 2 | Day 3 | Day 4 | Day 5 |
| 18G395-56 | ? | 1 | 1 | 1 | 1 | 1 |
| 18G395-57 | Yes | 3 | 3 | 3 | 3 | 3 |
| 18G395-58 | Yes | 3 | 3 | 3 | 3 | 3 |
| 18G395-59 | Yes | 2 | 3 | 3 | 3 | 3 |
| 18G395-60 | Yes | 1 | 1 | 2 | 2 | 2 |
| 18G395-61 | Yes | 3 | 3 | 3 | 3 | 3 |
| 18G395-62 | ? | 1 | 1 | 1 | 1 | 1 |
| 18G395-63 | Yes | 1 | 2 | 2 | 3 | 3 |
| 18G395-64 | Yes | 2 | 2 | 2 | 3 | 3 |
| 18G395-65 | Yes | 1 | 2 | 2 | 3 | 3 |
| 18G395-66 | Yes | 1 | 2 | 2 | 3 | 3 |
| 18G395-67 | Yes | 1 | 3 | 3 | 3 | 3 |
| 18G395-68 | No | 0 | 0 | 1 | 1 | 1 |
| 18G395-69 | Yes | 1 | 1 | 2 | 2 | 3 |
| 18G395-70 | Yes | 1 | 1 | 2 | 2 | 3 |
| 18G395-71 | Yes | 0 | 1 | 1 | 2 | 2 |
| 18G395-72 | Yes | 1 | 1 | 1 | 2 | 2 |
| 18G395-73 | ? | 1 | 1 | 2 | 2 | 2 |
| 18G395-74 | Yes | 1 | 1 | 2 | 2 | 2 |
| 18G395-75 | Yes | 1 | 2 | 2 | 3 | 3 |
| 18G395-76 | Yes | 1 | 1 | 2 | 2 | 3 |
| 18G395-77 | Yes | 1 | 2 | 2 | 3 | 3 |
| 18G395-78 | Yes | 1 | 2 | 2 | 3 | 3 |
| 18G395-79 | Yes | 3 | 3 | 3 | 3 | 3 |
| 18G395-80 | No | 0 | 0 | 1 | 1 | 1 |
| 18G395-81 | No | 1 | 1 | 1 | 1 | 2 |
| 18G395-82 | Yes | 1 | 2 | 2 | 3 | 3 |
| 18G395-83 | Yes | 0 | 1 | 1 | 1 | 2 |
| 18G395-84 | No | 1 | 1 | 1 | 1 | 1 |
| 18G395-85 | Yes | 2 | 3 | 3 | 3 | 3 |
| 18G395-86 | Yes | 1 | 2 | 2 | 3 | 3 |
| 18G395-87 | Yes | 1 | 2 | 3 | 3 | 3 |
| 18G395-88 | ? | 2 | 3 | 3 | 3 | 3 |
| 18G395-89 | Yes | 1 | 2 | 2 | 3 | 3 |
| 18G395-90 | ? | 1 | 1 | 2 | 3 | 3 |
| 18G395-91 | Yes | 2 | 3 | 3 | 3 | 3 |
| 18G395-92 | Yes | 0 | 1 | 2 | 2 | 2 |
| 18G395-93 | No | 0 | 0 | 1 | 1 | 1 |
| 18G395-94 | Yes | 0 | 0 | 1 | 2 | 2 |
| 18G395-95 | Yes | 0 | 0 | 1 | 2 | 2 |
| 18G395-96 | No | 0 | 0 | 0 | 0 | 0 |
| 18G395-97 | No | 0 | 1 | 1 | 1 | 1 |
| 18G395-98 | No | 1 | 1 | 1 | 2 | 2 |
| 18G395-99 | No | 0 | 0 | 1 | 1 | 1 |
| 18G395-100 | Yes | 0 | 1 | 1 | 1 | 2 |
| 18G395-101 | Yes | 2 | 3 | 3 | 3 | 3 |
| 18G395-102 | Yes | 1 | 1 | 1 | 2 | 2 |
| 18G395-103 | Yes | 0 | 1 | 2 | 2 | 3 |
| 18G395-104 | ? | 1 | 2 | 2 | 2 | 2 |
| 18G395-105 | ? | 1 | 3 | 3 | 3 | 3 |
| 18G395-106 | Yes | 1 | 2 | 2 | 3 | 3 |
| 18G395-107 | Yes | 2 | 3 | 3 | 3 | 3 |
| 18G395-108 | ? | 1 | 2 | 2 | 2 | 2 |
| 18G395-109 | Yes | 1 | 2 | 2 | 3 | 3 |
| 18G395-110 | No | 0 | 1 | 1 | 2 | 2 |
| 18G395-111 | Yes | 2 | 3 | 3 | 3 | 3 |
| 18G395-112 | No | 0 | 1 | 1 | 1 | 1 |
| 18G395-113 | No | 0 | 0 | 0 | 0 | 0 |
| 18G395-114 | Yes | 1 | 1 | 1 | 1 | 1 |
| 18G395-115 | Yes | 1 | 1 | 1 | 1 | 1 |
| 18G395-116 | No | 0 | 1 | 1 | 1 | 1 |
| 18G395-117 | Yes | 0 | 0 | 1 | 1 | 1 |
| 18G395-118 | Yes | 1 | 2 | 2 | 3 | 3 |
| 18G395-119 | ? | 1 | 2 | 2 | 2 | 2 |
| 18G395-120 | Yes | 0 | 1 | 1 | 1 | 2 |
| 18G395-121 | No | 0 | 0 | 0 | 0 | 0 |
| 18G395-122 | ? | 1 | 2 | 2 | 3 | 3 |
| 18G395-123 | Yes | 0 | 1 | 1 | 1 | 2 |
| 18G395-124 | No | 0 | 1 | 1 | 1 | 1 |
| 18G395-125 | No | 0 | 0 | 0 | 0 | 1 |
| 18G395-126 | Yes | 1 | 2 | 2 | 2 | 2 |
| 18G395-127 | Yes | 3 | 3 | 3 | 3 | 3 |
| 18G395-128 | No | 0 | 0 | 1 | 1 | 1 |

TABLE 11-continued

Phenotypic scoring of F2 mapping individuals. Tables 9 and 10 provide descriptions for the scoring used in this table.

| Plant Number | Untreated Score | Ethephon-treated Score | | | | |
|---|---|---|---|---|---|---|
| | | Day 1 | Day 2 | Day 3 | Day 4 | Day 5 |
| 18G395-129 | ? | 0 | 1 | 1 | 2 | 2 |
| 18G395-130 | Yes | 1 | 2 | 3 | 3 | 3 |
| 18G395-131 | No | 0 | 0 | 0 | 0 | 0 |
| 18G395-132 | ? | 1 | 2 | 3 | 3 | 3 |
| 18G395-133 | Yes | 0 | 0 | 1 | 1 | 1 |
| 18G395-134 | Yes | 0 | 1 | 1 | 1 | 1 |
| 18G395-135 | Yes | 0 | 1 | 2 | 2 | 3 |
| 18G395-136 | No | 0 | 0 | 0 | 0 | 1 |
| 18G395-137 | ? | 0 | 0 | 0 | 0 | 0 |
| 18G395-138 | ? | 1 | 2 | 2 | 1 | 1 |
| 18G395-139 | Yes | 0 | 1 | 1 | 2 | 2 |
| 18G395-140 | ? | 0 | 0 | 0 | 1 | 1 |
| 18G395-141 | Yes | 0 | 1 | 2 | 2 | 3 |
| 18G395-142 | No | 1 | 1 | 2 | 2 | 2 |
| 18G395-143 | ? | 0 | 1 | 1 | 1 | 1 |
| 18G395-144 | ? | 1 | 2 | 2 | 2 | 2 |
| 18G395-145 | ? | 0 | 1 | 2 | 2 | 2 |
| 18G395-146 | ? | 1 | 2 | 3 | 3 | 3 |
| 18G395-147 | Yes | 0 | 1 | 1 | 2 | 3 |
| 18G395-148 | No | 0 | 1 | 1 | 2 | 2 |
| 18G395-149 | Yes | 3 | 3 | 3 | 3 | 3 |
| 18G395-150 | No | 0 | 1 | 2 | 2 | 3 |
| 18G395-151 | Yes | 0 | 2 | 3 | 3 | 3 |
| 18G395-152 | No | 0 | 1 | 1 | 1 | 1 |
| 18G395-153 | Yes | 2 | 3 | 3 | 3 | 3 |
| 18G395-154 | Yes | 0 | 1 | 1 | 1 | 1 |
| 18G395-155 | Yes | 1 | 1 | 2 | 2 | 3 |
| 18G395-156 | No | 0 | 0 | 0 | 0 | 0 |
| 18G395-157 | ? | 0 | 0 | 1 | 1 | 1 |
| 18G395-158 | No | 0 | 0 | 0 | 0 | 0 |
| 18G395-159 | ? | 0 | 1 | 2 | 2 | 2 |
| 18G395-160 | No | 0 | 0 | 0 | 0 | 0 |
| 18G395-161 | Yes | 0 | 1 | 1 | 2 | 3 |
| 18G395-162 | No | 0 | 1 | 1 | 1 | 1 |
| 18G395-163 | No | 0 | 0 | 1 | 1 | 1 |
| 18G395-164 | No | 1 | 1 | 1 | 1 | 1 |
| 18G395-165 | Yes | 2 | 3 | 3 | 3 | 3 |
| 18G395-166 | No | 0 | 0 | 0 | 0 | 0 |
| 18G395-167 | ? | 1 | 2 | 2 | 2 | 2 |
| 18G395-168 | Yes | 2 | 3 | 3 | 3 | 3 |
| 18G395-169 | Yes | 1 | 2 | 3 | 3 | 3 |
| 18G395-170 | ? | 1 | 1 | 2 | 2 | 2 |
| 18G395-171 | Yes | 3 | 3 | 3 | 3 | 3 |
| 18G395-172 | Yes | 1 | 2 | 3 | 3 | 3 |
| 18G395-173 | Yes | 1 | 2 | 3 | 3 | 3 |
| 18G395-174 | Yes | 2 | 3 | 3 | 3 | 3 |
| 18G395-175 | No | 1 | 1 | 1 | 1 | 1 |

TABLE 12

Phenotypic scoring of control plants. Table 10 provides descriptions for the scoring used in this table. All control plants are NL Madole LC plants.

| Plant Number | Ethephon-treated Score | | | | |
|---|---|---|---|---|---|
| | Day 1 | Day 2 | Day 3 | Day 4 | Day 5 |
| 18F33-1 | 0 | 0 | 0 | 0 | 0 |
| 18F33-2 | 0 | 0 | 0 | 0 | 0 |
| 18F33-3 | 0 | 0 | 1 | 1 | 1 |
| 18F33-4 | 0 | 0 | 0 | 0 | 0 |
| 18F33-5 | 0 | 0 | 0 | 0 | 0 |
| 18F33-6 | 0 | 0 | 0 | 0 | 0 |
| 18F33-7 | 0 | 0 | 0 | 0 | 0 |
| 18F33-8 | 0 | 0 | 0 | 0 | 0 |
| 18F33-9 | 0 | 0 | 0 | 0 | 0 |
| 18F33-10 | 0 | 0 | 1 | 1 | 1 |
| 18F33-11 | 0 | 1 | 1 | 0 | 0 |
| 18F33-12 | 0 | 0 | 0 | 0 | 0 |
| 18F33-13 | 0 | 0 | 0 | 1 | 1 |
| 18F33-14 | 0 | 0 | 0 | 0 | 0 |
| 18F33-15 | 0 | 0 | 0 | 0 | 0 |
| 18F33-16 | 0 | 1 | 1 | 1 | 1 |
| 18F33-17 | 0 | 0 | 0 | 0 | 0 |
| 18F33-18 | 0 | 0 | 0 | 0 | 0 |
| 18F33-19 | 0 | 0 | 0 | 0 | 0 |

Ninety-three of the $F_2$ individuals scored in Table 12, as well as the parental lines (NL Madole LC and TI1372) are genotyped using a custom tobacco axiom array comprising approximately 170,000 SNPs positioned throughout the tobacco genome. The genotypic and phenotypic data are combined to identify quantitative trait loci to identify the genetic control of the pale yellow trait. A QTL on chromosome 15 (PY QTL) of the tobacco pseudomolecule explains 75% of the variance of the PY trait identified in this analysis. The PY QTL is positioned between the publicly available SSR/microsatellite markers PT51549 and PT55414. See Bindler et al., "A high density genetic map of tobacco (*Nicotiana tabacum* L.) obtained from large scale microstatellite marker development," *Theor. Appl. Genet.*, 123:219-230 (2011), which is incorporated by reference herein in its entirety. Additional publicly available tobacco markers can be found in Tong et al., "Large-scale development of SSR markers in tobacco and construction of a linkage map in flue-cured tobacco," *Breed Sci.*, 66:381-390 (2016), which is also incorporated by reference herein in its entirety.

Example 2. Design and Validation of High-Throughput KASP™ Assays

KASP™ is a system of genotyping assay that is based on competitive allele-specific PCR, which enables bi-allelic scoring of SNPs at specific loci. KASP™ primers are designed for five SNP markers within the QTL identified in Example 1. See Table 13.

TABLE 13

SNPs within the PY QTL assayed using KASPTM. The SNP position is in bold underline in the sequence columns of the table.

| Locus ID | Non-PY Nucleotide | PY Nucleotide | Non-PY Associated Sequence | PY Associated Sequence |
|---|---|---|---|---|
| PY_SNP2 (SEQ ID NO: 1) | A | G | SNP Position: nucleotide 121 of SEQ ID NO: 1 | GTCAAGCAGTTTTTGAACA AGTTCTACCCACCCAATAA GATTGCCAAGTAAGTTGAT CAGATATTGAGCTTCAGGG AGAATCCAACTGAAACACT ACAAGAAACGTAAGAGAGG TTCAAAAGGATACTGGTTA AGTGTCCACATCATGGTAT TCCAGATTAGATGTTGGGG CAAATGTTCTACATGGGAT TGACAGACAGCTTGAAGGC CAATGTTGATGCTTCAGCA AGTGGAGCATTTT (SEQ ID NO: 6) | GTCAAGCAGTTTTTGAACAAGT TCTACCCACCCAATAAGATTGC CAAGTAAGTTGATCAGATATTG AGCTTCAGGGAGAATCCAACTG AAACACTACAAGAAACGTAAGA GAGGTTCAAAGGGATACTGGTT AAGTGTCCACATCATGGTATTC CAGATTAGATGTTGGGGCAAAT GTTCTACATGGGATTGACAGAC AGCTTGAAGGCCAATGTTGATG CTTCAGCAAGTGGAGCATTTT (SEQ ID NO: 11) |
| PY_SNP3 (SEQ ID NO: 2) | A | G | SNP Position: nucleotide 121 of SEQ ID NO: 2 | CTTCTTCTACGCGTTCACA AGGTGCTGGTCACGTTCGC GAAGGTATGAGCTGGTAAA GCTTTGCATTCGCGAAGCC GTGGTCGCATTTGCGAAGG GTAAGAATTGTAAAGTTTC ACGTTCACGAAGGATTAAA TTGTGGGCAATCGAGTTGT GCTTCGCAAACGCAAGGGA CCTGTCGTGTTCGCGAAGA AGAGAGGTCAGGACAGAAG GTTTAAGTTCAGAAAATGG GACTTCGTCCCAT (SEQ ID NO: 7) | CTTCTTCTACGCGTTCACAAGG TGCTGGTCACGTTCGCGAAGGT ATGAGCTGGTAAAGCTTTGCAT TCGCGAAGCCGTGGTCGCATTT GCGAAGGGTAAGAATTGTAAAG TTTCACGTTCGCGAAGGATTAA ATTGTGGGCAATCGAGTTGTGC TTCGCAAACGCAAGGGACCTGT CGTGTTCGCGAAGAAGAGAGGT CAGGACAGAAGGTTTAAGTTCA GAAAATGGGACTTCGTCCCAT (SEQ ID NO: 12) |
| PY_SNP4 (SEQ ID NO: 3) | A | G | SNP Position: nucleotide 101 of SEQ ID NO: 3 | GAGAGCTTCGTGCTTTAAG TATGGTATCGTCTTTGTTA GAAAGTGTTTCACGTTATA TTATGGAGTTGTGCAAATC TGAATTTAGTCGGGGCCCA ATACGAAGACACCAGGTGG GACACTAAAAAAGAAAAGA AAAAAGAGGAGAAACAAAG TCCGAAGTCTACTAGATAC AAATGCATACGTCTCTATT AATAAATTTGT (SEQ ID NO: 8) | GAGAGCTTCGTGCTTTAAGTAT GGTATCGTCTTTGTTAGAAAGT GTTTCACGTTATATTATGGAGT TGTGCAAATCTGAATTTAGTCG GGGCCCAATACGGAGACACCAG GTGGGACACTAAAAAAGAAAAG AAAAAGAGGAGAAACAAAGTC CGAAGTCTACTAGATACAAATG CATACGTCTCTATTAATAAATT TGT (SEQ ID NO: 13) |
| PY_SNP5 (SEQ ID NO: 4) | A | T | SNP Position: nucleotide 121 of SEQ ID NO: 4 | AATAGTACAAGATGAGAGC AATTTCATATAGTCACTCT CAACTAATTAGGAAATATG AGGCGCTTGACTGATTGAA GTTTGTATGTTGAATATAC TAGAACTTCTGATGTAGAC ATGTAGAATTCTGTATATT TTAGAGCACATCACTTATA AGCAGCCAAGAATATTAC TGTATCTAAGACATAATTT AGTAAATAAAAGTATGTT TTCTTTGAAAGTTTAAGAT TTTTTATGAGATG (SEQ ID NO: 9) | AATAGTACAAGATGAGAGCAAT TTCATATAGTCACTCTCAACTA GTCACTCTCAACTAATTAGGAA ATATGAGGCGCTTGACTGATTG GTTTGTATGTTGAATATACT AAGTTTGTATGTTGAATATACT AGAACTTCTGATGTAGACATGT AGTTATTCTGTATATTTTAGAGC ACATCACTTATAAGCAGCCCAA GAATATTACTGTATCTAAGACA TAATTTAGTAAATAAAAAGTAT GTTTTCTTTGAAAGTTTAAGAT TTTTTATGAGATG (SEQ ID NO: 14) |

TABLE 13-continued

SNPs within the PY QTL assayed using KASPTM. The SNP position is in bold underline in the sequence columns of the table.

| Locus ID | Non-PY Nucleotide | PY Nucleotide | Non-PY Associated Sequence | PY Associated Sequence |
|---|---|---|---|---|
| PY_SNP6 (SEQ ID NO: 5) | A | G | TACCTCGGGAGTGCCGTTG TTGATATTTTCCTATTAGT GTACTTGTCTTGATTGTTT TATTTTTCCTTTAATATGT AAATTCCTGTTTGTCTTCC GTGATGTATTATTCGCCCT TACTCTAAGCAGTTAAATT CTGACATACTGCTTACTTG ATTCACTCTCATTGTTATT ATTTTATTATTATTATTAT TATTATTATTATTATTATT ATATTATTATATATTATTA TTATTATATATTA (SEQ ID NO: 10) | TACCTCGGGAGTGCCGTTGTTG ATATTTTCCTATTAGTGTACTT GTCTTGATTGTTTTATTTTTCC TTTAATATGTAAATTCCTGTTT GTCTTCCGTGATGTATTATTCG CCCTTACTCTGAGCAGTTAAAT TCTGACATACTGCTTACTTGAT TCACTCTCATTGTTATTATTTT ATTATTATTATTATTATTATTA TTATTATTATTATATTATTATA TATTATTATTATTATATATATTA (SEQ ID NO: 15) |
| | SNP Position: nucleotide 121 of SEQ ID NO: 5 | | | |

Eighty F₂ individuals phenotyped in Example 1 are screened at the SNP loci identified above in Table 13 in order to identify SNP markers associated with the PY trait. See Table 14.

TABLE 14

KASP™ SNP marker results. Genotype columns denote the nucleotide observed at the SNP position for each PY_SNP marker as noted above in Table 13. "?" indicates that data was inconclusive. "WT" refers to wild-type or non-PY genotype.

| Plant Number | PY_SNP2 Genotype | PY_SNP3 Genotype | PY_SNP4 Genotype | PY_SNP5 Genotype | PY_SNP6 Genotype | SNP Call |
|---|---|---|---|---|---|---|
| TI 1372 | G:G | G:G | G:G | T:T | G:G | Homozygous PY |
| NLM | A:A | A:A | A:A | A:A | A:A | WT |
| 18G395-1 | A:G | A:G | A:G | A:T | A:G | Heterozygous PY |
| 18G395-2 | A:G | A:G | A:G | A:T | A:G | Heterozygous PY |
| 18G395-3 | A:G | A:G | A:G | A:T | A:G | Heterozygous PY |
| 18G395-4 | A:G | A:G | A:G | A:T | A:G | Heterozygous PY |
| 18G395-5 | A:G | A:G | A:G | A:T | ? | Heterozygous PY |
| 18G395-6 | G:G | G:G | G:G | T:T | G:G | Homozygous PY |
| 18G395-7 | A:A | A:A | ? | A:A | A:A | WT |
| 18G395-8 | G:G | ? | G:G | T:T | G:G | Homozygous PY |
| 18G395-9 | A:G | A:G | A:G | A:T | A:G | Heterozygous PY |
| 18G395-10 | A:G | A:G | A:G | A:T | A:G | Heterozygous PY |
| 18G395-11 | A:G | A:G | A:G | A:T | A:G | Heterozygous PY |
| 18G395-12 | A:A | A:A | ? | A:A | A:A | WT |
| 18G395-13 | A:G | A:G | A:G | A:T | A:G | Heterozygous PY |
| 18G395-14 | A:G | A:G | A:G | A:T | A:G | Heterozygous PY |
| 18G395-15 | A:G | A:G | A:G | A:T | A:G | Heterozygous PY |
| 18G395-16 | G:G | ? | G:G | T:T | G:G | Homozygous PY |
| 18G395-17 | A:G | A:G | A:G | A:T | A:G | Heterozygous PY |
| 18G395-18 | G:G | G:G | G:G | T:T | G:G | Homozygous PY |
| 18G395-19 | A:G | A:G | A:G | A:T | A:G | Heterozygous PY |
| 18G395-20 | A:G | A:G | A:G | A:T | A:G | Heterozygous PY |
| 18G395-21 | G:G | G:G | G:G | T:T | G:G | Homozygous PY |
| 18G395-22 | A:A | A:A | A:A | A:A | A:A | WT |
| 18G395-23 | G:G | G:G | G:G | T:T | G:G | Homozygous PY |
| 18G395-24 | A:A | A:A | A:A | A:A | A:A | WT |
| 18G395-25 | A:A | A:A | ? | A:A | A:A | WT |
| 18G395-26 | A:G | A:G | A:G | A:T | A:G | Heterozygous PY |
| 18G395-27 | A:G | A:G | A:G | A:T | A:G | Heterozygous PY |
| 18G395-28 | A:A | A:A | A:A | A:A | A:A | WT |
| 18G395-29 | A:A | A:A | A:A | A:A | A:A | WT |
| 18G395-30 | A:A | A:A | A:A | A:A | ? | WT |
| 18G395-31 | A:G | A:G | A:G | A:T | A:G | Heterozygous PY |
| 18G395-32 | G:G | G:G | G:G | T:T | G:G | Homozygous PY |
| 18G395-33 | A:G | A:G | A:G | A:T | A:G | Heterozygous PY |
| 18G395-34 | G:G | G:G | G:G | T:T | G:G | Homozygous PY |
| 18G395-35 | A:A | A:A | A:A | A:A | A:A | WT |
| 18G395-36 | A:A | A:A | A:A | A:A | A:A | WT |
| 18G395-37 | A:G | A:G | A:G | A:T | A:G | Heterozygous PY |
| 18G395-38 | A:A | A:A | A:A | A:A | A:A | WT |
| 18G395-39 | A:G | A:G | A:G | A:T | A:G | Heterozygous PY |

TABLE 14-continued

KASP™ SNP marker results. Genotype columns denote the nucleotide observed at the SNP position for each PY_SNP marker as noted above in Table 13. "?" indicates that data was inconclusive. "WT" refers to wild-type or non-PY genotype.

| Plant Number | PY_SNP2 Genotype | PY_SNP3 Genotype | PY_SNP4 Genotype | PY_SNP5 Genotype | PY_SNP6 Genotype | SNP Call |
|---|---|---|---|---|---|---|
| 18G395-40 | G:G | ? | G:G | T:T | G:G | Homozygous PY |
| 18G395-41 | A:G | A:G | A:G | A:T | A:G | Heterozygous PY |
| 18G395-42 | G:G | G:G | G:G | T:T | G:G | Homozygous PY |
| 18G395-43 | A:A | A:A | A:A | A:A | A:A | WT |
| 18G395-44 | A:G | A:G | A:G | A:T | A:G | Heterozygous PY |
| 18G395-45 | A:G | A:G | A:G | A:T | A:G | Heterozygous PY |
| 18G395-46 | A:A | A:A | A:A | A:A | A:A | WT |
| 18G395-47 | A:G | A:G | A:G | A:T | A:G | Heterozygous PY |
| 18G395-48 | A:G | A:G | A:G | A:T | A:G | Heterozygous PY |
| 18G395-49 | G:G | G:G | G:G | T:T | G:G | Homozygous PY |
| 18G395-50 | A:A | A:A | ? | A:A | A:A | WT |
| 18G395-51 | A:G | A:G | A:G | A:T | ? | Heterozygous PY |
| 18G395-52 | G:G | G:G | G:G | T:T | G:G | Homozygous PY |
| 18G395-53 | A:A | A:A | ? | A:A | A:A | WT |
| 18G395-54 | A:G | A:G | A:G | A:T | A:G | Heterozygous PY |
| 18G395-55 | A:A | A:A | A:A | A:A | A:A | WT |
| 18G395-56 | A:A | ? | ? | A:A | A:A | WT |
| 18G395-57 | G:G | ? | G:G | T:T | ? | Homozygous PY |
| 18G395-58 | G:G | G:G | G:G | T:T | G:G | Homozygous PY |
| 18G395-59 | A:G | A:G | A:G | A:T | A:G | Heterozygous PY |
| 18G395-60 | A:G | A:G | A:G | A:T | A:G | Heterozygous PY |
| 18G395-61 | G:G | G:G | G:G | T:T | G:G | Homozygous PY |
| 18G395-62 | A:A | A:A | ? | A:A | A:A | WT |
| 18G395-63 | A:G | A:G | A:G | A:T | A:G | Heterozygous PY |
| 18G395-64 | A:G | A:G | A:G | A:T | A:G | Heterozygous PY |
| 18G395-65 | G:G | G:G | G:G | T:T | G:G | Homozygous PY |
| 18G395-66 | A:G | A:G | A:G | A:T | A:G | Heterozygous PY |
| 18G395-67 | A:G | A:G | A:G | A:T | A:G | Heterozygous PY |
| 18G395-68 | A:A | A:A | A:A | A:A | A:A | WT |
| 18G395-69 | A:G | A:G | A:G | A:T | A:G | Heterozygous PY |
| 18G395-70 | A:G | A:G | A:G | A:T | A:G | Heterozygous PY |
| 18G395-71 | G:G | ? | G:G | T:T | G:G | Homozygous PY |
| 18G395-72 | A:G | A:G | A:G | A:T | A:G | Heterozygous PY |
| 18G395-73 | A:G | A:G | A:G | A:T | A:G | Heterozygous PY |
| 18G395-74 | A:G | A:G | A:G | A:T | A:G | Heterozygous PY |
| 18G395-75 | A:G | A:G | A:G | A:T | A:G | Heterozygous PY |
| 18G395-76 | A:G | A:G | A:G | A:T | A:G | Heterozygous PY |
| 18G395-77 | A:G | A:G | A:G | A:T | A:G | Heterozygous PY |
| 18G395-78 | G:G | G:G | G:G | T:T | G:G | Homozygous PY |
| 18G395-79 | A:G | A:G | A:G | A:T | ? | Heterozygous PY |
| 18G395-80 | A:G | A:G | A:G | ? | A:G | Heterozygous PY |

Table 15 provides the physical position of the SNP markers identified herein in comparison to the publicly available markers PT51549 (GenBank Accession No; Pr032530969), PT55414 (GenBank Accession No. Pr032533458), PT50034 (GenBank Accession No. Pr032529969), and PT53131 (GenBank Accession No. Pr032531997).

TABLE 15

Physical position of markers and candidate genes on chromosome 15 of the tobacco genome.

| Locus | Physical Position (nucleotides) | Nucleotide Position in reference to Locus PT51549 |
|---|---|---|
| PT51549 | 8,127,257 | 0 |
| G58887 (SEQ ID NO: 16) | 9,201,319 to 9,203,140 | 1,074,062 to 1,075,883 |
| g58888 (SEQ ID NO: 17) | 9,217,954 to 9,218,864 | 1,090,697 to 1,091,607 |
| PY_SNP5 (SEQ ID NO: 4) | 9,391,163 | 1,263,906 |
| PY_SNP6 (SEQ ID NO: 5) | 9,417,146 | 1,289,889 |
| PY_SNP2 (SEQ ID NO: 1) | 9,468,719 | 1,341,462 |
| PY_SNP3 (SEQ ID NO: 2) | 9,478,625 | 1,351,368 |
| PY_SNP4 (SEQ ID NO: 3) | 9,493,144 | 1,365,887 |
| g58899 (SEQ ID NO: 18) | 9,509,010 to 9,514,972 | 1,381,753 to 1,387,715 |
| g58905 (SEQ ID NO: 20) | 9,720,661 to 9,729,412 | 1,593,404 to 1,602,155 |
| g58917 (SEQ ID NO: 19) | 10,510,970 to 10,513,162 | 2,383,713 to 2,385,905 |
| PT55414 | 11,475,118 | 3,347,861 |
| PT50034 | 130,163,141 | 122,035,884 |
| g61524 (SEQ ID NO: 21) | 130,257,374 to 130,257,844 | 122,130,177 to 122,130,587 |
| PT53131 | 131,471,751 | 123,344,494 |

Example 3. Identification of Candidate Genes Responsible for the PY Trait

Dark tobacco varieties KY171 (lacking the PY trait) and PYKY171 (KY171 comprising the PY trait introgressed from TI1372), and TI1372 are grown in a greenhouse until plants reach flowering stage. Upon reaching flowering stage, all plants are topped, and leaf samples are collected from plants 24 hours after topping, 48 hours after topping, 72 hours after topping, one week after topping, and two weeks after topping.

RNA is collected from all topped samples, as well as non-topped control samples for each variety at each time point. The collected RNA is subjected to 2×100 nucleotide paired-end sequencing on Illumina HiSeq at a depth of approximately 60,000,000 paired-end reads per sample.

Based on the RNAseq results, six candidate genes are identified on chromosome 15. See Table 16. g61524 does not fall within the PY QTL, but exhibited significantly changed expression between the two tested tobacco varieties.

KASP' SNP marker results (see Table 14). Approximately twenty-four $F_2$ individuals per group (homozygous PY, heterozygous PY, and WT) are screened for candidate gene expression.

Expression of candidate genes is measured in leaf tissue using quantitative RT-PCR (qPCR), TaqMan™ gene expression assays, and RNAseq. Leaf tissue is collected from each $F_2$ individual before topping, and at several time points after topping (e.g., 24 hours after topping, 48 hours after topping, 72 hours after topping, one week after topping, two weeks after topping). The same lines used in the RNAseq study of Example 3 are used here.

TABLE 16

Candidate genes.

| Gene ID | Genomic Sequence | Coding Sequence | Amino Acid Sequence | BLAST Description | KY171 vs. PYKY171 Expression Fold Change | KY171 vs. PYKY171 Fold Change p-value |
|---|---|---|---|---|---|---|
| G58887 | (SEQ ID NO: 16) | (SEQ ID NO: 22) | (SEQ ID NO: 28) | Laminin subunit beta-1 | −34.878 | 0.0078 |
| g58888 | (SEQ ID NO: 17) | (SEQ ID NO: 23) | (SEQ ID NO: 29) | Transposon protein, putative, CACTA, En/Spm sub-class | −24.417 | 0.0313 |
| g58899 | (SEQ ID NO: 18) | (SEQ ID NO: 24) | (SEQ ID NO: 30) | CAAX amino terminal protease; STAY-GREEN | −3.737 | $3.56 \times 10^{-8}$ |
| g58917 | (SEQ ID NO: 19) | (SEQ ID NO: 25) | (SEQ ID NO: 31) | PLATZ transcription factor family protein | −1.178 | .8038 |
| g58905 | (SEQ ID NO: 20) | (SEQ ID NO: 26) | (SEQ ID NO: 32) | ADP-ribosylation factor GTPase-activating protein AGD8 | 4.322 | 0.0003 |
| g61524 | (SEQ ID NO: 21) | (SEQ ID NO: 27) | (SEQ ID NO: 33) | Translation initiation factor IF-1, chloroplastic | −8.290 | $1.03 \times 10^{-10}$ |

Example 4. Validation of Identified Candidate Genes

Plants from the same seed lots scored in the $F_2$ mapping population described above (see Example 1) are used to track the expression of the candidate genes provided above in Example 3. Parental lines are used as controls. Gene expression is examined in plants that are scored homozygous PY, heterozygous PY, and WT as determined by the TaqMan™ gene expression assays (see Table 17 for primers and probes) are designed to track the expression of the candidate genes identified above in Example 3.

Figure 2:
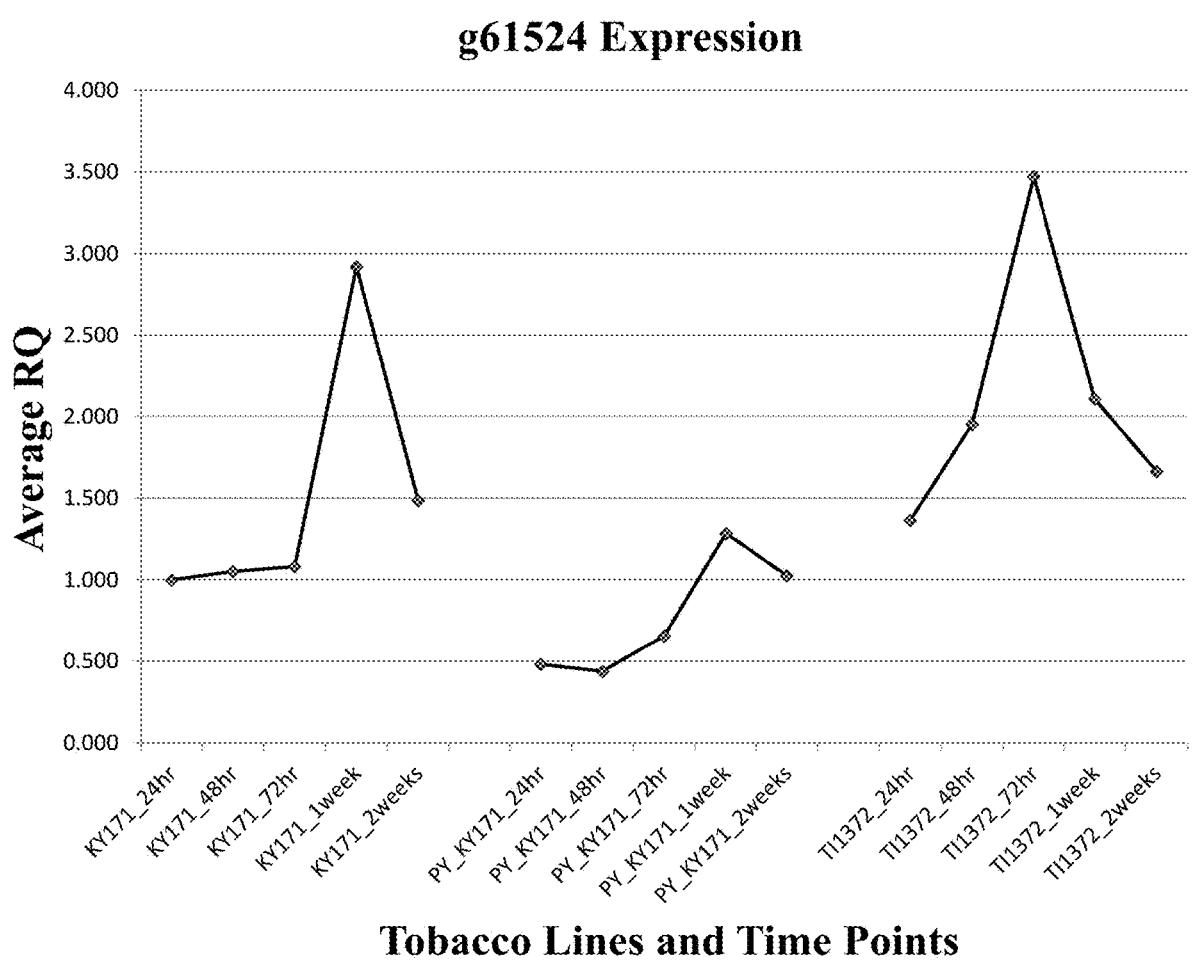
FIG. 2 depicts the expression of g61524 (SEQ ID NO: 27) as measured using quantitative RT-PCR. The average RQ (e.g., fold change) of g61524 as measured across three biological replicates is shown for tobacco varieties KY171, Pale Yellow KY171 (PY_KY171), and TI1372 at various timepoints after topping. Actin is used as a control.
Figure 3:
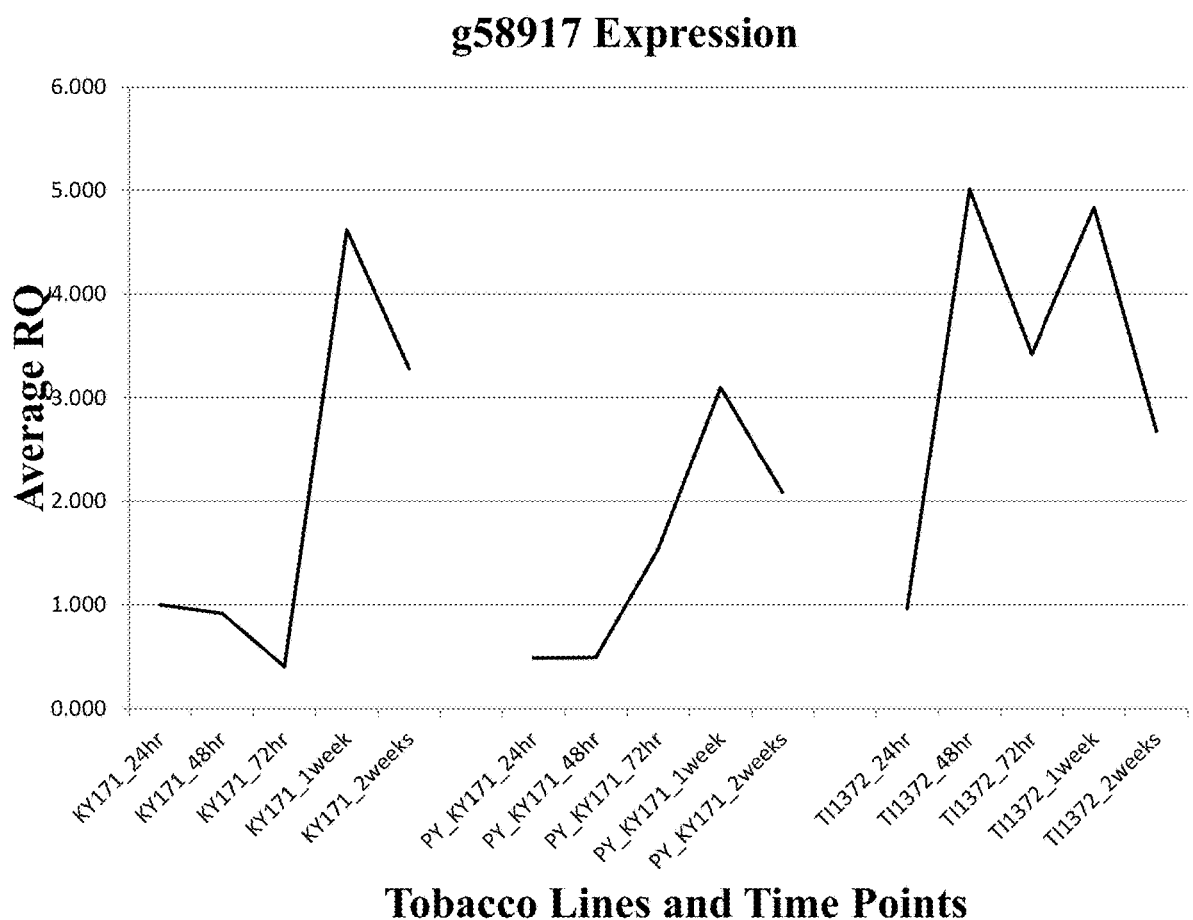
FIG. 3 depicts the expression of g58917 (SEQ ID NO: 25) as measured using quantitative RT-PCR. The average RQ (e.g., fold change) of g58917 as measured across three biological replicates is shown for tobacco varieties KY171, Pale Yellow KY171 (PY_KY171), and TI1372 at various timepoints after topping. Actin is used as a control.

Using qPCR, expression of g61524 and g58917 is shown to be similar in KY171, Pale Yellow KY171, and TI1372. See FIGS. 2 and 3. However, expression of g58899 is markedly lower in Pale Yellow KY171 and TI1372 as compared to KY171. See FIG. 1.

TABLE 17

TaqMan ™ primers and probes.

| Gene | | Sequence | Dye | Quencher |
|---|---|---|---|---|
| g58899 | Forward | TGTTAGCCCTTTACCTTGGGTTT (SEQ ID NO: 34) | | |
| | Reverse | TGTGATTATCGGTGCAAAAATGT (SEQ ID NO: 35) | | |

TABLE 17-continued

TaqMan™ primers and probes.

| Gene | | Sequence | Dye | Quencher |
|---|---|---|---|---|
| | Probe | AATGGATCCAGACAAAC (SEQ ID NO: 36) | VIC™ | MGB-NFQ (minor groove binder-non-fluorescent quencher) |
| g58917 | Forward | CACAGCAACAAGGTCCAAAGTTT (SEQ ID NO: 37) | | |
| | Reverse | TGGCCGTTTTGTAATTAACTGAAG (SEQ ID NO: 38) | | |
| | Probe | ACTCCGTCGACGCCCCCTCC (SEQ ID NO: 39) | JUN™ | QSY™ |
| g61524 | Forward | GGCATCTCTCTCATGGTGGAA (SEQ ID NO: 40) | | |
| | Reverse | GGATGTTGGAGTTGGAGAACAAG (SEQ ID NO: 41) | | |
| | Probe | CCTGCTCCTGCCACGACTGCAA (SEQ ID NO: 42) | ABY™ | QSY™ |

Example 5. Transformation and Regeneration of Modified Tobacco Plants to Overexpress Candidate Genes Candidate genes that exhibit increased expression that correlates with the PY trait (e.g., TI1372, $F_2$ individuals that are homozygous for the PY trait) are overexpressed in a non-PY background (e.g., NL Madole NC) and resulting phenotypes are observed.

An expression vector is used as a backbone to generate multiple transformation vectors comprising recombinant DNA constructs to overexpress candidate genes (e.g., a nucleic acid sequence encoding any one of SEQ ID NOs: 28-33, 46, 47, and 50; see also SEQ ID NOs: 53 and 54). The expression vector contains a CaMV 35S promoter, a NOS terminator, and a cassette comprising a kanamycin selection marker (NPT II) operably linked to an Actin2 promoter and a NOS terminator. Nucleic acid vectors comprising transgenes of interest are introduced into tobacco leaf discs via *Agrobacterium* transformation. See, for example, Mayo et al., 2006, Nat Protoc. 1:1105-11 and Horsch et al., 1985, Science 227:1229-1231.

NL Madole LC tobacco plants are grown in Magenta™ GA-7 boxes and leaf discs are cut and placed into Petri plates. *Agrobacterium tumefaciens* cells comprising a transformation vector are collected by centrifuging a 20 mL cell suspension in a 50 mL centrifuge tube at 3500 RPM for 10 minutes. The supernatant is removed and the *Agrobacterium tumefaciens* cell pellet is re-suspended in 40 mL liquid re-suspension medium. Tobacco leaves, avoiding the midrib, are cut into eight 0.6 cm discs with a #15 razor blade and placed upside down in a Petri plate. A thin layer of Murashige & Skoog (MS) with B5 vitamins liquid re-suspension medium is added to the Petri plate and the leaf discs are poked uniformly with a fine point needle. About 25 mL of the *Agrobacterium tumefaciens* suspension is added to the Petri plate and the leaf discs are incubated in the suspension for 10 minutes.

Leaf discs are transferred to co-cultivation Petri plates (½ MS medium) and discs are placed upside down in contact with filter paper overlaid on the co-cultivation TOM medium (MS medium with 30 g/L sucrose; 0.1 mg/L 1-napthaleneacetic acid (NAA); and 1 mg/L 6-benzyl aminopurine (BAP)). The Petri plate is sealed with parafilm prior to incubation in the dark for two days.

After incubation, leaf discs are transferred to regeneration/selection TOM-Hyg medium Petri plates (TOM medium plus 200 mg/L cefotaxime and 50 mg/L hygromycin). Calli formed from leaf discs are sub-cultured bi-weekly to fresh TOM-Hyg medium in dim light (between 60 mE/ms and 80 mE/ms) with photoperiods of 18 hours light, 6 hours dark at 24° C. until shoots (plantlets) become excisable. Plantlets formed from calli are removed with forceps and subcultured into MS rooting medium (MS medium with 3 g/L sucrose; 7 g/L dextrose; 200 mg/L cefotaxime; 50 mg/L hygromycin). Shoots on MS rooting medium are incubated at 24° C. with dim light and photoperiods of 18 hours light, 6 hours dark to induce rooting When plantlets comprising both shoots and roots grow large enough (e.g., over half the height of a Magenta™ GA-7 box), they are transferred Jiffy peat pellets for acclimatization in the growth room. Once established, seedlings are transferred to a greenhouse for further growth, breeding, and analysis.

Resulting plants are evaluated by visual observation or ethephone screening as described above in Example 1.

Figure 4:
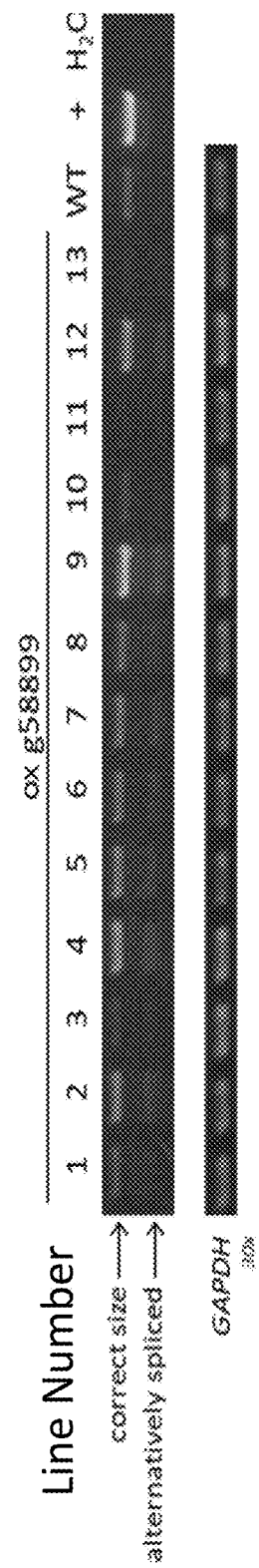
FIG. 4 depicts RNA expression of $T_0$ plants overexpressing g58899 (SEQ ID NO: 54).

FIG. 4 depicts semi-quantitative RT-PCR results (using RNA extracted from young leaves) from examining thirteen $T_0$ tobacco lines over-expressing g58899 (SEQ ID NO: 24, which encodes SEQ ID NO: 30). Some lines (e.g., Lines 3, 11) exhibit silenced expression as compared to the wildtype (WT) control, while other lines (e.g., Lines 9, 12) exhibit increased expression. Without being limited by any scientific theory, it is known in the art that the insertion of multiple copies of a single transgene can lead to gene silencing.

Figure 5:
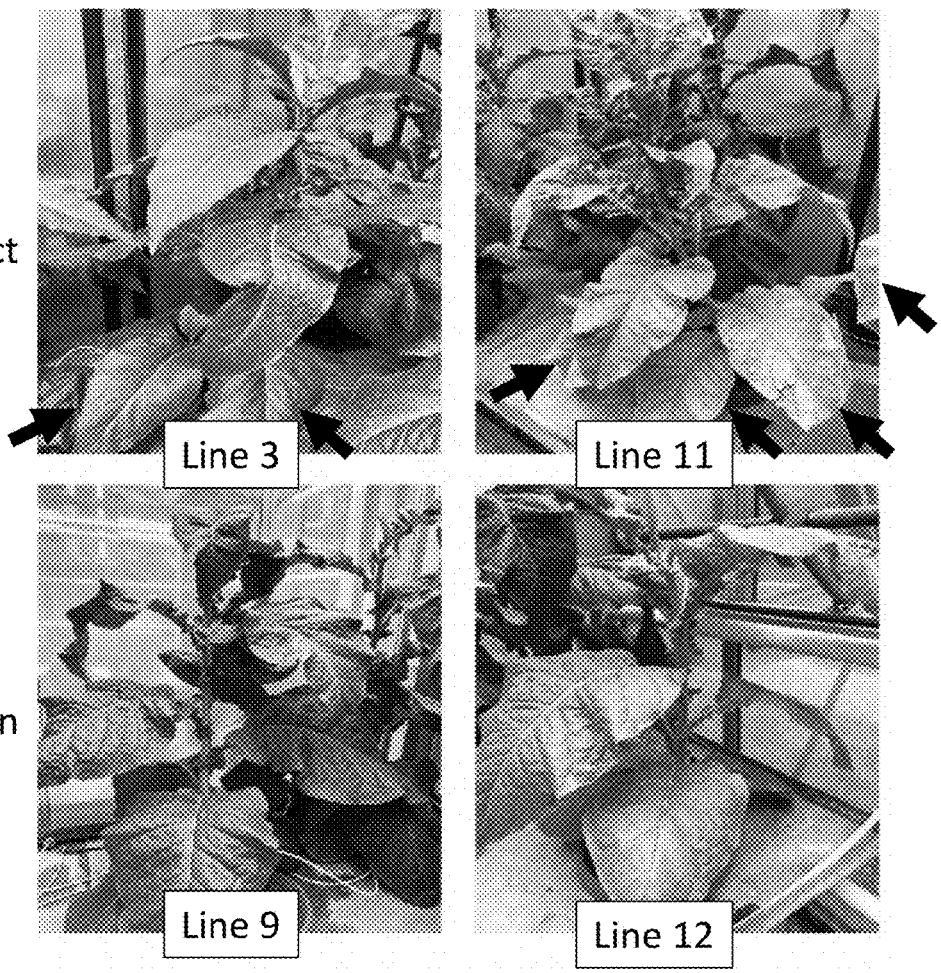
FIG. 5 depicts photographs of four plant lines overexpressing g58899 (SEQ ID NO: 54). Black arrows point to pale yellow tissue.

The $T_0$ lines tested in FIG. 4 are phenotypically examined. Lines 9 and 12, which were shown to overexpress g58899, show entirely green leaves. See FIG. 5. In contrast, Lines 3 and 11, which were shown to have reduced expression of g58899, exhibit a PY phenotype in older leaves. See FIG. 5, black arrows.

Example 6. Knockdown of Candidate Genes

Candidate genes that exhibit decreased expression that correlates with the PY trait (e.g., TI1372, $F_2$ individuals that are homozygous for the PY trait) are targets for having expression knocked down or knocked out in a non-PY background (e.g., NL Madole NC).

Artificial miRNAs or other RNAi constructs are generated to produce a miRNA or another non-coding RNA that is capable of reducing the expression of each of the candidate genes (e.g., SEQ ID NOs: 22-27). The artificial miRNA or RNAi construct is inserted into a plasmid under the control of a CaMV 35S promoter. The plasmid further comprises a NOS terminator, and a cassette comprising a kanamycin selection marker (NPT II) operably linked to an Actin2 promoter and a NOS terminator.

Tobacco leaf discs are transformed, and tobacco plants are regenerated, as described in Example 5.

Figure 6:
FIG. 6 depicts photographs of plants expressing an RNAi construct (SEQ ID NO: 52) designed to suppress g58899 (SEQ ID NO: 44) expression in tissue culture. Black arrows point to pale yellow tissue.

Plantlets comprising constructs designed to suppress g58899 (SEQ ID NOs: 51 and 52) began to exhibit a PY phenotype on some leaves prior to removal from Magenta™ GA-7 boxes. See FIG. 6; especially black arrows. This effect was not observed in plants expressing a g58905 (SEQ ID NO: 26) RNAi suppression construct or in wildtype controls.

Figure 7:
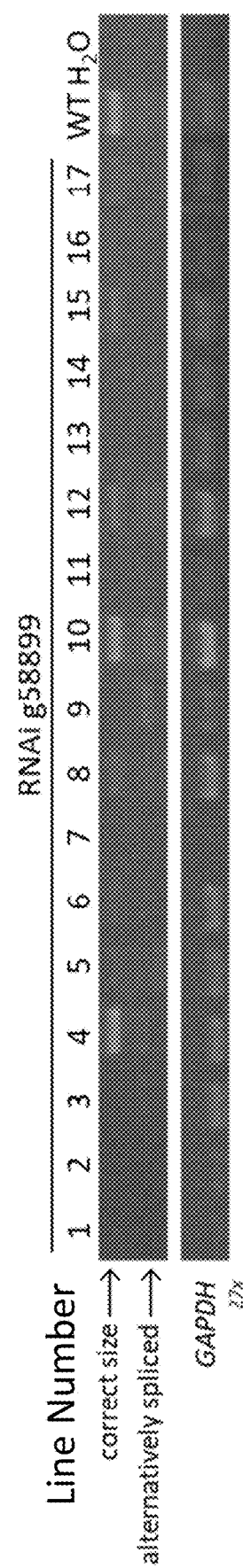
FIG. 7 depicts RNA expression of $T_0$ plants expressing an RNAi construct (SEQ ID NO: 52) designed to suppress g58899 (SEQ ID NO: 44) expression.
Figure 8:
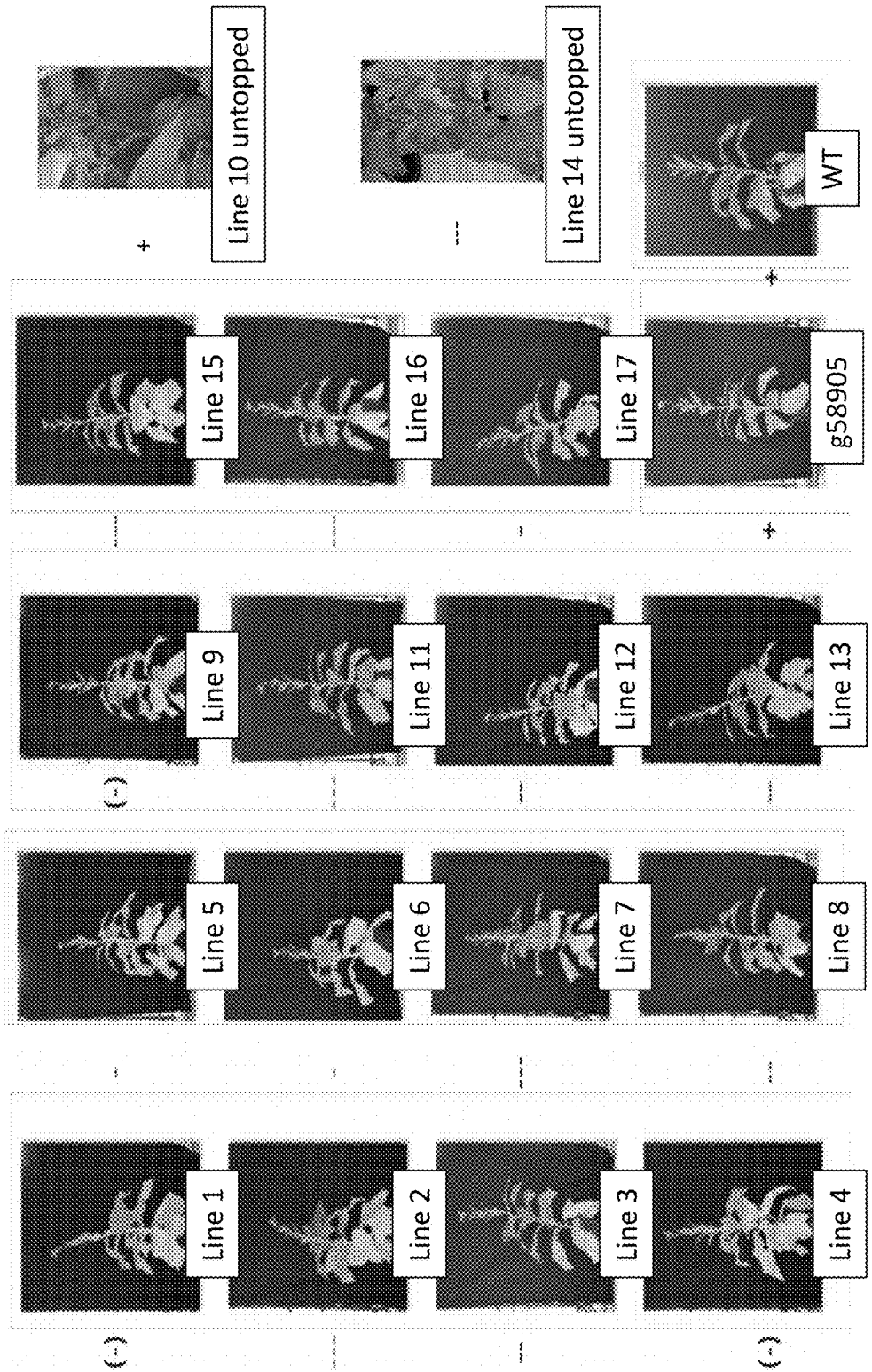
FIG. 8 depicts photographs of $T_0$ plants expressing an RNAi construct (SEQ ID NO: 52) designed to suppress g58899 (SEQ ID NO: 44) expression. A "+" symbol denotes wildtype-like expression. The symbols "(-)," "-," "--," and "---" refer to increasing levels of down-regulation as determined by semi-quantitative PCR, with (−) having the least down-regulation and −−− having the most down-regulation within that group.

Seventeen transgenic lines comprising the g58899 suppression construct are examined for g58899 expression levels using RNA extracted from young plants. See FIG. 7. FIG. 8 depicts phenotypes observed in plants comprising various levels of g58899 suppression as compared to a wildtype (WT) control. All of the plants exhibiting suppression of g58899 as compared to the wildtype control exhibit a PY phenotype in older leaves.

Example 7. Mutation of Candidate Genes

Candidate genes that exhibit decreased expression that correlates with the PY trait (e.g., TI1372, F2 individuals that are homozygous for the PY trait) are targets for having expression knocked down or knocked out in a non-PY background (e.g., NL Madole NC).

Mutations are generated in the genomic sequence of each of the candidate genes (e.g., SEQ ID NOs: 16-21 and 48). Tobacco protoplasts are transfected using polyethylene glycol (PEG) with plasmids encoding a CRISPR protein or a CRISPR protein and specific guide RNA (gRNA) targeting individual genes at desired positions.

Transfected protoplasts are then immobilized in 1% agarose beads and subjected to tissue culture. When calli grow to approximately 1 millimeter in diameter, they are spread on TOM2 plates. Calli are screened for mutations (e.g., insertions or deletions (indels)) at the target positions using fragment analysis. Candidates, showing size shifts compared to wildtype control, are selected for further culture and the consequent shoots are tested by fragment analysis again to confirm the presence of mutations.

Resulting plants are evaluated by visual observation or ethephone screening as described above in Example 1.

Example 7. Leaf Quality of Varieties Comprising Pale Yellow Trait

Leaf quality values were obtained from flue cured (Table 18), Burley (Table 19), and dark (Table 20) tobacco varieties at a field site in Virginia, United States of America in 2018. Each test comprised 3 or 4 replicates in a randomized complete block design. Grading was performed after curing was complete. Each replicate was given a USDA Grade Index by a certified tobacco leaf grader. Grading was performed separately for each of several leaf positions (A to D). At harvest, leaves are separated into positions for each three leaf increment. The top three leaves (e.g., the youngest leaves) are designated as position "A," leaves 4 to 6 designated as position "B," leaves 7 to 9 designated as position "C," leaves 10 to 12 designated as position "D," 13 to 15 designated as position "E," and so on to the last leaf.

TABLE 18

Leaf grade index values of flue cured tobacco.
PY refers to a variety comprising the
Pale Yellow trait. LA refers to a variety comprising low alkaloid levels.

| Variety | Position A | Position B | Position C | Position D |
|---|---|---|---|---|
| K326 | 100 | 95 | 90 | 90 |
| K326 | 70 | 80 | 80 | 80 |
| K326 | 35 | 90 | 85 | 85 |
| K326 | 35 | 80 | 80 | 75 |
| LA FC 53 | 40 | 70 | 1 | 1 |
| LA FC 53 | 1 | 1 | 1 | 1 |
| LA FC 53 | 35 | 35 | 30 | 1 |
| LA FC 53 | 10 | 35 | 80 | 80 |
| PY LA K326-1 | 60 | 85 | 80 | 1 |
| PY LA K326-1 | 70 | 80 | 80 | 80 |
| PY LA K326-1 | 50 | 70 | 40 | 40 |
| PY LA K326-1 | 80 | 90 | 85 | 90 |
| PY LA K326-2 | 60 | 80 | 85 | 85 |
| PY LA K326-2 | 60 | 70 | 30 | 80 |
| PY LA K326-2 | 50 | 80 | 80 | 85 |
| PY LA K326-2 | 80 | 90 | 80 | 90 |
| LA K326 | 80 | 85 | 95 | 85 |
| LA K326 | NG | 90 | 1 | 1 |
| LA K326 | 50 | 70 | 80 | 80 |
| LA K326 | 35 | 85 | 80 | 80 |

TABLE 19

Leaf grade index values of Burley tobacco.
PY refers to a variety comprising the Pale
Yellow trait. LA refers to a variety comprising low alkaloid levels.

| Variety | Position A | Position B | Position C | Position D |
|---|---|---|---|---|
| TN90 LC | 30 | 25 | 25 | 25 |
| TN90 LC | 50 | 60 | 35 | 22 |
| TN90 LC | 30 | 35 | 35 | 35 |
| TN90 LC | 30 | 35 | 35 | 35 |
| LA BU 21 | 10 | 5 | 5 | 5 |
| LA BU 21 | 5 | 5 | 5 | 5 |
| LA BU 21 | 10 | 5 | 5 | 5 |
| LA BU 21 | 10 | 10 | 5 | 5 |
| PY TN90-1 | 5 | 5 | 5 | 5 |
| PY TN90-1 | 5 | 5 | 5 | 5 |
| PY TN90-1 | 5 | 5 | 5 | 5 |
| PY TN90-1 | 5 | 5 | 5 | 5 |
| PY TN90-2 | 10 | 5 | 5 | 5 |
| PY TN90-2 | 5 | 5 | 5 | 5 |
| PY TN90-2 | 5 | 5 | 5 | 5 |
| PY TN90-2 | 5 | 5 | 5 | 5 |
| LA TN90 | 5 | 5 | 5 | 0 |
| LA TN90 | 5 | 5 | 5 | 5 |
| LA TN90 | 5 | 5 | 5 | 5 |

TABLE 20

Leaf grade index values of dark tobacco. PY refers to a variety comprising the Pale Yellow trait. LN refers to a variety comprising low nicotine levels. NG means no grade was given.

| Curing Style | Variety | Position A | Position B | Position C |
|---|---|---|---|---|
| KY | LN KY 171 | NG | NG | NG |
| | LN KY 171 | NG | NG | NG |
| | LN KY 171 | NG | NG | NG |
| | LN KY 171 | NG | NG | NG |
| | PY LN KY 171 | NG | NG | NG |
| | PY LN KY 171 | NG | NG | NG |
| | PY LN KY 171 | NG | NG | NG |
| | PY KY 171 | 13 | 5 | 5 |
| | PY KY 171 | 52 | 52 | 52 |
| | PY KY 171 | 13 | 52 | 5 |
| | PY KY 171 | 13 | 52 | 5 |
| | KY 171 | 13 | 52 | 5 |
| | KY 171 | 13 | 52 | 5 |
| | KY 171 | 13 | 52 | 5 |
| | KY 171 | 13 | 5 | 5 |
| VA | LN KY 171 | 1 | 1 | 1 |
| | LN KY 171 | 1 | 1 | 1 |
| | LN KY 171 | 1 | 1 | 1 |
| | LN KY 171 | 1 | 1 | 1 |
| | PY LN KY 171 | 1 | 1 | 1 |
| | PY LN KY 171 | 1 | 1 | 1 |
| | PY LN KY 171 | 1 | 1 | 1 |
| | PY KY 171 | 29 | 38 | 38 |
| | PY KY 171 | 29 | 38 | 38 |
| | PY KY 171 | 29 | 38 | 38 |
| | PY KY 171 | 29 | 38 | 38 |
| | KY 171 | 1 | 38 | 38 |
| | KY 171 | 3 | 74 | 74 |
| | KY 171 | 29 | 74 | 74 |
| | KY 171 | 3 | 74 | 74 |

Example 8. Additional Validation of Identified Candidate Genes

Expression of candidate genes g58899, g58917, and g61524 is further examined in the tobacco varieties Narrow Leaf Madole (NLM; lacking the pale yellow trait), ds1771 (F$_2$ population generated from crossing NLM with TI1372) wildtype (WT; no pale yellow phenotype), ds1771 heterzygous for the pale yellow trait (HT), ds1771 homozygous for the pale yellow trait (HM), and TI1372 (source of the pale yellow trait) before topping (UT) and 24 hours after topping (24 hr).

The ds1771 line was genotyped using the SNP markers identified in Table 13, and expression analysis was performed as described in Example 4 before topping at 24 hours after topping.

Figure 9:
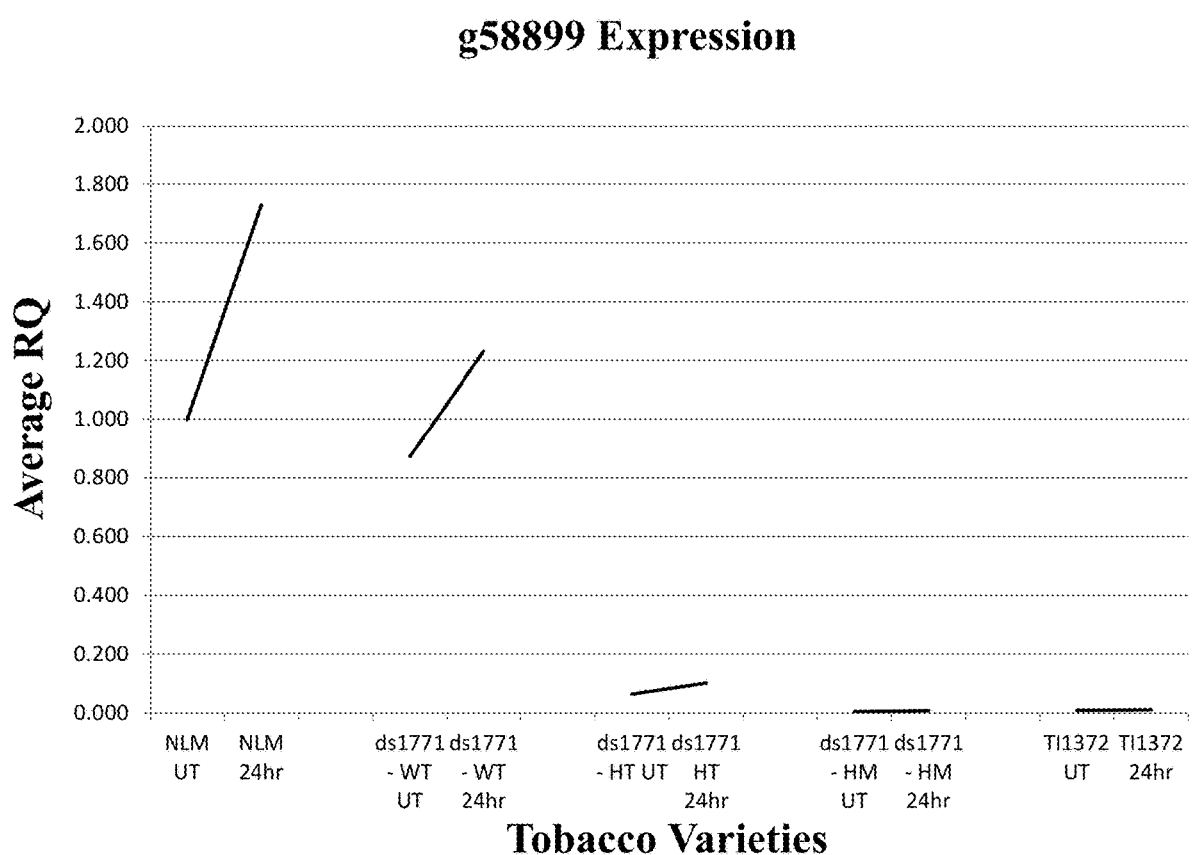
FIG. 9 depicts the expression of g58899 (SEQ ID NO: 24) as measured using quantitative RT-PCR. The average RQ are shown for the tobacco varieties Narrow Leaf Madole (NLM; lacks the pale yellow trait), ds1771 ($F_2$ population generated from crossing NLM with TI1372) wildtype (WT; no pale yellow phenotype), ds1771 heterozygous for the pale yellow trait (HT), ds1771 homozygous for the pale yellow trait (HM), and TI1372 (source of the pale yellow trait) before topping (UT) and 24 hours after topping (24 hr).
Figure 10:
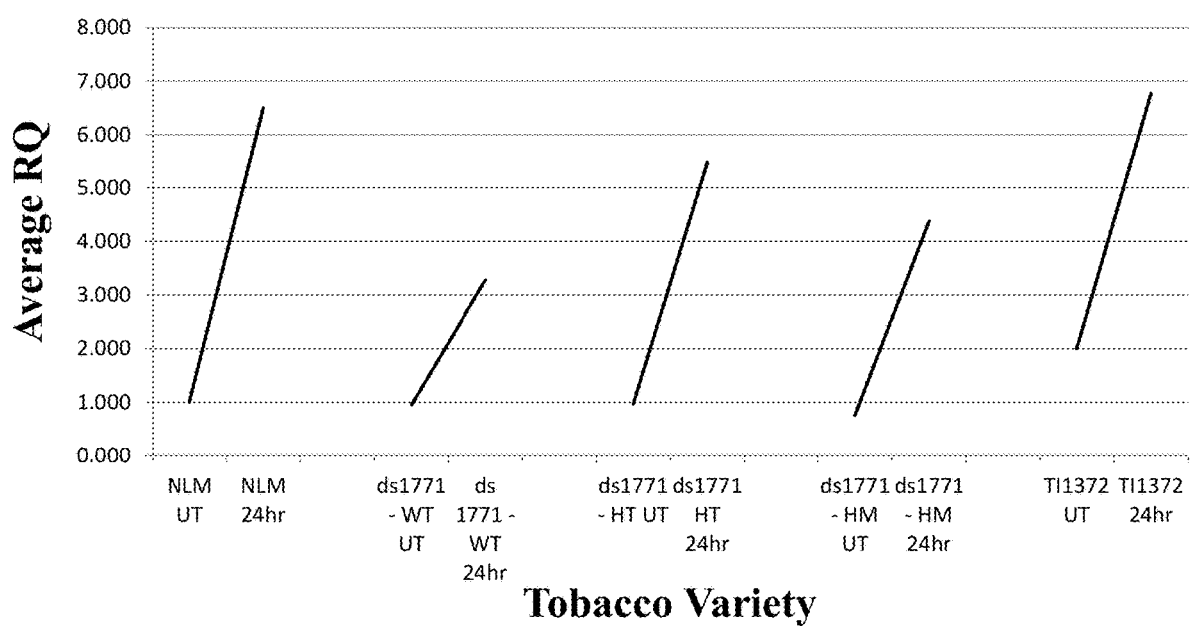
FIG. 10 depicts the expression of g58917 (SEQ ID NO: 25) as measured using quantitative RT-PCR. The average RQ are shown for the tobacco varieties Narrow Leaf Madole (NLM; lacks the pale yellow trait), ds1771 ($F_2$ population generated from crossing NLM with TI1372) wildtype (WT; no pale yellow phenotype), ds1771 heterozygous for the pale yellow trait (HT), ds1771 homozygous for the pale yellow trait (HM), and TI1372 (source of the pale yellow trait) before topping (UT) and 24 hours after topping (24 hr).
Figure 11:
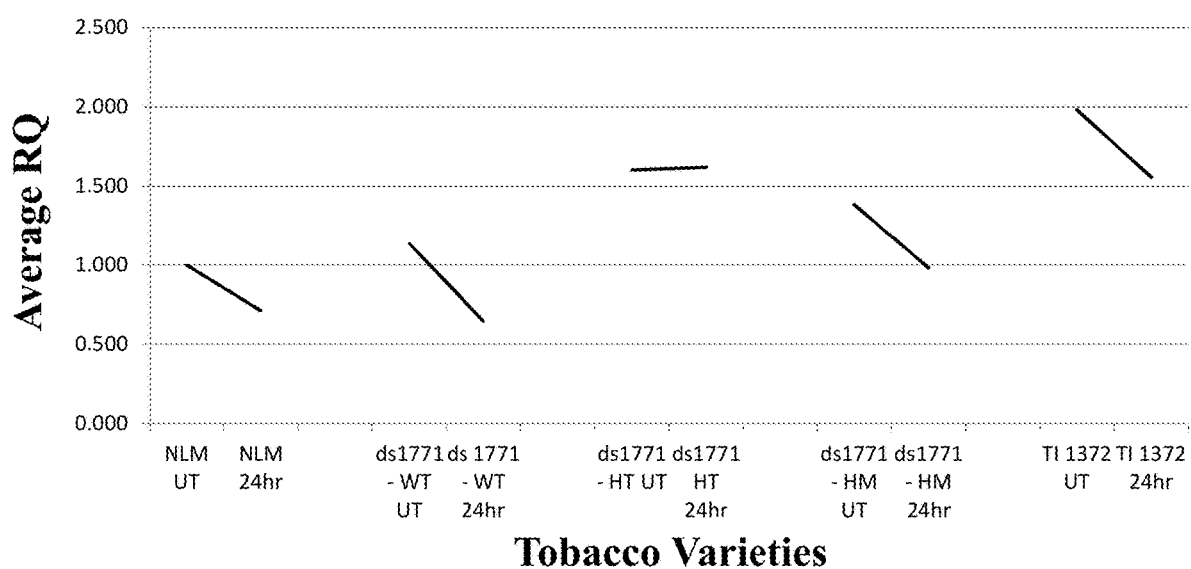
FIG. 11 depicts the expression of g61524 (SEQ ID NO: 27) as measured using quantitative RT-PCR. The average RQ are shown for the tobacco varieties Narrow Leaf Madole (NLM; lacks the pale yellow trait), ds1771 ($F_2$ population generated from crossing NLM with TI1372) wildtype (WT; no pale yellow phenotype), ds1771 heterozygous for the pale yellow trait (HT), ds1771 homozygous for the pale yellow trait (HM), and TI1372 (source of the pale yellow trait) before topping (UT) and 24 hours after topping (24 hr).

Expression of g58899 is markedly lower in the varieties ds1771-HT, ds1771-HM, and TI1372 as compared to NLM and ds1771-WT. See FIG. 9. Expression levels of g58917 and g61524 were similar across all lines. See FIGS. 10 and 11, respectively.

Example 9. Additional Sequence Analysis of g58899

Gene g58899 exhibits 87.77% sequence identity with the tomato (*Solanum lycopersicum*) STAY-GREEN gene (GenBank Accession No. NP 001358338.1; SEQ ID NO: 43). See Table 16. In tomato, the STAY-GREEN protein is required to trigger chlorophyll degradation during leaf senescence and fruit ripening.

Sequencing the cDNA sequence of g58899 in Narrow Leaf Madole (SEQ ID NO: 44), which lacks the PY trait, and TI1372 (SEQ ID NO: 45), which comprises the PY trait, indicates that the sequences share 100% identity at the nucleotide level. The amino acids encoded by SEQ ID NOs: 44 and 45, therefore, also share 100% identity at the protein (SEQ ID NOs: 46 and 47, respectively) level.

Alignments of the TI1372 cDNA (SEQ ID NO: 45) to an internal tobacco genome assembly indicate that the best match is g58899. Similarly, alignments of the Narrow Leaf Madole cDNA (SEQ ID NO: 44) to the internal tobacco genome assembly indicate that the best match is also g58899.

Alignments of the TN90 variety g58899 amino acid sequence (SEQ ID NO: 30) with the *Arabidopsis* proteins BALANCE OF CHLOROPHYLL METABOLISM1 (BCM1) and BCM2 demonstrate that g58899 shares 66.21% identity with BCM1 (SEQ ID NO: 55) and 64.13% identity with BCM2 (SEQ ID NO: 56). See FIG. 12. BCM1 and BCM2 have been shown to be involved with preventing or attenuating chlorophyll degradation. See Wang et al., *Nature Communications*, 11:1254 (2020).

Figure 13:
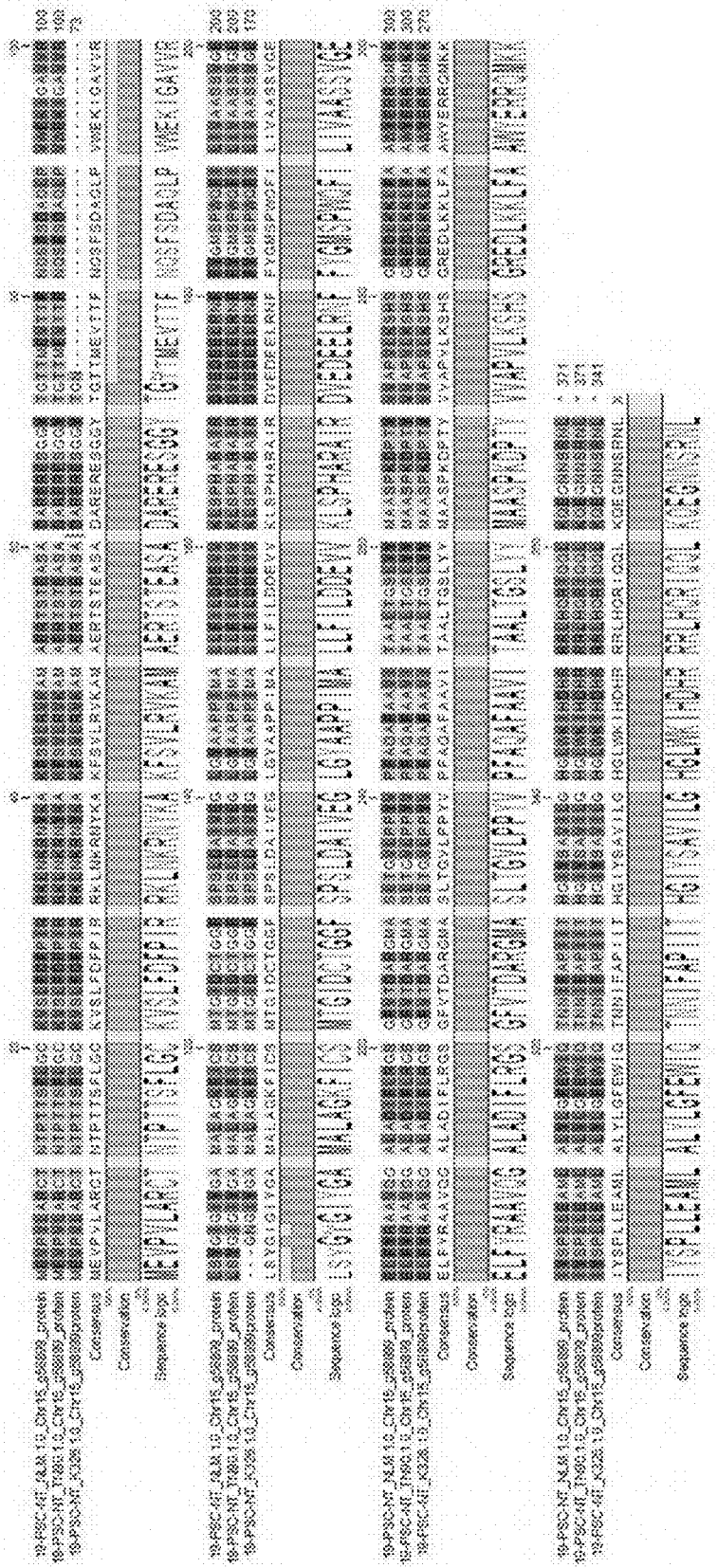
FIG. 13 depicts an alignment of g58899 amino acid sequences from the tobacco varieties Narrow Leaf Madole (NLM; SEQ ID NO: 46), TN90 (SEQ ID NO: 30), and K326 (SEQ ID NO: 57).

Alignments of the NLM g58899 amino acid sequence (SEQ ID NO: 46), the TN90 g58899 amino acid sequence (SEQ ID NO: 30), and the K326 g58899 amino acid sequence (SEQ ID NO: 57) enable the identification of a g58899 consensus amino acid sequence (SEQ ID NO: 58). See FIG. 13.

Example 10. Expression Profile of g58899

Figures 14, 14A:
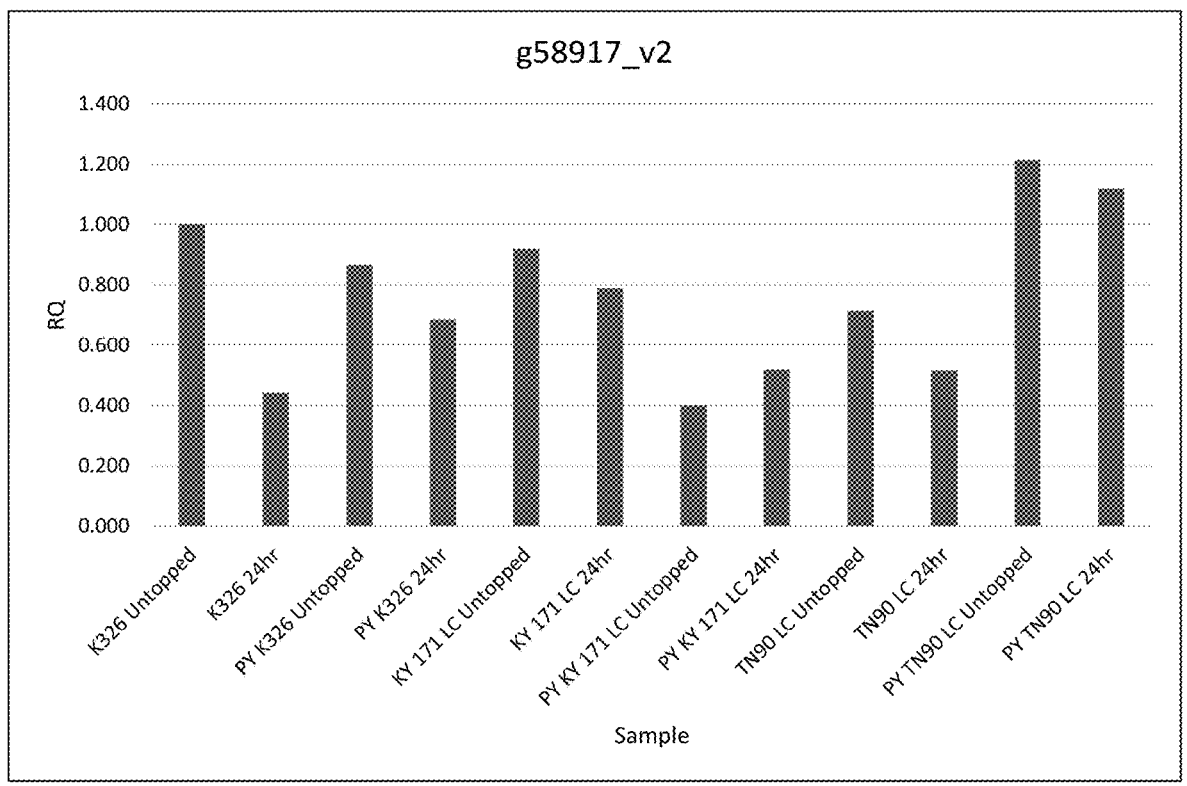
FIG. 14 comprises FIG. 14A, FIG. 14B, and FIG. 14C.
FIG. 14A depicts the relative quantification (RQ) of g58917 v2 (SEQ ID NO: 25).
Figures 14, 14B:
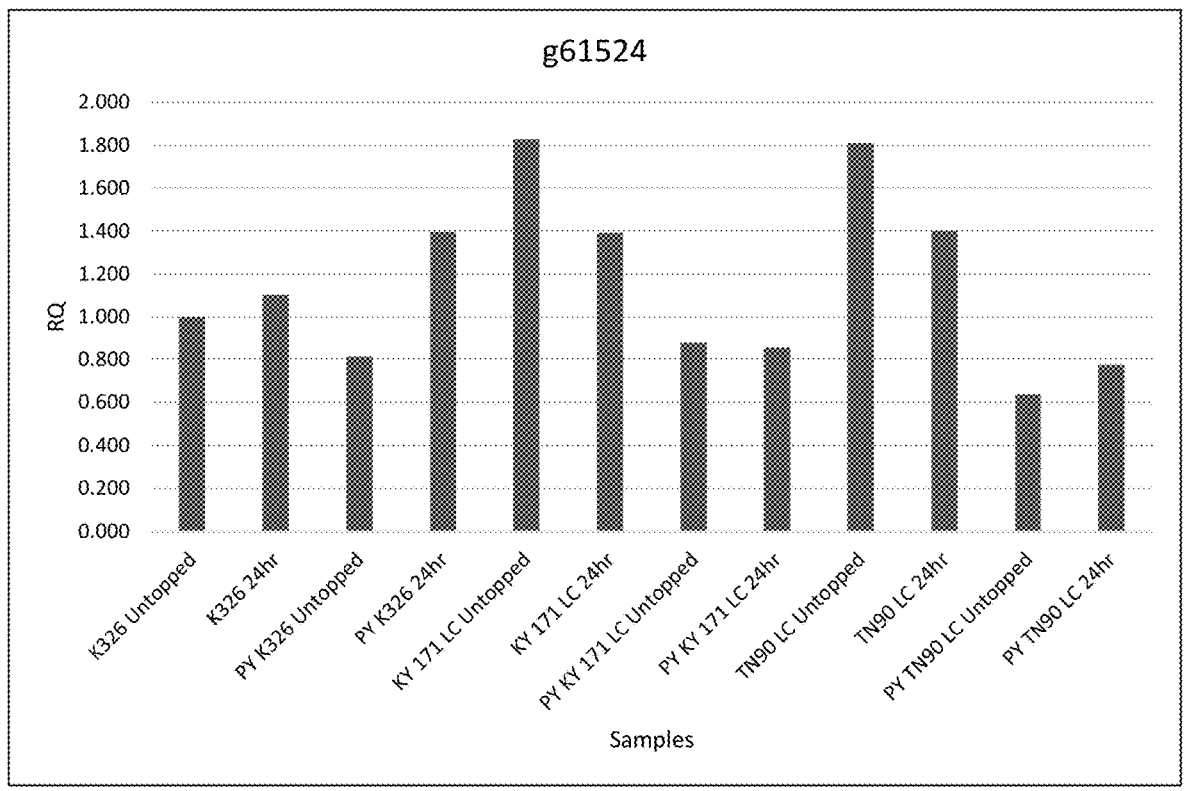
FIG. 14B depicts the RQ of g61524 (SEQ ID NO: 27).
Figures 14, 14C:
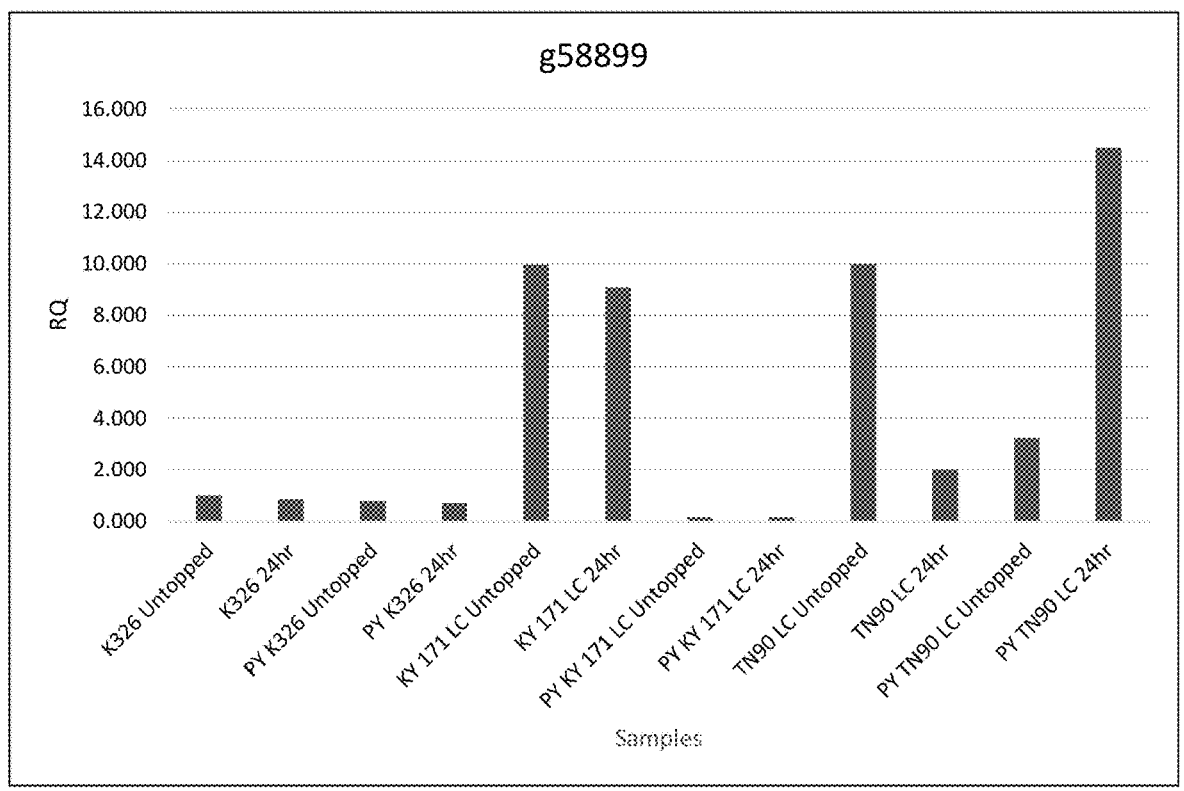
FIG. 14C depicts the RQ of g58899 (SEQ ID NO: 24. For each of FIGS. 14A, 14B, and 14C, the tobacco lines K326, Pale Yellow (PY) K326, KY171 LC, PY KY 171 LC, TN90 LC, and PY TN90 LC are sampled. Samples are taken before topping ("untopped") and 24 hours after topping ("24 hr").

The expression profile of g58899 (SEQ ID NO: 24) is examined in the tobacco lines K326, Pale Yellow (PY) K326, KY 171, Pale Yellow (PY) K171, TN90, and Pale Yellow (PY) TN 90 using qPCR. RNA samples are collected from leaves before topping and 24 hours after topping. The expression profiles of g61524 (SEQ ID NO: 27) and g58917 (SEQ ID NO: 25) are also examined. Actin is used as a control. Results are depicted in FIGS. 14A, 14B, and 14C.

The invention claimed is:

1. A modified tobacco plant, or part thereof, comprising a non-natural mutation in the nucleic acid sequence of SEQ ID NO:18, wherein said modified tobacco plant comprises a pale yellow phenotype, wherein said non-natural mutation results in a reduced level of expression of said polynucleotide as compared to a wildtype tobacco plant, and wherein said non-natural mutation is not present in said wildtype tobacco plant.

2. The modified tobacco plant, or part thereof, of claim 1, wherein said modified tobacco plant is of a tobacco variety selected from the group consisting of a flue-cured variety, a bright variety, a Burley variety, a Virginia variety, a Maryland variety, a dark variety, a Galpão variety, an Oriental variety, and a Turkish variety.

3. The modified tobacco plant, or part thereof, of claim 1, wherein said modified tobacco plant is of a variety selected from the group consisting of 400 (TC 225), 401 (TC 226), 401 Cherry Red (TC 227), 401 Cherry Red Free (TC 228), Cash (TC 250), Cash (TI 278), CC 101, CC 1063, CC 13, CC 143, CC 200, CC 27, CC 301, CC 33, CC 35, CC 37, CC 400, CC 500, CC 600, CC 65, CC 67, CC 700, CC 800, CC 900, Coker 139 (TC 259), Coker 139 yb1, yb2, Coker 140 (TC 260), Coker 176 (TC 262), Coker 187 (TC 263), Coker 187-Hicks (TC 265), Coker 209 (TC 267), Coker 258 (TC 270), Coker 298 (TC 272), Coker 316 (TC 273), Coker 319 (TC 274), Coker 347 (TC 275), Coker 371-Gold (TC 276), Coker 411 (TC 277), Coker 48 (TC 253), Coker 51 (TC 254), Coker 86 (TC 256), CU 263 (TC 619), CU 561, DH95-1562-1, Dixie Bright 101 (TC 290), Dixie Bright 102 (TC 291), Dixie Bright 244 (TC 292), Dixie Bright 27 (TC 288), Dixie Bright 28 (TC 289), GF 157, GF 318, GL 26H, GL 338, GL 350, GL 368, GL 395, GL 600, GL 737, GL 939, GL 939 (TC 628), Hicks (TC 310), Hicks Broadleaf (TC 311), K 149 (TC 568), K 317, K 326, K 326 (TC 319), K 340 (TC 320), K 346, K 346 (TC 569), K 358, K 394 (TC 321), K 399, K 399 (TC 322), K 730, Lonibow (TI 1573), Lonibow (TI 1613), McNair 10 (TC 330), McNair 135 (TC 337), McNair 30 (TC 334), McNair 373 (TC 338), McNair 944 (TC 339), MK94 (TI 1512), MS K 326, MS NC 71, MS NC 72, NC 100, NC 102, NC 1071 (TC 364), NC 1125-2, NC 12 (TC 346), NC 1226, NC 196, NC 2326 (TC 365), NC 27 NF (TC 349), NC 291, NC 297, NC 299, NC 37 NF (TC 350), NC 471, NC 55, NC 567 (TC 362), NC 60 (TC 352), NC 606, NC 6140, NC 71, NC 72, NC 729 (TC 557), NC 810 (TC 659), NC 82 (TC 356), NC 8640, NC 89 (TC 359), NC 92, NC 925, NC 95 (TC 360), NC 98 (TC 361), NC EX 24, NC PY 10 (TC 367), NC TG 61, Oxford 1 (TC 369), Oxford 1-181 (TC 370), Oxford 2 (TC 371), Oxford 207 (TC 632), Oxford 26 (TC 373), Oxford 3 (TC 372), Oxford 414 NF, PD 611 (TC 387), PVH 03, PVH 09, PVH 1118, PVH 1452, PVH 1600, PVH 2110, PVH 2275, R 83 (Line 256-1) (TI 1400), Reams 134, Reams 158, Reams 713, Reams 744, Reams Ml, RG 11 (TC 600), RG 13 (TC 601), RG 17 (TC 627), RG 22 (TC 584), RG 8 (TC 585), RG 81 (TC 618), RG H51, RG4H 217, RGH 12, RGH 4, RGH 51, RGH 61, SC 58 (TC 400), SC 72 (TC 403), Sp. G-168, SPEIGHT 168, Speight 168 (TC 633), Speight 172 (TC 634), Speight 178, Speight 179, Speight 190, Speight 196, SPEIGHT 220, SPEIGHT 225, SPEIGHT 227, SPEIGHT 236, Speight G-10 (TC 416), Speight G-102, Speight G-108, Speight G-111, Speight G-117, Speight G-126, Speight G-15 (TC 418), Speight G-23, Speight G-28 (TC 420), Speight G-33, Speight G-41, Speight G-5, Speight G-52, Speight G-58, Speight G-70, Speight G-70 (TC 426), Speight G-80 (TC 427), Speight NF3 (TC 629), STNCB, VA 182, VA 45 (TC 559), Vesta 30 (TC 439), Vesta 33 (TC 440), Vesta 5 (TC 438), Vesta 62 (TC 441), Virginia (TI 220), Virginia (TI 273), Virginia (TI 877), Virginia 115 (TC 444), Virginia 21 (TC 443), Virginia Bright (TI 964), Virginia Bright Leaf (TC 446), Virginia Gold (TC 447), White Stem Orinoco (TC 451), 4407 LC, AA-37-1, Burley 21 (TC 7), Burley 49 (TC 10), Burley 64 (TC 11), Burley Mammoth KY 16 (TC 12), Clay 402, Clay 403, Clay 502, Clays 403, GR 10 (TC 19), GR 10 (TC 19), GR 10A (TC 20), GR 13 (TC 21), GR 14 (TC 22), GR 149 LC, GR 153, GR 17 (TC 23), GR 17B (TC 24), GR 18 (TC 25), GR 19 (TC 26), GR 2 (TC 15), GR 24 (TC 27), GR 36 (TC 28), GR 38 (TC 29), GR 38A (TC 30), GR 40 (TC 31), GR 42 (TC 32), GR 42C (TC 33), GR 43 (TC 34), GR 44 (TC 35), GR 45 (TC 36), GR 46 (TC 37), GR 48 (TC 38), GR 5 (TC 16), GR 53 (TC 39), GR 6 (TC 17), GR 9 (TC 18), GR139 NS, GR139 S, HB 04P, HB 04P LC, HB 3307P LC, HB 4108P, HB 4151P, HB 4192P, HB 4194P, HB 4196, HB 4488, HB 4488P, HB04P, HB 4488 LC, HIB 21, HPB 21, HY 403, Hybrid 403 LC, Hybrid 404 LC, Hybrid 501 LC, KDH-959 (TC 576), KDH-960 (TC 577), KT 200 LC, KT 204 LC, KT 206 LC, KT 209 LC, KT 210 LC, KT 212 LC, KT 215 LC, KY 1 (TC 52), KY 10 (TC 55), KY 12 (TC 56), KY 14 (TC 57), KY 14×L8 LC, KY 15 (TC 58), KY 16 (TC 59), KY 17 (TC 60), KY 19 (TC 61), KY 21 (TC 62), KY 22 (TC 63), KY 24 (TC 64), KY 26 (TC 65), KY 33 (TC 66), KY 34 (TC 67), KY 35 (TC 68), KY 41A (TC 69), KY 5 (TC 53), KY 52 (TC 70), KY 54 (TC 71), KY 56 (TC 72), KY 56 (TC 72), KY 57 (TC 73), KY 58 (TC 74), KY 8654 (TC 77), KY 8959, KY 9 (TC 54), KY 907 LC, KY 908 (TC 630), NBH 98 (Screened), NC 1206, NC 129, NC 2000 LC, NC 2002 LC, NC 3 LC, NC 5 LC, NC 6 LC, NC 7 LC, NC BH 129 LC, NC03-42-2, Newton 98, R 610 LC, R 630 LC, R 7-11, R 7-12 LC, RG 17, TKF 1801 LC, TKF 2002 LC, TKF 4024 LC, TKF 4028 LC, TKF 6400 LC, TKF 7002 LC, TKS 2002 LC, TN 86 (TC 82), TN 90 LC, TN 97 Hybrid LC, TN 97 LC, VA 116, VA 119, Virgin A Mutante (TI 1406), Virginia 509 (TC 84), Maryland 10 (TC 498), Maryland 14 D2 (TC 499), Maryland 201 (TC 503), Maryland 21 (TC 500), Maryland 341 (TC 504), Maryland 40, Maryland 402, Maryland 59 (TC 501), Maryland 601, Maryland 609 (TC 505), Maryland 64 (TC 502), Maryland 872 (TC 506), Maryland Mammoth (TC 507), Black Mammoth (TC 461), Black Mammoth Small Stalk (TC 641), Certified Madole (TC 463), D-534-A-1 (TC 464), DAC ULT 302, DAC ULT 303, DAC ULT 306, DAC ULT 308, DAC ULT 312, DF 300 (TC 465), DF 485 (TC 466), DF 516 (TC 467), DF 911 (TC 468), DT 508, DT 518 (Screened), DT 538 LC, DT 592, Improved Madole (TC 471), Jernigan's Madole (TC 472), KT 14LC, KT D17LC, KT D4 LC, KT D6 LC, KT D8 LC, KY 153 (TC 216), KY 157 (TC 217), KY 160, KY 160 (TC 218), KY 163 (TC 219), KY 165 (TC 220), KY 170 (TC 474), KY 171 (PhPh), KY 171 (TC 475), KY 171 LC, KY 171 NS, KY 180 (TC 573), KY 190 (TC 574), Little Crittenden, Little Crittenden (TC 476), Little Crittenden LC (certified), Little Crittenden PhPh, Lizard Tail Turtle Foot, Madole (TC 478), Madole (TC 479), MS KY 171, MS NL Madole LC, MS TN D950 LC, Nance (TC 616), Narrow Leaf Madole LC (certified), Neal Smith Madole (TC 646), Newtons VH Madole, NL Madole, NL Madole (PhPh), NL Madole (TC 484), NL Madole LC, NL Madole LC (PhPh), NL Madole NS, One Sucker (TC 224), OS 400, PD 302H, PD 312H, PD 318H, PD 7302 LC, PD 7305, PD 7309 LC, PD 7312 LC, PD 7318 LC, PD 7319 LC, Petico M PG04, PY KY 160 (TC 612), PY KY 171 (TC 613), Shirey, TI 1372, TN D94, TN D94 (TC 621), TN D950, TN D950 (PhPh), TN D950, TN D950 (TC 622), TR Madole (TC 486), VA 309, VA 309 (TC 560), VA 309 LC (certified), VA 310 (TC 487), VA 331 (TC 592), VA 355 (TC 638), VA 359, VA 359 (Screened), VA 359 (TC 639), VA 359 LC (certified), VA 403 (TC 580), VA 405 (TC 581), VA 409 (TC 562), VA 510 (TC 572), Bafra (TI 1641), Bahce (TI 1730), Bahia (TI 1416), Bahia (TI 1455), Baiano (TI 128), Basma, Basma (TI 1666), Basma Drama, Basma Hybrid (PhPh), Basma Zihna I, Bitlis (TI 1667), Bitlis (TI 1725), Bubalovac (TI 1282), Bursa (TI 1650), Bursa (TI 1668), Canik (TI 1644), Djebel 174 (TI 1492), Djebel 359 (TI 1493), Djebel 81, Dubec 566 (TI 1409), Dubec 7 (TI 1410), Dubek 566 (TI 1567), Duzce (TI 1670), Edirne (TI 1671), Ege (TI 1642), Ege-64 (TI 1672), Izmir (Akhisar) (TI 1729), Izmir (Gavurkoy) (TI 1727), Izmir Ege 64, Izmir-Incekara (TI 1674), Izmir-Ozbas (TI 1675), Jaka Dzebel (TI 1326), Kaba-Kulak, Kagoshima Maruba (TI 158), Katerini, Katerini S53, Krumovgrad 58, MS Basma, MS Katerini S53, Nevrokop 1146, Ozbas (TI 1645), Perustitza (TI 980), Prilep (TI 1291), Prilep (TI 1325), Prilep 12-2/1, Prilep 23, Samsun (TC 536), Samsun 959 (TI 1570), Samsun Evkaf (TI 1723), Samsun Holmes NN (TC 540), Samsun Maden (TI 1647), Samsun NO 15 (TC 541), Samsun-BLK SHK Tol (TC 542), Samsun-Canik (TI 1678), Samsun-Maden (TI 1679), Saribaptar 407—Izmir Region, Smyrna (TC 543), Smyrna No. 23 (TC 545), Smyrna No. 9 (TC 544), Smyrna-Blk Shk Tol (TC 546), Trabzon (TI 1649), Trabzon (TI 1682), Trapezund 161 (TI 1407), Turkish (TC 548), Turkish Angshit (TI 90), Turkish Samsum (TI 92), Turkish Tropizoid (TI 93), Turkish Varotic (TI 89), Xanthi (TI 1662), Bahai (TI 62), Beinhart 1000, Beinhart 1000 (TI 1562), Beinhart 1000-1 (TI 1561), Bergerac C, Bergerac C (TI 1529), Big Cuban (TI 1565), Castillo Negro, Blanco, Pina (TI 448), Castillo Negro, Blanco, Pina (TI 448A), Castillo Negro, Blanco, Pina (TI 449), Caujaro (TI 893), Chocoa (TI 289), Chocoa (TI 313), Connecticut 15 (TC 183), Connecticut Broadleaf, Connecticut Broadleaf (TC 186), Connecticut Shade (TC 188), Criollo Colorado (TI 1093), Enshu (TI 1586), Florida 301, Florida 301 (TC 195), PA Broadleaf (TC 119), Pennsylvania Broadleaf, Pennsylvania Broadleaf (TC 119), Petite Havana SR1, Petite Havana SR1 (TC 105), Chocoa (TI 319), Hoja Parada (TI 1089), Hoja Parado (Galpoa) (TI 1068), Perique (St. James Parrish), Perique (TC 556), Perique (TI 1374), *Sylvestris* (TI 984), and TI 179.

4. The modified tobacco plant, or part thereof, of claim 1, wherein said tobacco plant, or part thereof, is heterozygous for said mutation.

5. The modified tobacco plant, or part thereof, of claim 1, wherein said tobacco plant, or part thereof, is homozygous for said mutation.

6. The modified tobacco plant, or part thereof, of claim 1, wherein said modified tobacco plant is a hybrid.

7. The modified tobacco plant, or part thereof, of claim 1, wherein said modified tobacco plant is male sterile or cytoplasmically male sterile.

8. The modified tobacco plant, or part thereof, of claim 1, wherein said non-natural mutation results in a reduced level of activity of a protein or polypeptide encoded by the polynucleotide comprising the non-natural mutation as compared to a protein or polypeptide encoded by the polynucleotide lacking the non-natural mutation.

9. The modified tobacco plant, or part thereof, of claim 1, wherein the mutation is in a sequence region selected from the group consisting of a promoter, a 5'-UTR, an intron, an exon, a 3'-UTR, a terminator, and any combination thereof.

10. The modified tobacco plant, or part thereof, of claim 1, wherein said non-natural mutation is selected from the group consisting of a nonsense mutation, a missense mutation, a frameshift mutation, a splice-site mutation, and any combination thereof.

11. The modified tobacco plant, or part thereof, of claim 1, wherein said non-natural mutation is selected from the group consisting of a substitution, a deletion, an insertion, a duplication, and an inversion of one or more nucleotides.

12. Cured tobacco material from a modified tobacco plant, or part thereof, comprising a non-natural mutation in the nucleic acid sequence of SEQ ID NO: 18, wherein said modified tobacco plant comprises a pale yellow phenotype, wherein said non-natural mutation results in a reduced level of expression of said polynucleotide as compared to a wildtype tobacco plant, and wherein said non-natural mutation is not present in said wildtype tobacco plant.

13. The cured tobacco material of claim 12, wherein the cured tobacco material is selected from the group consisting of air-cured tobacco material, fire-cured tobacco material, sun-cured tobacco material, and flue-cured tobacco material.

14. The cured tobacco material of claim 12, wherein the cured tobacco material is selected from the group consisting of leaf material, stem material, flower material, and bud material.

15. A tobacco product comprising the cured tobacco material of claim 12.

16. The tobacco product of claim 15, wherein the tobacco product is selected from the group consisting of a cigarillo, non-ventilated recess filter cigarette, vented recess filter cigarette, cigar, snuff, pipe tobacco, cigar tobacco, cigarette tobacco, chewing tobacco, leaf tobacco, hookah tobacco, shredded tobacco, and cut tobacco.

17. The tobacco product of claim 15, wherein the tobacco product is a smokeless tobacco product.

18. The tobacco product of claim 17, wherein the smokeless tobacco product is selected from the group consisting of chewing tobacco, moist smokeless tobacco, snus, and dry snuff.

19. The tobacco product of claim 15, wherein the tobacco product further comprises fermented tobacco.

20. The tobacco product of claim 15, wherein the tobacco product further comprises reconstituted tobacco.

* * * * *